United States Patent
Li et al.

(10) Patent No.: US 10,081,629 B2
(45) Date of Patent: Sep. 25, 2018

(54) AMIDE DERIVATIVES AND PHARMACEUTICALLY ACCEPTABLE SALTS THEREOF, PREPARATION METHOD THEREOF AND MEDICINAL APPLICATION THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Xin Li, Shanghai (CN); Wei He, Shanghai (CN); Xianbo Liu, Shanghai (CN); Bin Wang, Shanghai (CN); Qiyue Hu, Shanghai (CN); Fangfang Jin, Shanghai (CN); Qing Dong, Shanghai (CN); Piaoyang Sun, Jiangsu (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/303,704

(22) PCT Filed: Mar. 31, 2015

(86) PCT No.: PCT/CN2015/075531
§ 371 (c)(1),
(2) Date: Oct. 12, 2016

(87) PCT Pub. No.: WO2015/158204
PCT Pub. Date: Oct. 22, 2015

(65) Prior Publication Data
US 2017/0037044 A1 Feb. 9, 2017

(30) Foreign Application Priority Data
Apr. 14, 2014 (CN) .......................... 2014 1 0148152

(51) Int. Cl.
| | |
|---|---|
| C07D 307/78 | (2006.01) |
| C07D 307/87 | (2006.01) |
| C07D 471/04 | (2006.01) |
| C07C 233/47 | (2006.01) |
| C07C 233/63 | (2006.01) |
| C07D 209/10 | (2006.01) |
| C07D 209/44 | (2006.01) |
| C07D 231/56 | (2006.01) |
| C07D 235/18 | (2006.01) |
| C07D 263/57 | (2006.01) |
| C07D 401/04 | (2006.01) |
| C07D 401/12 | (2006.01) |
| C07D 405/12 | (2006.01) |

(Continued)

(52) U.S. Cl.
CPC .......... C07D 471/04 (2013.01); C07C 233/47 (2013.01); C07C 233/63 (2013.01); C07D 209/10 (2013.01); C07D 209/44 (2013.01); C07D 231/56 (2013.01); C07D 235/18 (2013.01); C07D 263/57 (2013.01); C07D 401/04 (2013.01); C07D 401/12 (2013.01); C07D 405/12 (2013.01); C07D 405/14 (2013.01); C07D 413/12 (2013.01); C07D 417/12 (2013.01); C07C 2601/02 (2017.05)

(58) Field of Classification Search
CPC .. C07D 307/78; C07D 307/87; C07D 333/52; C07D 333/72; C07D 209/04; C07D 209/44; C07D 235/04; C07D 231/56; C07D 261/20; C07D 263/54; C07D 277/62
USPC ......... 548/469, 470, 304.4, 361.1, 241, 217, 548/152; 549/462, 49
See application file for complete search history.

(56) References Cited

FOREIGN PATENT DOCUMENTS

| | | |
|---|---|---|
| CN | 101490000 A | 7/2009 |
| WO | 2012087771 A1 | 6/2012 |

(Continued)

OTHER PUBLICATIONS

Int'l Search Report dated Jun. 30, 2015 in Int'l Application No. PCT/CN2015/075531.

*Primary Examiner* — Niloofar Rahmani
(74) *Attorney, Agent, or Firm* — Panitch Schwarze Belisario & Nadel LLP

(57) ABSTRACT

Amide derivatives and pharmaceutically acceptable salts thereof, preparation method thereof and medicinal application thereof are provided. Specifically, amide derivatives represented by general formula (I) are provided. The amide derivatives represented by general formula (I) can be used as a therapeutic agent, particularly as an inhibitor for microsomal prostaglandin E synthase-1 (mPGES-1), and also to treat and/or prevent diseases or illnesses such as inflammation and/or pain etc. The definition of each substituent group in general formula (I) is the same as the definition in the description.

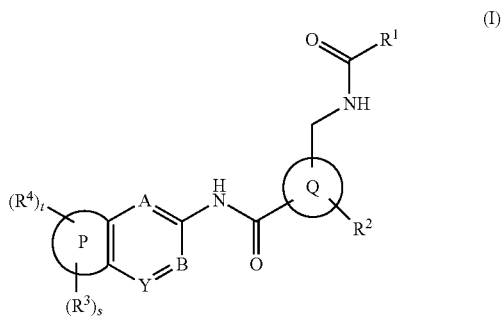

16 Claims, No Drawings

(51) Int. Cl.
*C07D 405/14* (2006.01)
*C07D 413/12* (2006.01)
*C07D 417/12* (2006.01)

(56) References Cited

FOREIGN PATENT DOCUMENTS

| | | | |
|---|---|---|---|
| WO | 2012161965 | A1 | 11/2012 |
| WO | 2013038308 | * | 3/2013 |
| WO | 2013038308 | A1 | 3/2013 |
| WO | 2013072825 | A1 | 5/2013 |
| WO | 2013118071 | A1 | 8/2013 |

* cited by examiner

AMIDE DERIVATIVES AND PHARMACEUTICALLY ACCEPTABLE SALTS THEREOF, PREPARATION METHOD THEREOF AND MEDICINAL APPLICATION THEREOF

CROSS-REFERENCE TO RELATED APPLICATION

This application is a Section 371 of International Application No. PCT/CN2015/075531, filed Mar. 31, 2015, which was published in the Chinese language on Oct. 22, 2015, under International Publication No. WO 2015/158204 A1, and the disclosure of which is incorporated herein by reference.

FIELD OF THE INVENTION

The present invention relates to novel amide derivatives, preparation method thereof and pharmaceutical compositions containing the same, as well as use thereof as a therapeutic agent, especially as an inhibitor of microsomal prostaglandin E synthase-1 (mPGES-1), and use thereof in the preparation of a medicament for the treatment and/or prevention of diseases or disorders such as inflammation and/or pain etc.

BACKGROUND OF THE INVENTION

Many diseases and/or disorders are essentially inflammatory. A main existing problem associated with the treatment of inflammatory diseases is the lack of efficacy and/or the presence of common side effects. Inflammatory diseases affecting humans include asthma, inflammatory bowel disease, rheumatoid arthritis, osteoarthritis, rhinitis, conjunctivitis, dermatitis and the like. Inflammation is a common cause of pain, which can be caused by a variety of reasons, such as infection, surgery, or other injuries. Meanwhile, some diseases, including malignant tumor and cardiovascular disease, also have the symptoms of inflammation.

Prostaglandin E2 (prostaglandin E2, PGE2) is one of the most common prostaglandins (PG), which belongs to strong proinflammatory mediator and can induce fever and pain, and participate in a variety of physiological and pathological processes of the body. Its chemical synthesis consists of three consecutive enzymatic reactions: (1) arachidonic acid (AA) is released from glycerol phospholipid on the membranes by the catalysis of the phospholipase A2 (PLA2); (2) AA generates PGG2 and PGH2 by the action of cyclooxygenase (COX); and (3) PGH2 generates PGE2, PGF2, and PGD2, prostacylin and thromboxane A2 by the catalysis of PGE2 synthase (PGES).

There are two forms of cyclooxygenase (COX). One is constitutively expressed as COX-1 in many of the cells and tissues, and the other is COX-2 induced by proinflammatory stimulators such as cytokines during an inflammatory reaction. Currently, there are kinds of COX-1 and/or COX-2 inhibitors that control inflammation by reducing the final formation of PGE2, such as "NSAID" (non-steroid anti-inflammatory drug) and "coxib" (selective cox-2 inhibitor). However, inhibiting target COX will reduce the generation of all the metabolites from arachidonic acid (AA), including some metabolites that are beneficial to the human body. Therefore the COX inhibitors may cause adverse biological effects to the human body. Therefore, developing more safe and effective new drugs for inflammatory disease is of great clinical significance and market value.

The PGES targeting PGE2 synthesis is a terminal rate-limiting enzyme during the process of synthesis of PGE2. As we all know, there are at least three kinds of PGES, named cytoplasmic PGES (cPGES) (or called PGE-3), membrane-bound PGES-1 (mPGES-1) and membrane-bound PGES-2 (mPGES-2). The cPGES is a GSH dependent constitutively expressed enzyme, which belongs to the enzyme widely expressed by housekeeping genes in multiple tissues and cells and is not affected by inflammation stimulating factor. The mPGES-2 is a GSH independent constitutively expressed enzyme, which is mainly expressed in tissues with relatively low expression of mPGES-1, such as brain, heart, kidney, and intestine, and is not induced by tissue inflammation and damage. The mPGES-1 belongs to the GSH dependent inducible expression enzyme, which can be expressed a lot due to inducement by inflammatory factor and plays an important role in a variety of diseases, such as arthritis, inflammation-associated fever and pain, atherosclerosis, and the pathological and physiological process of cancer. mPGES-1 gene is on the chromosome 9q34.3, and contains three exons and two introns, with a length of approximately 14.8 Kb. Its cDNA encodes a polypeptide containing 152 amino acids. The mPGES-1 primary protein structure from different species has more than 80% homology. The research shows that the expression of COX-2 and mPGES-1 are significantly increased in a variety of cultured cells stimulated with an inflammatory factor (LPS, IL-1, etc.), which is accompanied by an increase of the synthesis of PGE2. Immunohistochemical experiments also show that COX-2 and mPGES-1 are all located in the microsome membrane, which indicates that mPGES-1 is mainly coupled with COX-2, and mediates the increased synthesis of PGE2 in the delayed reaction caused by inflammation factors. However, enzymatic dynamics research shows that the inductions of COX-2 and mPGES-1 are not completely consistent, and in certain cases, COX-2 can be coupled with mPGES-2, and mPGES-1 can also be coupled with COX-1 at the same time. Moreover, PGH2 generated by the catalysis of COX-2 either can be synthesized into PGE2 or other types of prostaglandin by the action of mPGES-1. Thus, the regulatory mechanisms of the expression of COX-2 and mPGES-1 are both overlapping and different.

Currently, there are two kinds of mPGES-1 inhibitors, AAD-2004 of Korean GNT (Neurotech) pharmaceutical company and LY-3023703 of Eli Lilly Company. AAD-2004 indications are not aimed at pain, but it is a potent spin trapping molecule and microsomal prostaglandin E synthase-1 inhibitor which can be used in the treatment of Alzheimer's disease, Parkinson's disease and motor neurone disease. LY-3023703 is used in the treatment of osteoarthritis pain, and entered the clinical stage on June 2016.

At present, there are only two patent applications WO2012087771 and WO2012161965 about mPGES-1 disclosed by Eli Lilly Company.

Although a series of microsomal prostaglandin E synthetase-1 (mPGES-1) inhibitors have been disclosed by now, new compounds with better efficacy still need to be developed. The present invention obtained a series of compounds of general formula (I) upon continuous efforts, and found that these compounds have excellent effect and function.

SUMMARY OF THE INVENTION

The present invention is directed to a compound of formula (I), or a tautomer, mesomer, racemate, enantiomer, diastereomer, or mixture thereof, or pharmaceutically acceptable salt thereof,

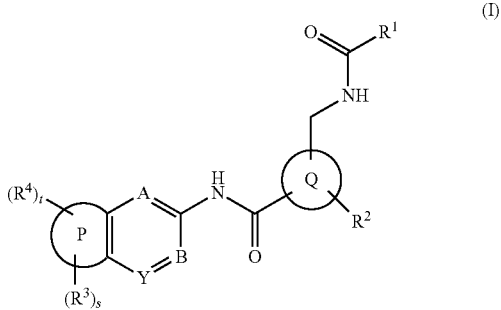

wherein:
ring P is selected from the group consisting of five-membered heteroaryl and five-membered heterocyclyl;
ring Q is selected from the group consisting of aryl and heteroaryl, preferably phenyl, pyridyl or pyrimidinyl;
A, B or Y is selected from the group consisting of —CH and N;
$R^1$ is selected from the group consisting of alkyl and cycloalkyl, wherein said alkyl or cycloalkyl is optionally further substituted by one or more groups selected from the group consisting of alkyl, halogen and haloalkyl;
$R^2$ is selected from the group consisting of halogen and haloalkyl;
each $R^3$ is the same or different, and each is independently selected from the group consisting of hydrogen, halogen, alkoxy, cyano, nitro, alkyl, cycloalkyl, heterocyclyl, oxo, —C(O)OR$^5$, —OC(O)R$^5$, —NHS(O)mR$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein said alkyl, cycloalkyl and heterocyclyl are each optionally further substituted by one or more groups selected from the group consisting of halogen, hydroxyl, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)mR$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$;
$R^4$ is selected from the group consisting of aryl and heteroaryl, preferred phenyl, wherein said aryl and heteroaryl are each optionally further substituted by one or more groups selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR$^5$, —OC(O)R$^5$, —NHS(O)mR$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein said haloalkyl is preferably trifluoromethyl;
$R^5$ is selected from the group consisting of alkyl, alkenyl, alkynyl, cycloalkyl, heterocyclyl, aryl and heteroaryl, wherein said alkyl, cycloalkyl, aryl and heteroaryl are each optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group;
$R^6$ and $R^7$ are each independently selected from the group consisting of hydrogen, alkyl, alkoxy, cycloalkyl, heterocyclyl, aryl and heteroaryl, wherein said alkyl, alkoxy, cycloalkyl, heterocyclyl, aryl and heteroaryl are each optionally substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group; or $R^6$ and $R^7$ can be taken together with the nitrogen atom to which they are attached to form heterocyclyl, wherein said heterocyclyl can contain one or more heteroatoms selected from the group consisting of N, O and S(O)$_m$, and wherein said heterocyclyl is optionally further substituted by one or more groups selected from the group consisting of alkyl, halogen, hydroxyl, alkoxy, hydroxyalkyl, cycloalkyl, heterocyclyl, aryl, heteroaryl, carboxylic acid and carboxylate group;
m is 0, 1 or 2;
s is an integer between 0 to 3;
t is 0 or 1.

In a preferred embodiment of the present invention, in a compound of formula (I), or a tautomer, mesomer, racemate, enantiomer, diastereomer, or mixture thereof, or pharmaceutically acceptable salt thereof, wherein when said $R^2$ is halogen, t is 1.

In another preferred embodiment of the present invention, a compound of formula (I), or a tautomer, mesomer, racemate, enantiomer, diastereomer, or mixture thereof, or pharmaceutically acceptable salt thereof, is a compound of formula (II), or a tautomer, mesomer, racemate, enantiomer, diastereomer, or mixture thereof, or pharmaceutically acceptable salt thereof:

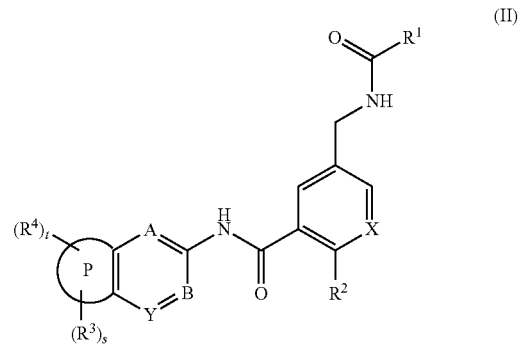

wherein:
X is selected from the group consisting of —CH— and N;
ring P, A, B, Y, s, t and $R^1$ to $R^4$ are as defined in general formula (I).

In another preferred embodiment of the present invention, a compound of formula (I), or a tautomer, mesomer, racemate, enantiomer, diastereomer, or mixture thereof, or pharmaceutically acceptable salt thereof, is a compound of formula (III), formula (IV), or formula (V), or a tautomer, mesomer, racemate, enantiomer, diastereomer, or mixture thereof, or pharmaceutically acceptable salt thereof:

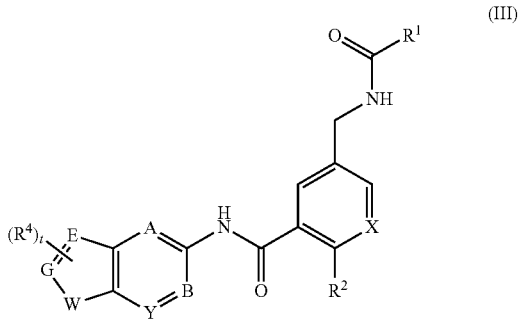

-continued

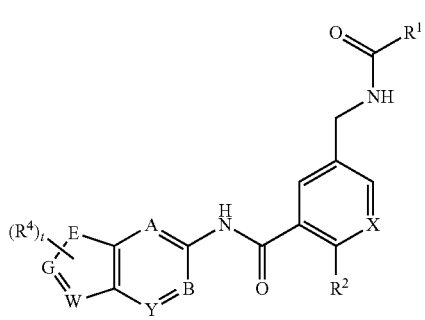

(IV)

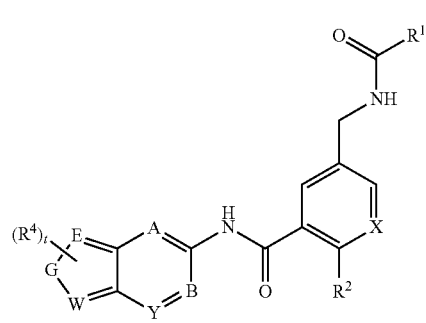

(V)

wherein:
X is selected from the group consisting of —CH— and N;
E, G and W are each independently selected from the group consisting of $CR^aNR^b$, N, O and S;
$R^a$ and $R^b$ are each independently selected from the group consisting of hydrogen, halogen, alkoxy, cyano, nitro, alkyl, cycloalkyl, heterocyclyl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein said alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$; and
A, B, Y, t, $R^1$ to $R^2$ and $R^4$ to $R^7$ are as defined in general formula (I).

In another preferred embodiment of the present invention, a compound of formula (I), or a tautomer, mesomer, racemate, enantiomer, diastereomer, or mixture thereof, or pharmaceutically acceptable salt thereof, is a compound of formula (VI), or a tautomer, mesomer, racemate, enantiomer, diastereomer, or mixture thereof, or pharmaceutically acceptable salt thereof:

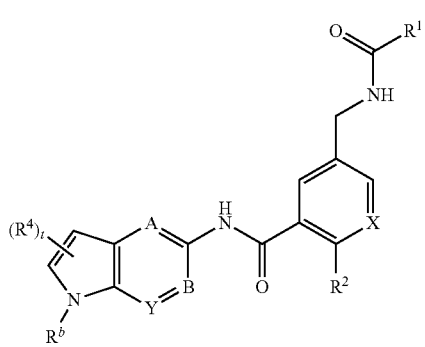

(VI)

wherein:
X is selected from the group consisting of —CH— and N;
$R^b$ is selected from the group consisting of hydrogen, halogen, alkoxy, cyano, nitro, alkyl, cycloalkyl, heterocyclyl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein said alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O) NR$^6$R$^7$ and —C(O)NR$^6$R$^7$; preferably C$_1$ to C$_4$ alkyl, C$_1$ to C$_4$ alkoxy or tetrahydrofuryl; and
A, B, Y, t, $R^1$ to $R^2$ and $R^4$ to $R^7$ are as defined in general formula (I).

In another preferred embodiment of the present invention, a compound of formula (I), or a tautomer, mesomer, racemate, enantiomer, diastereomer, or mixture thereof, or pharmaceutically acceptable salt thereof, is a compound of formula (VII), or a tautomer, mesomer, racemate, enantiomer, diastereomer, or mixture thereof, or pharmaceutically acceptable salt thereof:

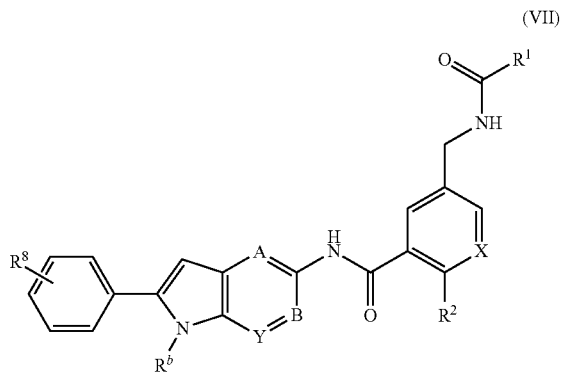

(VII)

wherein:
X is selected from the group consisting of —CH— and N;
$R^b$ is selected from the group consisting of hydrogen, halogen, alkoxy, cyano, nitro, alkyl, cycloalkyl, heterocyclyl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein said alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O) NR$^6$R$^7$ and —C(O)NR$^6$R$^7$;
$R^8$ is selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O) NR$^6$R$^7$, wherein said haloalkyl is preferably trifluoromethyl; and
A, B, Y, $R^1$ to $R^2$ and $R^5$ to $R^7$ are as defined in general formula (I).

In another preferred embodiment of the present invention, a compound of formula (VII), or a tautomer, mesomer, racemate, enantiomer, diastereomer, or mixture thereof, or pharmaceutically acceptable salt thereof, is a compound of formula (VII-A) or formula (VII-B), or a tautomer, mesomer, racemate, enantiomer, diastereomer, or mixture thereof, or pharmaceutically acceptable salt thereof:

include, but are not limited to:

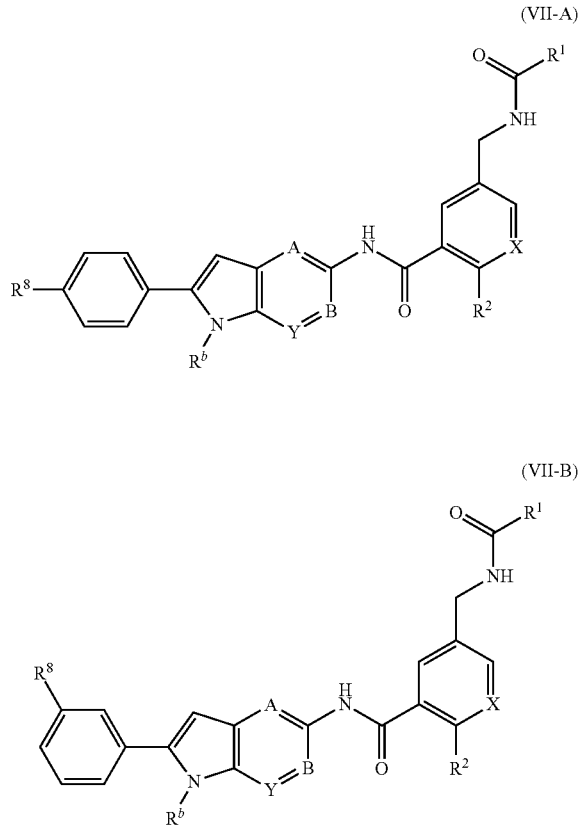

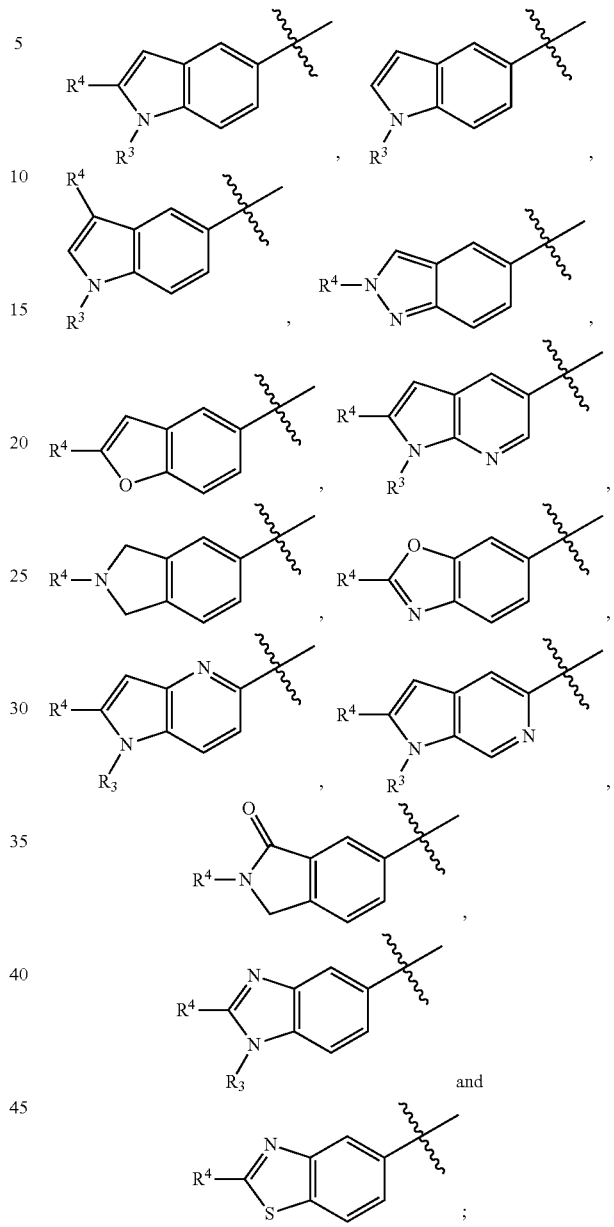

A, B, X, Y, $R^1$ to $R^2$, $R^8$ and $R^b$ are as defined in formula (VII).

In another preferred embodiment of the present invention, a compound of formula (I), or a tautomer, mesomer, racemate, enantiomer, diastereomer, or mixture thereof, or pharmaceutically acceptable salt thereof, wherein said A, B and Y are CH.

In another preferred embodiment of the present invention, a compound of formula (I), or a tautomer, mesomer, racemate, enantiomer, diastereomer, or mixture thereof, or pharmaceutically acceptable salt thereof, wherein one of A, B and Y is N, the other two are —CH—.

In another embodiment of the present invention, a compound of formula (I), or a tautomer, mesomer, racemate, enantiomer, diastereomer, or mixture thereof, or pharmaceutically acceptable salt thereof, wherein said groups

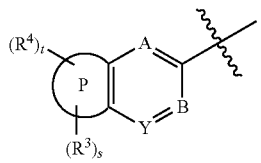

$R^3$ and $R^4$ are as defined in general formula (I).

In another preferred embodiment of the present invention, a compound of formula (I), or a tautomer, mesomer, racemate, enantiomer, diastereomer, or mixture thereof, or pharmaceutically acceptable salt thereof, wherein said $R^1$ is selected from the group consisting of alkyl and haloalkyl, preferably tertiary butyl, isopropyl,

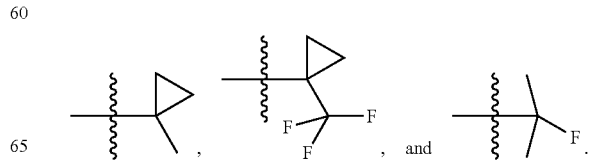

In another preferred embodiment of the present invention, a compound of formula (I), or a tautomer, mesomer, racemate, enantiomer, diastereomer, or mixture thereof, or pharmaceutically acceptable salt thereof, wherein said $R^1$ is cycloalkyl, wherein said cycloalkyl is further substituted by haloalkyl, $R^1$ is preferably

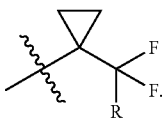

In another preferred embodiment of the present invention, a compound of formula (I), or a tautomer, mesomer, racemate, enantiomer, diastereomer, or mixture thereof, or pharmaceutically acceptable salt thereof, wherein said $R^2$ is haloalkyl, preferably —$CHF_2$.

In another preferred embodiment of the present invention, a compound of formula (I), or a tautomer, mesomer, racemate, enantiomer, diastereomer, or mixture thereof, or pharmaceutically acceptable salt thereof, wherein said $R^2$ is haloalkyl and t is 0.

In another preferred embodiment of the present invention, a compound of formula (I), or a tautomer, mesomer, racemate, enantiomer, diastereomer, or mixture thereof, or pharmaceutically acceptable salt thereof, wherein said $R^2$ is halogen, preferably chlorine.

In another preferred embodiment of the present invention, a compound of formula (III), or a tautomer, mesomer, racemate, enantiomer, diastereomer, or mixture thereof, or pharmaceutically acceptable salt thereof, wherein said t is 1.

Typical compounds of the present invention include, but are not limited to:

| Example No. | Structure and name |
| --- | --- |
| 1 | 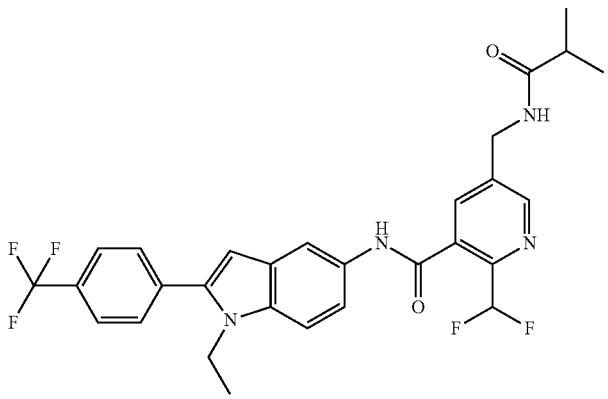<br>1<br>2-(difluoromethyl)-N-(1-ethyl-2(4-(trifluoromethyl)phenyl)-1H-indol-5-yl)-5((2-methylpropanoylamino)methyl)nicotinamide |
| 2 | 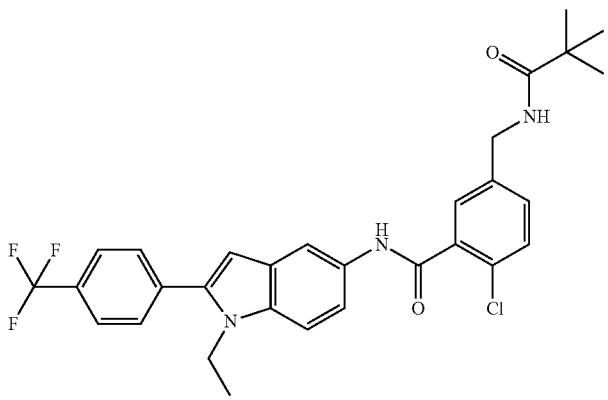<br>2<br>2-chloro-N-(1-ethyl-2-(4-(trifluoromethyl)phenyl)-1H-indol-5-yl)-5-((2,2-dimethylpropanoylamino)methyl)benzamide |

| Example No. | Structure and name |
|---|---|
| 3 | 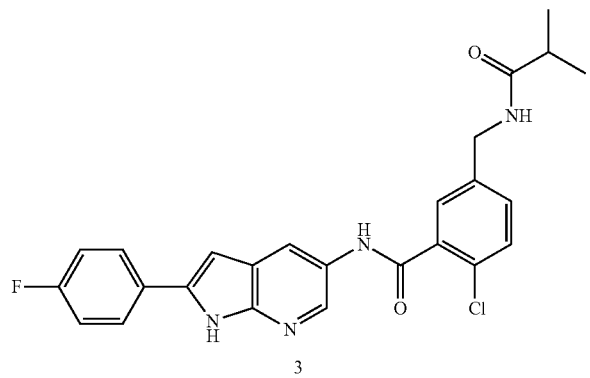 [SMILES: CC(C)C(=O)NCc1ccc(Cl)c(C(=O)Nc2cnc3[nH]c(-c4ccc(F)cc4)cc3c2)c1]
2-chloro-N-(2-(4-fluorophenyl)-1H-pyrrolo[2,3-b]pyridin-5-yl)-5-((2,2-dimethylpropanoylamino)methyl)benzamide |
| 4 | 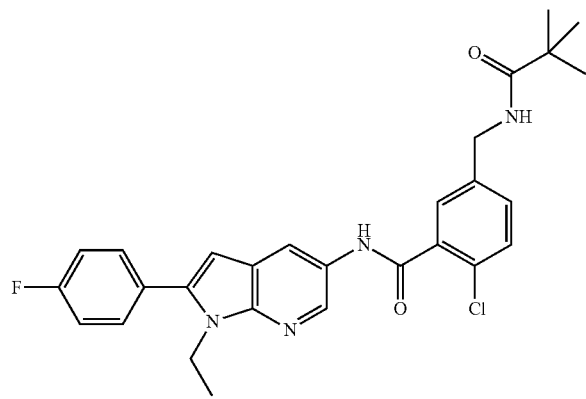
2-chloro-N-(1-ethyl-2-(4-fluorophenyl)-1H-pyrrolo[2,3-b]pyridin-5-yl)-5-((2,2-dimethylpropanoylamino)methyl)benzamide |
| 5 | 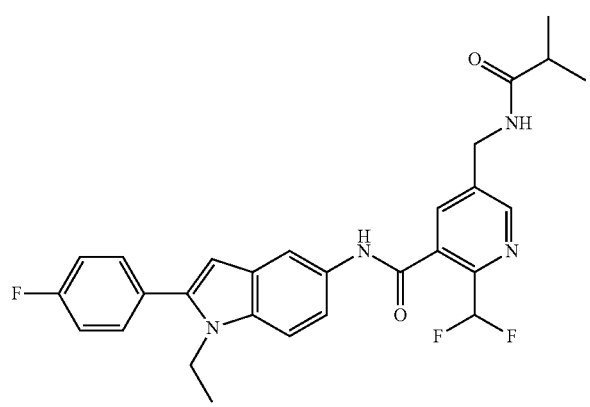
2-(difluoromethyl)-N-(1-ethyl-2-(4-fluorophenyl)-1H-indol-5-yl)-5-((2-methylpropanoylamino)methyl)nicotinamide |

-continued
| Example No. | Structure and name |
|---|---|
| 6 | 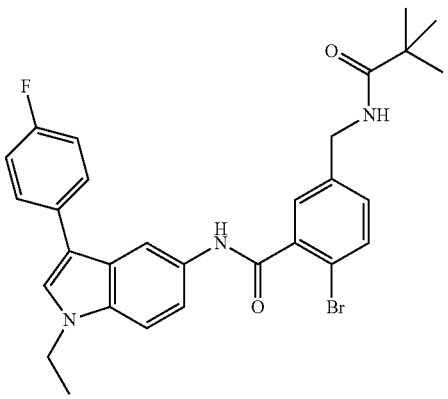<br>6<br>2-bromo-N-[1-ethyl-3-(4-fluorophenyl)-1H-indol-5-yl)-5-((2,2-dimethylpropanoylamino)methyl)benzamide |
| 7 | 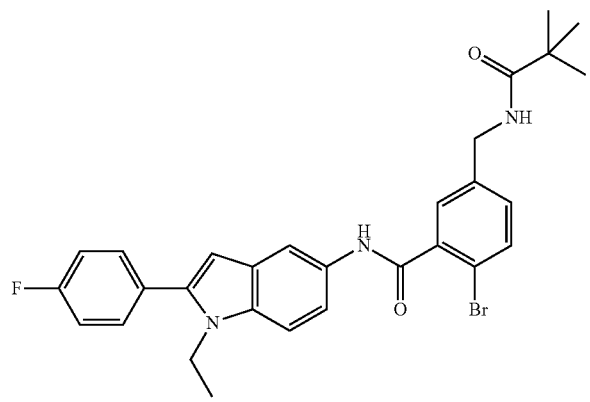<br>7<br>2-bromo-N-(1-ethyl-2-(4-fluorophenyl)-1H-indol-5-yl)-5-((2,2-dimethylpropanoylamino)methyl)benzamide |
| 8 | 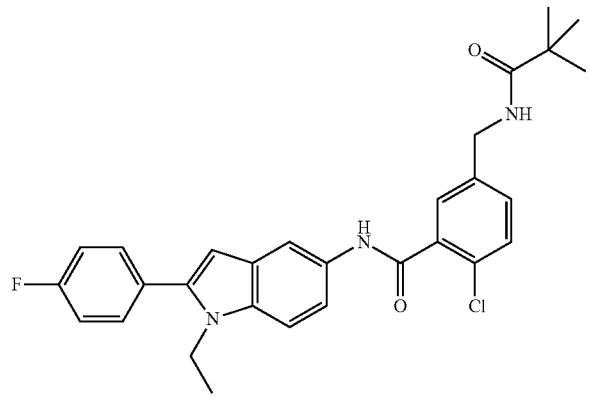<br>8<br>2-chloro-N-(1-ethyl-2-(4-fluorophenyl)-1H-indol-5-yl)-5-((2,2-dimethylpropanoylamino)methyl)benzamide |

| Example No. | Structure and name |
|---|---|
| 9 | 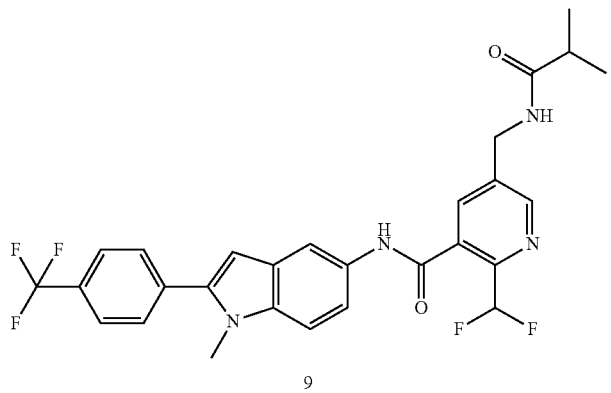 [SMILES: CC(C)C(=O)NCc1cnc(C(F)F)c(C(=O)Nc2ccc3c(c2)cc(-c2ccc(C(F)(F)F)cc2)n3C)c1]
2-(difluoromethyl)-N-(1-methyl-2-(4-(trifluoromethyl)phenyl)-1H-indol-5-yl)-5-((2-methylpropanoylamino)methyl)nicotinamide |
| 10 | 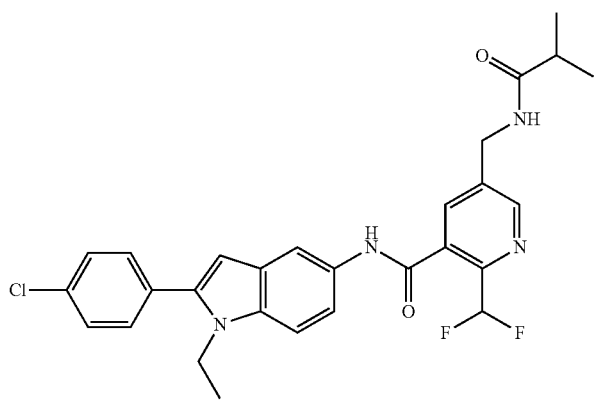
2-(difluoromethyl)-N-(1-ethyl-2-(4-chlorophenyl)-1H-indol-5-yl)-5-((2-methylpropanoylamino)methyl)nicotinamide |
| 11 | 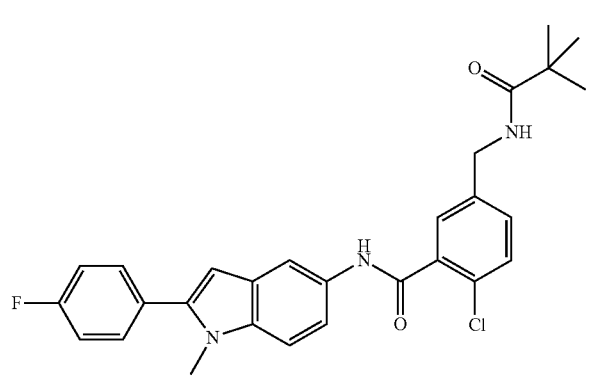
2-chloro-N-(2-(4-fluorophenyl)-1-methyl-1H-indol-5-yl)-5-((2,2-dimethylpropanoylamino)methyl)benzamide |

| Example No. | Structure and name |
|---|---|
| 12 | 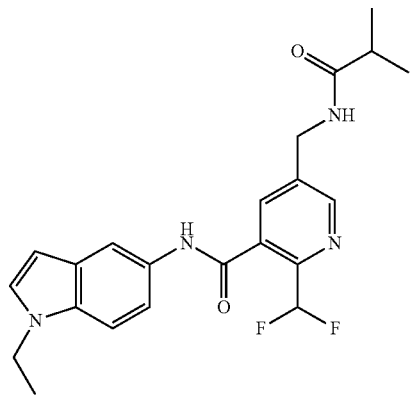
12
2-(difluoromethyl)-N-(1-ethyl-1H-indol-5-yl)-5-((2-methylpropanoyl-amino)methyl)nicotinamide |
| 13 | 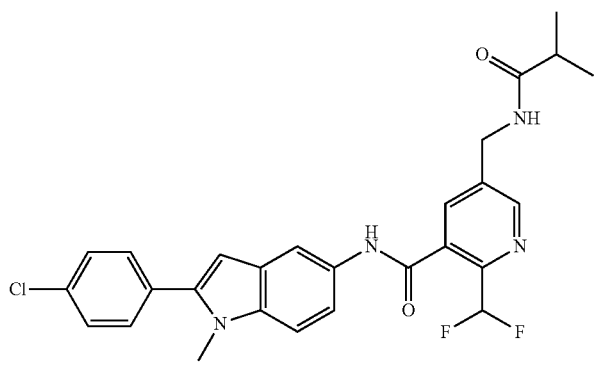
13
N-(2-(4-chlorophenyl)-1-methyl-1H-indol-5-yl)-2-(difluoromethyl)-5-((2-methylpropanoylamino)methyl)nicotinamide |
| 14 | 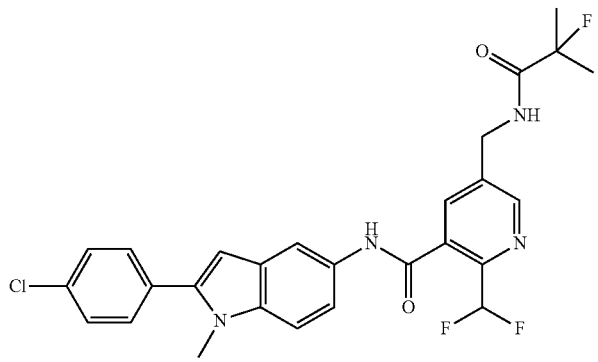
14
N-(2-(4-chlorophenyl)-1-methyl-1H-indol-5-yl)-2-(difluoromethyl)-5-(((2-fluoro-2-methyl-propanoyl)amino)methyl)nicotinamide |

| Example No. | Structure and name |
|---|---|
| 15 | 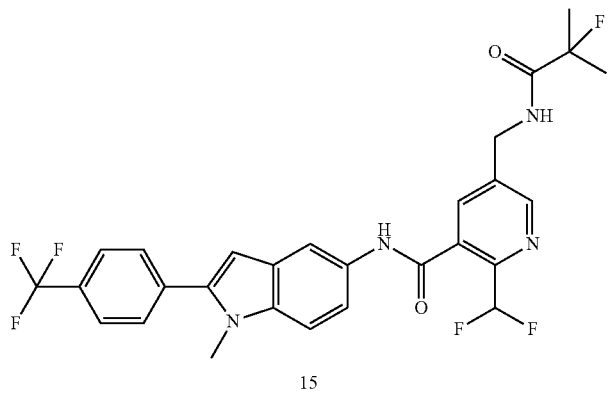 [SMILES: Cn1c(-c2ccc(C(F)(F)F)cc2)cc2cc(NC(=O)c3cc(CNC(=O)C(C)(C)F)cnc3C(F)F)ccc21]
2-(difluoromethyl)-5-(((2-fluoro-2-methyl-propanoyl)amino)methyl)-
N-(1-methyl-2-(4-(trifluoromethyl)phenyl)-1H-indol-5-yl)nicotinamide |
| 16 | 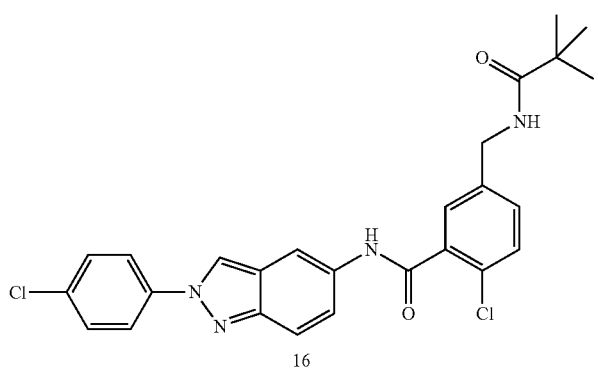 [SMILES: CC(C)(C)C(=O)NCc1ccc(Cl)c(C(=O)Nc2ccc3nn(-c4ccc(Cl)cc4)cc3c2)c1]
2-chloro-N-(2-(4-chlorophenyl)-2H-indazol-5-yl)-5-((2,2-dimethyl-
propanoylamino)methyl)benzamide |
| 17 | 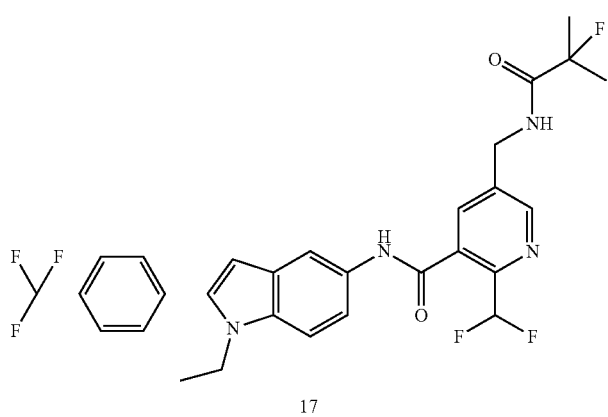
2-(difluoromethyl)-N-(1-ethyl-2-(4-(trifluoromethyl)phenyl)-1H-indol-
5-yl)-5-(((2-fluoro-2-methyl-propanoyl)amino)methyl)nicotinamide |

| Example No. | Structure and name |
|---|---|
| 18 | 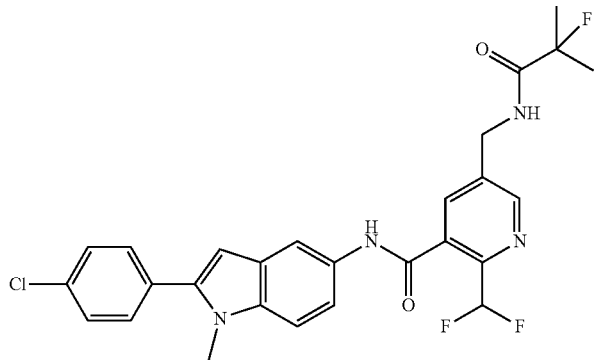<br>N-(2-(4-chlorophenyl)-1-methyl-1H-indol-5-yl)-2-(difluoromethyl)-5-(((2-fluoro-2-methyl-propanoyl)amino)methyl)nicotinamide |
| 19 | 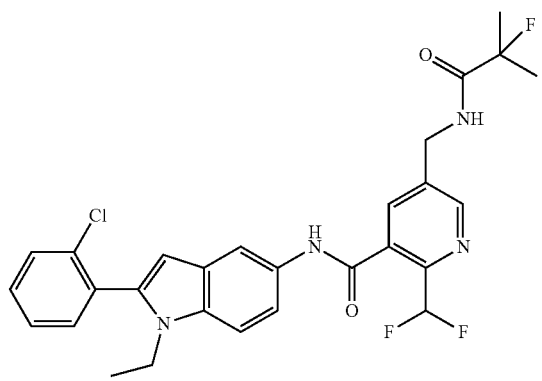<br>N-(2-(2-chlorophenyl)-1-ethyl-1H-indol-5-yl)-2-(difluoromethyl)-5-(((2-fluoro-2-methyl-propanoyl)amino)methyl)nicotinamide |
| 20 | 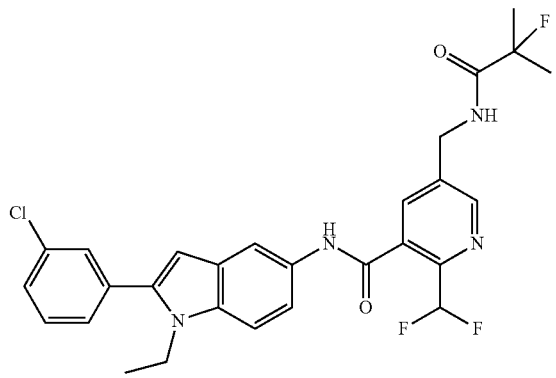<br>N-(2-(3-chlorophenyl)-1-ethyl-1H-indol-5-yl)-2-(difluoromethyl)-5-(((2-fluoro-2-methyl-propanoyl)amino)methyl)nicotinamide |

| Example No. | Structure and name |
|---|---|
| 21 | 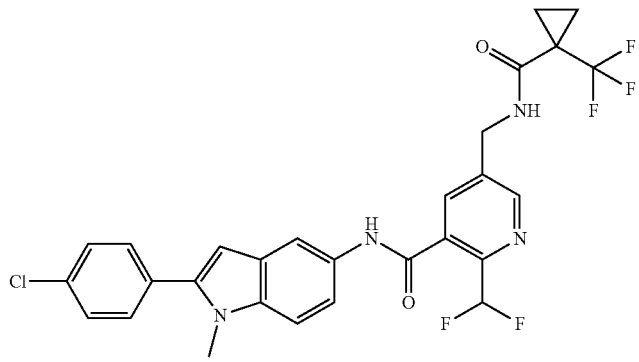
N-(2-(4-chlorophenyl)-1-methyl-1H-indol-5-yl)-2-(difluoromethyl)-
5-((1-(trifluoromethyl)cyclopropanecarbonyl)amino)methyl)nicotinamide |
| 22 | 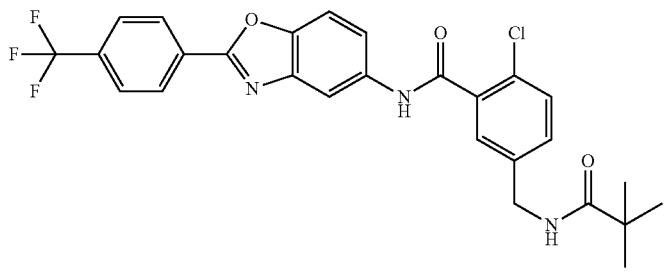
2-chloro-5-((2,2-dimethylpropanoylamino)methyl)-N-(2-(4-(trifluoro-
methyl)phenyl)-1,3-benzoxazol-5-yl)benzamide |
| 23 | 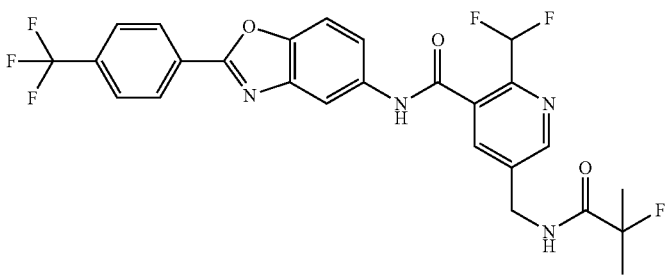
2-(difluoromethyl)-5-(((2-fluoro-2-methyl-propanoyl)amino)methyl)-
N-(2-(4-(trifluoromethyl)phenyl)-1,3-benzoxazol-5-yl)nicotinamide |

| Example No. | Structure and name |
|---|---|
| 24 | 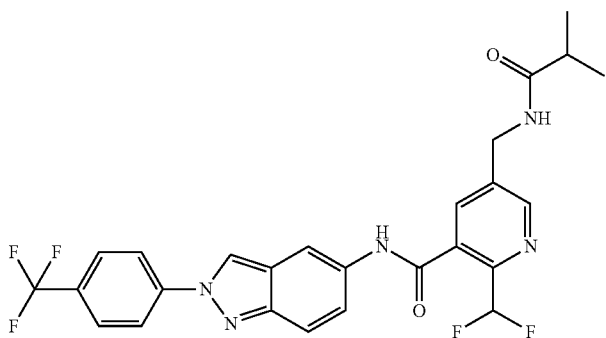
2-(difluoromethyl)-5-(((2-methylpropanoylamino)methyl)-N-(2-(4-(trifluoromethyl)phenyl)-2H-indol-5-yl)nicotinamide |
| 25 | 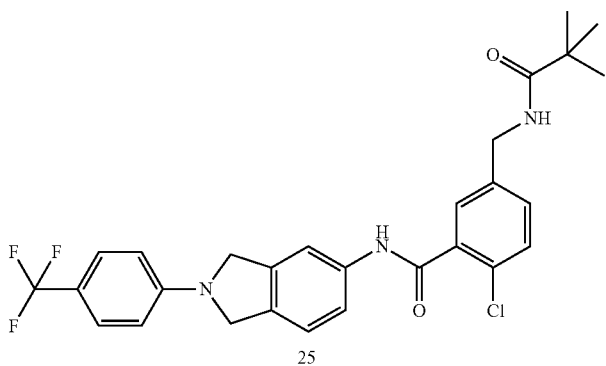 [SMILES: CC(C)(C)C(=O)NCc1ccc(Cl)c(C(=O)Nc2ccc3c(c2)CN(c2ccc(C(F)(F)F)cc2)C3)c1]
2-chloro-5-((2,2-dimethylpropanoylamino)methyl)-N-(2-(4-(trifluoromethyl)phenyl)isoindolin-5-yl)benzamide |
| 26 | 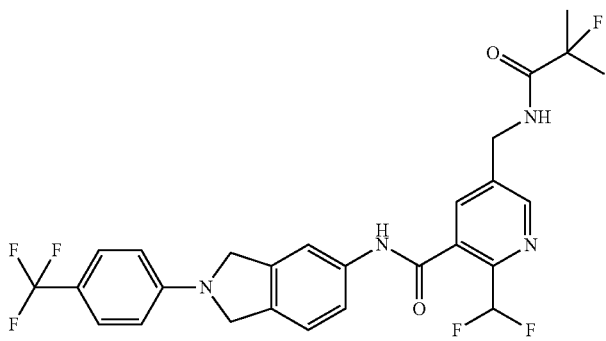
2-(difluoromethyl)-5-(((2-fluoro-2-methyl-propanoylamino)methyl)-N-(2-(4-(trifluoromethyl)phenyl)isoindolin-5-yl)nicotinamide |

| Example No. | Structure and name |
|---|---|
| 27 | 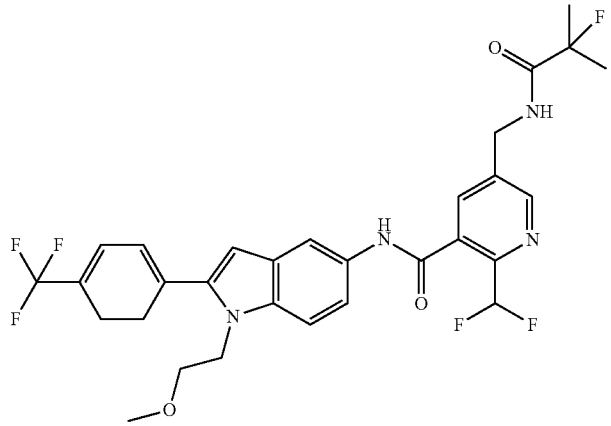

2-(difluoromethyl)-5-(((2-fluoro-2-methyl-propanoyl)amino)methyl)-N-(1-(2-methoxyethyl)-2-(4-(trifluoromethyl)phenyl)-1H-indol-5-yl)nicotinamide |
| 28 | 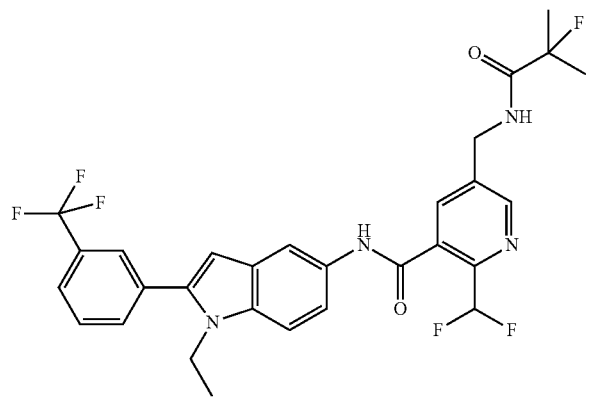

2-(difluoromethyl)-N-(1-ethyl-2-(3-(trifluoromethyl)phenyl)-1H-indol-5-yl)-5-(((2-fluoro-2-methyl-propanoyl)amino)methyl)nicotinamide |
| 29 | 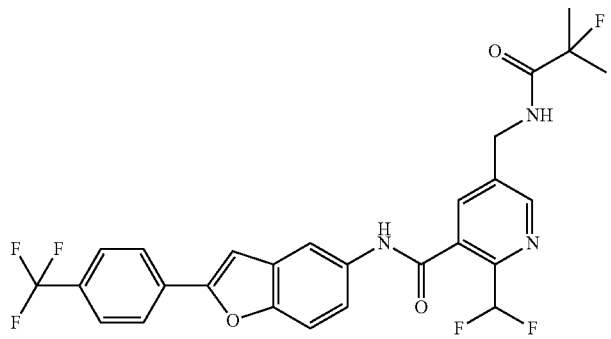

2-(difluoromethyl)-5-(((2-fluoro-2-methyl-propanoyl)amino)methyl)-N-(2-(4-(trifluoromethyl)phenyl)benzofuran-5-yl)nicotinamide |

| Example No. | Structure and name |
|---|---|
| 30 | 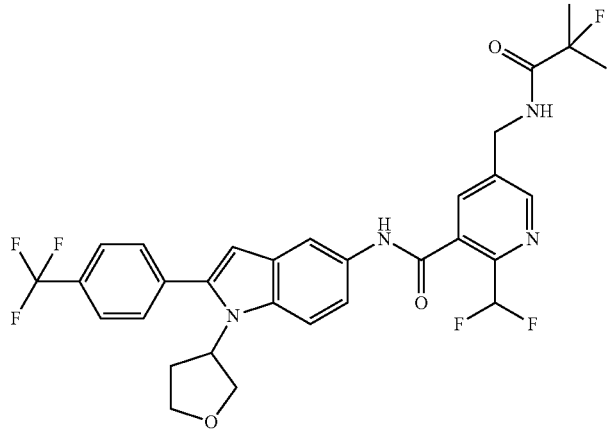<br>30<br>2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide |
| 31 | 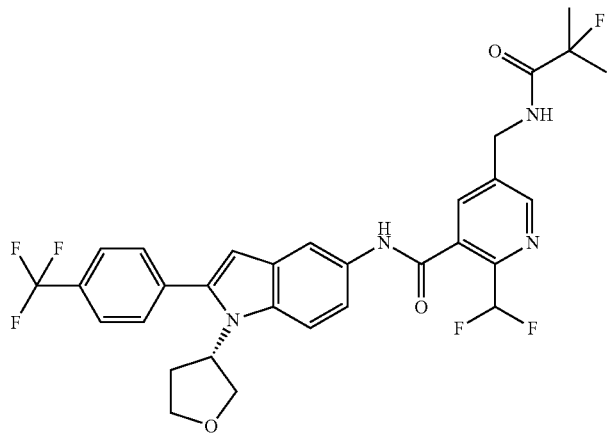<br>31<br>(S)-2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide |

| Example No. | Structure and name |
|---|---|
| 32 | 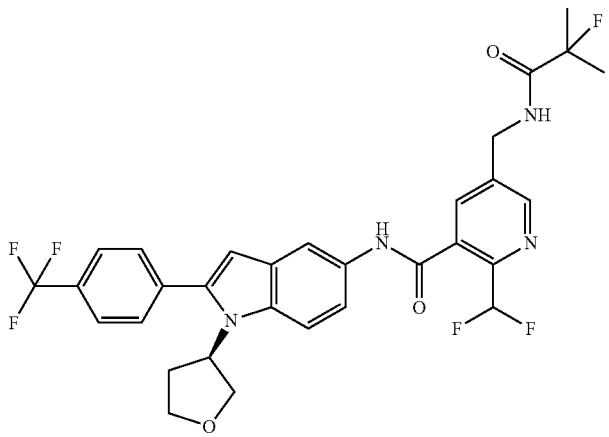<br>(R)-2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide |
| 33 | 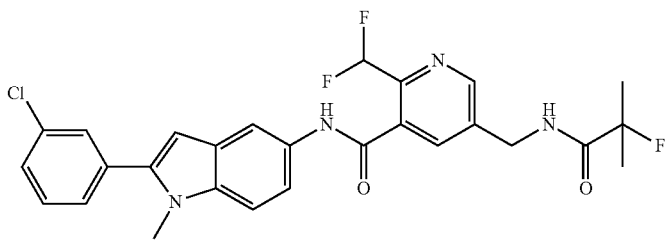<br>N-(2-(3-chlorophenyl)-1-methyl-1H-indol-5-yl)-2-(difluoromethyl)-5-(((2-fluoro-2-methyl-propanoyl)amino)methyl)nicotinamide |
| 34 | 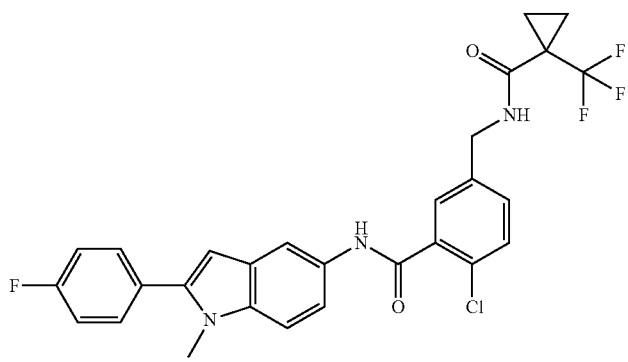<br>2-chloro-N-(2-(4-fluorophenyl)-1-methyl-1H-indol-5-yl)-5-(((1-(trifluoromethyl)cyclopropanecarbonyl)amino)methyl)benzamide |

| Example No. | Structure and name |
|---|---|
| 35 | 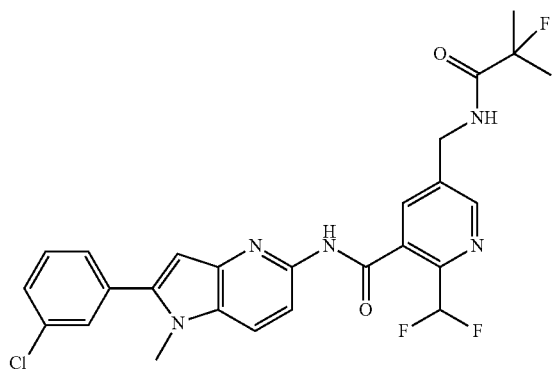<br>N-(2-(3-chlorophenyl)-1-methyl-1H-pyrrolo[3,2-b]pyridin-5-yl)-2-(difluoromethyl)-5-(((2-fluoro-2-methyl-propanoyl)amino)methyl)nicotinamide |
| 36 | 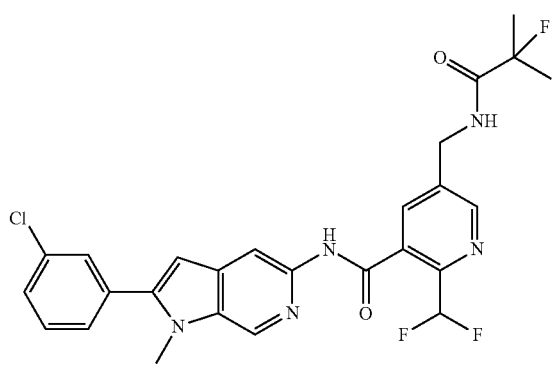<br>N-(2-(3-chlorophenyl)-1-methyl-1H-pyrrolo[2,3-c]pyridin-5-yl)-2-(difluoromethyl)-5-(((2-fluoro-2-methyl-propanoyl)amino)methyl)nicotinamide |
| 37 | 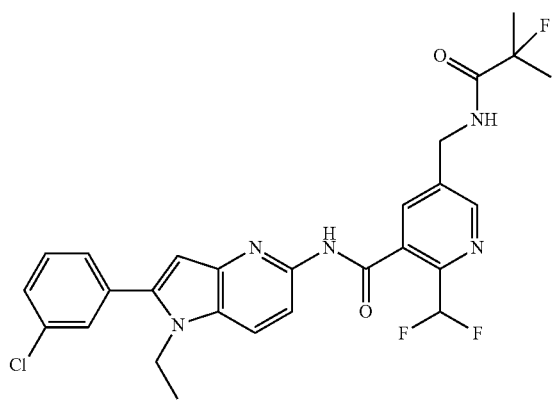 [SMILES: Cn1c(-c2cccc(Cl)c2)cc2nc(NC(=O)c3cc(CNC(=O)C(C)(C)F)cnc3C(F)F)ccc21]<br>N-(2-(3-chlorophenyl)-1-ethyl-1H-pyrrolo[3,2-b]pyridin-5-yl)-2-(difluoromethyl)-5-(((2-fluoro-2-methyl-propanoyl)amino)methyl)nicotinamide |

| Example No. | Structure and name |
|---|---|
| 38 | 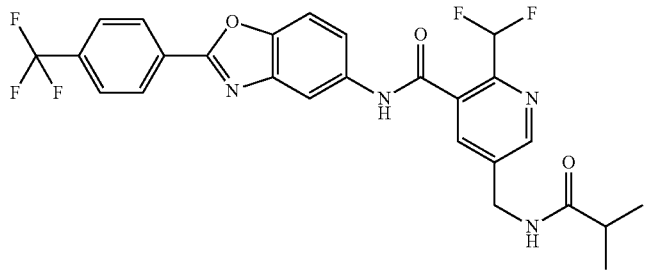<br>38<br>2-(difluoromethyl)-5-((2-methylpropanoylamino)methyl)-N-(2-(4-(trifluoromethyl)phenyl)-1,3-benzoxazol-5-yl)nicotinamide |
| 39 | 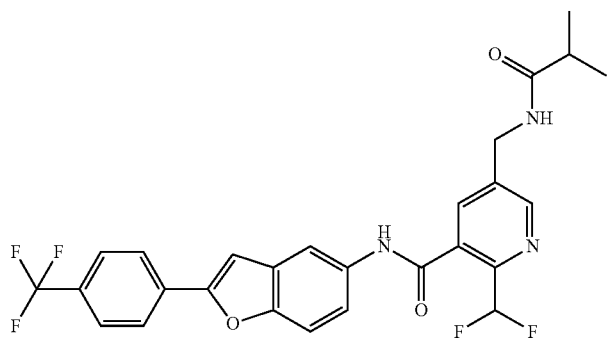<br>39<br>2-(difluoromethyl)-5-((2-methylpropanoylamino)methyl)-N-(2-(4-(trifluoromethyl)phenyl)benzofuran-5-yl)nicotinamide |
| 40 | 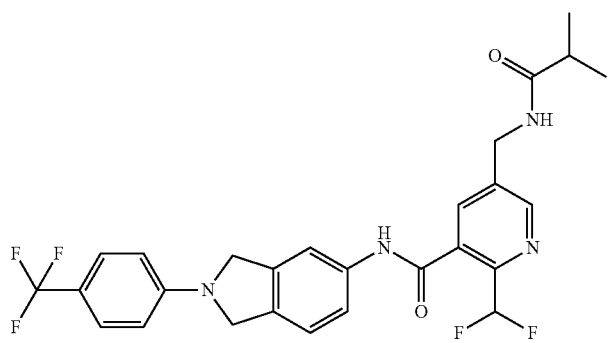<br>40<br>2-(difluoromethyl)-5-((2-methylpropanoylamino)methyl)-N-(2-(4-(trifluoromethyl)phenyl)isoindolin-5-yl)nicotinamide |

| Example No. | Structure and name |
|---|---|
| 41 | 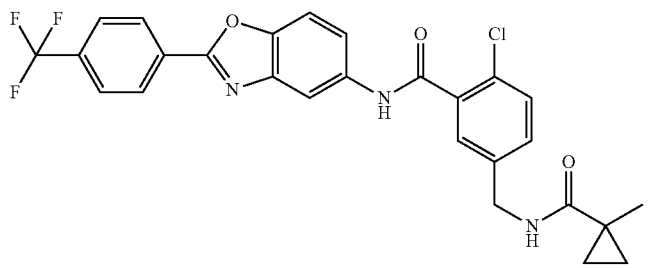

41

2-chloro-5-(((1-methylcyclopropanecarbonyl)amino)methyl)-N-(2-
(4-(trifluoromethyl)phenyl)-1,3-benzoxazol-5-yl)benzamide |
| 42 | 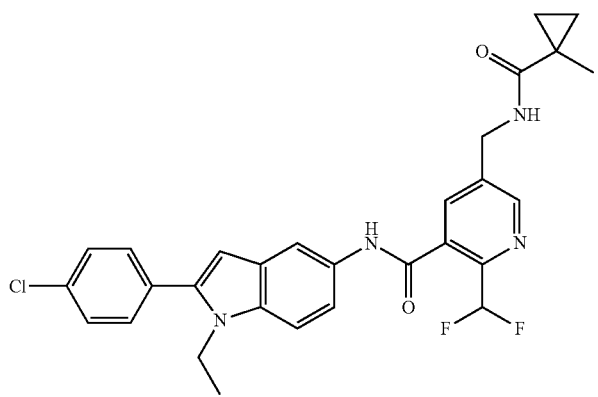

42

N-(2-(4-chlorophenyl)-1-ethyl-1H-indol-5-yl)-2-(difluoromethyl)-5-
(((1-methylcyclopropanecarbonyl)amino)methyl)nicotinamide |
| 43 | 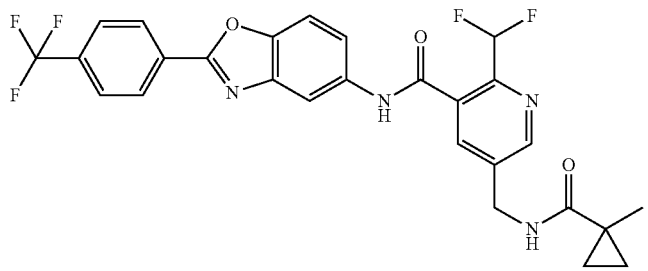

43

2-(difluoromethyl)-5-(((1-methylcyclopropanecarbonyl)amino)methyl)-
N-(2-(4-(trifluoromethyl)phenyl)-1,3-benzoxazol-5-yl)nicotinamide |
| 44 | 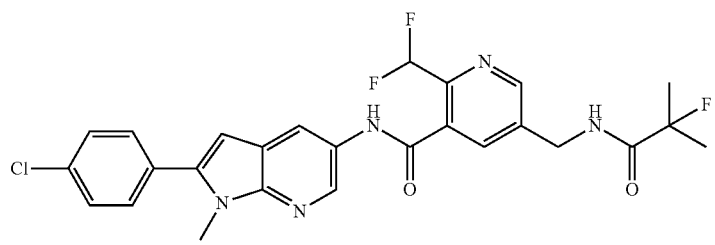

44

N-(2-(4-chlorophenyl)-1-methyl-1H-pyrrolo(2,3-b)pyridin-5-yl)-2-
(difluoromethyl)-5-(((2-fluoro-2-methyl-propanoyl)amino)methyl)
nicotinamide |

| Example No. | Structure and name |
|---|---|
| 45 | 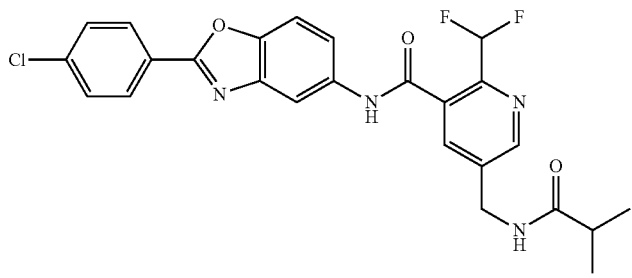

45

N-(2-(4-chlorophenyl)-1,3-benzoxazol-5-yl)-2-(difluoromethyl)-5-
((2-methylpropanoylamino)methyl)nicotinamide |
| 46 | 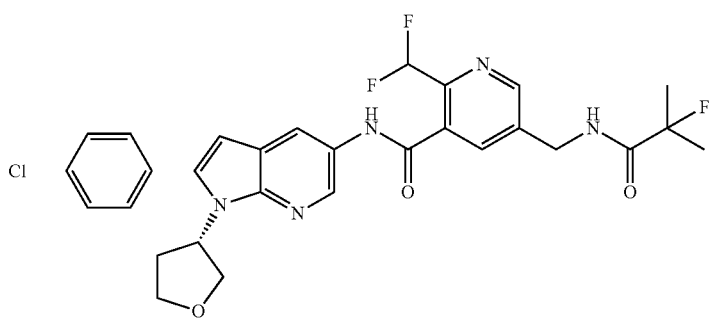

46

(4-chlorophenyl)-1-(tetrahydrofuran-3-yl)-1H-indol-5-yl)-
7-(difluoromethyl)-5-(((2-fluoro-2-methyl-propanoyl)amino)methyl)
nicotinamide |
| 47 | 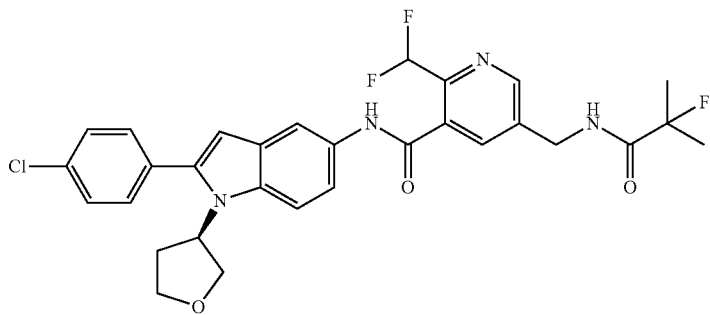

47

(R)-N-(2-(4-chlorophenyl)-1-(tetrahydrofuran-3-yl)-1H-indol-5-yl)-
2-(difluoromethyl)-5-(((2-fluoro-2-methyl-propanoyl)amino)methyl)
nicotinamide |
| 48 | 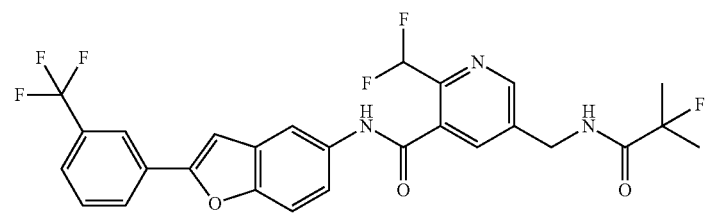

48

2-(difluoromethyl)-5-(((2-fluoro-2-methyl-propanoyl)amino)methyl)-
N-(2-(3-(trifluoromethyl)phenyl)benzofuran-5-yl)nicotinamide |

| Example No. | Structure and name |
|---|---|
| 49 | 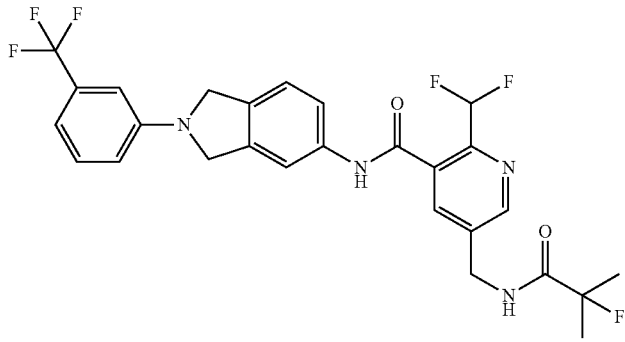

49

2-(difluoromethyl)-5-(((2-fluoro-2-methyl-propanoyl)amino)methyl)-N-(2-(3-(trifinornmethyl)phenyl)isoindolin-5-yl)nicotinamide |
| 50 | 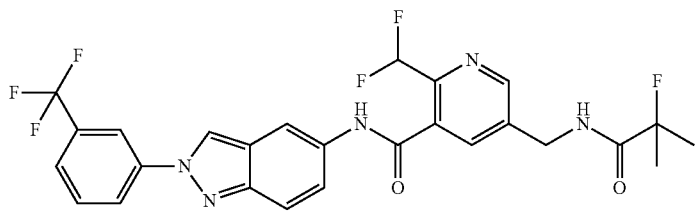

50

2-(difluoromethyl)-5-(((2-fluoro-2-methyl-propanoyl)amino)methyl)-N-(2-(3-(trifluoromethyl)phenyl)-2H-indazol-5-yl)nicotinamide |
| 51 | 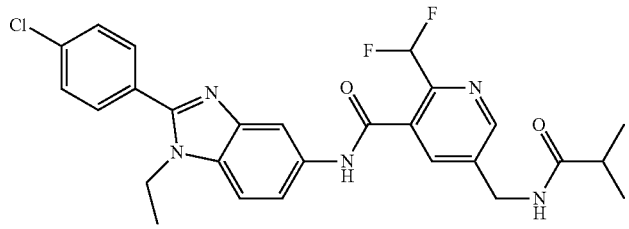

51

N-(2-(4-chlorophenyl)-1-ethyl-1H-benzo[d]imidazol-5-yl)-2-(difluoromethyl)-5-((2-methylpropanoylamino)methyl)nicotinamide |
| 52 | 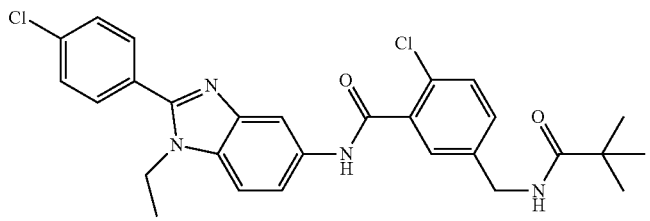

52

2-chloro-N-(2-(4-chlorophenyl)-1-ethyl-1H-benzo[d]imidazol-5-yl)-5-((2,2-dimethylpropanoylamino)methyl)benzamide |

| Example No. | Structure and name |
|---|---|
| 53 | 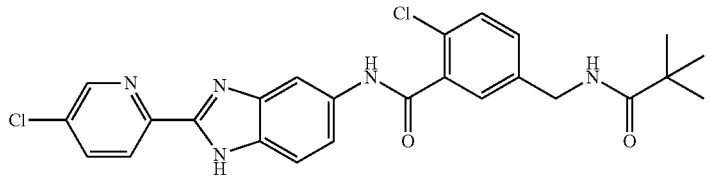<br>2-chloro-N-(2-(5-chloropyridin-2-yl)-1H-benzo[d]imidazol-5-yl)-5-((2,2-dimethylpropanoylamino)methyl)benzamide |
| 54 | 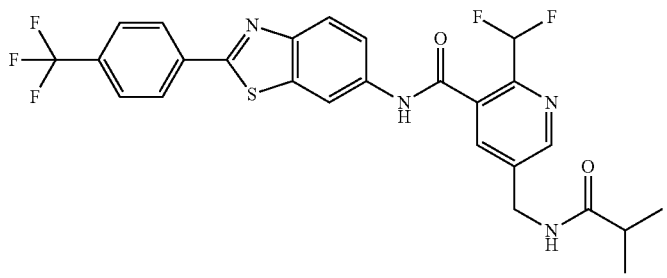<br>2-(difluoromethyl)-5-((2-methylpropanoylamino)methyl)-N-(2-(4-(trifluoromethyl)phenyl)-1benzo[d]thiazol-6-yl)nicotinamide |
| 55 | 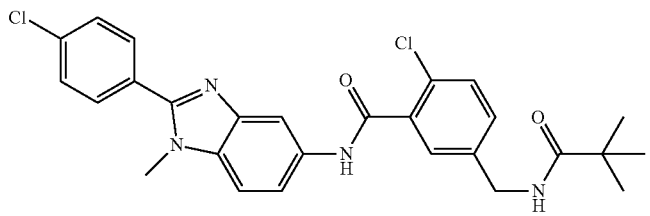<br>2-chloro-N-(2-(4-chlorophenyl)-1-methyl-1H-benzo[d]imidazol-5-yl)-5-((2,2-dimethylpropanoylamino)methyl)benzamide |
| 56 | 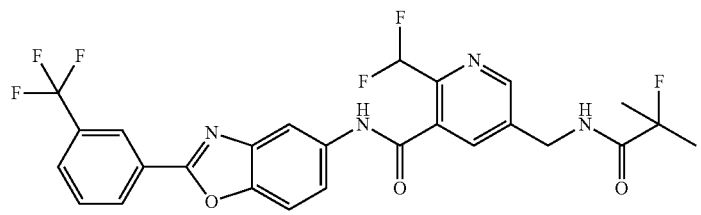<br>2-(difluoromethyl)-5-(((2-fluoro-2-methyl-propanoyl)amino)methyl)-N-(2-(3-(trifluoromethyl)phenyl)-benzo[d]oxazol-5-yl)nicotinamide |

| Example No. | Structure and name |
|---|---|
| 57 | 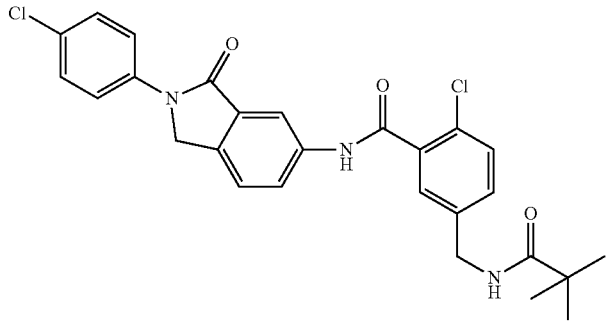<br>57<br>2-chloro-N-(2-(4-chlorophenyl)-3-oxo-isoindolin-5-yl)-5-((2,2-dimethyl-propanoylamino)methyl)benzamide |
| 58 | 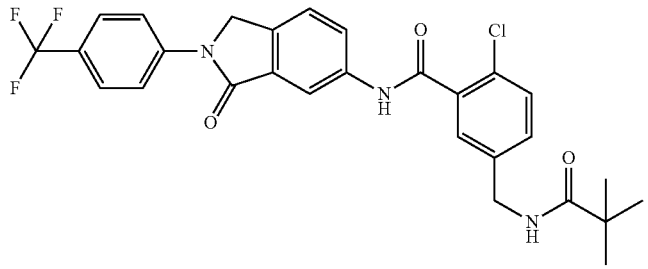<br>58<br>2-chloro-N-(3-oxo-2-(4-(trifluoromethyl)phenyl)isoindolin-5-yl)-5-((2,2-dimethylpropanoylamino)methyl)-benzamide |
| 59 | 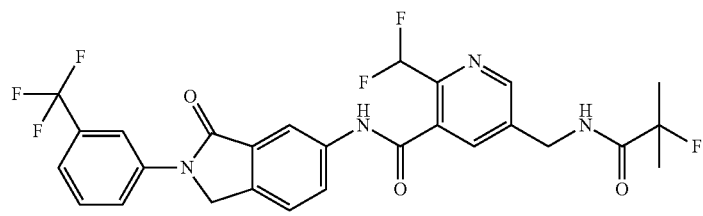<br>59<br>2-(difluoromethyl)-5-(((2-fluoro-2-methyl-propanoyl)amino)methyl)-N-(3-oxo-2-(3-(trifluoromethyl)phenyl)isoindolin-5-yl)nicotinamide | or a tautomer, mesomer, racemate, enantiomer, diastereomer, or mixture thereof, or pharmaceutically acceptable salt thereof.

In another aspect, the present invention provides a process for preparing the compound of formula (I), or a tautomer, mesomer, racemate, enantiomer, diastereomer, or mixture thereof, or pharmaceutically acceptable salt thereof, comprising a step of:

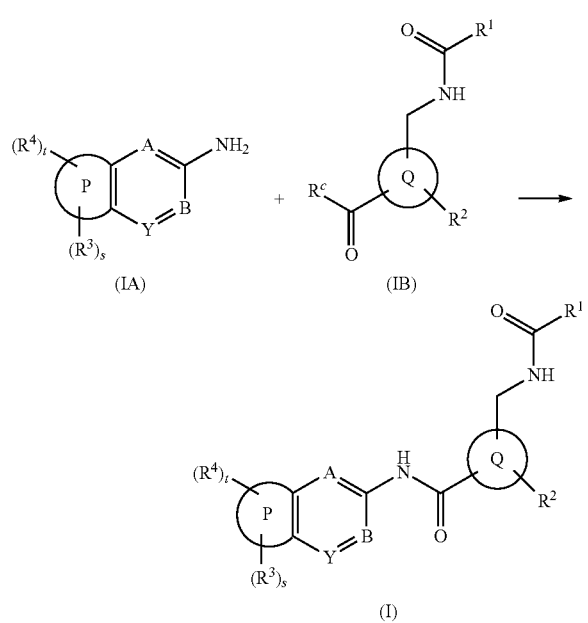

a compound of general formula (IA) or salts thereof is subject to a condensation reaction with a compound of general formula (IB) under an alkaline condition to give a compound of formula (I);
wherein:
$R^c$ is selected from the group consisting of hydroxy and halogen; and
ring P, ring Q, A, B, Y, s, t and $R^1$ to $R^4$ are as defined in general formula (I).

The alkaline reagents include organic base and inorganic base, wherein said organic base includes, but is not limited to, triethylamine, N,N-diisopropylethylamine, pyridine, sodium bis(trimethylsilyl)amide, n-butyllithium, potassium tert-butanolate, or tetrabutylammonium bromide, wherein said inorganic base includes, but is not limited to, lithium hydroxide, sodium hydroxide, potassium hydroxide, sodium hydride, sodium carbonate, sodium bicarbonate, potassium carbonate, potassium bicarbonate, or cesium carbonate, preferably triethylamine.

The catalysts include, but are not limited to, Pd/C and Raney nickel.

The condensating agents include, but are not limited to, 1-(3-dimethylaminopropyl)-3-ethylcarbodiimide hydrochloride, N,N'-dicyclohexylcarbodiimide, N,N'-diisopropylcarbondiimide, O-(benzotriazole-1-yl)-N,N,N',N'-tetramethyluronium tetrafluoroborate, 1-hydroxybenzotriazole, 1-hydroxy-7-azobenzotriazole, O-(benzotriazole-1-yl)-N,N,N'N'-tetramethyluronium hexafluorophosphate, 2-(7-azobenzotriazol-1-yl)-N,N,N'N'-tetramethyluronium hexafluorophophate, benzotriazol-1-yl-oxy-tris(dimethylamino)-phophonium hexaflurophosphate, and benzotriazol-1-yl-oxy-tripyrrolidinyl-phosphonium hexafluorophosphate.

In another aspect, the present invention provides a compound of formula (IA), or a tautomer, mesomer, racemate, enantiomer, diastereomer, or mixture thereof, or pharmaceutically acceptable salt thereof,

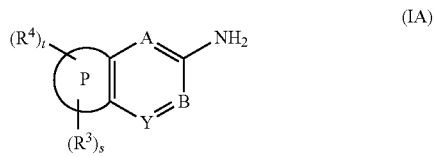

comprising the following groups:

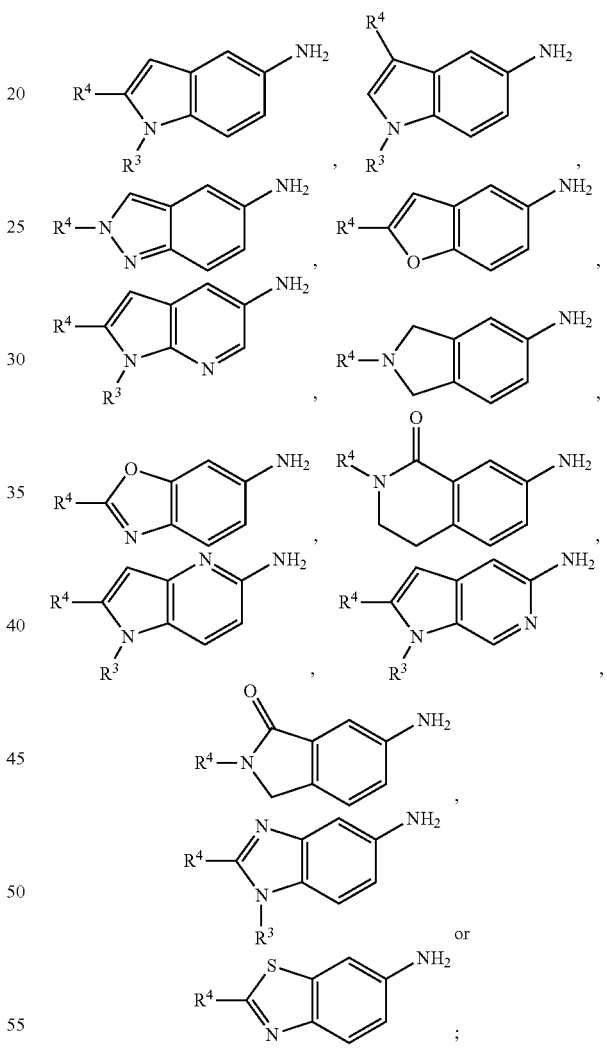

wherein:
$R^3$ is selected from the group consisting of hydrogen, alkyl, and heterocyclyl, wherein said alkyl is optionally further substituted by one or more groups selected from the group consisting of alkoxy and heterocyclyl, preferably $C_1$ to $C_4$ alkyl, $C_1$ to $C_4$ alkoxy or tetrahydrofuranyl;
$R^4$ is selected from the group consisting of aryl and heteroaryl, wherein said aryl or heteroaryl is optionally further substituted by one or more groups selected from the group consisting of halogen and haloalkyl, wherein said haloalkyl is preferably trifluoromethyl; $R^4$ is preferably phenyl, wherein said phenyl is further substituted by one halogen or one haloalkyl.

t is 1;

provided that:

when general formula (IA) is one of the following groups:

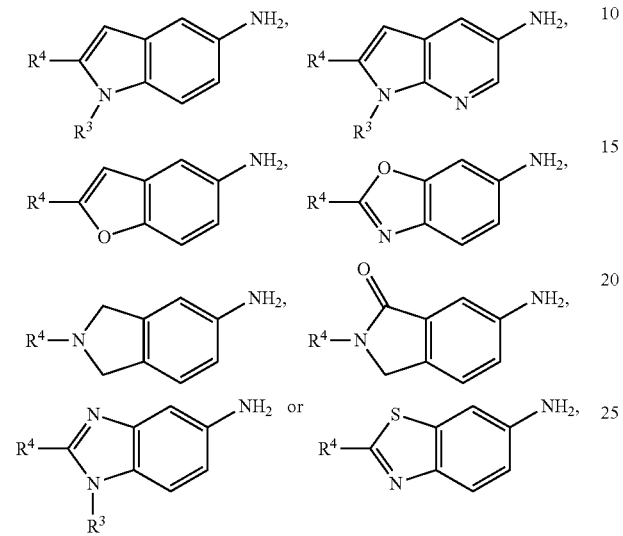

$R^3$ is selected from the group consisting of hydrogen and alkyl, wherein said alkyl is optionally further substituted by one or more groups selected from the group consisting of alkoxy and heterocyclyl; and $R^4$ is phenyl, wherein said phenyl is further substituted by one haloalkyl, wherein said haloalkyl is preferably trifluoromethyl; or $R^3$ is heterocyclyl; and $R^4$ is phenyl, wherein said phenyl is further substituted by one halogen or one haloalkyl.

The compounds of general formula (IA) include, but are not limited to:

| Example No. | Structure and name |
|---|---|
| 1k | 1-ethyl-5-amino-2-(4-(trifluoromethyl)phenyl)-1H-indole 1k |
| 3e | 2-(4-fluorophenyl)-5-amino-1H-pyrrolo(2,3-b)pyridine 3e |
| 4b | 1-ethyl-2-(4-fluorophenyl)-5-amino-1H-pyrrolo(2,3-b)pyridine 4b |
| 6c | 1-ethyl-3-(4-fluorophenyl)-5-amino-1H-indole 6c |
| 9c | 1-methyl-5-amino-2-(4-(trifluoromethyl)phenyl)-1H-indole 9c |
| 10c | 1-ethyl-2-(4-chlorophenyl)-5-amino-1H-indole 10c |
| 11b | 2-(4-fluorophenyl)-1-methyl-5-amino-1H-indole 11b |
| 13b | 2-(4-chlorophenyl)-1-methyl-5-amino-1H-indole 13b |

| Example No. | Structure and name |
|---|---|
| 16c | 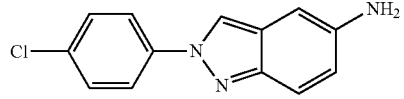 [SMILES: Nc1ccc2nn(-c3ccc(Cl)cc3)cc2c1]

2-(4-chlorophenyl)-5-amine-indazole
16c |
| 19c | 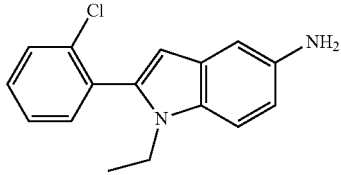 [SMILES: CCn1c(-c2ccccc2Cl)cc2cc(N)ccc21]

2-(2-chlorophenyl)-1-ethyl-1H-indol-5-amine19c |
| 20c | 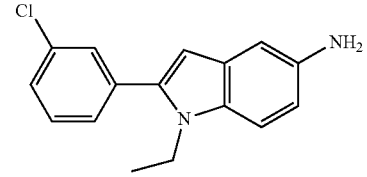 [SMILES: CCn1c(-c2cccc(Cl)c2)cc2cc(N)ccc21]

2-(3-chlorophenyl)-1-ethyl-1H-indol-5-amine
20c |
| 22c | 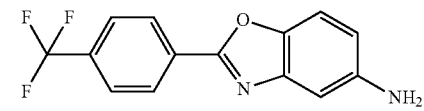

2-(4-(trifluoromethyl)phenyl)-benzo[d]oxazol-5-amine
22c |
| 24f | 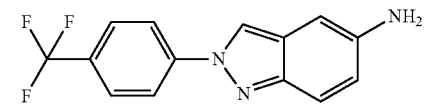 [SMILES: Nc1ccc2nn(-c3ccc(C(F)(F)F)cc3)cc2c1]

2-(4-(trifluoromethyl)phenyl)-2H-indazol-5-amine
24f |
| 25c | 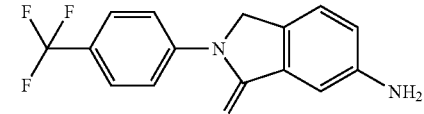

6-amino-2-(4-(trifluoromethyl)phenyl)isoindolin-1-one
25c |
| 25d | 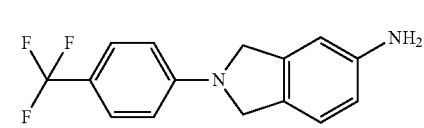 [SMILES: Nc1ccc2c(c1)CN(c1ccc(C(F)(F)F)cc1)C2]

2-(4-(trifluoromethyl)phenyl)isoindolin-5-amine
25d |
| 27c | 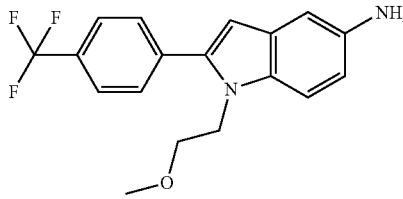

1-(2-methoxyethyl-5-amino-2-(4-(trifluoromethyl)phenyl)-1H-indol
27c |
| 28c | 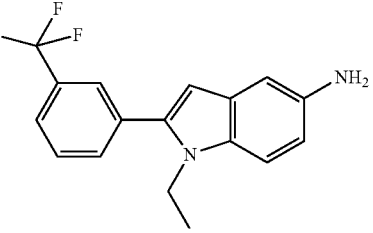

1-ethyl-5-amino-2-(3-(trifluoromethyl)phenyl)-1H-indole
28c |
| 29d | 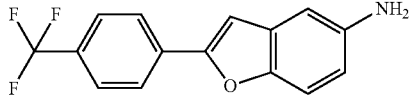 [SMILES: Nc1ccc2oc(-c3ccc(C(F)(F)F)cc3)cc2c1]

5-amino-2-(4-(trifluoromethyl)phenyl)benzofuran-
29d |
| 30e | 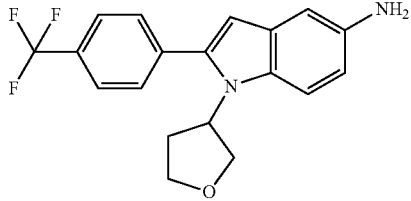 [SMILES: Nc1ccc2c(c1)cc(-c1ccc(C(F)(F)F)cc1)n2C1CCOC1]

5-amino-1-(tetrahydrofuran-3-yl)-2-(4-(trifluoromethyl)phenyl)-1H-indole
30e |
| 31d | 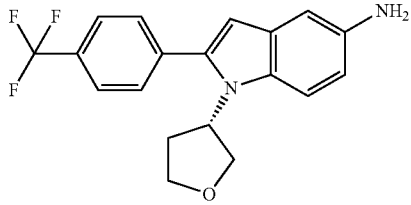 [SMILES: Nc1ccc2c(c1)cc(-c1ccc(C(F)(F)F)cc1)n2[C@H]1CCOC1]

(S)-5-amino-1-(tetrahydrofuran-3-yl)-2-(4-(trifluoromethyl)phenyl)-1H-indole
31d |

| Example No. | Structure and name |
|---|---|
| 32d | 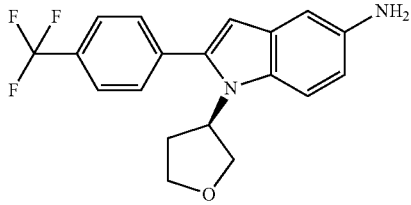 [SMILES: Nc1ccc2c(c1)cc(-c1ccc(C(F)(F)F)cc1)n2[C@@H]1CCOC1]<br>(R)-5-amino-1-(tetrahydrofuran-3-yl)-2-(4-(trifluoromethyl)phenyl)-1H-indole<br>32d |
| 33b | 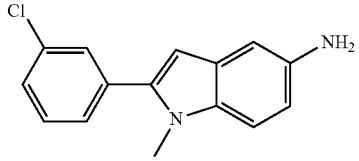 [SMILES: Cn1c(-c2cccc(Cl)c2)cc2cc(N)ccc21]<br>2-(3-chlorophenyl)-1-methyl-1H-indol-5-amine<br>33b |
| 35j | 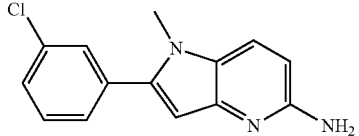 [SMILES: Cn1c(-c2cccc(Cl)c2)cc2nc(N)ccc21]<br>2-(3-chorophenyl)-1-methyl-1H-pyrrolo[3,2-b]pyridinyl-5-amine<br>35j |
| 36d | 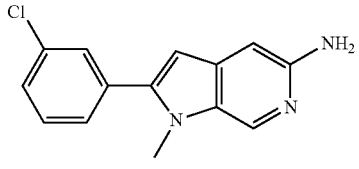 [SMILES: Cn1c(-c2cccc(Cl)c2)cc2cc(N)ncc21]<br>2-(3-chlorophenyl)-1-methyl-1H-pyrrolo[2,3-c]pyridinyl-5-amine<br>36d |
| 37d | 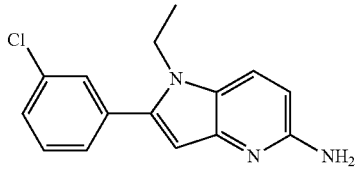 [SMILES: CCn1c(-c2cccc(Cl)c2)cc2nc(N)ccc21]<br>2-(3-chlorophenyl)-1-ethyl-1H-pyrrolo[3,2-b]pyridinyl-5-amine<br>37d |
| 44f | 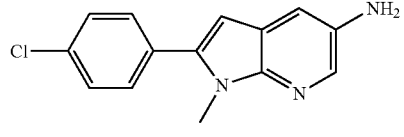 [SMILES: Cn1c(-c2ccc(Cl)cc2)cc2cc(N)cnc21]<br>2-(4-chlorophenyl)-1-methyl-1H-pyrrolo(2,3-b)pyridinyl-5-amine<br>44f |
| 45a | 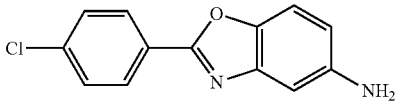 [SMILES: Nc1ccc2oc(-c3ccc(Cl)cc3)nc2c1]<br>2-(4-chlorophenyl)-benzo[d]oxazol-5-amine<br>45a |
| 46c | 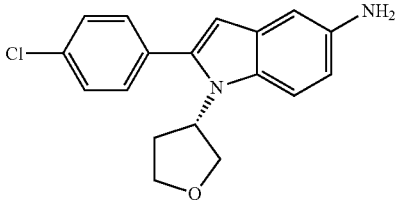 [SMILES: Nc1ccc2c(c1)cc(-c1ccc(Cl)cc1)n2[C@H]1CCOC1]<br>(S)-2-(4-chlorophenyl)-(tetrahydrofuran-3-yl)-1H-indol-5-amine<br>46c |
| 47b | 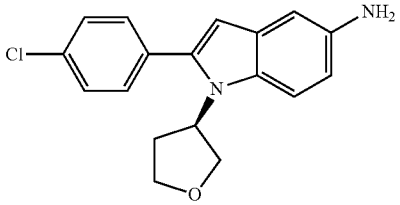 [SMILES: Nc1ccc2c(c1)cc(-c1ccc(Cl)cc1)n2[C@@H]1CCOC1]<br>(R)-2-(4-chlorophenyl)-1-(tetrahydrofuran-3-yl)-1H-indol-5-amine<br>47b |
| 48d | 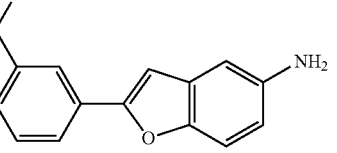<br>2-(3-(trifluoromethyl)phenyl)benzofuran-5-amine<br>48d |
| 49c | 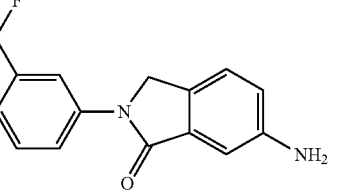<br>6-amino-2-(3-(trifluoromethyl)phenyl)isoindolin-1-one<br>49b |
| 50c | 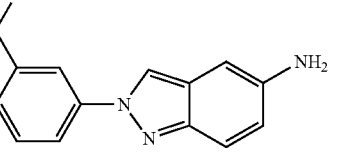<br>2-(3-(trifluoromethyl)phenyl)-2H-indazolyl-5-amine<br>50c |

-continued

| Example No. | Structure and name |
|---|---|
| 51g | 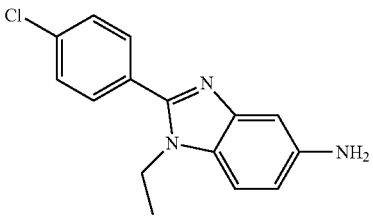 [SMILES: CCn1c(-c2ccc(Cl)cc2)nc2cc(N)ccc21]<br>2-(4-chlorophenyl)-1-ethyl-1H-benzo[d]imidazol-5-amine<br>51g |
| 53d | 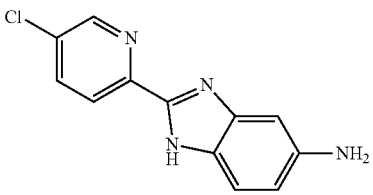 [SMILES: Nc1ccc2[nH]c(-c3ccc(Cl)cn3)nc2c1]<br>2-(5-chloropyridin-2-yl)-1H-benzo[d]imidazol-5-amine<br>53d |
| 54c | 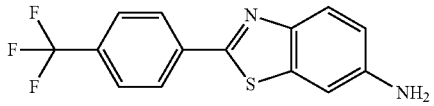<br>2-(4-(trifluoromethyl)phenyl)benzo[d]thiazol-6-amino<br>54c |
| 55b | 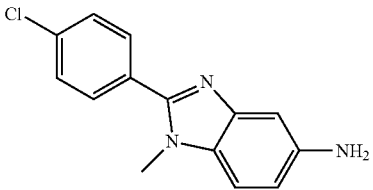 [SMILES: Cn1c(-c2ccc(Cl)cc2)nc2cc(N)ccc21]<br>2-(4-chlorophenyl)-1-methyl-benzo[d]imidazol-5-amine<br>55b |
| 56d | 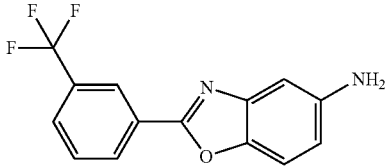 [SMILES: Nc1ccc2oc(-c3cccc(C(F)(F)F)c3)nc2c1]<br>2-(3-(trifluoromethyl)phenyl)-benzo[d]oxazol-5-amine<br>56d |
| 57b | 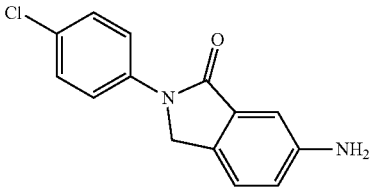 [SMILES: Nc1ccc2c(c1)C(=O)N(c1ccc(Cl)cc1)C2]<br>6-amino-2-(4-chlorophenyl)isoindolin-1-one<br>57b | or a tautomer, mesomer, racemate, enantiomer, diastereomer, or mixture thereof, or pharmaceutically acceptable salt thereof.

In another aspect, the present invention provides a compound of formula (IB), or a tautomer, mesomer, racemate, enantiomer, diastereomer, or mixture thereof, or pharmaceutically acceptable salt thereof:

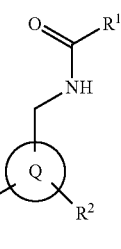

(IB)

wherein, $R^c$ is selected from the group consisting of hydroxy and halogen; and ring Q, $R^1$ and $R^2$ are as defined in general formula (I).

The compounds of general formula (IB) include, but are not limited to:

| Example No. | Structure and name |
|---|---|
| 1f | 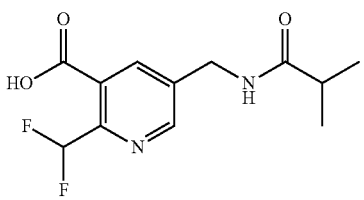 [SMILES: CC(C)C(=O)NCc1cnc(C(F)F)c(C(=O)O)c1]<br>2-(difluoromethyl)-5-((2-methylpropanoylamino)methyl)nicotinic acid 1f |
| 1g | 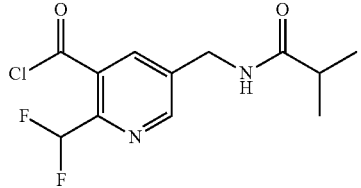 [SMILES: CC(C)C(=O)NCc1cnc(C(F)F)c(C(=O)Cl)c1]<br>2-(difluoromethyl)-5-((2-methylpropanoylamino)methyl)nicotinoyl chloride<br>1g |
| 2a | 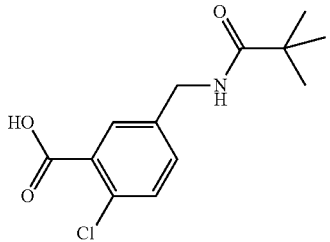 [SMILES: CC(C)(C)C(=O)NCc1ccc(Cl)c(C(=O)O)c1]<br>2-chloro-5-((2,2-dimethylpropanoylamino)methyl)benzoic acid<br>2a |

-continued

| Example No. | Structure and name |
|---|---|
| 2b | 2-chloro-5-((2,2-dimethylpropanoylamino)methyl)benzoyl chloride 2b |
| 6b | 2-bromo-5-((2,2-dimethylpropanoylamino)methyl)benzoyl chloride 6b |
| 14b | 2-(difluoromethyl)-5-(((2-fluoro-2-methyl-propanoyl)amino)methyl)nicotinic acid 14b |
| 21c | 2-(difluoromethyl)-5-(((1-(trifluoromethyl)cyclopropanecarbonyl)amino)methyl)nicotinic acid 21c |
| 34d | 2-chloro-5-(((1-(trifluoromethyl)cyclopropanecarbonyl)amino)methyl)benzoyl chloride 34d |

-continued

| Example No. | Structure and name |
|---|---|
| 37a | 2-(difluoromethyl)-5-(((2-fluoro-2-methyl-propanoyl)amino)methyl)nicotinoyl chloride 37a |
| 41b | 2-chloro-5-(((1-methylcyclopropanecarbonyl)amino)methyl)benzoic acid 41b |
| 41c | 2-chloro-5-(((1-methylcyclopropanecarbonyl)amino)methyl)benzoyl chloride 41c |
| 42c | 2-(difluoromethyl)-5-(((1-methylcyclopropanecarbonyl)amino)methyl)nicotinic acid 42c | or a tautomer, mesomer, racemate, enantiomer, diastereomer, or mixture thereof, or pharmaceutically acceptable salt thereof.

Another aspect of this invention is directed to a pharmaceutical composition comprising a therapeutically effective amount of the compound of formula (I), or a tautomer, mesomer, racemate, enantiomer, diastereomer, or mixture thereof, or pharmaceutically acceptable salt thereof and pharmaceutically acceptable carriers, diluents or excipients.

Another aspect of this invention is directed to use of the compound of formula (I), or a tautomer, mesomer, racemate, enantiomer, diastereomer, or mixture thereof, or pharmaceutically acceptable salt thereof, or the pharmaceutical composition comprising the same, in the preparation of a medicament for the treatment of microsomal prostaglandin E synthase-1 (mPGES-1) mediated diseases.

Another aspect of this invention is directed to use of the compound of formula (I), or a tautomer, mesomer, racemate, enantiomer, diastereomer, or mixture thereof, or pharmaceutically acceptable salt thereof, or the pharmaceutical composition comprising the same, in the preparation of a medicament for the inhibition of microsomal prostaglandin E synthase-1 (mPGES-1).

Another aspect of this invention is directed to use of the compound of formula (I), or a tautomer, mesomer, racemate, enantiomer, diastereomer, or mixture thereof, or pharmaceutically acceptable salt thereof, or the pharmaceutical composition comprising the same, in the preparation of a medicament for the treatment or prevention of diseases or disorders, wherein said diseases or disorders are selected from the group consisting of inflammation, pain, cancer, diabetes and diabetic complications and neurodegenerative disorders and the like, wherein said inflammation includes inflammation associated autoimmune disease, skin disease, lung disease, visceral disease, ear, nose, mouth and throat disease and cardiovascular disease and the like; wherein autoimmune disease includes arthritis, osteoarthritis, juvenile arthritis, rheumatoid arthritis, ankylosing spondylitis, gout, rheumatic fever, bursitis, systemic lupus erythematosus (SLE) and multiple sclerosis and the like; said skin disease includes dermatitis, eczema, psoriasis, burns or tissue trauma, and the like; said lung disease includes asthma, chronic obstructive pulmonary disease (COPD), and pulmonary fibrosis, and the like; said visceral disease includes inflammatory bowel disease, Crohn's disease, ulcerative colitis, irritable bowel disease (IBS), peptic ulcers, cystitis, prostatitis, pancreatitis and nephritis, and the like; said ear, nose, mouth and throat disease includes influenza, virus infection, bacterial infection, fever, rhinitis, pharyngitis, tonsillitis, conjunctivitis, iritis, scleritis and uveitis, and the like; said cardiovascular disease includes atherosclerosis, thrombosis, stroke and coronary heart disease, and the like; said pain includes neuropathic pain, inflammatory pain, visceral pain, cancer pain, chemotherapy pain, trauma pain, surgery pain, postoperative pain, delivery pain, childbirth ache, chronic pain, persistent pain, peripheral mediated pain, central mediated pain, chronic headache, migraine, sinus headaches, tension headaches, phantom limb pain, peripheral nerve injury or combination thereof, and the like; said cancer includes prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma and skin B-cell lymphoma, and the like; said diabetes and diabetic complications include diabetic vasculopathy, diabetic neuropathy and diabetic retinopathy, and the like; said neurodegenerative disorder includes Alzheimer's disease and Parkinson's disease; wherein said diseases or disorders are preferably selected from inflammation and pain, more preferably selected from osteoarthritis, rheumatoid arthritis, bursitis, ankylosing spondylitis, and the pain associated with any one of the diseases or disorders listed above.

Another aspect of this invention is directed to a method for the treatment of a microsomal prostaglandin E synthase-1 (mPGES-1) mediated disease, wherein the method comprises administering to a subject in need thereof a therapeutically effective amount of the compound of formula (I), or a tautomer, mesomer, racemate, enantiomer, diastereomer, or mixture thereof, or pharmaceutically acceptable salt thereof, or the pharmaceutical composition comprising the same.

Another aspect of this invention is directed to a method for the inhibition of microsomal prostaglandin E synthase-1 (mPGES-1), wherein the method comprises administering to a subject in need thereof a therapeutically effective amount of the compound of formula (I), or a tautomer, mesomer, racemate, enantiomer, diastereomer, or mixture thereof, or pharmaceutically acceptable salt thereof, or the pharmaceutical composition comprising the same.

Another aspect of this invention is directed to a method for the treatment or prevention of diseases or disorders, wherein the method comprises administering to a subject in need thereof a therapeutically effective amount of the compound of formula (I), or a tautomer, mesomer, racemate, enantiomer, diastereomer, or mixture thereof, or pharmaceutically acceptable salt thereof, or the pharmaceutical composition comprising the same; wherein said diseases or disorders are selected from the group consisting of inflammation, pain, cancer, diabetes and diabetic complications and neurodegenerative disorders and the like, wherein said inflammation includes inflammation associated autoimmune disease, skin disease, lung disease, visceral disease, ear, nose, mouth and throat disease and cardiovascular disease and the like; wherein autoimmune disease includes arthritis, osteoarthritis, juvenile arthritis, rheumatoid arthritis, ankylosing spondylitis, gout, rheumatic fever, bursitis, systemic lupus erythematosus (SLE) and multiple sclerosis and the like; said skin disease includes dermatitis, eczema, psoriasis, burns and tissue trauma, and the like; said lung disease includes asthma, chronic obstructive pulmonary disease (COPD), and pulmonary fibrosis, and the like; said visceral disease includes inflammatory bowel disease, Crohn's disease, ulcerative colitis, irritable bowel disease (IBS), peptic ulcers, cystitis, prostatitis, pancreatitis and nephritis, and the like; said ear, nose, mouth and throat disease includes influenza, virus infection, bacterial infection, fever, rhinitis, pharyngitis, tonsillitis, conjunctivitis, iritis, scleritis and uveitis, and the like; said cardiovascular disease includes atherosclerosis, thrombosis, stroke and coronary heart disease, and the like; said pain includes neuropathic pain, inflammatory pain, visceral pain, cancer pain, chemotherapy pain, trauma pain, surgery pain, postoperative pain, delivery pain, childbirth ache, chronic pain, persistent pain, peripheral mediated pain, central mediated pain, chronic headache, migraine, sinus headaches, tension headaches, phantom limb pain, peripheral nerve injury and a combination thereof, and the like; said cancer includes prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma and skin B-cell lymphoma, and the like; said diabetes and diabetic complications include diabetic vasculopathy, diabetic neuropathy and diabetic retinopathy, and the like; said neurodegenerative disorder includes Alzheimer's disease and Parkinson's disease; wherein said diseases or disorders are preferably selected from inflammation and pain, more preferably selected from osteoarthritis, rheumatoid arthritis, bursitis, ankylosing spondylitis, and the pain associated with any one of the diseases or disorders listed above.

Another aspect of this invention is directed to a compound of formula (I), or a tautomer, mesomer, racemate, enantiomer, diastereomer, or mixture thereof, or pharmaceutically acceptable salt thereof, or a pharmaceutical composition comprising the same, for use as a drug for the treatment of microsomal prostaglandin E synthase-1 (mPGES-1) mediated diseases.

Another aspect of this invention is directed to a compound of formula (I), or a tautomer, mesomer, racemate, enantiomer, diastereomer, or mixture thereof, or pharmaceutically acceptable salt thereof, or a pharmaceutical composition comprising the same, for use as a drug for the inhibition of microsomal prostaglandin E synthase-1 (mPGES-1).

Another aspect of this invention is directed to a compound of formula (I), or a tautomer, mesomer, racemate, enantiomer, diastereomer, or mixture thereof, or pharmaceutically acceptable salt thereof, or a pharmaceutical composition comprising the same, for use as a drug for the treatment or prevention of diseases or disorders, wherein said diseases or disorders are selected from the group consisting of inflammation, pain, cancer, diabetes and diabetic complications and neurodegenerative disorders and the like, wherein said inflammation includes inflammation associated autoimmune disease, skin disease, lung disease, visceral disease, ear, nose, mouth and throat disease and cardiovascular disease and the like; wherein autoimmune disease includes arthritis, osteoarthritis, juvenile arthritis, rheumatoid arthritis, ankylosing spondylitis, gout, rheumatic fever, bursitis, systemic lupus erythematosus (SLE) and multiple sclerosis and the like; said skin disease includes dermatitis, eczema, psoriasis, burns and tissue trauma, and the like; said lung disease includes asthma, chronic obstructive pulmonary disease (COPD), and pulmonary fibrosis, and the like; said visceral disease includes inflammatory bowel disease, Crohn's disease, ulcerative colitis, irritable bowel disease (IBS), peptic ulcers, cystitis, prostatitis, pancreatitis and nephritis, and the like; said ear, nose, mouth and throat disease includes influenza, virus infection, bacterial infection, fever, rhinitis, pharyngitis, tonsillitis, conjunctivitis, iritis, scleritis and uveitis, and the like; said cardiovascular disease includes atherosclerosis, thrombosis, stroke or coronary heart disease, and the like; said pain includes neuropathic pain, inflammatory pain, visceral pain, cancer pain, chemotherapy pain, trauma pain, surgery pain, postoperative pain, delivery pain, childbirth ache, chronic pain, persistent pain, peripheral mediated pain, central mediated pain, chronic headache, migraine, sinus headaches, tension headaches, phantom limb pain, peripheral nerve injury and a combination thereof, and the like; said cancer includes prostate cancer, kidney cancer, liver cancer, pancreatic cancer, gastric cancer, breast cancer, lung cancer, head and neck cancer, thyroid cancer, glioblastoma, melanoma, lymphoma, leukemia, skin T-cell lymphoma and skin B-cell lymphoma, and the like; said diabetes and diabetic complications include diabetic vasculopathy, diabetic neuropathy and diabetic retinopathy, and the like; said neurodegenerative disorder includes Alzheimer's disease and Parkinson's disease; wherein said diseases or disorders are preferably selected from inflammation and pain, more preferably selected from osteoarthritis, rheumatoid arthritis, bursitis, ankylosing spondylitis, and the pain associated with any one of the diseases or disorders listed above.

DETAILED DESCRIPTION OF THE INVENTION

Unless otherwise stated, the terms used herein have the following meanings.

"Alkyl" refers to a linear or branched saturated aliphatic hydrocarbon group including 1 to 20 carbon atoms, preferably $C_1$ to $C_{10}$ alkyl, more preferably $C_1$ to $C_6$ alkyl. Unlimited examples include methyl, ethyl, n-propyl, isopropyl, n-butyl, isobutyl, tert-butyl, sec-butyl, n-pentyl, 1,1-dimethyl propyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the branched isomers thereof. More preferably an alkyl group is a lower alkyl having 1 to 6 carbon atoms, and unlimited examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Alkenyl" refers to an alkyl defined as above that has at least two carbon atoms and at least one carbon-carbon double bond, for example, ethenyl, 1-propenyl, 2-propenyl, 1-, 2- or 3-butenyl and the like, preferably $C_{2-10}$ alkenyl, more preferably $C_{2-6}$ alkenyl, most preferably $C_{2-4}$ alkenyl. The alkenyl group can be substituted or unsubstituted. When substituted, the substituent group(s) is preferably one or more groups independently selected from the group consisting of alkyl, alkenyl, alkynyl, alkoxyl, alkylthio, alkylamino, halogen, thiol, hydroxyl, nitro, cyano, cycloalkyl, heterocyclyl, aryl, heteroaryl, cycloalkoxyl, heterocylic alkoxyl, cycloalkylthio, heterocyclylthio, oxo, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Alkynyl" refers to an alkyl defined as above that has at least two carbon atoms and at least one carbon-carbon triple bond, for example, ethynyl, 1-propynyl, 2-propynyl, 1-, 2- or 3-butynyl and the like, preferably $C_{2-10}$ alkynyl, more preferably $C_{2-6}$ alkynyl, most preferably $C_{2-4}$ alkynyl. The alkynyl group can be substituted or unsubstituted. When substituted, the substituent group(s) is preferably one or more groups independently selected from the group consisting of alkyl, alkenyl, alkynyl, alkoxyl, alkylthio, alkylamino, halogen, thiol, hydroxyl, nitro, cyano, cycloalkyl, heterocyclyl, aryl, heteroaryl, cycloalkoxyl, heterocylic alkoxyl, cycloalkylthio, heterocyclylthio, oxo, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Unlimited examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like, preferably cyclopropyl and cyclohexenyl. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the common spiro atoms, spiro cycloalkyl can be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Unlimited examples of spiro cycloalkyls include, but are not limited to:

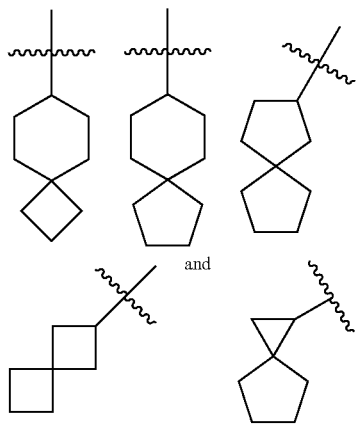

"Fused cycloalkyl" refers to a 5 to 20 membered full-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Unlimited examples of fused cycloalkyl include, but are not limited to:

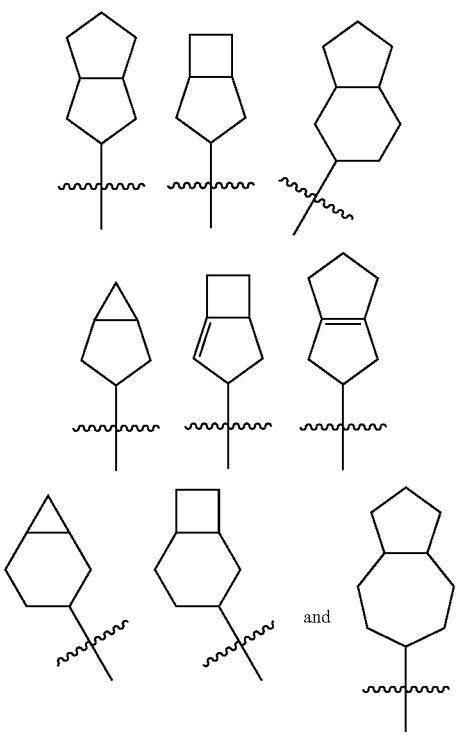

"Bridged cycloalkyl" refers to a 5 to 20 membered full-carbon polycyclic group, wherein every two rings in the system share two disconnected atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Unlimited examples of bridged cycloalkyls include, but are not limited to:

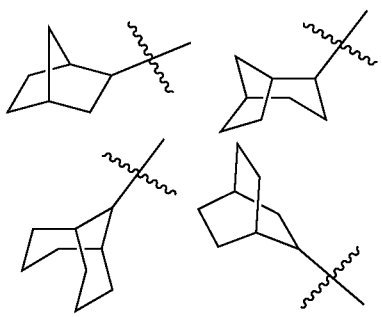

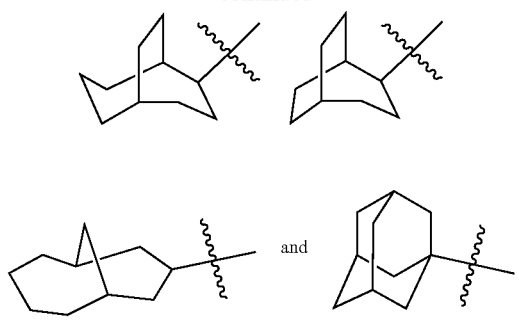

Said cycloalkyl can be fused to aryl, heteroaryl or heterocyclyl, wherein the ring bound to the parent structure is cycloalkyl. Unlimited examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Heterocyclyl" refers to a 3 to 20 membered saturated and/or partially unsaturated monocyclic or polycyclic hydrocarbon group having one or more heteroatoms selected from the group consisting of N, O, and S(O)$_m$ (wherein m is an integer selected from 0 to 2) as ring atoms, but excluding —O—O—, —O—S— and —S—S— in the ring, and the remaining ring atoms being carbon atoms. Preferably, heterocyclyl has 3 to 12 atoms with 1 to 4 heteroatoms, more preferably 3 to 10 atoms, and most preferably 5 to 6 atoms. Unlimited examples of monocyclic heterocyclyl include, but are not limited to, pyrrolidinyl, piperidyl, piperazinyl, morpholinyl, thiomorpholinyl, homopiperazinyl, pyranyl, tetrahydrofuranyl, and the like. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common carbon atom (called a spiro atom), wherein said rings have one or more heteroatoms selected from the group consisting of N, O, and S(O)$_m$ (wherein m is an integer selected from 0 to 2) as ring atoms and the remaining ring atoms being carbon atoms, wherein one or more rings can contain one or more double bonds, but none of the rings has a completely conjugated pi-electron system; preferably 6 to 14 membered spiro heterocyclyl, and more preferably 7 to 10 membered spiro heterocyclyl. According to the number of common spiro atoms, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Unlimited examples of spiro heterocyclyls include, but are not limited to:

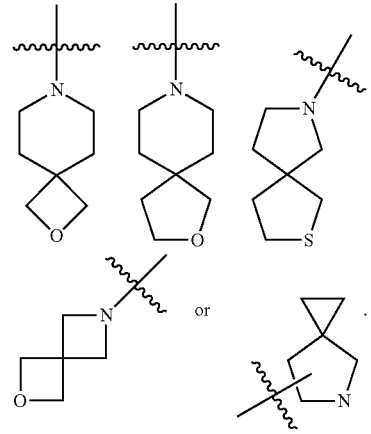

"Fused heterocyclyl" refers to a 5 to 20 membered polycyclic heterocyclyl group, wherein each ring in the system shares an adjacent pair of carbon atoms with another ring, wherein one or more rings can contain one or more double bonds, but none of the rings has a completely conjugated pi-electron system, and wherein said rings have one or more heteroatoms selected from the group consisting of N, O, and S(O)$_m$ (wherein m is an integer selected from 0 to 2) as ring atoms, and the remaining ring atoms being carbon atoms; preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Unlimited examples of fused heterocyclyl include, but are not limited to:

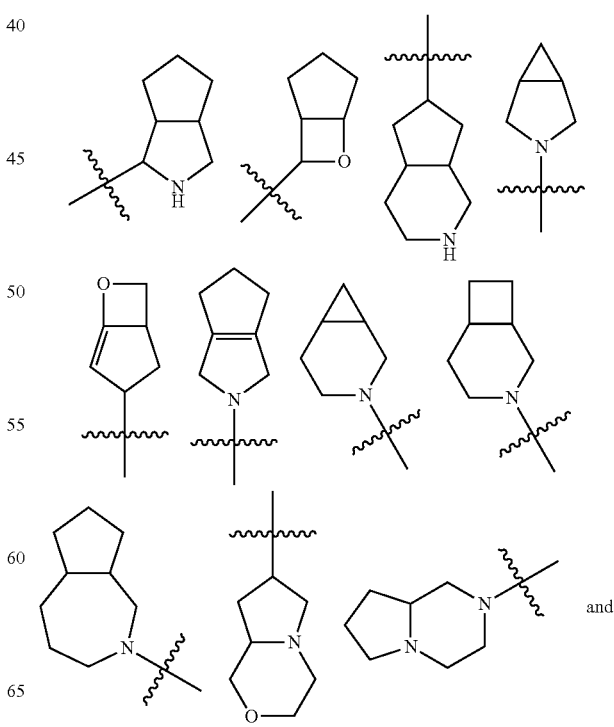

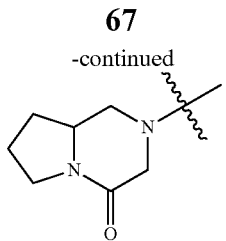

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S $(O)_m$ (wherein m is an integer selected from 0 to 2) as ring atoms, and the remaining ring atoms being carbon atoms; preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Unlimited examples of bridged heterocyclyls include, but are not limited to:

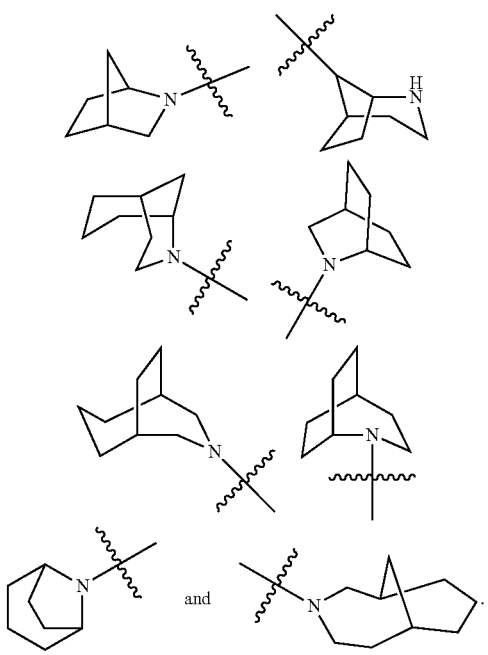

Said heterocyclyl can be fused to aryl, heteroaryl or cycloalkyl, wherein the ring bound to the parent structure is heterocyclyl. Unlimited examples include, but are not limited to:

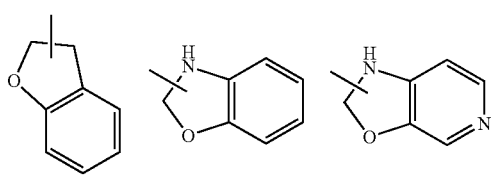

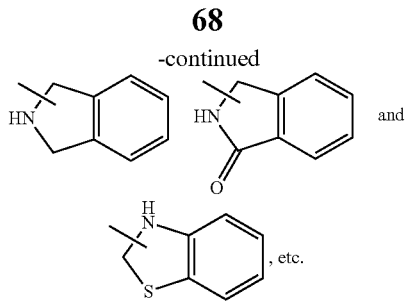

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylylthio, oxo, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Aryl" refers to a 6 to 14 membered full-carbon monocyclic ring or polycyclic fused ring (i.e., each ring in the system shares an adjacent pair of carbon atoms with another ring in the system) having a completely conjugated pi-electron system; preferably 6 to 10 membered aryl, more preferably phenyl and naphthyl, and most preferably phenyl. The aryl can be fused to heteroaryl, heterocyclyl or cycloalkyl, wherein the ring bound to the parent structure is aryl. Unlimited examples include, but are not limited to:

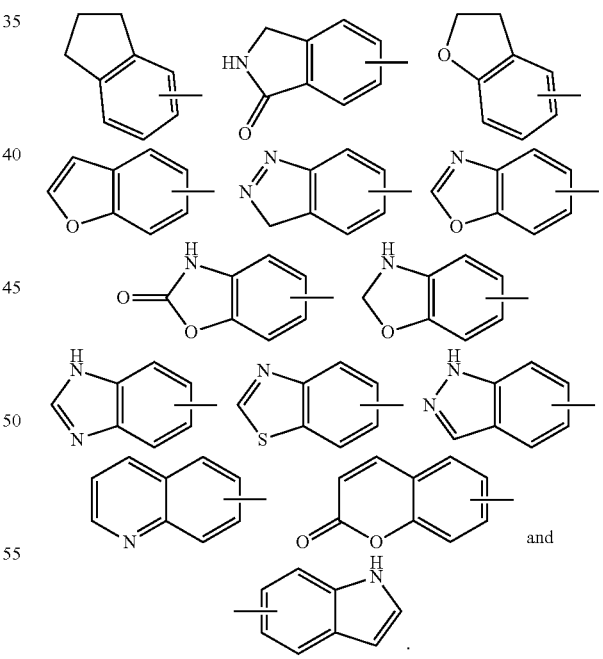

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclylthio, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Heteroaryl" refers to a 5 to 14 membered aryl having 1 to 4 heteroatoms selected from the group consisting of O, S and N as ring atoms and remaining ring atoms being carbon atoms; preferably a 5 to 10 membered heteroaryl, more preferably a 5- or 6-membered heteroaryl such as furyl, thienyl, pyridyl, pyrrolyl, N-alkyl pyrrolyl, pyrimidinyl, pyrazinyl, imidazolyl, tetrazolyl, oxazolyl, thiazolyl, pyrazolyl and the like. The heteroaryl can be fused to aryl, heterocyclyl or cycloalkyl, wherein the ring bound to the parent structure is heteroaryl. Unlimited examples include, but are not limited to:

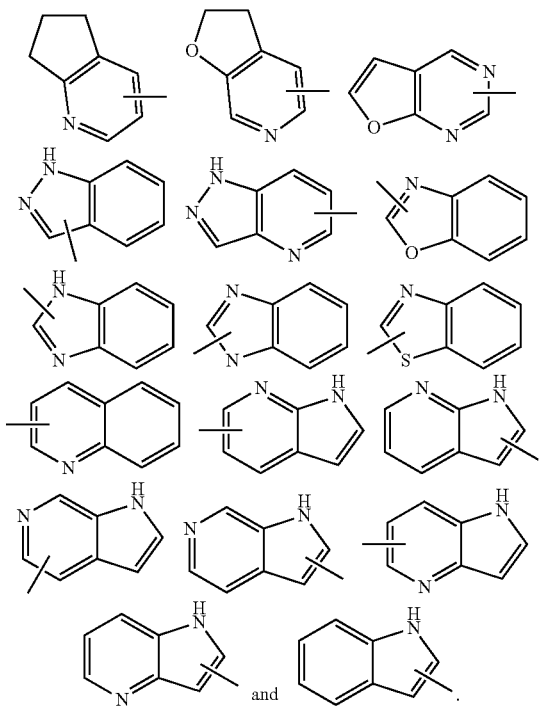

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Alkoxy" refers to an —O-(alkyl) or an —O-(unsubstituted cycloalkyl) group, wherein the alkyl is as defined above. Unlimited examples include, but are not limited to, methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, carboxylic ester, —C(O)OR$^5$, —OC(O)OR$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$.

"Haloalkyl" refers to an alkyl substituted with one or more halogen, wherein alkyl is as defined above.

"Hydroxy" refers to an —OH group.

"Hydroxyalkyl" refers to an alkyl substituted with hydroxy, wherein alkyl is as defined above.

"Halogen" refers to fluorine, chlorine, bromine or iodine.

"Amino" refers to a —NH$_2$ group.

"Cyano" refers to a —CN group.

"Nitro" refers to a —NO$_2$ group.

"Benzyl" refers to —CH$_2$-phenyl group.

"Oxo" refers to a =O group.

"Carboxyl" refers to a —C(O)OH group.

"Carboxylic ester" refers to a —C(O)O(alkyl) or (cycloalkyl) group, wherein the alkyl and cycloalkyl are as defined above.

"Amino protecting group" refers to a group preventing an amino from reaction when other parts of the molecular are subject to a reaction which can be easily removed. Unlimited examples include, but are not limited to formyl, alkyl carbonyl, alkoxy carbonyl, benzoyl, aralkyl carbonyl, aralkoxy carbonyl, trityl, phthalyl group, N,N-dimethylaminomethylenyl, substituted silyl, and the like. These groups can be optionally substituted with one to three groups independently selected from the group consisting of halogen, alkoxy and nitro. An amino protecting group is preferably t-butyloxycarbonyl.

"Optional" or "optionally" means that the event or circumstance described subsequently can, but need not, occur, and such description includes the situation in which the event or circumstance may or may not occur. For example, "the heterocyclic group optionally substituted with an alkyl" means that an alkyl group can be, but need not be, present, and such description includes the situation of the heterocyclic group being substituted with an alkyl and the heterocyclic group being not substituted with an alkyl.

"Substituted" refers to one or more hydrogen atoms in a group, preferably up to 5, more preferably 1 to 3 hydrogen atoms, independently substituted with a corresponding number of substituents. It goes without saying that the substituents only exist in their possible chemical position. The person skilled in the art is able to determine if the substitution is possible or impossible by experiments or theory without paying excessive efforts. For example, the combination of amino or hydroxy having free hydrogen with carbon atoms having unsaturated bonds (such as olefinic) may be unstable.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biological activity.

m and R$^5$ to R$^7$ are as defined in the compound of formula (I).

Synthesis Method of the Present Invention

In order to obtain the object of the present invention, the present invention applies the following synthesis technical solutions.

Scheme 1

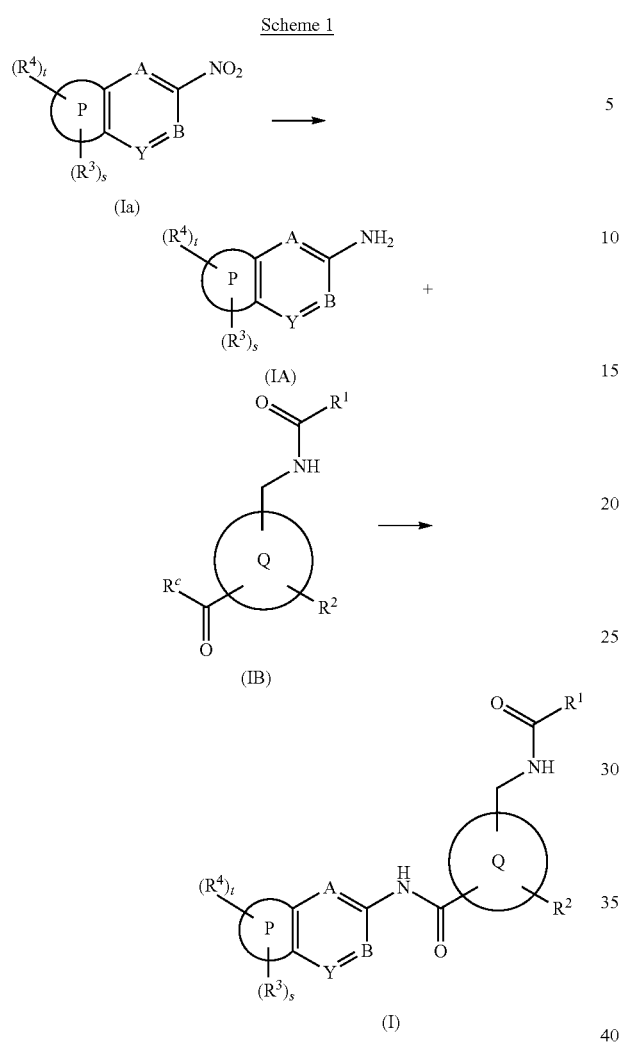

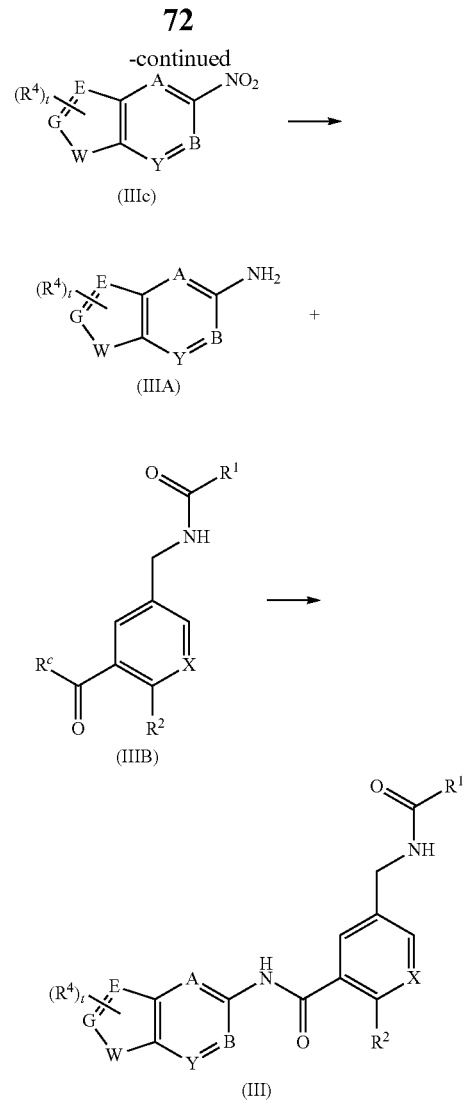

A process for preparing a compound of formula (I) of the present invention, or a tautomer, mesomer, racemate, enantiomer, diastereomer, or mixture thereof, or pharmaceutically acceptable salt thereof, comprising the following steps:
a compound of formula (Ia) is subject to a reduction reaction in the presence of a catalyst to give a compound of formula (IA) or a salt thereof; the compound of formula (IA) or the salt thereof is subject to a condensation reaction with a compound of formula (IB) under an alkaline condition to give the compound of formula (I);
wherein:
$R^c$ is selected from hydroxy and halogen;
ring P, ring Q, A, B, Y, s, t and $R^1$ to $R^4$ are as defined in general formula (I).

Scheme 2

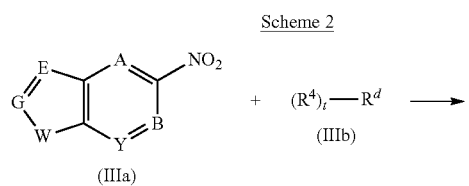

A process for preparing a compound of formula (III), or a tautomer, mesomer, racemate, enantiomer, diastereomer, or mixture thereof, or pharmaceutically acceptable salt thereof, comprising the following steps:
a compound of formula (IIIa) is subject to a coupling reaction with a compound of formula (IIIb) in the presence of a catalyst to give a compound of formula (IIIc); the compound of formula (IIIc) is subject to a reduction reaction in the presence of a catalyst to give a compound of formula (IIIA) or a salt thereof; the compound formula (IIIA) or the salt thereof is subject to a condensation reaction with a compound of formula (IIIB) under an alkaline condition to give the compound of formula (III);
Wherein:
$R^c$ is selected from hydroxy and halogen;
$R^d$ is selected from halogen, preferably bromine and iodine;
E, G and W are each independently selected from $CR^a$, $NR^b$, N, O and S;
A, B, X, Y, t, $R^1$, $R^2$ and $R^4$ are as defined in formula (I).
A process for preparing a compound of formula (IV) and formula (V) is the same or similar as that of the compound of formula (III).

Scheme 3

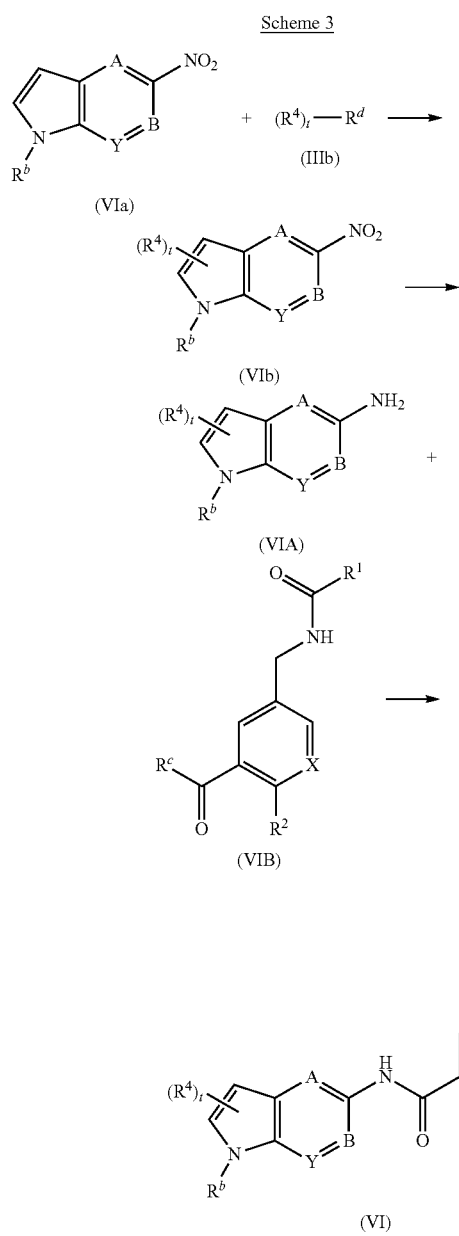

Scheme 4

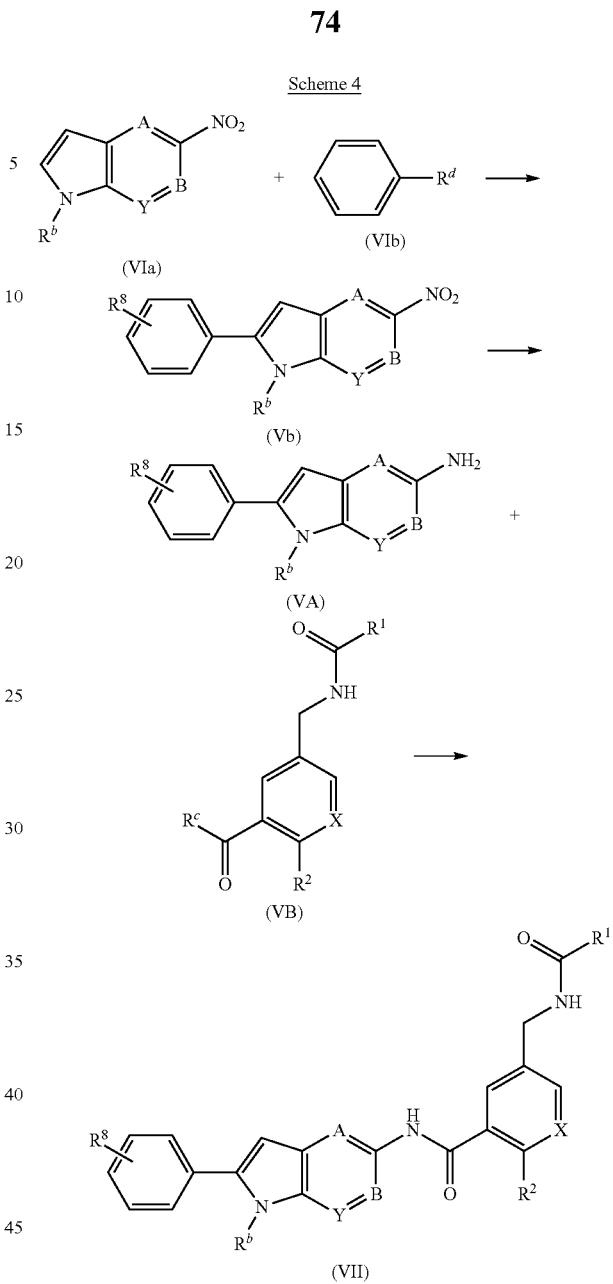

A process for preparing a compound of formula (VI), or a tautomer, mesomer, racemate, enantiomer, diastereomer, or mixture thereof, or pharmaceutically acceptable salt thereof, comprising the following steps:

a compound of formula (Via) is subject to a coupling reaction with a compound of formula (IIIb) in the presence of a catalyst to give a compound of formula (VIb); the compound of formula (VIb) is subject to a reduction reaction in the presence of a catalyst to give a compound of formula (VIA) or a salt thereof; the compound of formula (VIA) or salt thereof is subject to a condensation reaction with a compound of formula (VIB) under an alkaline condition to give the compound of formula (VI);

$R^c$ is selected from hydroxy and halogen;

$R^d$ is selected from halogen, preferably bromine and iodine;

A, B, X, Y, t, $R^1$, $R^2$ and $R^4$ are as defined in formula (I);

$R^b$ is as defined in formula (IV).

a compound of formula (VIa) is subject to a coupling reaction with a compound of formula (VIb) in the presence of a catalyst to give a compound of formula (Vb); the compound of formula (Vb) is subject to a reduction reaction in the presence of a catalyst to give a compound of formula (VA) or a salt thereof; the compound of formula (VA) or salt thereof is subject to a condensation reaction with a compound of formula (VB) under an alkaline condition to give the compound of formula (VII);

$R^c$ is selected from hydroxy and halogen;

$R^d$ is selected from halogen, preferably bromine and iodine;

A, B, X, Y, $R^1$ and $R^2$ are as defined in formula (I);

$R^b$ is as defined in formula (IV);

$R^8$ is as defined in formula (VII).

Alkaline reagents include organic base and inorganic base, wherein said organic base includes, but is not limited to, triethylamine, N,N-disopropylethylamine, pyridine, sodium bis(trimethylsilyl)amide, n-butyllithium, potassium tert-butanolate, and tetrabutylammonium bromide, wherein said inorganic base includes, but is not limited to, lithium hydroxide, sodium hydroxide, potassium hydroxide, sodium hydride, sodium carbonate, sodium bicarbonate, potassium carbonate, potassium bicarbonate, and cesium carbonate, preferably triethylamine.

Catalysts include, but are not limited to, Pd/C, raney nickel, Tetrakis(triphenylphosphine)palladium, palladium chloride, palladium diacetate, (1,1'-Bis(dibenzylphosphino) ferrocene)dichloropalladium(II), and Tris(dibenzylideneacetone)dipalladium.

Condensing agents include, but are not limited to, 1-(3-dimethylaminopropyl)-3-ethylcarbodiimide hydrochloride, N,N'-dicyclohexylcarbodiimide, N,N'-diisopropylcarbondiimide, O-benzotriazol-1-yl)-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, 2-(7-azobenzotriazol-1-yl)-N,N,N',N'-tertramethyluronium hexafluorophophate, benzotriazol-1-yl-oxy-tris(dimethylamino)-phophonium hexaflurophosphate, and benzotriazol-1-yl-oxy-tripyrrolidinophosphonium hexafluorophosphate.

The present invention will be further described with the following examples, but the examples should not be considered as limiting the scope of the invention.

Conditions that are not specified in the examples will be the common conditions in the art or the recommended conditions of the raw materials by the product manufacturer.

The reagents for which an origin is not indicated are the commercially available, conventional reagents.

EXAMPLES

Compound structures were identified by nuclear magnetic resonance (NMR) and/or mass spectrometry (MS). NMR is determined by Bruker AVANCE-400. The solvents were deuterated-dimethyl sulfoxide (DMSO-$d_6$), deuterated-chloroform (CDCl$_3$) and deuterated-methanol (CD$_3$OD) with tetramethylsilane (TMS) as an internal standard. NMR chemical shifts ($\delta$) are given in $10^{-6}$ (ppm).

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ values were determined by a NovoStar ELISA (BMG Co., Germany).

Yantai Huanghai HSGF254 or Qingdao GF254 silica gel plate was used for thin-layer silica gel chromatography (TLC). The dimensions of the silica gel plate used in TLC were 0.15 mm to 0.2 mm, and the dimension of the silica gel plate used in product purification were 0.4 mm to 0.5 mm.

Yantai Huanghai 200 to 300 mesh silica gel was used as carrier for column chromatography.

The known raw materials of the present invention can be prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions were carried out under nitrogen atmosphere or argon atmosphere.

The term "nitrogen atmosphere" or "argon atmosphere" means that a reaction flask was equipped with a 1 L nitrogen or argon balloon.

The term "hydrogen atmosphere" means that a reaction flask was equipped with a 1 L hydrogen balloon.

Pressured hydrogenation reactions were performed with a Parr 3916EKX hydrogenation instrument and a QL-500 hydrogen generator or HC2-SS hydrogenation instrument.

In hydrogenation reactions, the reaction system was generally vacuumed and filled with hydrogen, with the above operation repeated three times.

CEM Discover-S 908860 type microwave reactor was used for microwave reactions.

Unless otherwise stated, the solution used in the reactions refers to an aqueous solution.

Unless otherwise stated, the reaction temperature in the reactions refers to room temperature, and the range of the temperature was 20° C. to 30° C.

The reaction process was monitored by thin layer chromatography (TLC), the elution system included: A: dichloromethane and methanol, B: n-hexane and ethyl acetate, C: petroleum ether and ethyl acetate, D: acetone. The ratio of the volume of the solvent was adjusted according to the polarity of the compounds.

The elution system for purification of the compounds by column chromatography and thin layer chromatography included: A: dichloromethane and methanol, B: n-hexane and ethyl acetate, C: n-hexane and acetone, D: n-hexane, E: ethyl acetate. The ratio of the volume of the solvent was adjusted according to the polarity of the compounds, and sometimes a little alkaline reagent such as triethylamine or acidic reagent was added.

Example 1

2-(difluoromethyl)-N-(1-ethyl-2-(4-(trifluoromethyl) phenyl)-1H-indol-5-yl)-5-((2-methylpropanoylamino)methyl)nicotinamide

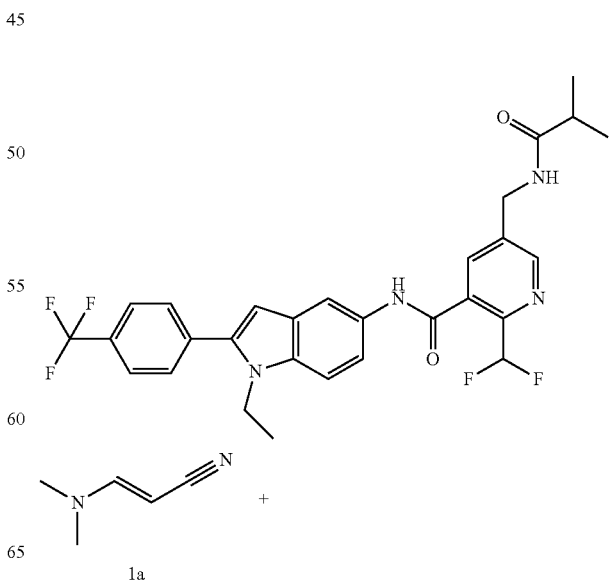

1a

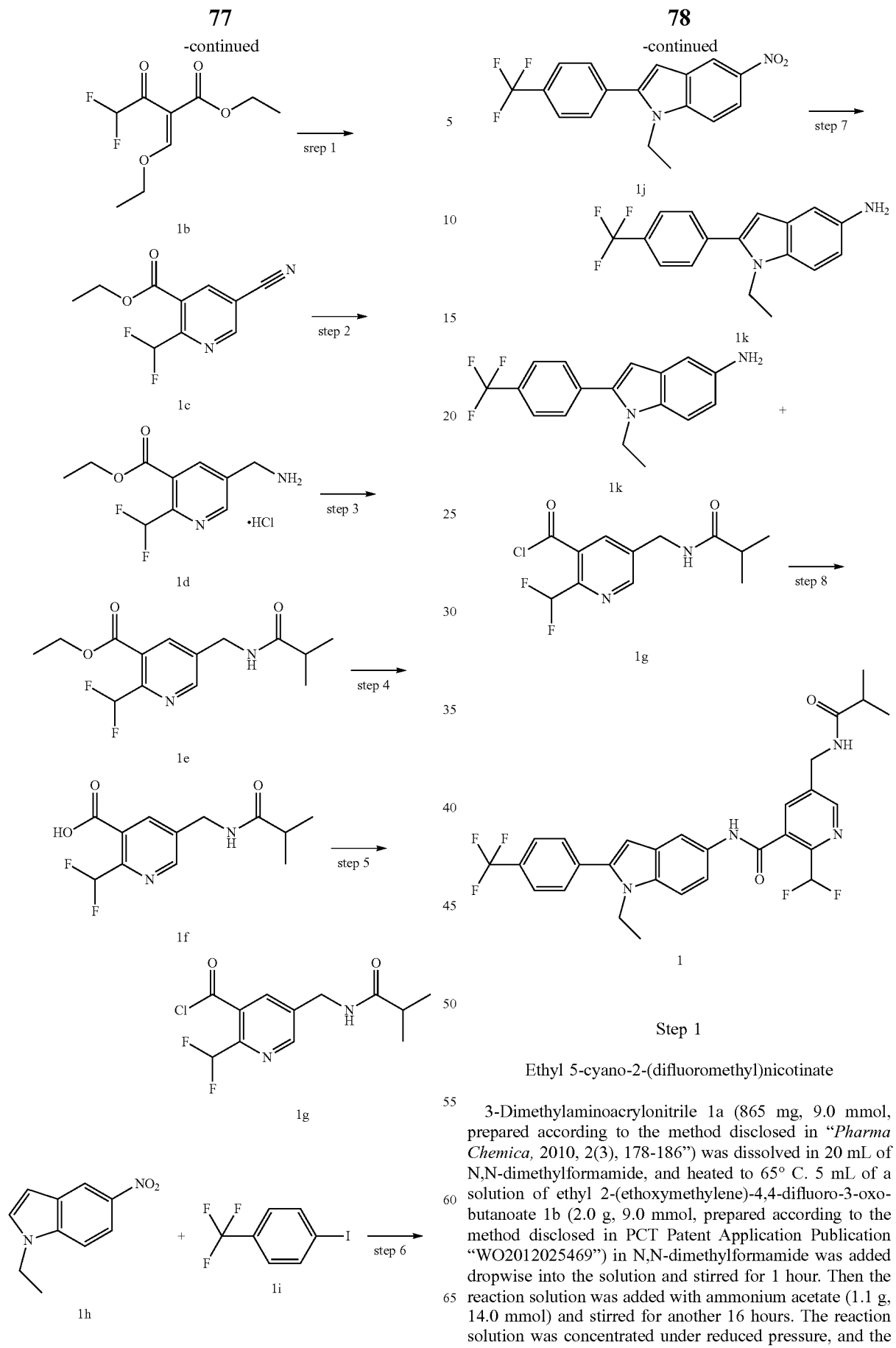

Step 1

Ethyl 5-cyano-2-(difluoromethyl)nicotinate

3-Dimethylaminoacrylonitrile 1a (865 mg, 9.0 mmol, prepared according to the method disclosed in "*Pharma Chemica*, 2010, 2(3), 178-186") was dissolved in 20 mL of N,N-dimethylformamide, and heated to 65° C. 5 mL of a solution of ethyl 2-(ethoxymethylene)-4,4-difluoro-3-oxo-butanoate 1b (2.0 g, 9.0 mmol, prepared according to the method disclosed in PCT Patent Application Publication "WO2012025469") in N,N-dimethylformamide was added dropwise into the solution and stirred for 1 hour. Then the reaction solution was added with ammonium acetate (1.1 g, 14.0 mmol) and stirred for another 16 hours. The reaction solution was concentrated under reduced pressure, and the residue was added with 100 mL of water and extracted with ethyl acetate (100 mL×3). The organic phases were combined, dried over anhydrous sodium sulfate, and filtered. The filtrate was concentrated under reduced pressure. The residues were purified via thin layer chromatography (TLC) with elution system C to obtain the title compound ethyl 5-cyano-2-(difluoromethyl)nicotinate 1c (606 mg, 30%) as a light yellow oil.

MS m/z (ESI): 227.1 [M+1]

Step 2

Ethyl 5-(aminomethyl)-2-(difluoromethyl)nicotinate hydrochloride

Ethyl 5-cyano-2-(difluoromethyl) nicotinate 1c (606 mg, 2.7 mmol) was dissolved in 15 mL of ethanol, and added with concentrated hydrochloric acid (1.0 mL, 37%) and Pd/C (180 mg, 10%). The reaction mixture was stirred for 2 hours under a hydrogen atmosphere. The reaction solution was filtered via celatom, and the filtrate was concentrated under reduced pressure to obtain the title compound ethyl 5-(aminomethyl)-2-(difluoromethyl) nicotinate hydrochloride 1d (709 mg, 99%) as a yellow solid.

MS m/z (ESI): 231.1 [M+1]

Step 3

Ethyl 2-(difluoromethyl)-5-((2-methylpropanoylamino)methyl)nicotinate

Ethyl 5-(aminomethyl)-2-(difluoromethyl)nicotinate hydrochloride 1d (709 mg, 2.7 mmol) was dissolved in 50 mL of dichloromethane, and added with N,N-diisopropylethylamine (1.9 mL, 10.6 mmol). Upon the completion of the addition, the reaction mixture was added dropwise with a solution of isobutyryl chloride in dichloromethane (0.7 M, 5 mL) and then stirred for 2 hours. The reaction mixture was washed with water (50 mL) and saturated sodium bicarbonate solution (50 mL) successively. The organic phase was concentrated under reduced pressure to obtain the title compound ethyl 2-(difluoromethyl)-5-((2-methylpropanoylamino)methyl)nicotinate 1e (790 mg, 99%) as a light yellow solid.

MS m/z (ESI): 301.1 [M+1]

Step 4

2-(Difluoromethyl)-5-((2-methylpropanoylamino)methyl)nicotinic acid

Ethyl 2-(difluoromethyl)-5-((2-methylpropanoylamino)methyl)nicotinate 1e (790 mg, 2.6 mmol) was dissolved in 10 mL of 1,4-dioxane, and added with 5 mL water and lithium hydroxide hydrate (291 mg, 6.9 mmol). The reaction mixture was stirred for 16 hours. The reaction mixture was concentrated under reduced pressure. The residues were added with 5 mL of water, and adjusted to pH 2 by 5M hydrochloric acid. A lot of solid was precipitated and filtered out. The filtrate was extracted with ethyl acetate (50 mL×3). The organic phases were combined and concentrated under reduced pressure. The residues were combined with the filter cake above, washed with water, and dried to obtain the title compound 2-(difluoromethyl)-5-((2-methylpropanoylamino)methyl)nicotinic acid 1f (420 mg, 56%) as a light yellow solid.

MS m/z (ESI): 273.1 [M+1]

Step 5

2-(Difluoromethyl)-5-((2-methylpropanoylamino)methyl)nicotinoyl chloride 2-(Difluoromethyl)-5-((2-methylpropanoylamino)methyl)nicotinic acid 1f (150 mg, 0.55 mmol) was dissolved in 5 mL of dichloromethane, and added with one drop of N,N-Dimethylformamide and thionyl chloride (197 mg, 1.65 mmol). Upon the completion of the addition, the reaction mixture was stirred for 2 hours. The reaction mixture was concentrated under reduced pressure to obtain the title compound 2-(difluoromethyl)-5-((2-methylpropanoylamino)methyl)nicotinoyl chloride 1g (160 mg) as a light yellow oil, which was used in the next step without further purification.

Step 6

1-Ethyl-5-nitro-2-(4-(trifluoromethyl)phenyl)-1H-indole

1-Ethyl-5-nitro-1H-indole 1h (500 mg, 2.63 mmol, prepared according to the method disclosed in "*Bioorganic & Medicinal Chemistry*, 2005, 13(10), 3531-3541") was dissolved in 5 mL of N,N-dimethylacetamide, and added with 4-iodotrifluorotoluene 1i (790 mg, 2.92 mmol), triphenylphosphine (140 mg, 0.53 mmol), palladium acetate (30 mg, 0.13 mmol) and cesium acetate (1.6 g, 5.21 mmol), successively. Upon the completion of the addition, the resulting mixture was heated to 140° C. and stirred for 18 hours under an argon atmosphere. The reaction mixture was concentrated under reduced pressure. The residues were added with 50 mL of ethyl acetate, washed with water (20 mL×2), dried over anhydrous sodium sulfate, and filtered. The filtrate was concentrated under reduced pressure, and the residues were purified by thin layer chromatography (TLC) with elution system C to obtain the title compound 1-ethyl-5-nitro-2-(4-(trifluoromethyl)phenyl)-1H-indole 1j (130 mg, 14.8%) as a yellow solid.

MS m/z (ESI): 335.1 [M+1]

Step 7

1-Ethyl-5-amino-2-(4-(trifluoromethyl)phenyl)-1H-indole

1-Ethyl-5-nitro-2-(4-(trifluoromethyl)phenyl)-1H-indole 1j (130 mg, 0.39 mmol) was dissolved in 10 mL of a mixture of tetrahydrofuran and methanol (V:V=1:1), and added with Raney nickel (30 mg). The reaction mixture was stirred for 2 hours under a hydrogen atmosphere. The reaction mixture was filtered with celatom, and the filtrate was concentrated under reduced pressure to obtain the crude title compound 1-ethyl-5-amino-2-(4-(trifluoromethyl)phenyl)-1H-indole 1k (120 mg) as a light yellow solid, which was used in the next step without further purification.

MS m/z (ESI): 305.1 [M+1]

Step 8

2-(Difluoromethyl)-N-(1-ethyl-2-(4-(trifluoromethyl)phenyl)-1H-indol-5-yl)-5-((2-methylpropanoylamino)methyl)nicotinamide 1-Ethyl-5-amino-2-(4-(trifluoromethyl)phenyl)-1H-indole 1k (120 mg, 0.39 mmol) was dissolved in 10 mL of tetrahydrofuran, and added with triethylamine (0.10 mL, 0.78 mmol), and a 5 mL solution of 2-(difluoromethyl)-5-((2-methylpropanoylamino)methyl)nicotinoyl chloride 1g (160 mg, 0.55 mmol) in tetrahydrofuran dropwise. The reaction mixture was stirred for 1 hour. The reaction mixture was filtered, and the filtrate was concentrated under reduced pressure. The residues were purified via thin layer chromatography (TLC) with elution system A to obtain the title compound 2-(difluoromethyl)-N-(1-ethyl-2-(4-(trifluoromethyl)phenyl)-1H-indol-5-yl)-5-((2-methylpropanoylamino)methyl)nicotinamide 1 (25 mg, 11.5%) as a yellow solid.

MS m/z (ESI): 559.3 [M+1]

$^1$H NMR (400 MHz, DMSO-d$_6$): δ 10.61 (s, 1H), 8.68 (s, 1H), 8.46 (t, 1H), 8.07 (s, 1H), 8.01 (s, 1H), 7.93-7.86 (d, 2H), 7.85-7.78 (d, 2H), 7.61-7.55 (d, 1H), 7.47-7.42 (d, 1H), 7.19 (t, 1H), 6.70 (s, 1H), 4.47-4.39 (d, 2H), 4.31-4.20 (m, 2H), 2.49-2.41 (m, 1H), 1.21 (t, 3H), 1.09-1.03 (d, 6H).

Example 2

2-Chloro-N-(1-ethyl-2-(4-(trifluoromethyl)phenyl)-1H-indol-5-yl)5-((2,2-dimethylpropanoylamino)methyl)-benzamide "WO2012025469") was dissolved in 10 mL dichloromethane, and added dropwise with thionyl chloride (0.4 mL, 5.58 mmol) and one drop of N,N-dimethylformamide. Upon the completion of the addition, the reaction mixture was stirred for 2 hours. The reaction mixture was concentrated under reduced pressure to obtain the title compound 2-chloro-5-((2,2-dimethylpropanoylamino)-methyl)benzoyl chloride 2b (550 mg) as a yellow oil which was used in the next step without further purification.

Step 2

2-Chloro-N-(1-ethyl-2-(4-(trifluoromethyl)phenyl)-1H-indol-5-yl) 5-((2,2-dimethylpropanoylamino)methyl)-benzamide 1-Ethyl-5-amino-2-(4-(trifluoromethyl)phenyl)-1H-indol-1k (90 mg, 0.27 mmol) was dissolved in 5 mL tetrahydrofuran, and added with triethylamine (75 µL, 0.54 mmol), and 2 mL of a solution of 2-chloro-5-((2,2-dimethylpropanoylamino)methyl)benzoyl chloride 2b (77 mg, 0.27 mmol) in tetrahydrofuran dropwise. Upon the completion of the addition, the reaction mixture was stirred for 1 hour. The

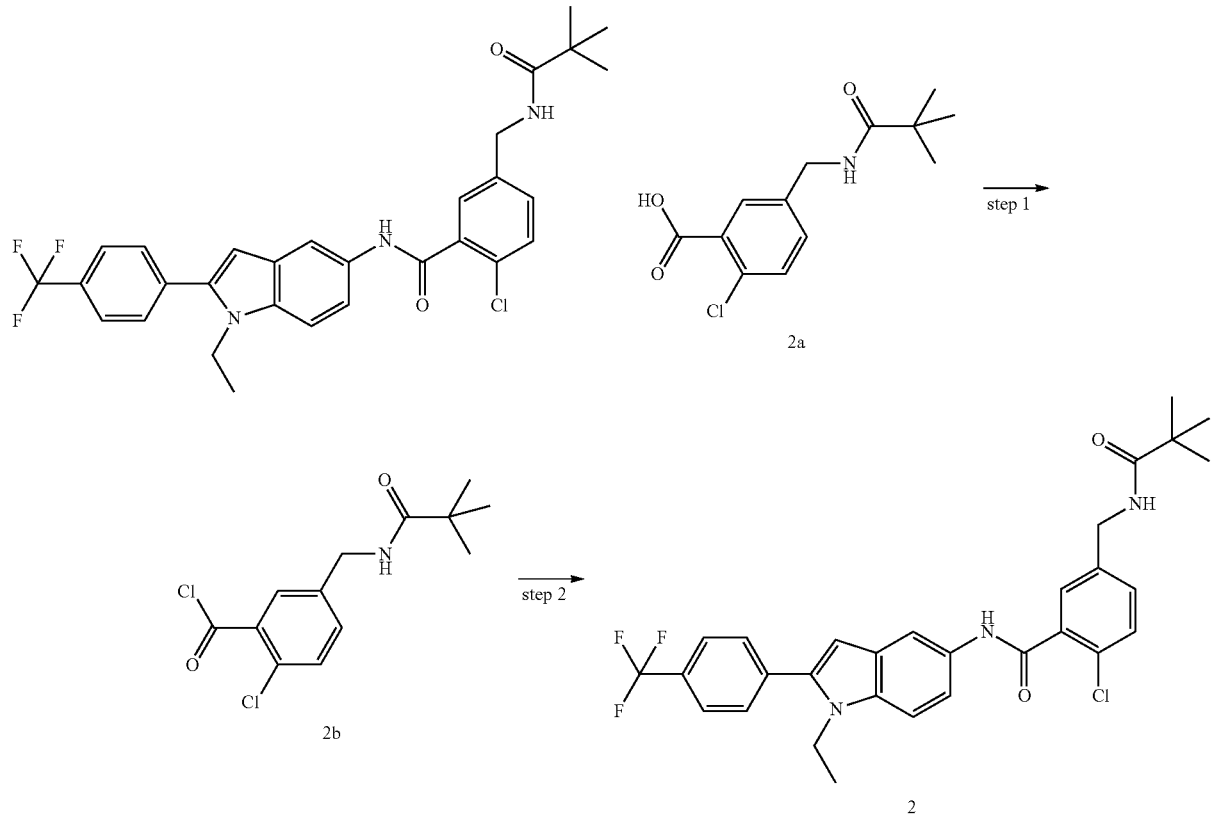

Step 1

2-Chloro-5-((2,2-dimethylpropanoylamino)methyl) benzoyl chloride

2-Chloro-5-((2,2-dimethylpropanoylamino)methyl)benzoic acid 2a (500 mg, 1.86 mmol, prepared according to the method disclosed in PCT Patent Application Publication reaction mixture was filtered. The filtrate was concentrated under reduced pressure. The residues were purified by thin layer chromatography (TLC) with elution system A to obtain the title compound 2-chloro-N-(1-ethyl-2-(4-(trifluoromethyl)phenyl)-1H-indol-5-yl)5-((2,2-dimethylpropanoylamino)methyl)-benzamide 2 (45 mg, 30%) as a light yellow solid.

MS m/z (ESI): 557.1 [M+1]

¹H NMR (400 MHz, DMSO-d₆): δ 10.40 (s, 1H), 8.18 (t, 1H), 8.10 (s, 1H), 7.92-7.87 (d, 2H), 7.84-7.79 (d, 2H), 7.58-7.53 (d, 1H), 7.52-7.48 (d, 1H), 7.47-7.41 (m, 2H), 7.36-7.30 (d, 1H), 6.69 (s, 1H), 4.34-4.29 (d, 2H), 4.29-4.21 (m, 2H), 1.21 (t, 3H), 1.13 (s, 9H).

Example 3

2-chloro-N-(2-(4-fluorophenyl)-1H-pyrrolo(2,3-b)pyridin-5-yl)-5-((2,2-dimethylpropanoylamino)methyl)-benzamide

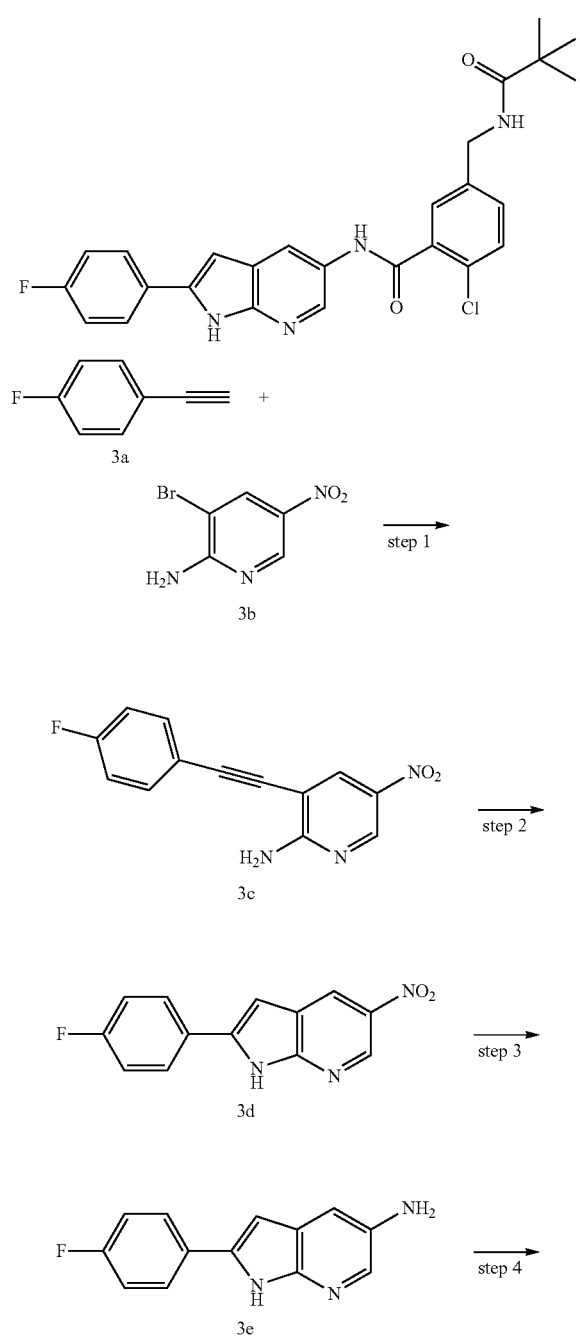

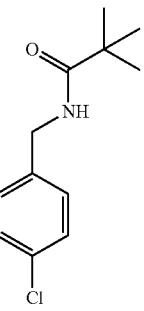

Step 1

3-((4-Fluorophenyl)ethynyl)-5-nitro-pyridin-2-amine

2-Amino-3-bromo-5-nitro-pyridine 3b (1.0 g, 4.6 mmol), 1-ethynyl-4-fluoro-benzene 3a (1.24 g, 10.3 mmol), Bis(triphenylphosphine)palladium (II) chloride (0.25 g, 0.35 mmol), copper iodine (7 mg, 0.35 mmol) and triethylamine (0.7 mL, 4.6 mmol) were added into 20 mL N,N-dimethylformamide. The reaction mixture was stirred for 16 hours under an argon atmosphere. The reaction mixture was filtered with celatom, and the filtrate was concentrated under reduced pressure. The residues were purified by silica gel column chromatography with elution system C to obtain the crude title compound 3-((4-fluorophenyl)ethynyl)-5-nitro-pyridin-2-amine 3c (1.7 g) as a brown solid, which was used in the next step without further purification.

MS m/z (ESI): 256.0 [M−1]

Step 2

2-(4-Fluorophenyl)-5-nitro-1H-pyrrolo[2,3-b]pyridine 3-((4-Fluorophenyl)ethynyl)-5-nitro-pyridin-2-amine 3c (1.7 g, 4.6 mmol) and potassium tert-butoxide (1.0 g, 9.2 mmol) were dissolved in 20 mL N, N-dimethylformamide. The reaction mixture was heated to 70° C. and stirred for 16 hours. The reaction solution was concentrated under reduced pressure. The residues were added with 200 mL water, and then filtered with celatom. The filter cake was purified by silica gel column chromatography with elution system C, and then added with 20 mL dichloromethane and then filtered. The residues were dried to obtain the crude title compound 2-(4-fluorophenyl)-5-nitro-1H-pyrrolo[2,3-b]pyridine 3 d (564 mg) as a yellow solid which was used in the next step without further purification.

Step 3

2-(4-Fluorophenyl)-5-amino-1H-pyrrolo[2,3-b]pyridine 2-(4-Fluorophenyl)-5-nitro-1H-pyrrolo[2,3-b]pyridine 3d (64 mg, 0.25 mmol) was dissolved in 10 mL of a mixture of tetrahydrofuran and methanol (V:V=1:1), and then added with Raney nickel (30 mg). The reaction mixture was stirred for 1 hour under a hydrogen atmosphere and then filtered with celatom. The filtrate was concentrated under reduced pressure to obtain the crude title compound 2-(4-fluorophenyl)-5-amino-1H-pyrrolo[2,3-b]pyridine 3e (60 mg) as a brown oil which was used in the next step without further purification.

MS m/z (ESI): 226.1 [M−1]

Step 4

2-Chloro-N-(2-(4-fluorophenyl)-1H-pyrrolo[2,3-b]pyridin-5-yl)5-((2,2-dimethylpropanoylamino)methyl)-benzamide 2-(4-Fluorophenyl)-5-amino-1H-pyrrolo[2,3-b]pyridine 3e (60 mg, 0.25 mmol) was dissolved in 8 mL tetrahydrofuran, and added with triethylamine (0.43 mL, 0.31 mmol) and 5 mL of a solution of 2-chloro-5-((2,2-dimethylpropanoylamino)methyl)benzoyl chloride 2b (220 mg, 0.76 mmol) in tetrahydrofuran dropwise. The reaction mixture was stirred for 1 hour and then filtered. The filtrate was concentrated under reduced pressure. The residues were purified by thin layer chromatography (TLC) with elution system A to obtain the title compound 2-chloro-N-(2-(4-fluorophenyl)-1H-pyrrolo[2,3-b]pyridin-5-yl)5-((2,2-dimethylpropanoylamino)methyl)-benzamide 3 (5 mg, 4.2% for two steps) as a light yellow solid.

MS m/z (ESI): 479.4 [M+1]

$^1$H NMR (400 MHz, DMSO-$d_6$): δ 9.16 (s, 1H), 8.06 (s, 1H), 7.94 (s, 1H), 7.65-7.56 (m, 1H), 7.55-7.46 (m, 2H), 7.48-7.36 (m, 2H), 7.27-7.16 (m, 3H), 6.41 (s, 1H), 5.15 (m, 1H), 4.26-4.21 (m, 2H), 1.13 (s, 9H).

Example 4

2-Chloro-N-(1-ethyl-2-(4-fluorophenyl)-1H-pyrrolo[2,3-b]pyridin-5-yl)5-((2,2-dimethylpropanoylamino)methyl)-benzamide

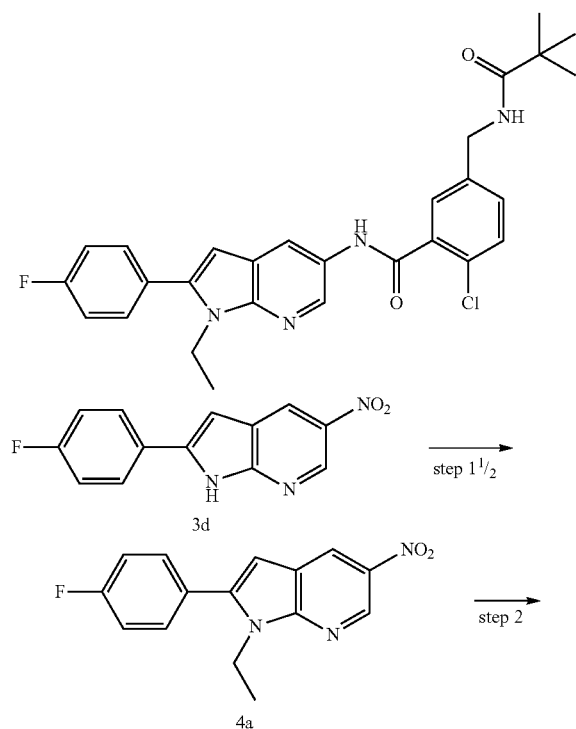

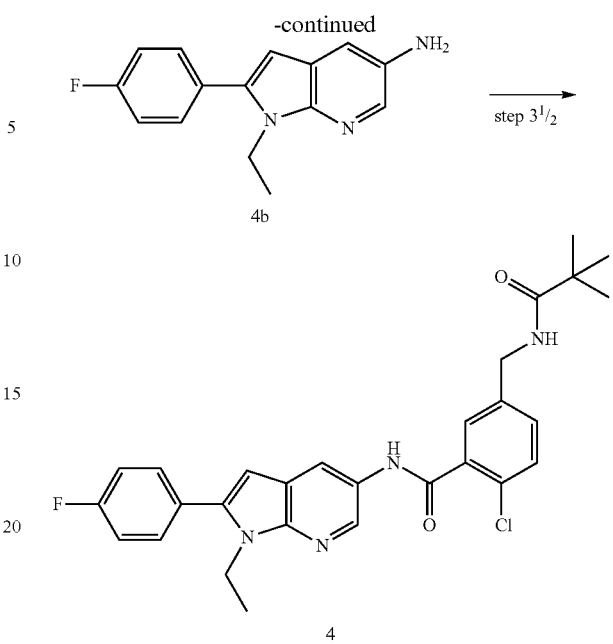

Step 1

1-Ethyl-2-(4-fluorophenyl)-5-nitro-1H-pyrrolo[2,3-b]pyridine 2-(4-Fluorophenyl)-5-nitro-1H-pyrrolo[2,3-b]pyridine 3d (60 mg, 0.23 mmol), iodoethane (40 μL, 0.47 mmol) and cesium carbonate (150 mg, 0.47 mmol) were added into 5 mL N,N-dimethylformamide. The reaction mixture was stirred for 16 hours, and then added with 20 mL water, and extracted with ethyl acetate (20 mL×4). The organic phases were combined, washed with saturated sodium chloride solution (30 mL×2), dried over anhydrous sodium sulfate, filtered, and the filtrate was concentrated under reduced pressure. The residues were purified by silica gel column chromatography with elution system C to obtain the crude title compound 1-ethyl-2-(4-fluorophenyl)-5-nitro-1H-pyrrolo[2,3-b]pyridine 4a (70 mg) as a yellow solid which was used in the next step without further purification.

MS m/z (ESI): 286.1 [M+1]

Step 2

1-Ethyl-2-(4-fluorophenyl)-5-amino-1H-pyrrolo[2,3-b]pyridine

1-Ethyl-2-(4-fluorophenyl)-5-nitro-1H-pyrrolo[2,3-b]pyridine 4a (70 mg, 0.23 mmol) was dissolved in 10 mL of a mixture of tetrahydrofuran and methanol (V:V=1:1), and then added with Raney nickel (20 mg). The reaction mixture was stirred for 2 hours under a hydrogen atmosphere and then filtered with celatom. The filtrate was concentrated under reduced pressure to obtain the crude title compound 1-ethyl-2-(4-fluorophenyl)-5-amino-1H-pyrrolo[2,3-b]pyridine 4b (60 mg) as a light yellow solid which was used in the next step without further purification.

MS m/z (ESI): 256.2 [M+1]

Step 3

2-Chloro-N-(1-ethyl-2-(4-fluorophenyl)-1H-pyrrolo[2,3-b]pyridin-5-yl)-5-((2,2-dimethylpropanoylamino)methyl)-benzamide 5

1-Ethyl-2-(4-fluorophenyl)-5-amino-1H-pyrrolo[2,3-b]pyridine 4b (60 mg, 0.23 mmol) was dissolved in 5 mL tetrahydrofuran, and added with triethylamine (65 µL, 0.47 mmol) and 5 mL of a solution of 2-chloro-5-((2,2-dimethylpropanoylamino)methyl)benzoyl chloride 2b (220 mg, 0.76 mmol) in tetrahydrofuran dropwise. The reaction mixture was stirred for 1 hour and then filtered. The filtrate was concentrated under reduced pressure. The residues were purified by thin layer chromatography (TLC) with elution system A to obtain the title compound 2-chloro-N-(1-ethyl-2-(4-fluorophenyl)-1H-pyrrolo[2,3-b]pyridin-5-yl)-5-((2,2-dimethylpropanoylamino)methyl)-benzamide 4 (5 mg, 4.2% for three steps) as a yellow solid.

MS m/z (ESI): 507.3 [M+1]

$^1$H NMR (400 MHz, DMSO-d$_6$): δ 9.15 (s, 1H), 8.05 (s, 1H), 7.93 (s, 1H), 7.66-7.56 (m, 1H), 7.55-7.48 (m, 2H), 7.48-7.38 (m, 2H), 7.27-7.17 (m, 3H), 6.56 (s, 1H), 4.34-4.28 (d, 2H), 4.29-4.20 (m, 2H), 1.23 (t, 3H), 1.12 (s, 9H).

Example 5

2-(Difluoromethyl)-N-(1-ethyl-2-(4-fluorophenyl)-1H-indol-5-yl)-5-((2-methylpropanoylamino)methyl)nicotinamide

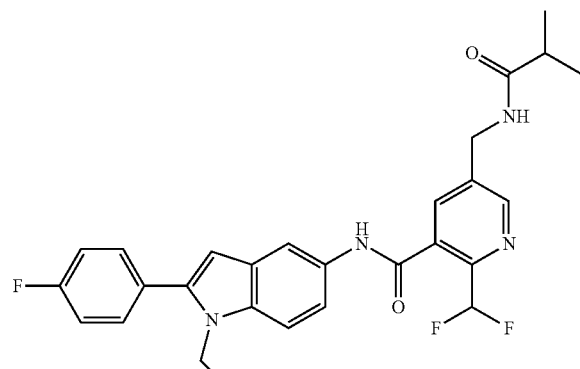

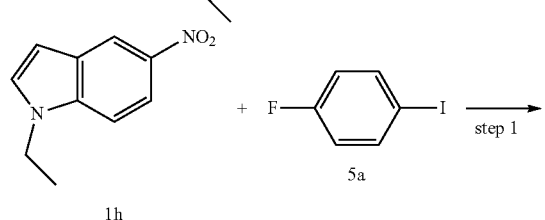

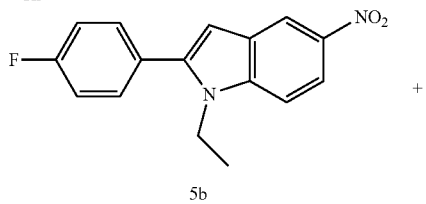

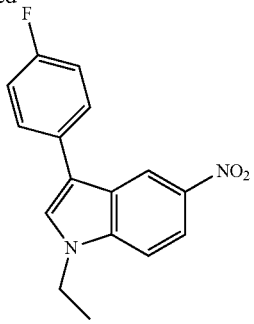

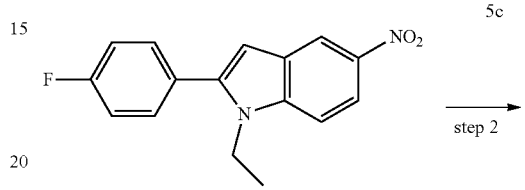

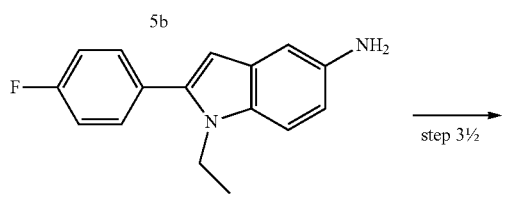

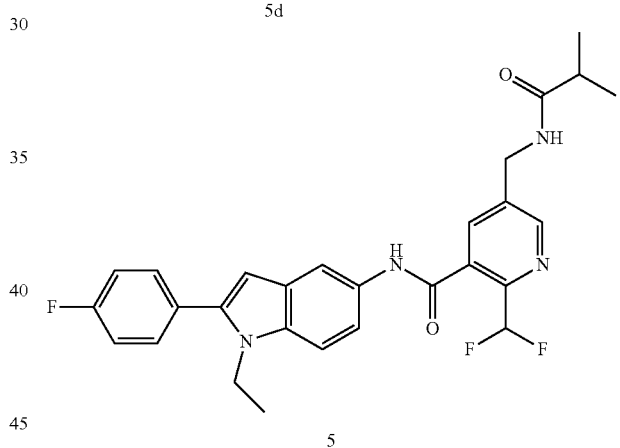

Step 1

1-Ethyl-2-(4-fluorophenyl)-5-nitro-1H-indole 5b

1-Ethyl-3-(4-fluorophenyl)-5-nitro-1H-indole 5c

1-Ethyl-5-nitro-1H-indole 1h (1.64 g, 6.17 mmol) was dissolved in 20 mL N,N-dimethylacetamide, and then added with 1-fluoro-4-iodo-benzene 5a (4.65 g, 21.0 mmol), triphenylphosphine (360 mg, 1.36 mmol), palladium acetate (70 mg, 0.31 mmol), and cesium acetate (4.0 g, 12.3 mmol), successively. The reaction mixture was heated to 140° C. and stirred for 18 hours under an argon atmosphere. The reaction mixture was concentrated under reduced pressure. The residues were purified by thin layer chromatography (TLC) with elution system C to obtain the title compound 1-ethyl-2-(4-fluorophenyl)-5-nitro-1H-indole 5b (0.51 g, 29.1%) as a yellow solid and 1-ethyl-3-(4-fluorophenyl)-5-nitro-1H-indole 5c (125 mg, 7.1%) as a yellow solid.

5b: MS m/z (ESI): 285.0 [M+1]
5c: MS m/z (ESI): 285.1 [M+1]

Step 2

1-Ethyl-2-(4-fluorophenyl)-5-amino-1H-indole

1-Ethyl-2-(4-fluorophenyl)-5-nitro-1H-indole 5b (35 mg, 0.12 mmol) was dissolved in 10 mL of a mixture of tetrahydrofuran and methanol (V:V=1:1), and then added with Raney nickel (10 mg). The reaction mixture was stirred for 2 hours under a hydrogen atmosphere and then filtered with celatom. The filtrate was concentrated under reduced pressure to obtain the crude title compound 1-ethyl-2-(4-fluorophenyl)-5-amino-1H-indole 5d (31 mg) as yellow solid which was used in the next step without further purification.

MS m/z (ESI): 255.2 [M+1]

Step 3

2-(Difluoromethyl)-N-(1-ethyl-2-(4-fluorophenyl)-1H-indol-5-yl)-5-((2-methylpropanoylamino)methyl)nicotinamide 1-Ethyl-2-(4-fluorophenyl)-5-amino-1H-indole 5d (31 mg, 0.12 mmol) was dissolved in 5 mL acetonitrile, and then added with triethylamine (31 μL, 0.22 mmol) and 5 mL of a solution of 2-(difluoromethyl)-5-((2-methylpropanoylamino)methyl)nicotinoyl chloride 1g (32 mg, 0.11 mmol) in acetonitrile dropwise. The reaction mixture was stirred for 1 hour and then filtered. The filtrate was concentrated under reduced pressure. The residues were purified by thin layer chromatography (TLC) with elution system A to obtain the title compound 2-(difluoromethyl)-N-(1-ethyl-2-(4-fluorophenyl)-1H-indol-5-yl)-5-((2-methylpropanoylamino)methyl)nicotinamidenicotinamide 5 (35 mg, 62.5%) as a yellow solid.

MS m/z (ESI): 509.3 [M+1]

$^1$H NMR (400 MHz, DMSO-d$_6$): δ 8.70 (s, 1H), 8.07 (s, 1H), 7.94 (s, 1H), 7.63-7.54 (m, 2H), 7.46-7.51 (d, 2H), 7.44-7.39 (d, 2H), 7.32-7.25 (m, 2H), 7.12 (t, 1H), 6.51 (s, 1H), 5.36 (t, 1H), 4.53 (s, 2H), 4.30-4.21 (m, 2H), 1.27 (t, 3H), 1.20-1.14 (d, 6H).

Example 6

2-Bromo-N-(1-ethyl-3-(4-fluorophenyl)-1Hindol-5-yl)5-((2,2-dimethylpropanoylamino)methyl)-benzamide

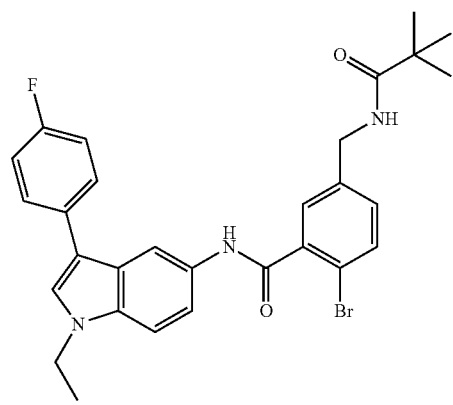

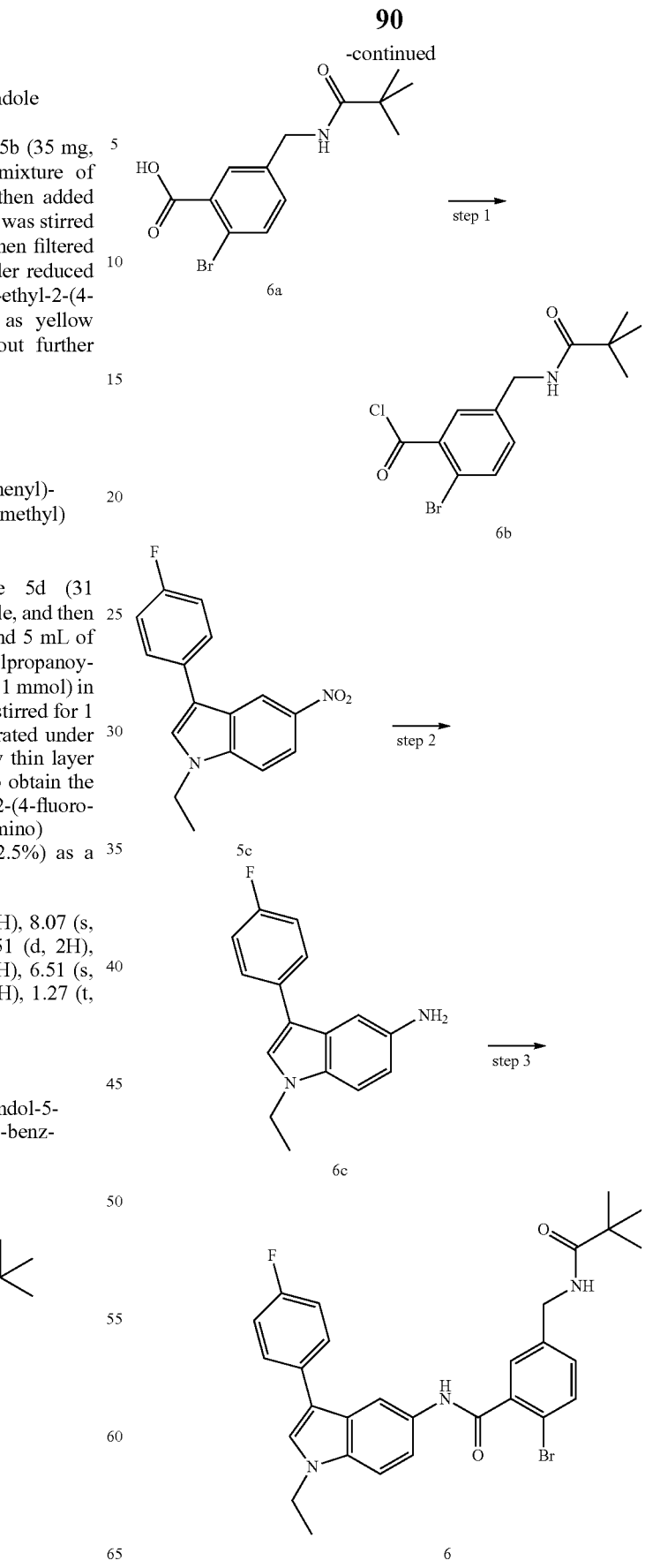

Step 1

2-Bromo-5-((2,2-dimethylpropanoylamino)methyl)benzoyl chloride

2-Bromo-5-((2,2-dimethylpropanoylamino)methyl)benzoic acid 6a (500 mg, 1.59 mmol, prepared according to the method disclosed in patent application publication "US20120157506") was dissolved in 10 mL dichloromethane, and then added with thionyl chloride (0.4 mL, 4.78 mmol) and one drop of N,N-dimethylformamide. The reaction mixture was stirred for 2 hours, and then concentrated under reduced pressure to obtain the crude title compound 2-bromo-5-((2,2-dimethylpropanoylamino)-methyl)benzoyl chloride 6b (530 mg) as a light yellow solid which was used in the next step without further purification.

MS m/z (ESI): 331.1 [M−1]

Step 2

1-Ethyl-3-(4-fluorophenyl)-5-amino-1H-indole

1-Ethyl-3-(4-fluorophenyl)-5-nitro-1H-indole 5c (110 mg, 0.39 mmol) was dissolved in 10 mL of a mixture of tetrahydrofuran and methanol (V:V=1:1), and added with Raney nickel (20 mg). The reaction mixture was stirred for 2 hours under a hydrogen atmosphere and then filtered with celatom. The filtrate was concentrated under reduced pressure to obtain the crude title compound 1-ethyl-3-(4-fluorophenyl)-5-amino-1H-indole 6c (100 mg) as a gray solid which was used in the next step without further purification.

MS m/z (ESI): 255.2 [M+1]

Step 3

2-Bromo-N-(1-ethyl-3-(4-fluorophenyl)-1H-indol-5-yl)-5-((2,2-dimethylpropanoylamino)methyl)-benzamide 1-Ethyl-3-(4-fluorophenyl)-5-amino-1H-indole 6c (100 mg, 0.39 mmol) was dissolved in 5 mL tetrahydrofuran, and added with triethylamine (63 μL, 0.45 mmol) and 5 mL of a solution of 2-bromo-5-((2,2-dimethylpropanoylamino) methyl)benzoyl chloride 6b (50 mg, 0.15 mmol) in tetrahydrofuran dropwise. The reaction was stirred for 16 hours and then filtered. The filtrate was concentrated under reduced pressure. The residues were purified by thin layer chromatography (TLC) with elution system A to obtain the title compound 2-bromo-N-(1-ethyl-3-(4-fluorophenyl)-1H-indol-5-yl)-5-((2,2-dimethylpropanoylamino)methyl)-benzamide 6 (15 mg, 18.2%) as a yellow solid.

MS m/z (ESI): 551.3 [M+1]

$^1$H NMR (400 MHz, DMSO-d$_6$): δ 8.17 (s, 1H), 7.99 (s, 1H), 7.66-7.56 (m, 4H), 7.55-7.50 (m, 3H), 7.43-7.37 (m, 1H), 7.25-7.19 (m, 1H), 7.15 (t, 1H), 6.28 (s, 1H), 4.46-4.36 (d, 2H), 4.30-4.20 (m, 2H), 1.55 (t, 3H), 1.25 (s, 9H).

Example 7

2-Bromo-N-(1-ethyl-2-(4-fluorophenyl)-1H-indol-5-yl)5-((2,2-dimethylpropanoylamino)methyl)-benzamide

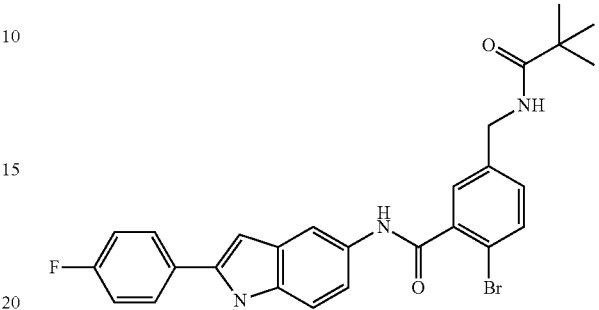

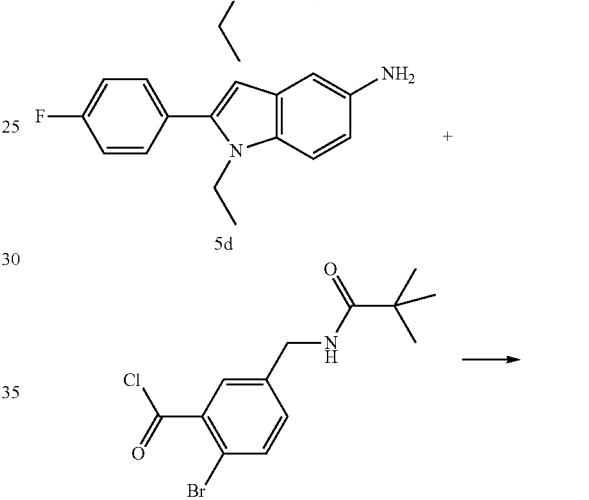

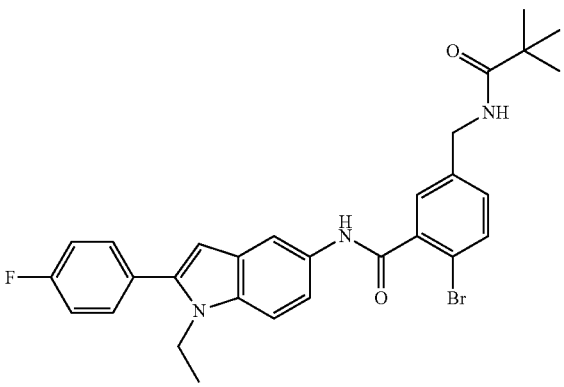

1-Ethyl-2-(4-fluorophenyl)-5-amino-1H-indole 5d (30 mg, 0.12 mmol) was dissolved in 5 mL tetrahydrofuran, and then added with triethylamine (63 μL, 0.45 mmol) and 5 mL of a solution of 2-bromo-5-((2,2-dimethylpropanoylamino) methyl)benzoyl chloride 6b (50 mg, 0.15 mmol) in tetrahydrofuran dropwise. The reaction mixture was stirred for 16 hours and then filtered. The filtrate was concentrated under reduced pressure. The residues were purified by thin layer chromatography (TLC) with elution system A to obtain the title compound 2-bromo-N-(1-ethyl-2-(4-fluorophenyl)-1H- indol-5-yl) 5-((2,2-dimethylpropanoylamino)methyl)-benzamide 7 (5 mg, 10.4%) as a yellow solid.

MS m/z (ESI): 551.3 [M+1]

$^1$H NMR (400 MHz, DMSO-d$_6$): δ 8.00 (s, 1H), 7.90 (s, 1H), 7.65-7.56 (m, 2H), 7.54-7.48 (m, 2H), 7.47-7.38 (m, 2H), 7.28-7.17 (m, 3H), 6.52 (s, 1H), 6.22 (s, 1H), 4.50-4.40 (d, 2H), 4.25-4.16 (m, 2H), 1.33 (t, 3H), 1.27 (s, 9H).

Example 8

2-Chloro-N-(1-ethyl-2-(4-fluorophenyl)-1H-indol-5-yl)5-((2,2-dimethylpropanoylamino)methyl)-benzamide

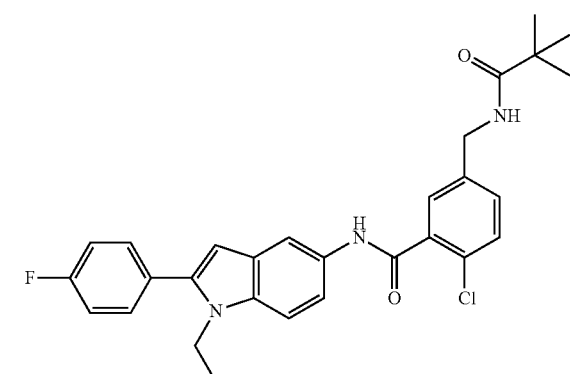

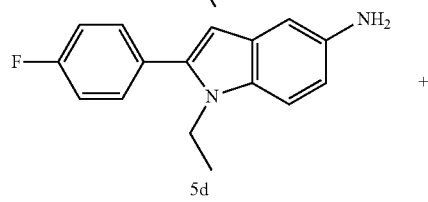

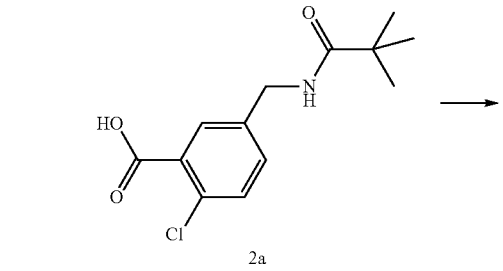

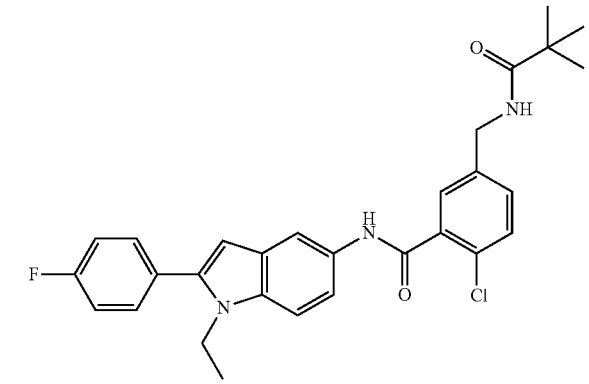

1-Ethyl-2-(4-fluorophenyl)-5-amino-1H-indole 5d (38 mg, 0.15 mmol), 2-chloro-5-((2,2-dimethylpropanoylamino)methyl)benzoic acid 2a (40 mg, 0.15 mmol), 1-ethyl-(3-dimethylaminopropyl)-carbodiimide hydrochloride (57 mg, 0.3 mmol), 1-hydroxybenzotriazole (2 mg, 0.015 mmol) and N,N-diisopropylethylamine (38 mg, 0.3 mmol) were dissolved in 5 mL of N,N-dimethylformamide. The reaction mixture was stirred for 16 hours and then filtered. The filtrate was concentrated under reduced pressure. The residues were purified by thin layer chromatography (TLC) with elution system A to obtain the title compound 2-chloro-N-(1-ethyl-2-(4-fluorophenyl)-1H-indol-5-yl) 5-((2,2-dimethylpropanoylamino)methyl)-benzamide 8 (5 mg, 6.7%) as a yellow solid.

MS m/z (ESI): 506.0 [M+1]

$^1$H NMR (400 MHz, DMSO-d$_6$): δ 10.64 (s, 1H), 8.12 (s, 1H), 8.09 (s, 1H), 7.95-7.90 (d, 2H), 7.82-7.77 (d, 2H), 7.57-7.47 (d, 2H), 7.48-7.45 (m, 2H), 7.30-7.22 (m, 1H), 6.72 (s, 1H), 4.40-4.36 (d, 2H), 4.33-4.29 (m, 2H), 1.21 (t, 3H), 1.12 (s, 9H)

Example 9

2-(Difluoromethyl)-N-(1-methyl-2-(4-(trifluoromethyl)phenyl)-1Hindol-5-yl)5-((2-methylpropanoylamino)methyl)-nicotinamide

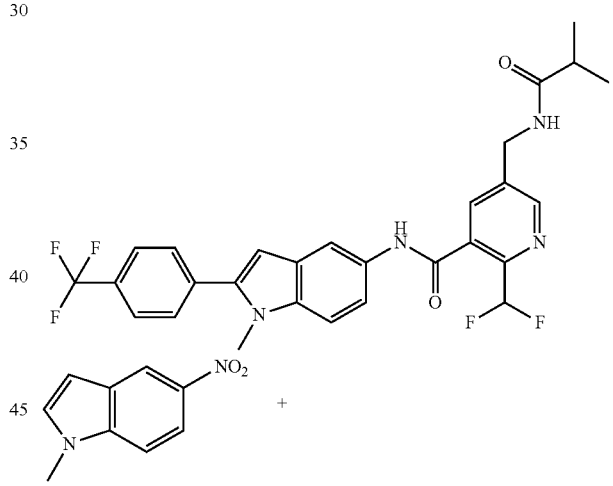

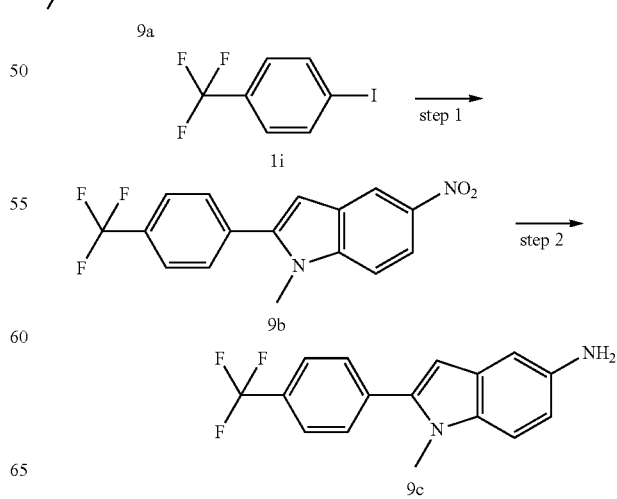

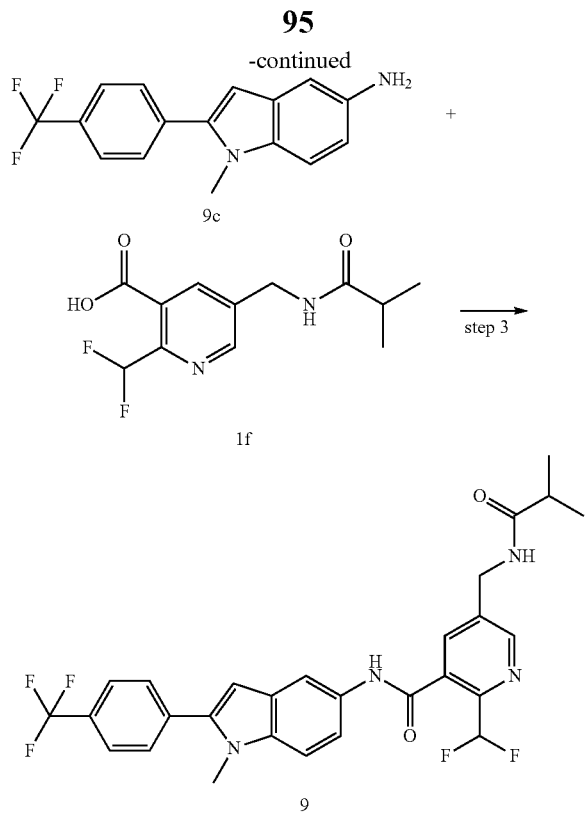

amino-2-(4-(trifluoromethyl)phenyl)-1H-indole 9c (300 mg) as a brown oil which was use in the next step without further purification.

MS m/z (ESI): 291.2 [M+1]

Step 3

2-(difluoromethyl)-N-(1-methyl-2-(4-(trifluoromethyl)phenyl)-1H-indol-5-yl)5-((2-methylpropanoylamino)methyl)-nicotinamide 1-Methyl-5-amino-2-(4-(trifluoromethyl)phenyl)-1H-indole 9c (150 mg, 0.52 mmol), 2-(difluoromethyl)-5-((2-methylpropanoylamino)methyl)nicotinic acid 1f (141 mg, 0.52 mmol), O-benzotriazol-1-yl)-N,N,N',N'-tetramethyluronium (250 mg, 0.78 mmol) and N,N-diisopropylethylamine (100 mg, 0.78 mmol) were dissolved in 5 mL N,N-dimethylformamide. The reaction mixture was heated to 75° C. and then stirred for 16 hours. The reaction mixture was concentrated under reduced pressure. The residues were purified by thin layer chromatography (TLC) with elution system A to obtain the title compound 2-(difluoromethyl)-N-(1-methyl-2-(4-(trifluoromethyl)phenyl)-1Hindol-5-yl)5-((2-methylpropanoylamino)methyl)-nicotinamidenicotinamide 9 (10 mg, 2.0%) as a brown solid.

MS m/z (ESI): 545.2 [M+1]
$^1$H NMR (400 MHz, DMSO-$d_6$): δ 10.64 (s, 1H), 8.68 (s, 1H), 8.50-8.47 (m, 1H), 8.09 (s, 1H), 8.03 (s, 1H), 7.90-7.85 (m, 4H), 7.56-7.54 (m, 1H), 7.48-7.45 (m, 1H), 7.28-7.20 (m, 1H), 6.75 (s, 1H), 4.44-4.42 (d, 2H), 3.80 (s, 3H), 2.47-2.46 (m, 1H), 1.07-1.05 (d, 6H)

Example 10

2-(Difluoromethyl)-N-(1-ethyl-2-(4-chlorophenyl)-1H-indol-5-yl)-5-((2-methylpropanoylamino)methyl)nicotinamide

Step 1

1-Methyl-5-nitro-2-(4-(trifluoromethyl)phenyl)-1H-indole 9b

1-Methyl-5-nitro-1H-indole 9a (1.0 g, 5.7 mmol) was dissolved in 40 mL N,N-dimethylacetamide, and added with 4-iodotrifluorobenzene 1i (1.7 g, 6.2 mmol), triphenylphosphine (300 mg, 1.4 mmol), palladium acetate (130 mg, 0.57 mmol), and cesium acetate (2.2 g, 1.4 mmol), successively. The reaction mixture was heated to 140° C., and stirred for 18 hours under an argon atmosphere. The reaction mixture was concentrated under reduced pressure. The residues were added with 50 mL ethyl acetate, washed with water (20 mL×2), dried over anhydrous sodium sulfate, and then filtered. The filtrate was concentrated under reduced pressure. The residues were purified by silica gel column chromatography with elution system B to obtain the title compound 1-methyl-5-nitro-2-(4-(trifluoromethyl)phenyl)-1H-indole 9b (350 mg, 19.4%) as a yellow solid.

MS m/z (ESI): 321.1 [M+1]

Step 2

1-Methyl-5-amino-2-(4-(trifluoromethyl)phenyl)-1H-indole

1-Methyl-5-nitro-2-(4-(trifluoromethyl)phenyl)-1H-indole 9b (350 mg, 1.1 mmol) was dissolved in 10 mL tetrahydrofuran, and then added with Raney nickel (35 mg). The reaction mixture was stirred for 2 hours under a hydrogen atmosphere. The reaction mixture was filtered with celatom, and the filtrate was concentrated under reduced pressure to obtain the crude title compound 1-methyl-5-

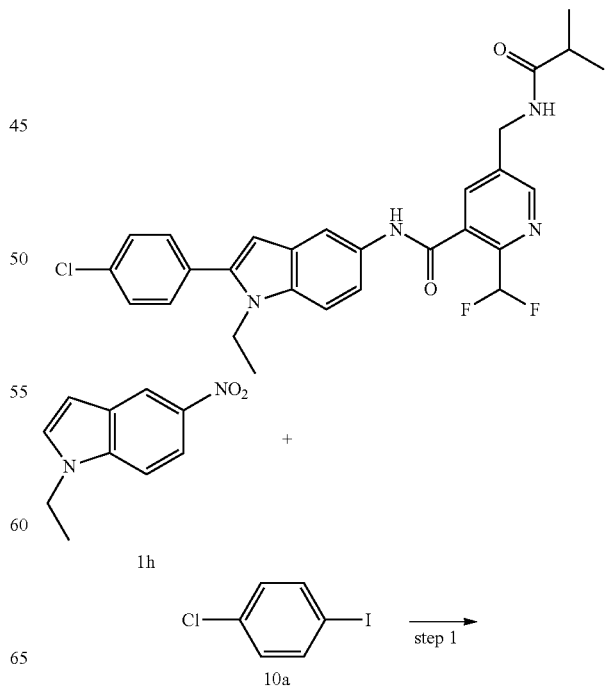

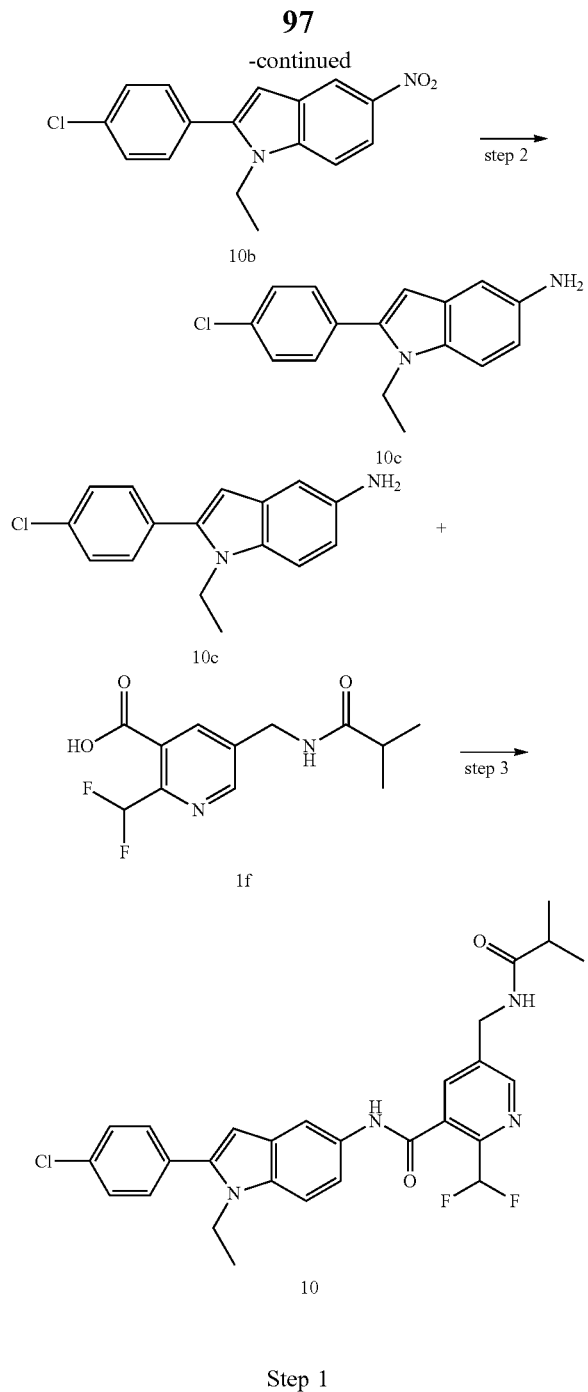

title compound 1-ethyl-2-(4-chlorophenyl)-5-nitro-1H-indole 10b (80 mg, 12.7%) as a yellow solid.

Step 2

1-Ethyl-2-(4-chlorophenyl)-5-amino-1H-indole

1-Ethyl-2-(4-chlorophenyl)-5-nitro-1H-indole 10b (80 mg, 0.27 mmol) was dissolved in 20 mL of a mixture of tetrahydrofuran and methanol (V:V=1:1), and then added with Raney nickel (10 mg). The reaction mixture was stirred for 2 hours under a hydrogen atmosphere was and then filtered with celatom. The filtrate was concentrated under reduced pressure to obtain the crude title compound 1-ethyl-2-(4-chlorophenyl)-5-amino-1H-indole 10c (72 mg) as a gray solid which was used in the next step without further purification.

MS m/z (ESI): 271.1 [M+1]

Step 3

2-(Difluoromethyl)-N-(1-ethyl-2-(4-chlorophenyl)-1H-indol-5-yl)-5-((2-methylpropanoylamino)methyl)nicotinamide 1-Ethyl-2-(4-chlorophenyl)-5-amino-1H-indole 10c (50 mg, 0.18 mmol), 2-(difluoromethyl)-5-((2-methylpropanoylamino)methyl)nicotinic acid 1f (55 mg, 0.18 mmol), 1-ethyl-(3-dimethylaminopropyl) carbodiimide hydrochloride (70 mg, 0.37 mmol) and 1-hydroxybenzotriazole (25 mg, 0.18 mmol) were dissolved in 3 mL N, N-dimethylformamide, successively. The reaction mixture was heated to 40° C., and then stirred for 5 hours. The reaction mixture was concentrated under reduced pressure, and the residues were purified by thin layer chromatography (TLC) with elution system A to obtain the title compound 2-(difluoromethyl)-N-(1-ethyl-2-(4-chlorophenyl)-1H-indol-5-yl)-5-((2-methylpropanoylamino)methyl)nicotinamidenicotinamide 10 (20 mg, 27.8%) as a yellow solid.

MS m/z (ESI): 525.2 [M+1]

$^1$H NMR (400 MHz, DMSO-$d_6$): δ 10.57 (s, 1H), 8.65 (s, 1H), 8.44 (t, 1H), 8.02 (s, 1H), 7.89 (s, 1H), 7.59 (s, 2H), 7.52 (d, 1H), 7.41 (d, 1H), 7.39 (s, 1H), 6.57 (s, 1H), 4.42 (d, 2H), 4.21 (d, 2H), 3.89 (s, 1H), 1.25 (d, 3H), 1.22 (t, 2H), 1.03 (d, 6H).

Example 11

2-Chloro-N-(2(4-fluorophenyl)-1-methyl-1H-indol-5-yl)-5-((2,2-dimethylpropanoylamino)methyl)benzamide

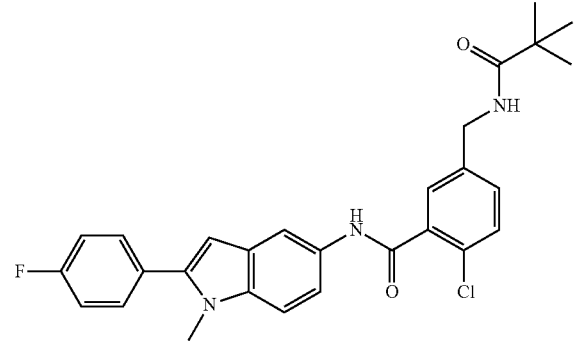

Step 1

1-Ethyl-2-(4-chlorophenyl)-5-nitro-1H-indole

1-Ethyl-5-nitro-1H-indole 1h (439 mg, 2.3 mmol) was dissolved in 5 mL N,N-dimethylacetamide, and added with 1-chloro-4-iodo-benzene 10a (500 mg, 2.1 mmol), triphenylphosphine (110 mg, 0.42 mmol), palladium acetate (24 mg, 0.11 mmol), and cesium acetate (806 mg, 4.2 mmol), successively. The reaction mixture was heated to 140° C. and then stirred for 18 hours under an argon atmosphere. The reaction mixture was filtered. The filtrate was added with 150 mL ethyl acetate, and then washed with water (20 mL×1). The organic phase was dried over anhydrous sodium sulfate, filtered, and the filtrate was concentrated under reduced pressure. The residues were purified by silica gel column chromatography with elution system C to obtain the

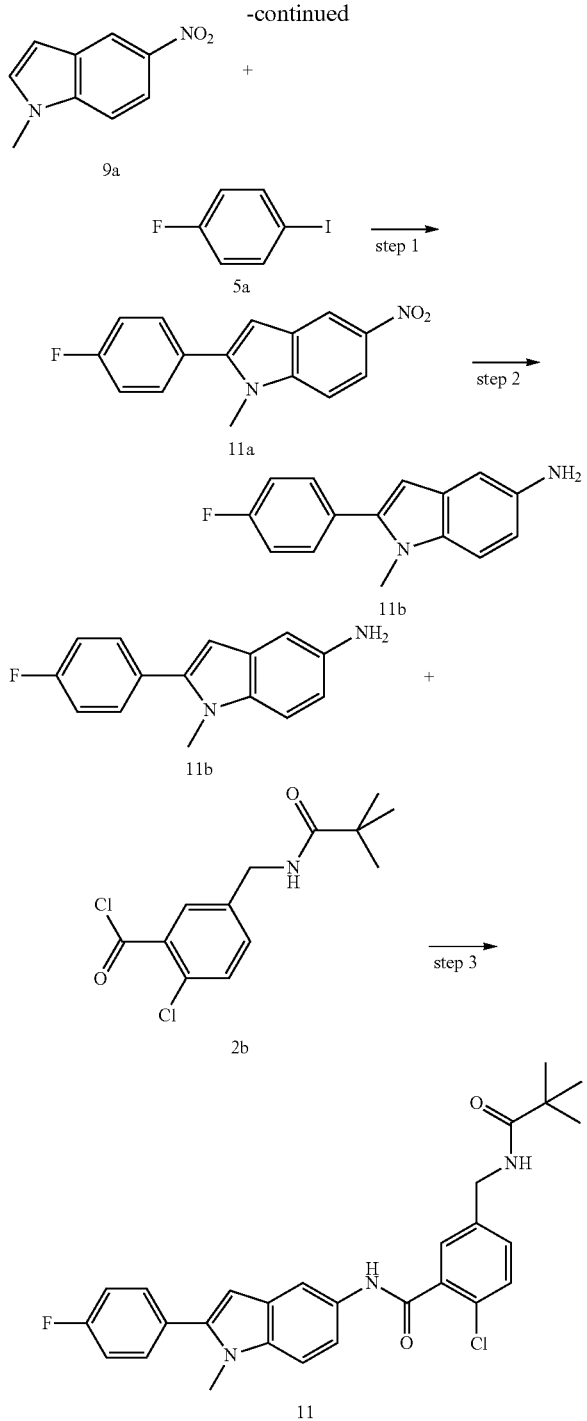

added with 50 mL water, and extracted with ethyl acetate (50 mL). The organic phase was dried over anhydrous sodium sulfate, filtered, and the filtrate was concentrated under reduced pressure. The residues were purified by silica gel column chromatography with elution system C to obtain the title compound 2-(4-fluorophenyl)-1-methyl-5-nitro-1H-indole 11a (130 mg, 10.7%) as a yellow solid.

MS m/z (ESI): 271.1 [M+1]

Step 2

2-(4-Fluorophenyl)-1-methyl-5-amino-1H-indole 2-(4-Fluorophenyl)-1-methyl-5-nitro-1H-indole 11a (130 mg, 0.48 mmol) was dissolved in 16 mL of a mixture of tetrahydrofuran and methanol (V:V=1:1), and then added with Raney nickel (15 mg). The reaction mixture was stirred for 2 hours under a hydrogen atmosphere and then filtered with celatom. The filtrate was concentrated under reduced pressure to obtain the crude title compound 2-(4-fluorophenyl)-1-methyl-5-amino-1H-indole 11b (130 mg) as a yellow solid which was used in the next step without further purification.

Step 3

2-Chloro-N-(2-(4-fluorophenyl)-1-methyl-1H-indol-5-yl)5-((2,2-dimethylpropanoylamino)methyl)benzamide 2-(4-Fluorophenyl)-1-methyl-5-amino-1H-indole 11b (70 mg 0.29 mmol) was dissolved in 20 mL tetrahydrofuran, and then added with triethylamine (85 µL, 0.60 mmol) and 5 mL of a solution of 2-chloro-5-((2,2-dimethylpropanoylamino)methyl)benzoyl chloride 2b (83 mg, 0.29 mmol) in tetrahydrofuran dropwise. The reaction mixture was stirred for 2 hours and then filtered. The filtrate was concentrated under reduced pressure, and the residues were purified by thin layer chromatography (TLC) with elution system A to obtain the title compound 2-chloro-N-(2-(4-fluorophenyl)-1-methyl-1H-indol-5-yl)-5-((2,2-dimethylpropanoylamino)methyl)benzamide 11 (40 mg, 28.0%) as a yellow solid.

MS m/z (ESI): 492.2 [M+1]

$^1$H NMR (400 MHz, DMSO-$d_6$): δ 8.01 (s, 1H), 7.91 (s, 1H), 7.65-7.56 (m, 2H), 7.54-7.49 (m, 2H), 7.48-7.38 (m, 2H), 7.28-7.17 (m, 3H), 6.52 (s, 1H), 6.22 (s, 1H), 4.25-4.16 (m, 2H), 3.83 (t, 3H), 1.27 (s, 9H).

Example 12

2-(Difluoromethyl)-N-(1-ethyl-1H-indol-5-yl)-5-((2-methylpropanoylamino)methyl)nicotinamide

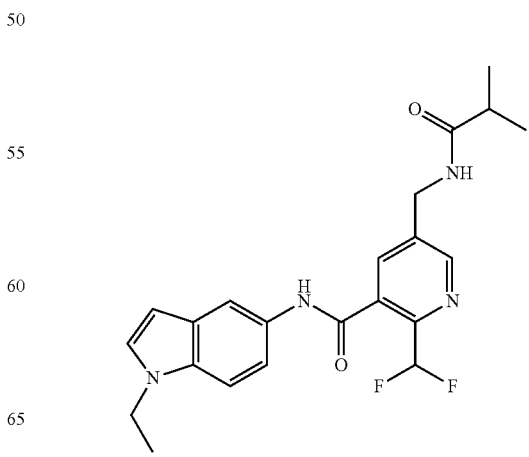

101

-continued

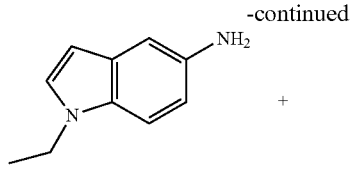

12a

+

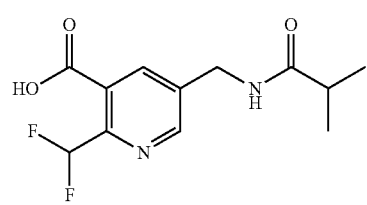

1f

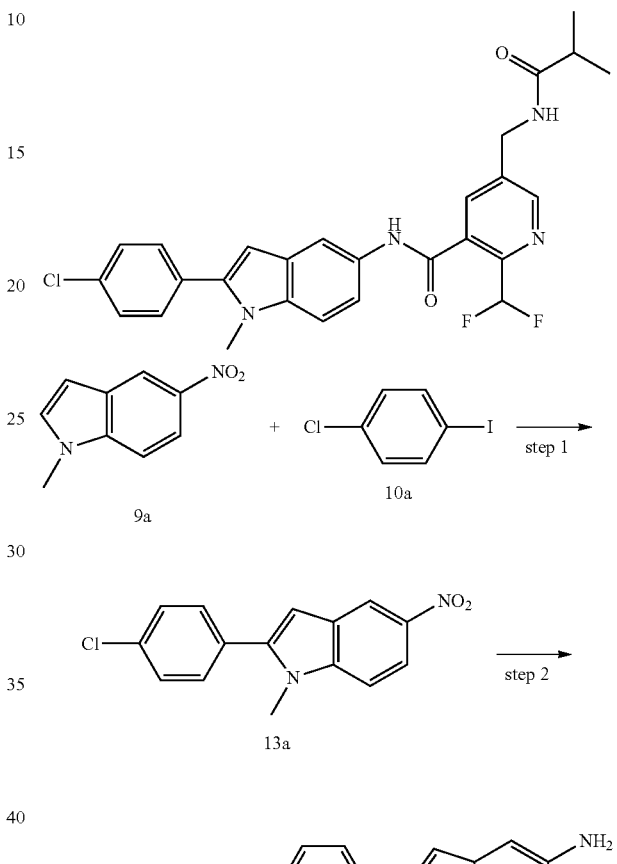

30

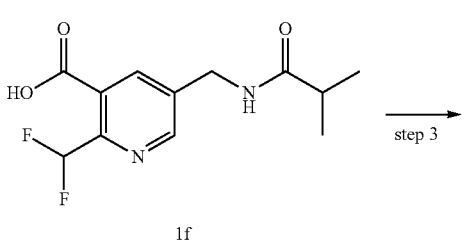

12

1-Ethyl-1H-indol-5-amine 12a (50 mg, 0.31 mmol, prepared according to "*Bioorganic & Medicinal Chemistry*, 2005, 13(10), 3531-3541"), 2-(difluoromethyl)-5-((2-methylpropanoylamino)methyl)nicotinic acid 1f (70 mg, 0.26 mmol), O-benzotriazol-1-yl)-N,N,N',N'-tetramethyluronium tetrafluoroborate (124 mg, 0.39 mmol), and N,N-diisopropylethylamine (100 mg, 0.78 mmol) were dissolved in 5 mL N,N-dimethylformamide, successively. The reaction mixture was heated to 75° C. and then stirred for 16 hours. The reaction mixture was concentrated under reduced pressure, and the residues were purified by thin layer chromatography (TLC) with elution system A to obtain the title compound 2-(difluoromethyl)-N-(1-ethyl-1H-indol-5-yl)-5-((2-methylpropanoylamino)methyl)nicotinamide 12 (20 mg, 18.9%) as a brown solid.

MS m/z (ESI): 415.1[(M+1])

$^1$H NMR (400 MHz, DMSO-d$_6$): δ 10.53 (s, 1H), 8.67 (s, 1H), 8.46 (t, 1H), 7.99 (s, 2H), 7.50-7.44 (d, 1H), 7.42-7.34 (m, 2H), 7.18 (t, 1H), 6.46-6.40 (d, 1H), 4.47-4.39 (d, 2H), 4.25-4.15 (m, 2H), 2.49-2.41 (m, 1H), 1.36 (t, 3H), 1.10-1.01 (d, 6H).

102

Example 13

N-(2-(4-Chlorophenyl)-1-methyl-1H-indol-5-yl-2-(difluoromethyl)-5-((2-methylpropanoylamino)methyl)nicotinamide

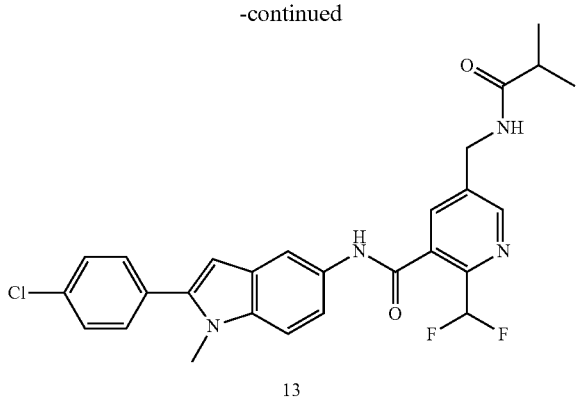

13

Step 1

2-(4-Chlorophenyl)-1-methyl-5-nitro-1H-indole

1-Methyl-5-nitro-1H-indole 9a (3.30 g, 18.7 mmol) was dissolved in 20 mL N,N-dimethylacetamide, and then added with 1-chloro-4-iodo-benzene 10a (4.96 g, 20.8 mmol), triphenylphosphine (982 mg, 3.75 mmol), palladium acetate (210 mg, 0.94 mmol), and cesium acetate (7.20 g, 3.75 mmol), successively. The reaction mixture was heated to 140° C., and then stirred for 18 hours under an argon atmosphere. The reaction solution was cooled to room temperature and then added with 50 mL water, and extracted with ethyl acetate (50 mL). The organic phase was washed with saturated sodium chloride solution (50 mL), dried over anhydrous sodium sulfate, and filtered. The filtrate was concentrated under reduced pressure, and the residues were purified by silica gel column chromatography with elution system C to obtain the title compound 2-(4-chlorophenyl)-1-methyl-5-nitro-1H-indole 13a (270 mg, 5.0%) as a yellow solid.

Step 2

2-(4-Chlorophenyl)-1-methyl-5-amino-1H-indole 2-(4-Chlorophenyl)-1-methyl-5-nitro-1H-indole 13a (80 mg, 0.28 mmol) was dissolved in 20 mL of a mixture of tetrahydrofuran and methanol (V:V=1:1), and then added with Raney nickel (8 mg). The reaction mixture was stirred for 1 hour under a hydrogen atmosphere. The reaction mixture was filtered with celatom, and the filtrate was concentrated under reduced pressure to obtain the crude title compound 2-(4-chlorophenyl)-1-methyl-5-amino-1H-indole 13b (72 mg) as an off-white solid which was used in the next step without further purification.

Step 3

N-(2-(4-chlorophenyl)-1-methyl-1H-indol-5-yl)-2-(difluoromethyl)-5-((2-methylpropanoylamino)methyl)nicotinamide 2-(4-Chlorophenyl)-1-methyl-5-amino-1H-indole 13b (72 mg, 0.28 mmol), 2-(difluoromethyl)-5-((2-methylpropanoylamino)methyl)nicotinic acid 1f (77 mg, 0.28 mmol), 1-ethyl-(3-dimethylaminopropyl)-3-ethylcarbodiimide hydrochloride (81 mg, 0.42 mmol) and 1-hydroxybenzotriazole (38 mg, 0.28 mmol) were dissolved in 5 mL N,N-dimethylformamide, successively. The reaction mixture was heated to 40° C. and then stirred for 2 hours. The reaction mixture was concentrated under reduced pressure, and the residues were purified by thin layer chromatography (TLC) with elution system A to obtain a solid. The solid was added with 20 mL dichloromethane, and stirred for 20 minutes to obtain the title compound N-(2-(4-chlorophenyl)-1-methyl-1H-indol-5-yl)-2-(difluoromethyl)-5-((2-methylpropanoylamino)methyl)nicotinamide 13 (20 mg, 14.0%) as a yellow solid.

MS m/z (ESI): 511.2 [M+1]

$^1$H NMR (400 MHz, DMSO-d$_6$): δ 10.59 (s, 1H), 8.68 (s, 1H), 8.45 (s, 1H), 8.04 (d, 2H), 7.62 (dd, 4H), 7.47 (dd, 2H), 7.20 (t, 1H), 6.64 (s, 1H), 4.43 (d, 2H), 3.76 (s, 3H), 2.46 (m, 1H), 1.06 (d, 6H).

Example 14

N-(2-(4-Chlorophenyl)-1-methyl-1H-indol-5-yl)-2-(difluoromethyl)-5-(((2-fluoro-2-methyl-propanoyl)amino)methyl)nicotinamide

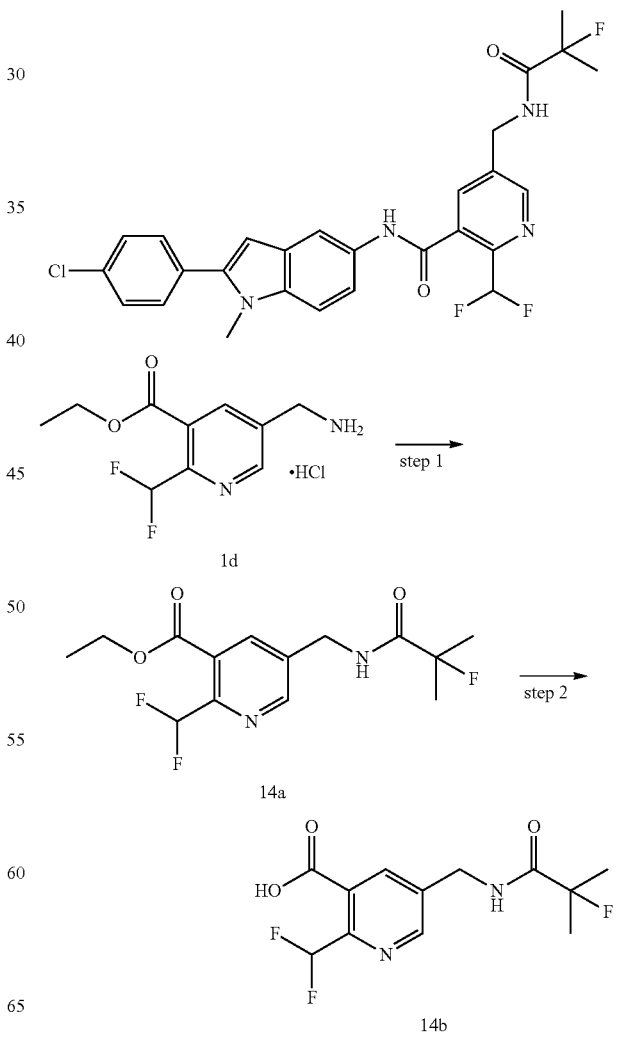

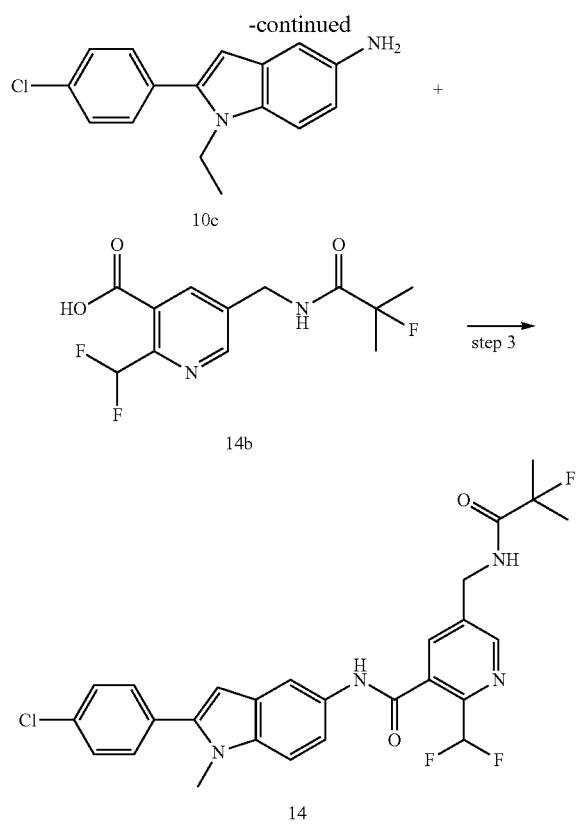

Step 1

Ethyl 2-(difluoromethyl)-5-(((2-fluoro-2-methyl-propanoyl)amino)methyl)nicotinate Ethyl 5-(aminomethyl)-2-(difluoromethyl)nicotinate hydrochloride 1d (2.18 g, 8.20 mmol) was dissolved in 20 mL of N,N-dimethylformamide, and then added with 2-fluoroisobutyric acid (1.04 g, 9.83 mmol), 1-(3-dimethylaminopropyl)-3-ethylcarbodiimide hydrochloride (2.36 g, 12.30 mmol), 1-hydroxybenzotriazole (1.66 g, 12.30 mmol) and triethylamine (7 mL, 49.2 mmol), successively. The reaction mixture was stirred for 16 hours and then added with 100 mL ethyl acetate and 50 mL water. The organic phase was concentrated under reduced pressure. The residues were purified via TLC with elution system A to obtain the title compound ethyl 2-(difluoromethyl)-5-(((2-fluoro-2-methyl-propanoyl)amino)methyl)nicotinate 14a (1.6 g, 61.3%) as a yellow solid.

MS m/z (ESI): 319.1[M+1]

Step 2

2-(Difluoromethyl)-5-(((2-fluoro-2-methyl-propanoyl)amino)methyl)nicotinic acid Ethyl 2-(difluoromethyl)-5-(((2-fluoro-2-methyl-propanoyl)amino)methyl)nicotinate 14a (1.6 g, 5.03 mmol) was dissolved in 50 mL 1,4-dioxane, and then added with 25 mL water and lithium hydroxide hydrate (529 mg, 12.6 mmol). The reaction mixture was stirred for 16 hours. The reaction mixture was concentrated under reduced pressure. The residues were added with 5 mL water, and then adjusted to pH 3 by 5M hydrochloric acid. A lot of solid was precipitated from the reaction solution and then filtered out. The filtrate was extracted with ethyl acetate (50 mL×3). The organic phases were combined and concentrated under reduced pressure. The residues were combined with the filter cake above, and then washed with water to obtain the title compound 2-(difluoromethyl)-5-(((2-fluoro-2-methyl-propanoyl)amino)methyl)nicotinic acid 14b (500 mg, 34.2%) as a white solid.

MS m/z (ESI): 291.1 [M+1]

Step 3

N-(2-(4-Chlorophenyl)-1-methyl-1H-indol-5-yl)-2-(difluoromethyl)-5-(((2-fluoro-2-methyl-propanoyl)amino)methyl)nicotinamide 1-Ethyl-2-(4-chlorophenyl)-5-amino-1H-indole 10c (100 mg, 0.37 mmol), 2-(difluoromethyl)-5-(((2-fluoro-2-methyl-propanoyl)amino)methyl)nicotinic acid 14b (107 mg, 0.37 mmol), 1-ethyl-(3-dimethylaminopropyl) carbodiimide hydrochloride (142 mg, 0.74 mmol) and 1-hydroxybenzotriazole (191 mg, 1.48 mmol) was dissolved in 5 mL N,N-dimethylformamide, successively. The reaction mixture was heated to 70° C. and then stirred for 2 hours. The reaction mixture was concentrated under reduced pressure. The residues were purified by thin layer chromatography (TLC) with elution system A to obtain the title compound N-(2-(4-chlorophenyl)-1-methyl-1H-indol-5-yl)-2-(difluoromethyl)-5-(((2-fluoro-2-methyl-propanoyl)amino)methyl) nicotinamide 14 (40 ing, 19.9%) as a white solid.

MS m/z (ESI): 543.3 [M+1]

$^1$H NMR (400 MHz, DMSO-$d_6$): δ 10.60 (s, 1H), 8.87 (s, 1H), 8.69 (m, 1H), 8.04-8.02 (m, 2H), 7.60-7.58 (m, 4H), 7.54-7.53 (m, 1H), 7.43-7.42 (m, 1H), 7.19 (t, 1H), 6.59 (s, 1H), 4.48-4.46 (m, 2H), 4.24-4.19 (m, 2H), 1.54-1.48 (d, 6H), 1.26-1.15 (m, 3H).

Example 15

2-(Difluoromethyl)-5-(((2-fluoro-2-methyl-propanoyl)amino)methyl)-N-(1-methyl-2-(4-(trifluoromethyl)phenyl)-1H-indol-5-yl)nicotinamide

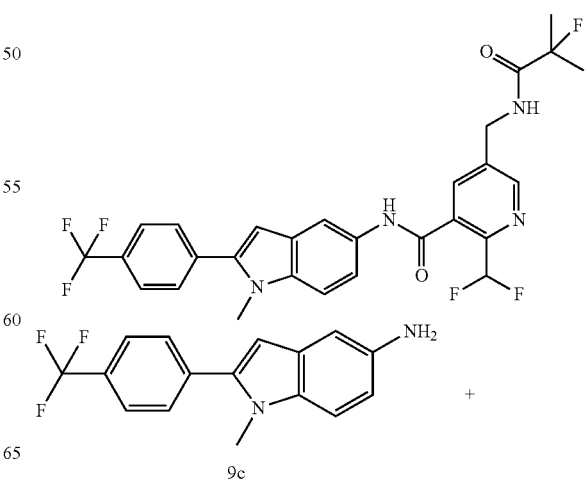

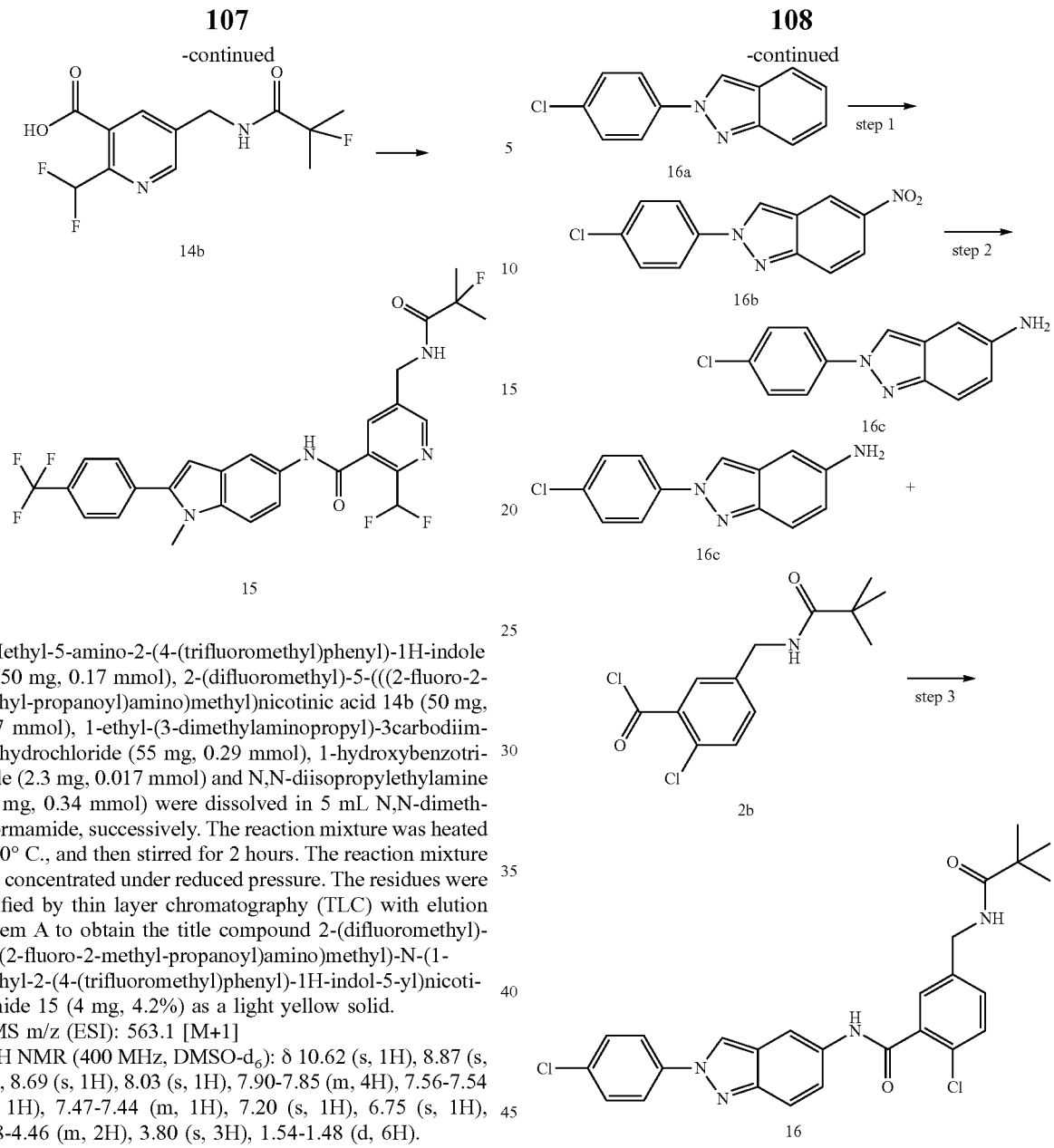

1-Methyl-5-amino-2-(4-(trifluoromethyl)phenyl)-1H-indole 9c (50 mg, 0.17 mmol), 2-(difluoromethyl)-5-(((2-fluoro-2-methyl-propanoyl)amino)methyl)nicotinic acid 14b (50 mg, 0.17 mmol), 1-ethyl-(3-dimethylaminopropyl)-3carbodiimide hydrochloride (55 mg, 0.29 mmol), 1-hydroxybenzotriazole (2.3 mg, 0.017 mmol) and N,N-diisopropylethylamine (44 mg, 0.34 mmol) were dissolved in 5 mL N,N-dimethylformamide, successively. The reaction mixture was heated to 70° C., and then stirred for 2 hours. The reaction mixture was concentrated under reduced pressure. The residues were purified by thin layer chromatography (TLC) with elution system A to obtain the title compound 2-(difluoromethyl)-5-(((2-fluoro-2-methyl-propanoyl)amino)methyl)-N-(1-methyl-2-(4-(trifluoromethyl)phenyl)-1H-indol-5-yl)nicotinamide 15 (4 mg, 4.2%) as a light yellow solid.

MS m/z (ESI): 563.1 [M+1]

$^1$H NMR (400 MHz, DMSO-$d_6$): δ 10.62 (s, 1H), 8.87 (s, 1H), 8.69 (s, 1H), 8.03 (s, 1H), 7.90-7.85 (m, 4H), 7.56-7.54 (m, 1H), 7.47-7.44 (m, 1H), 7.20 (s, 1H), 6.75 (s, 1H), 4.48-4.46 (m, 2H), 3.80 (s, 3H), 1.54-1.48 (d, 6H).

Example 16

2-Chloro-N-(2-(4-chlorophenyl)indazol-5-yl)-5-((2,2-dimethylpropanoylamino)methyl)benzamide

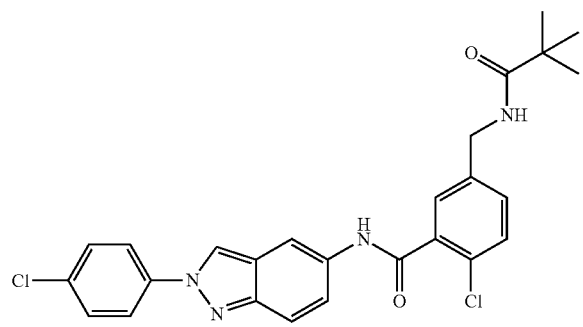

Step 1

2-(4-Chlorophenyl)-5-nitro-indazole

Sodium nitrate (1.6 g, 19.2 mmol) was added into 10 mL sulfuric acid in an ice-water bath. Then 2-(4-chlorophenyl)-2H-indazole 16a (2.2 g, 9.6 mmol) was added portion-wise. The reaction mixture was then heated to 70° C., and stirred for 1 hour. The reaction mixture was poured into 30 mL ice-water, and adjusted to pH>7 by saturated sodium bicarbonate solution. The mixture was extracted with ethyl acetate (40 mL×3). The organic phases were combined, dried over anhydrous sodium sulfate, and then filtered. The filtrate was concentrated under reduced pressure, and the residues were purified by silica gel column chromatography with elution system B to obtain the title compound 2-(4-chlorophenyl)-5-nitro-2H-indazole 16b (500 mg, 19.2%) as a yellow solid.

MS m/z (ESI): 274.0 [M+1]

Step 2

2-(4-Chlorophenyl)-5-amino-indazole 2-(4-Chlorophenyl)-5-nitro-indazole 16b (500 mg, 1.8 mmol) was dissolved in 20 mL of tetrahydrofuran, and then added with Raney nickel (50 mg). The reaction mixture was stirred for 2 hours under a hydrogen atmosphere. The reaction mixture was filtered with celatom, and the filter cake was washed with ethyl acetate (5 mL×3). The filtrate was concentrated under reduced pressure to obtain the crude title compound 2-(4-chlorophenyl)-5-amino-indazole 16c (200 mg, 45%) as a brown solid.

MS m/z (ESI): 244.1 [M+1]

Step 3

2-Chloro-N-(2-(4-chlorophenyl)-2H-indazol-5-yl)-5-((2,2-dimethylpropanoylamino)methyl)benzamide 2-(4-Chlorophenyl)-5-amino-indazole 16c (200 mg, 0.37 mmol), 2-chloro-5-((2,2-dimethylpropanoylamino)methyl)benzoyl chloride 2b (300 mg, 1.04 mmol) and N,N-diisopropylethylamine (300 mg, 2.32 mmol) were dissolved in 10 mL dichloromethane, successively. The resulting mixture was stirred for 1 hour and then concentrated under reduced pressure. The residues were purified by thin layer chromatography (TLC) with elution system A to obtain the title compound 2-chloro-N-(2-(4-chlorophenyl)-2H-indazol-5-yl)-5-((2,2-dimethylpropanoylamino)methyl)benzamide 16 (5 mg, 1.3%) as a light yellow solid.

MS m/z (ESI): 495.1 [M+1]

$^1$H NMR (400 MHz, DMSO-d$_6$): δ 10.56 (s, 1H), 9.12 (s, 1H), 8.38 (s, 1H), 8.19-8.11 (m, 3H), 7.73-7.66 (m, 3H), 7.51 (m, 1H), 7.45-7.44 (m, 2H), 7.36-7.34 (m, 1H), 4.31-4.30 (m, 2H), 1.14 (s, 9H)

Example 17

2-(Difluoromethyl)-N-(1-ethyl-2-(4-(trifluoromethyl)phenyl)-1H-indol-5-yl)-5-(((2-fluoro-2-methyl-propanoyl)amino)methyl)nicotinamide

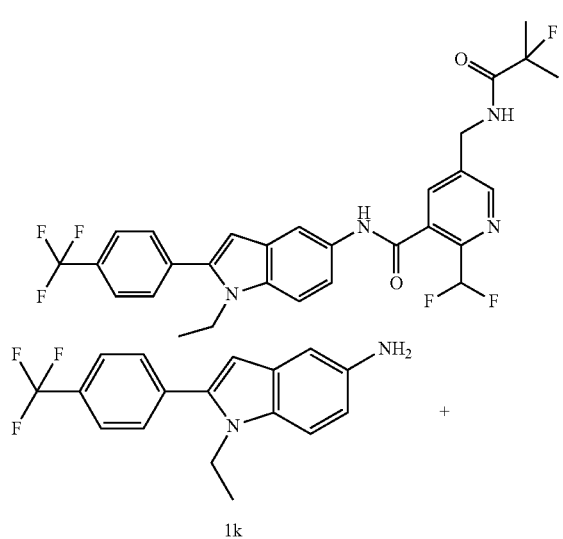

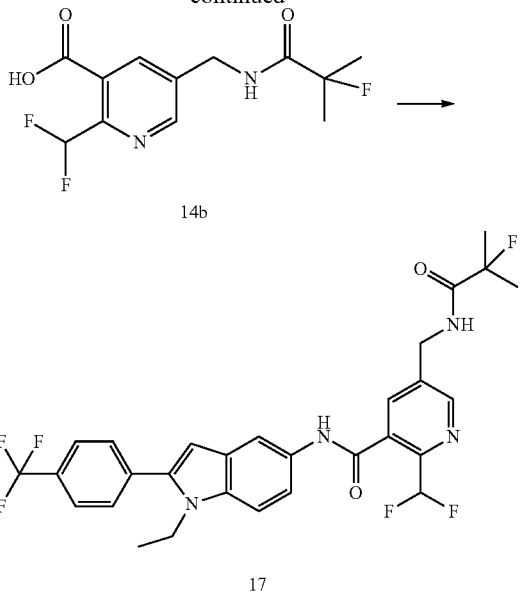

1-Ethyl-5-amino-2-(4-(trifluoromethyl)phenyl)-1H-indole 1k (105 mg, 0.34 mmol), 2-(difluoromethyl)-5-(((2-fluoro-2-methyl-propanoyl)amino)methyl)nicotinic acid 14b (100 mg, 0.34 mmol), 1-ethyl-(3-dimethylaminopropyl)carbodiimide hydrochloride (97 mg, 0.51 mmol), 1-hydroxybenzotriazole (4.6 mg, 0.034 mmol) and N,N-diisopropylethylamine (88 mg, 0.68 mmol) was dissolved in 5 mL N,N-dimethylformamide, successively. The resulting mixture was stirred for 2 hours and then concentrated under reduced pressure. The residues were purified by thin layer chromatography (TLC) with elution system A to obtain the title compound 2-(difluoromethyl)-N-(1-ethyl-2-(4-(trifluoromethyl)phenyl)-1H-indol-5-yl)-5-(((2-fluoro-2-methyl-propanoyl)amino)methyl)nicotinamide 17 (20 mg, 25.5%) as a yellow solid.

MS m/z (ESI): 577.3 [M+1]

$^1$H NMR (400 MHz, DMSO-d$_6$): δ 10.60 (s, 1H), 8.86 (s, 1H), 8.68 (s, 1H), 8.06 (s, 1H), 8.01 (s, 1H), 7.90-7.88 (m, 2H), 7.82-7.80 (m, 2H), 7.58-7.56 (m, 1H), 7.45-7.43 (m, 1H), 7.32 (t, 1H), 6.69 (s, 1H), 4.47-4.46 (m, 2H), 4.28-4.26 (m, 2H), 1.53-1.48 (d, 6H), 1.22-1.09 (m, 3H).

Example 18

N-(2-(4-Chlorophenyl)-1-methyl-1H-indol-5-yl)-2-(difluoromethyl)-5-(((2-fluoro-2-methyl-propanoyl)amino)methyl)nicotinamide

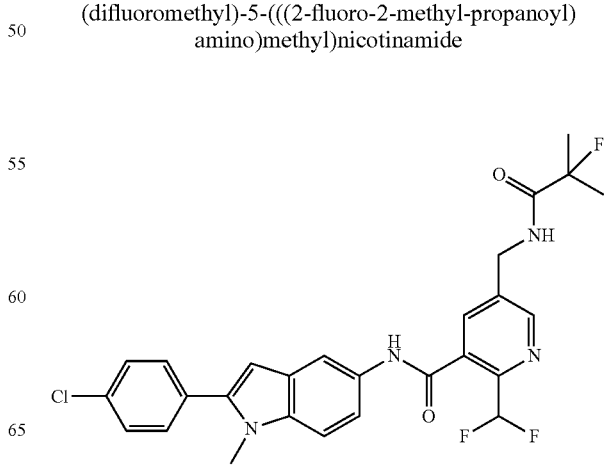

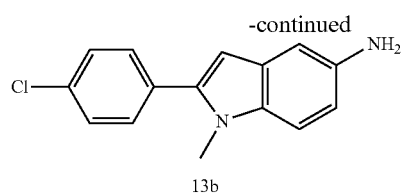
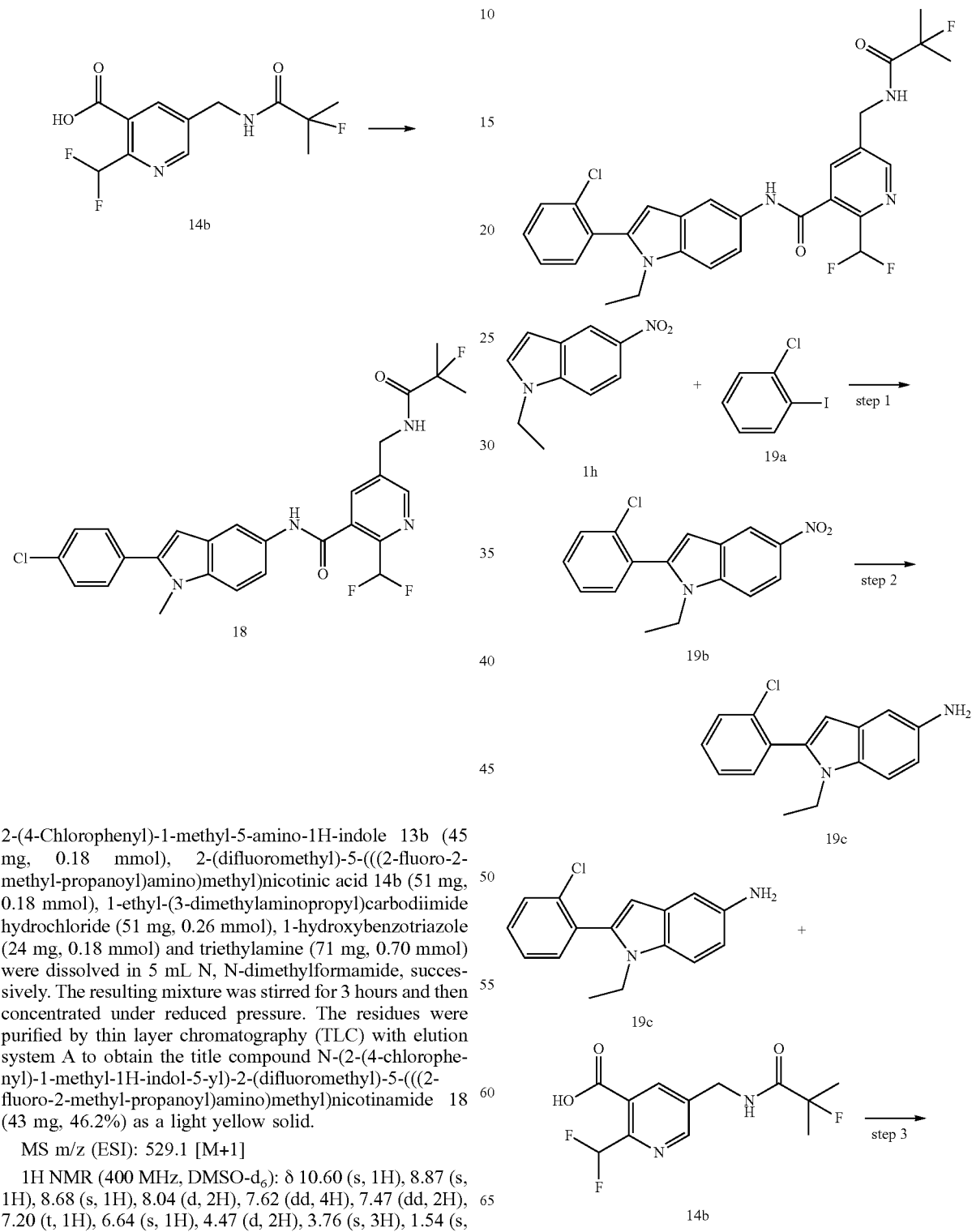

Example 19

N-(2-(2-Chlorophenyl)-1-ethyl-1H-indol-5-yl)-2-(difluoromethyl)-5-(((2-fluoro-2-methyl-propanoyl)amino)methyl)nicotinamide 2-(4-Chlorophenyl)-1-methyl-5-amino-1H-indole 13b (45 mg, 0.18 mmol), 2-(difluoromethyl)-5-(((2-fluoro-2-methyl-propanoyl)amino)methyl)nicotinic acid 14b (51 mg, 0.18 mmol), 1-ethyl-(3-dimethylaminopropyl)carbodiimide hydrochloride (51 mg, 0.26 mmol), 1-hydroxybenzotriazole (24 mg, 0.18 mmol) and triethylamine (71 mg, 0.70 mmol) were dissolved in 5 mL N, N-dimethylformamide, successively. The resulting mixture was stirred for 3 hours and then concentrated under reduced pressure. The residues were purified by thin layer chromatography (TLC) with elution system A to obtain the title compound N-(2-(4-chlorophenyl)-1-methyl-1H-indol-5-yl)-2-(difluoromethyl)-5-(((2-fluoro-2-methyl-propanoyl)amino)methyl)nicotinamide 18 (43 mg, 46.2%) as a light yellow solid.

MS m/z (ESI): 529.1 [M+1]

1H NMR (400 MHz, DMSO-$d_6$): δ 10.60 (s, 1H), 8.87 (s, 1H), 8.68 (s, 1H), 8.04 (d, 2H), 7.62 (dd, 4H), 7.47 (dd, 2H), 7.20 (t, 1H), 6.64 (s, 1H), 4.47 (d, 2H), 3.76 (s, 3H), 1.54 (s, 3H), 1.48 (s, 3H).

-continued

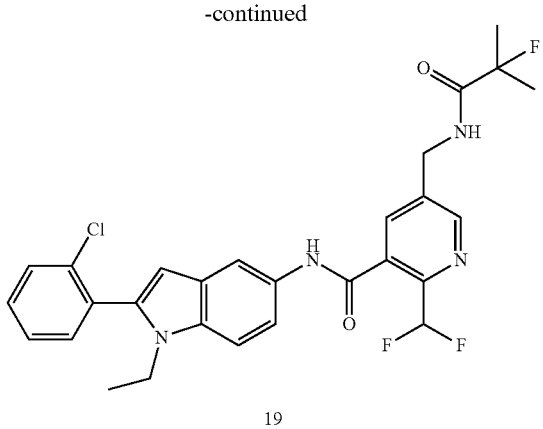

19

Step 1

2-(2-Chlorophenyl)-1-ethyl-5-nitro-1H-indole

1-Ethyl-5-nitro-1H-indole 1b (1.0 g, 5.3 mmol) was dissolved in 10 mL N,N-dimethylacetamide, and then added with 1-chloro-2-iodo-benzene 19a (1.25 g, 5.3 mmol), triphenylphosphine (300 mg, 1.1 mmol), palladium acetate (120 mg, 0.53 mmol), and cesium acetate (2.1 g, 11 mmol), successively. The reaction mixture was heated to 140° C., and then stirred for 18 hours under an argon atmosphere. The reaction mixture was concentrated under reduced pressure, and the residues were purified by thin layer chromatography (TLC) with elution system B to obtain the title compound 2-(2-chlorophenyl)-1-ethyl-5-nitro-H-indole 19b (300 mg, 18.9%) as a yellow solid.

MS m/z (ESI): 301.3 [M+1]

Step 2

2-(2-Chlorophenyl)-1-ethyl-1H-indol-5-amine 2-(2-Chlorophenyl)-1-ethyl-5-nitro-1H-indole 19b (300 mg, 1.0 mmol) was dissolved in 10 mL of a mixture of tetrahydrofuran and methanol (V:V=1:1), and then added with Raney nickel (50 mg). The reaction mixture was stirred for 2 hours under a hydrogen atmosphere. The reaction mixture was filtered with celatom. The filtrate was concentrated under reduced pressure to obtain the crude title compound 2-(2-chlorophenyl)-1-ethyl-1H-indol-5-amine 19c (270 mg) as a yellow solid which was used in the next step without further purification.

MS m/z (ESI): 271.1 [M+1]

Step 3

N-(2-(2-Chlorophenyl)-1-ethyl-1H-indol-5-yl)-2-(difluoromethyl)-5-(((2-fluoro-2-methyl-propanoyl)amino)methyl)nicotinamide 2-(2-Chlorophenyl)-1-ethyl-1H-indol-5-amine 19c (80 mg, 0.30 mmol), 2-(difluoromethyl)-5-(((2-fluoro-2-methyl-propanoyl)amino)methyl)nicotinic acid 14b (86 mg, 0.30 mmol), 1-ethyl-(3-dimethylaminopropyl)carbodiimide hydrochloride (115 mg, 0.60 mmol), 1-hydroxybenzotriazole (40 mg, 0.30 mmol) and triethylamine (118 mg, 1.17 mmol) were dissolved in 5 mL N,N-dimethylformamide, successively. The reaction mixture was heated to 40° C. and stirred for 4 hours. The reaction mixture was concentrated under reduced pressure, and the residues were purified by thin layer chromatography (TLC) with elution system C to obtain the title compound N-(2-(2-chlorophenyl)-1-ethyl-1H-indol-5-yl)-2-(difluoromethyl)-5-(((2-fluoro-2-methyl-propanoyl)amino)methyl)nicotinamide 19 (10 mg, 14.3%) as a yellow solid.

MS m/z (ESI): 543.9 [M+1]

$^1$H NMR (400 MHz, DMSO-$d_6$): δ 10.59 (s, 1H), 8.87 (s, 1H), 8.68 (s, 1H), 8.02 (d, 2H), 7.65 (d, 1H), 7.52-7.49 (m, 3H), 7.42 (d, 1H), 6.48 (s, 1H), 4.46 (d, 2H), 3.99-3.97 (m, 2H), 2.88 (s, 1H), 2.73 (s, 1H), 1.53 (s, 3H), 1.46 (s, 3H), 1.09 (t, 3H)

Example 20

N-(2-(3-Chlorophenyl)-1-ethyl-1H-indol-5-yl)-2-(difluoromethyl)-5-(((2-fluoro-2-methyl-propanoyl)amino)methyl)nicotinamide

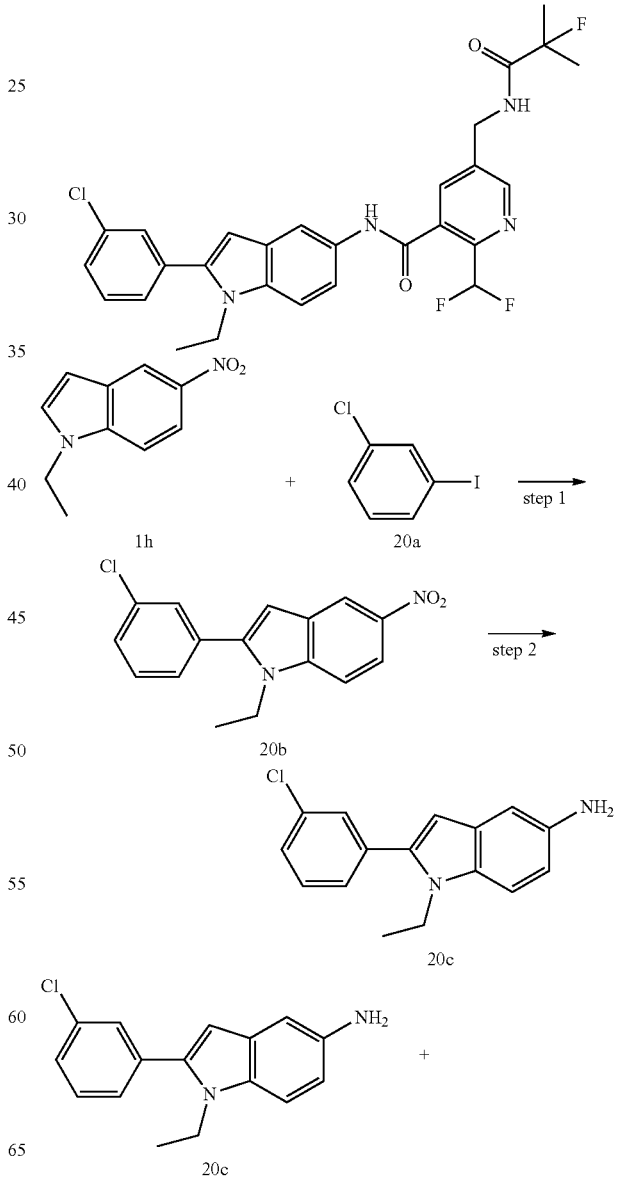

115

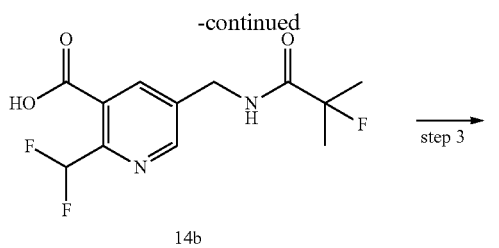

14b

-continued step 3 →

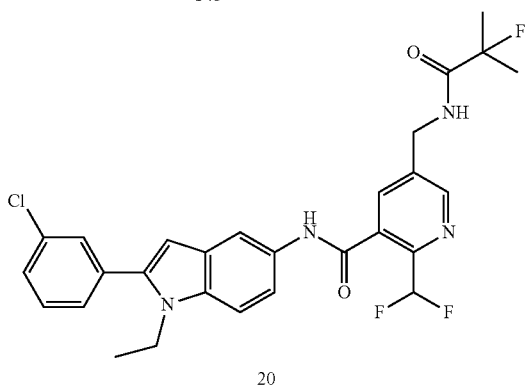

20

Step 1

2-(3-Chlorophenyl)-1-ethyl-5-nitro-1H-indole

1-Ethyl-5-nitro-1H-indole 1b (1.0 g, 5.3 mmol) was dissolved in 10 mL N,N-dimethylacetamide, and then added with 1-chloro-3-iodo-benzene 20a (1.4 g, 5.8 mmol), triphenylphosphine (276 mg, 1.1 mmol), palladium acetate (119 mg, 0.53 mmol), and cesium acetate (2.0 g, 11 mmol), successively. The reaction mixture was heated to 140° C., and stirred for 18 hours under an argon atmosphere. The reaction mixture was concentrated under reduced pressure, and the residues were purified by silica gel column chromatography with elution system C to obtain the title compound 2-(3-chlorophenyl)-1-ethyl-5-nitro-1H-indole 20b (120 mg, 7.6%) as a yellow solid.

MS m/7 (ESI): 301.1 [M+1]

Step 2

2-(3-Chlorophenyl)-1-ethyl-1H-indol-5-amine 2-(3-Chlorophenyl)-1-ethyl-5-nitro-1H-indole 20b (50 mg, 0.17 mmol) was dissolved in 10 mL of a mixture of tetrahydrofuran and methanol (V:V=1:1), and then added with Raney nickel (5 mg). The reaction mixture was stirred for 2 hours under a hydrogen atmosphere. The reaction mixture was filtered with celatom. The filtrate was concentrated under reduced pressure to obtain the crude title compound 2-(3-chlorophenyl)-1-ethyl-1H-indol-5-amine 20c (45 mg) as a red oil which was used in the next step without further purification.

MS m/z (ESI): 271.1 [M+1]

Step 3

N-(2-(3-Chlorophenyl)-1-ethyl-1H-indol-5-yl)-2-(difluoromethyl)-5-(((2-fluoro-2-methyl-propanoyl)amino)methyl)nicotinamide 2-(3-Chlorophenyl)-1-ethyl-1H-indol-5-amine 20c (45 mg, 0.17 mmol), 2-(difluoromethyl)-5-(((2-fluoro-2-

116 methyl-propanoyl)amino)methyl)nicotinic acid 14b (49 mg, 0.17 mmol), 1-ethyl-(3-dimethylaminopropyl)carbodiimide hydrochloride (48 mg, 0.25 mmol), 1-hydroxybenzotriazole (23 mg, 0.17 mmol) and triethylamine (68 mg, 0.66 mmol) were dissolved in 5 mL N, N-dimethylformamide, successively. The resulting mixture was stirred for 16 hours and then concentrated under reduced pressure. The residues were purified by thin layer chromatography (TLC) with elution system A to obtain the title compound N-(2-(3-chlorophenyl)-1-ethyl-1H-indol-5-yl)-2-(difluoromethyl)-5-(((2-fluoro-2-methyl-propanoyl)amino)methyl)nicotinamide 20 (45 mg, 50% for two steps) as an off-white solid.

MS m/z (ESI): 543.1 [M+1]

$^1$H NMR (400 MHz, DMSO-d$_6$): δ 10.62 (s, 1H), 8.88 (s, 1H), 8.69 (s, 1H), 8.03 (d, 2H), 7.57-7.55 (m, 6H), 7.43 (t, 1H), 7.19 (s, 1H), 6.64 (d, 2H), 4.49-4.47 (m, 2H), 1.54 (s, 3H), 1.49 (s, 3H), 1.19 (t, 3H).

Example 21

N-(2-(4-Chlorophenyl)-1-methyl-1H-indol-5-yl)-2-(difluoromethyl)-5-(((1-(trifluoromethyl)cyclopropanecarbonyl)amino)methyl)nicotinamide

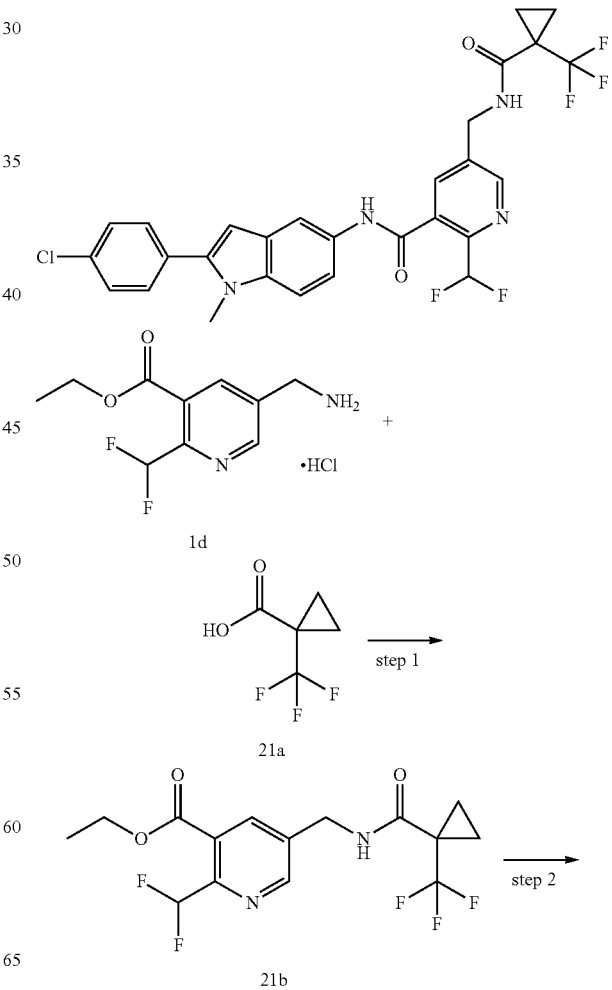

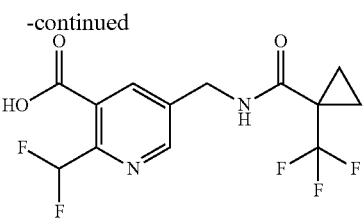

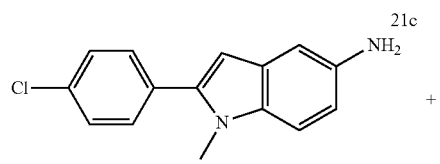

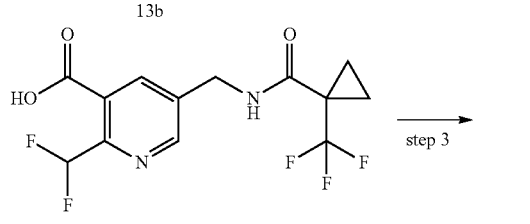

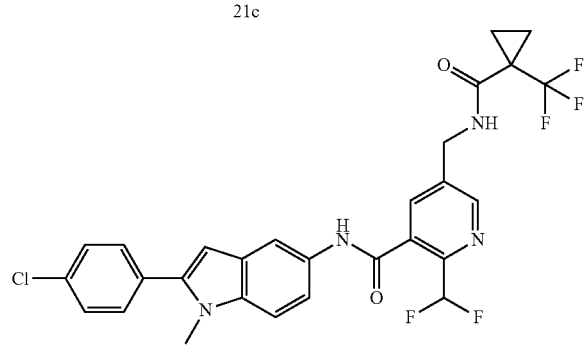

Step 1

Ethyl 2-(difluoromethyl)-5-(((1-(trifluoromethyl) cyclopropanecarbonyl)amino)methyl)nicotinate Ethyl 5-(aminomethyl)-2-(difluoromethyl)nicotinate hydrochloride 1d (4.0 g, 13.2 mmol) was dissolved in 50 mL N, N-dimethylformamide, and then added with 1-(trifluoromethyl)cyclopropane-1-carboxylic acid 21a (2.03 g, 13.2 mmol), 1-ethyl-(3-dimethylaminopropyl)carbodiimide hydrochloride (5.07 g, 26.4 mmol), 1-hydroxybenzotriazole (178 mg, 1.32 mmol) and triethylamine (5.3 g, 52.8 mmol), successively. The resulting mixture was stirred for 16 hours and then concentrated under reduced pressure. The residues were washed with ethyl acetate (50 mL) and water (50 mL), and dried to obtain the crude title compound ethyl 2-(difluoromethyl)-5-(((1-(trifluoromethyl)cyclopropanecarbonyl)amino)methyl)nicotinate 21b (4.83 g) as a brown oil which was used in the next step without further purification.

MS m/z (ESI): 367.1 [M+1]

Step 2

2-(Difluoromethyl)-5-(((1-(trifluoromethyl)cyclopropanecarbonyl)amino)methyl)nicotinic acid Ethyl 2-(difluoromethyl)-5-(((1-(trifluoromethyl)cyclopropanecarbonyl)amino)methyl) nicotinate 21b (4.83 g, 13.2 mmol) was dissolved in 150 mL of a mixture of 1,4-dioxane and water (V:V=2:1), and then added with lithium hydroxide hydrate (1.38 g, 33.0 mmol). The reaction mixture was stirred for 1 hour. The ethanol was removed under reduced pressure, and the residue was adjusted to pH 4 to 5 with 6M hydrochloric acid. A lot of solid was precipitated and added with 100 mL ethyl acetate. The solid was filtered out and dried to obtain the title compound 2-(difluoromethyl)-5-(((1-(trifluoromethyl)cyclopropanecarbonyl)amino)-methyl)nicotinic acid 21c (2.0 g, 44.8% for two steps) as a white solid.

MS m/z (ESI): 339.1 [M+1]

Step 3

N-(2-(4-Chlorophenyl)-1-methyl-1H-indol-5-yl)-2-(difluoromethyl)-5-(((1-(trifluoromethyl)cyclopropanecarbonyl)amino)methyl)nicotinamide 2-(4-Chlorophenyl)-1-methyl-5-amino-1H-indole 13b (45 mg, 0.17 mmol), 2-(difluoromethyl)-5-(((1-(trifluoromethyl)cyclopropanecarbonyl)amino)methyl)nicotinic acid 21c (59 mg, 0.17 mmol), 1-ethyl-(3-dimethylaminopropyl) carbodiimide hydrochloride (51 mg, 0.26 mmol), 1-hydroxybenzotriazole (24 mg, 0.17 mmol) and triethylamine (71 mg, 0.70 mmol) were dissolved in 5 mL N,N-dimethylformamide, successively. The resulting mixture was stirred for 16 hours and then concentrated under reduced pressure. The residues were purified by thin layer chromatography (TLC) with elution system A to obtain the title compound N-(2-(4-chlorophenyl)-1-methyl-1H-indol-5-yl)-2-(difluoromethyl)-5-(((1-(trifluoromethyl)cyclopropanecarbonyl)amino)methyl)nicotinamide 21 (20 mg, 20%) as a light yellow solid.

MS m/z (ESI): 577.1 [M+1]

$^1$H NMR (400 MHz, DMSO-$d_6$): δ 10.61 (s, 1H), 8.67 (s, 1H), 8.59-8.57 (m, 1H), 8.03 (d, 2H), 7.62 (dd, 4H), 7.47 (dd, 2H), 7.19 (t, 1H), 6.64 (s, 1H), 4.46 (d, 2H), 3.76 (s, 3H), 1.28-1.26 (m, 4H).

Example 22

2-Chloro-5-((2,2-dimethylpropanoylamino)methyl)-N-(2-(4-(trifluoromethyl)phenyl)benzo[d]oxazol-5-yl)benzamide

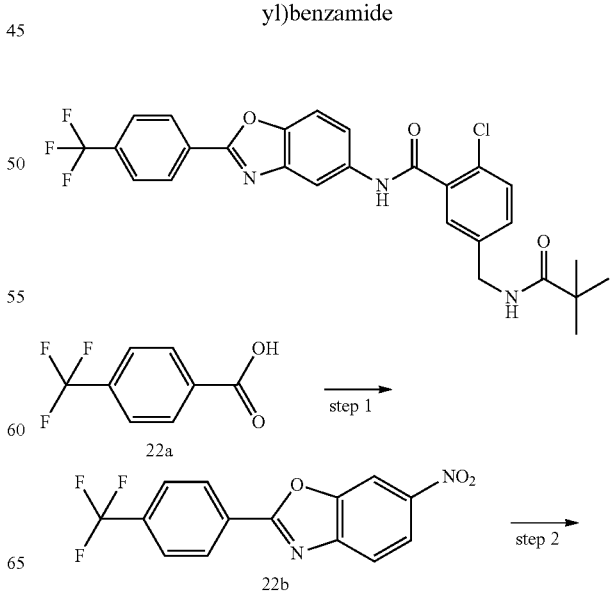

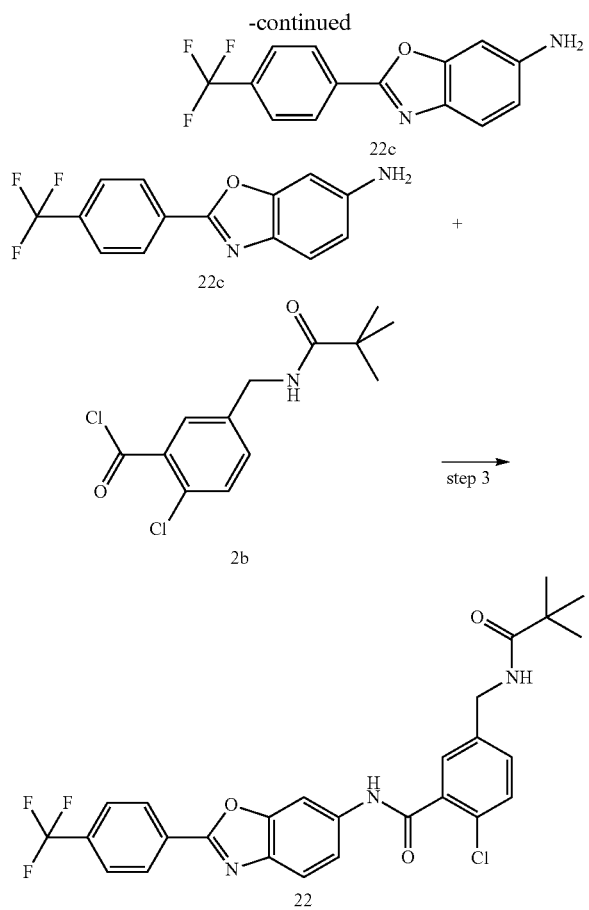

trated under reduced pressure to obtain the crude title compound 2-(4-(trifluoromethyl)phenyl) benzo[d]oxazole-5-amine 22c (150 mg) as brown solid which was used in the next step without further purification.

MS m/z (ESI): 279.1 [M+1]

Step 3

2-Chloro-5-((2,2-dimethylpropanoylamino)methyl)-N-(2-(4-(trifluoromethyl)phenyl)benzo[d]oxazol-5-yl)benzamide 2-(4-(Trifluoromethyl)phenyl) benzo[d]oxazole-5-amine 22c (50 mg, 0.18 mmol) was dissolved in 10 mL tetrahydrofuran, and then added with trifluoroacetic acid (54 μL, 0.39 mmol) and 2 mL of a solution of 2-chloro-5-((2,2-dimethylpropanoylamino)methyl)benzoyl chloride 2b (52 mg, 0.18 mmol) in tetrahydrofuran dropwise. The resulting mixture was stirred for 1 hour. The reaction mixture was filtered. The filtrate was concentrated under reduced pressure, and the residue was purified by thin layer chromatography (TLC) with elution system A to obtain a solid, which was added with 10 mL ethyl acetate and filtered. The filter cake was dried to obtain the title compound 2-chloro-5-((2, 2-dimethyl propanoylamino)methyl)-N-(2-(4-(trifluoromethyl)phenyl)benzo[d]oxazol-5-yl)benzamide 22 (15 mg, 15.3% for two steps) as a light yellow solid.

MS m/z (ESI): 530.3 [M+1]

$^1$H NMR (400 MHz, DMSO-d$_6$): δ 10.41 (s, 1H), 8.19 (t, 1H), 8.11 (s, 1H), 7.91-7.87 (d, 2H), 7.83-7.79 (d, 2H), 7.59-7.53 (d, 2H), 7.53-7.48 (d, 2H), 7.48-7.41 (m, 1H), 4.29-4.22 (m, 2H), 1.13 (s, 9H).

Step 1

5-Nitro-2-(4-(trifluoromethyl)phenyl)benzo[d]oxazole 4-(Trifluoromethyl)benzoic acid 22a (2.0 g, 10.5 mmol) was dissolved in 14 mL polyphosphoric acid, and then added with 2-amino-4-nitrophenol (1.62 g, 10.5 mmol). The reaction mixture was heated to 120° C. and stirred for 16 hours. The reaction mixture was cooled to room temperature, and then poured into 500 mL water. The solution was adjusted to pH 7 by addition of sodium hydroxide portionwise, and then extracted with ethyl acetate (500 mL×3). The organic phases were combined, dried over anhydrous sodium sulfate, and filtered. The filtrate was concentrated under reduced pressure to obtain the title compound 5-nitro-2-(4-(trifluoromethyl)phenyl) benzo[d]oxazole 22b (1.5 g) as a brown solid which was used in the next step without further purification.

Step 2

2-(4-(Trifluoromethyl)phenyl)benzo[d]oxazole-5-amine

5-Nitro-2-(4-(trifluoromethyl)phenyl)benzo[d]oxazole 22b (170 mg, 0.55 mmol) was dissolved in 10 mL mixture of tetrahydrofuran and methanol (V:V=1:1), and then added with Raney nickel (20 mg). The reaction mixture was stirred for 2 hours under a hydrogen atmosphere. The reaction mixture was filtered with celatom. The filtrate was concen- Example 23

2-(Difluoromethyl)-5-(((2-fluoro-2-methyl-propanoyl)amino)methyl)-N-(2-(4-(trifluoromethyl)phenyl)benzo[d]oxazol-5-yl)nicotinamide

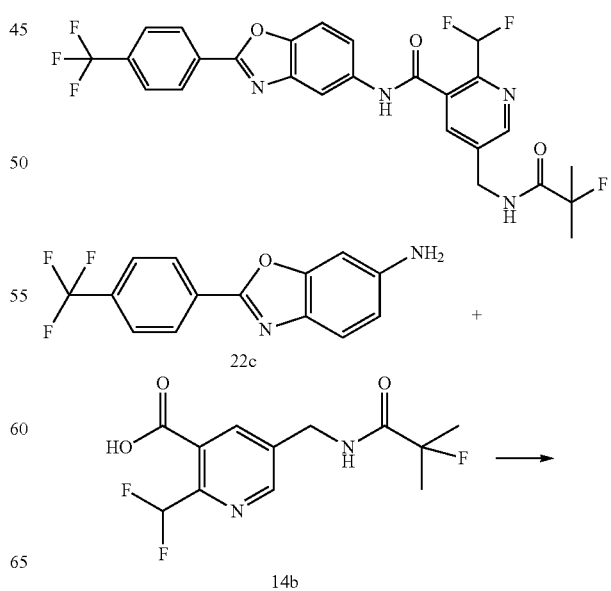

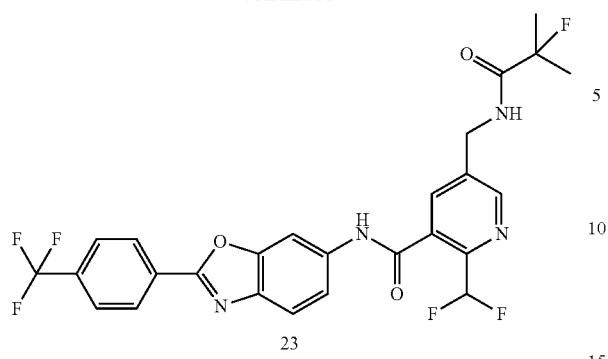

2-(4-(Trifluoromethyl)phenyl)benzo[d]oxazole-5-amine 22c (50 mg, 0.18 mmol) was dissolved in 10 mL of N,N-dimethylformamide, and then added with 2-(difluoromethyl)-5-(((2-fluoro-2-methyl-propanoyl)amino)methyl) nicotinic acid 14b (52 mg, 0.18 mmol), 1-ethyl-(3-dimethylaminopropyl) carbodiimide hydrochloride (75 mg, 0.39 mmol), 1-hydroxybenzotriazole (2.4 mg, 0.02 mmol) and triethylamine (73 mg, 0.72 mmol), successively. The resulting mixture was heated to 70° C. and stirred for 2 hours. The reaction mixture was cooled to room temperature. The reaction mixture was concentrated under reduced pressure, and the residues were purified by thin layer chromatography (TLC) with elution system A to obtain a solid. The solid was added with 10 mL diethyl ether, and filtered. The filter cake was dried to obtain the title compound 2-(difluoromethyl)-5-(((2-fluoro-2-methyl-propanoyl)amino)methyl)-N-(2-(4-(trifluoromethyl)phenyl) benzo[d]oxazole-5-yl)nicotinamide 23 (10 mg, 10.1%) as a light yellow solid.

MS m/z (ESI): 551.3 [M+1]

$^1$H NMR (400 MHz, DMSO-d$_6$): δ 10.60 (s, 1H), 8.69 (s, 1H), 8.45 (t, 1H), 8.08 (s, 1H), 8.01 (s, 1H), 7.92-7.86 (d, 2H), 7.85-7.79 (d, 2H), 7.61-7.56 (d, 1H), 7.46-7.42 (d, 1H), 7.20 (t, 1H), 4.31-4.21 (m, 2H), 2.49-2.40 (m, 1H), 1.09-1.02 (d, 6H).

Example 24

2-(Difluoromethyl)-5-((2-methylpropanoylamino)methyl)-N-(2-(4-(trifluoromethyl)phenyl)-2H-indazol-5-yl)nicotinamide

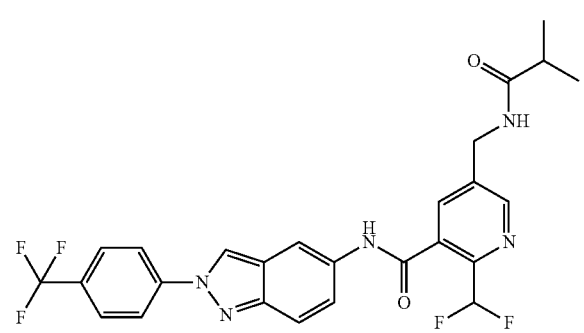

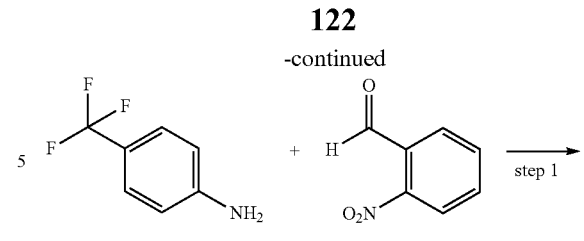

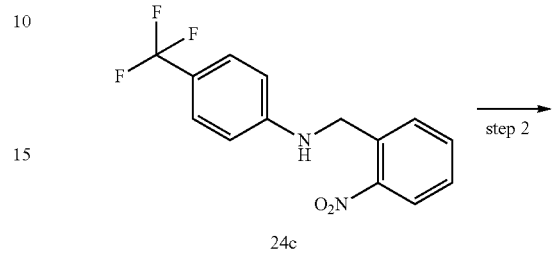

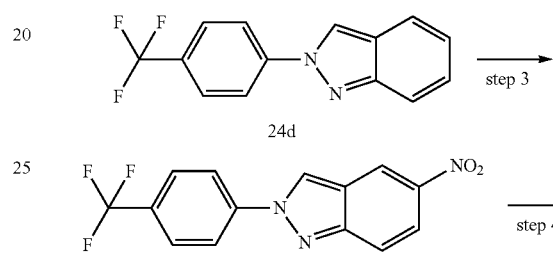

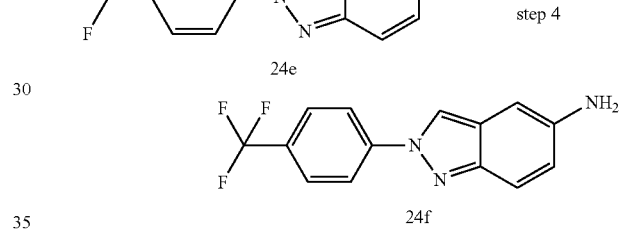

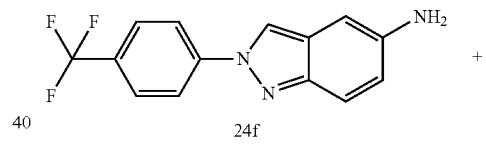

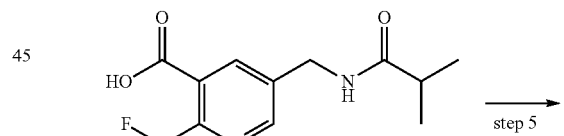

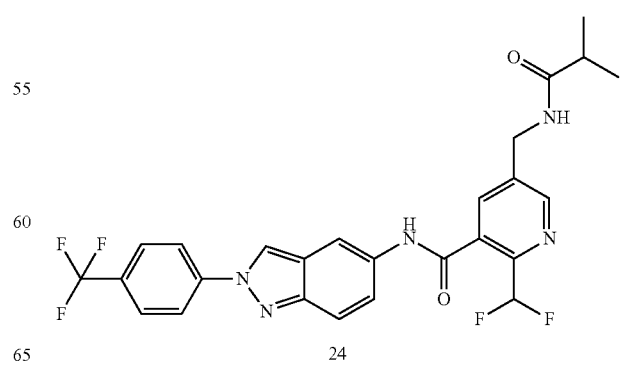

Step 1

N-(2-nitrobenzyl)-4-(trifluoromethyl)aniline

4-Aminobenzotrifluoride 24a (2.35 g, 14.56 mmol) was dissolved in 50 mL 1,2-dichloroethane, and then added with 2-nitrobenzaldehyde 24b (2.0 g, 13.23 mmol). The resulting mixture was stirred for 0.5 hour, and then added with sodium triacetoxyborohydride (5.6 g, 26.46 mmol) and stirred for another 16 hours. The reaction mixture was added with 100 mL dichloromethane and 100 mL water. The organic phase was concentrated under reduced pressure, and the residues were purified by thin layer chromatography (TLC) with elution system C to obtain the title compound N-(2-nitrobenzyl)-4-(trifluoromethyl)aniline 24c (3.5 g, 89.4%) as yellow oil.

MS m/z (ESI): 297.1 [M+1]

Step 2

2-(4-(Trifluoromethyl)phenyl)-2H-indazole

Zinc powder (1.73 g, 27.04 mmol) was added in 50 mL tetrahydrofuran, and then added with titanium tetrachloride (2.57 g, 13.55 mmol). The reaction mixture was heated to 70° C., and stirred for 2 hours. The reaction solution was cooled to room temperature and adjusted to pH 8 with triethylamine. N-(2-nitrobenzyl)-4-(trifluoromethyl)aniline 24c (1.0 g, 3.38 mmol) was dissolved in 20 mL of tetrahydrofuran and then added into the resulting mixture above. The reaction mixture was continually stirred for another 30 minutes and then adjusted to pH 3 with 6 M hydrochloric acid. The solution was extracted with dichloromethane (100 mL×3). The organic phases were combined, dried over anhydrous sodium sulfate, and filtered. The filtrate was concentrated under reduced pressure, and the residues were purified by thin layer chromatography (TLC) with elution system C to obtain the title compound 2-(4-(trifluoromethyl)phenyl)-2H-indazole 24d (100 mg, 11.3%) as a white solid.

MS m/z (ESI): 263.1 [M+1]

Step 3

5-Nitro-2-(4-(trifluoromethyl)phenyl)-2H-indazole

Sodium nitrate (29 mg, 0.67 mmol) was added into 1 mL sulfuric acid under an ice bath, and then added with 2-(4-(trifluoromethyl)phenyl)-2H-indazole 24d (50 mg, 0.19 mmol) portionwise. The reaction mixture was heated to 70° C., and stirred for 1 hour. The reaction mixture was poured into 30 mL of ice-water, and the pH was adjusted to >7. The solution was extracted with ethyl acetate (40 mL×3). The organic phases were combined, dried over anhydrous sodium sulfate, and filtered. The filtrate was concentrated under reduced pressure, and the residues were purified by thin layer chromatography (TLC) with elution system C to obtain the title compound 5-nitro-2-(4-(trifluoromethyl)phenyl)-2H-indazole 24e (30 mg, 25.6%) as a yellow solid.

MS m/z (ESI): 308.1 [M+1]

Step 4

2-(4-(Trifluoromethyl)phenyl)-2H-indazol-5-amine

5-Nitro-2-(4-(trifluoromethyl)phenyl)-2H-indazole 24e (30 mg, 0.098 mmol) was dissolved in 10 mL of a mixture of tetrahydrofuran and methanol (V:V=1:1), and then added with Raney nickel (3 mg). The reaction mixture was stirred for 1 hour under a hydrogen atmosphere. The reaction mixture was filtered with celatom. The filtrate was concentrated under reduced pressure to obtain the crude title compound 2-(4-(trifluoromethyl)phenyl)-2H-indazol-5-amine 24f (27 mg) as a light yellow solid which was used in the next step without further purification.

MS m/z (ESI): 278.1 [M+1]

Step 5

2-(Difluoromethyl)-5-((2-methylpropanoylamino)methyl)-N-(2-(4-(trifluoromethyl)phenyl)-2H-indazol-5-yl)nicotinamide 2-(4-(Trifluoromethyl)phenyl)-2H-indazol-5-amine 24f (27 mg, 0.098 mmol), 2-(difluoromethyl)-5-((2-methylpropanoylamino)methyl)nicotinic acid 1f (27 mg, 0.10 mmol), 1-ethyl-(3-dimethylaminopropyl)carbodiimide hydrochloride (29 mg, 0.15 mmol) and 1-hydroxybenzotriazole (14 mg, 0.10 mmol) were added to 5 mL of N,N-dimethylformamide, successively. The resulting mixture was heated to 40° C. and stirred for 1 hour. The reaction mixture was concentrated under reduced pressure, and the residue was purified by thin layer chromatography (TLC) with elution system A to obtain a solid. The solid was added with 20 mL of dichloromethane and stirred for 20 minutes. The mixture was filtered and the filter cake was washed with dichloromethane (5 mL×3) and dried to obtain the title compound 2-(difluoromethyl)-5-((2-methylpropanoylamino)methyl)-N-(2-(4-(trifluoromethyl)phen yl)-2H-indazol-5-yl)nicotinamide 24 (27 mg, 50.9%) as a white solid.

MS m/z (ESI): 532.1 [M+1]

$^1$H NMR (400 MHz, DMSO-d$_6$): δ 10.78 (s, 1H), 9.25 (s, 1H), 8.70 (s, 1H), 8.47 (t, 1H), 8.38-8.33 (m, 3H), 8.08-7.97 (m, 3H), 7.76 (d, 1H), 7.49 (d, 1H), 7.19 (t, 1H), 4.44 (d, 2H), 2.49-2.41 (m, 1H), 1.06 (d, 6H).

Example 25

2-Chloro-5-((2,2-dimethylpropanoylamino)methyl)-N-(2-(4-(trifluoromethyl)phenyl)isoindolin-5-yl)benzamide

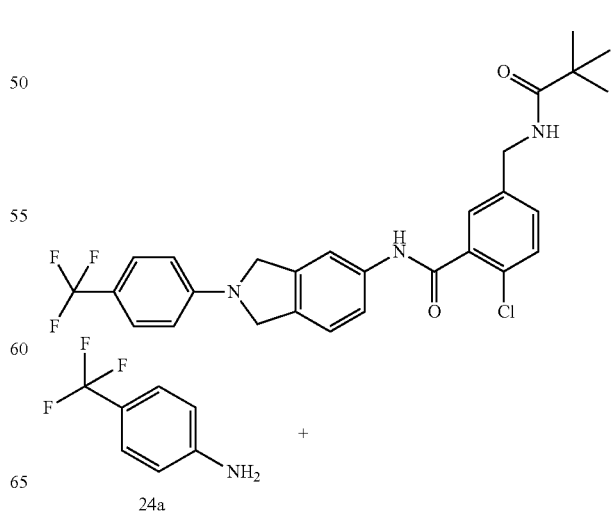

24a

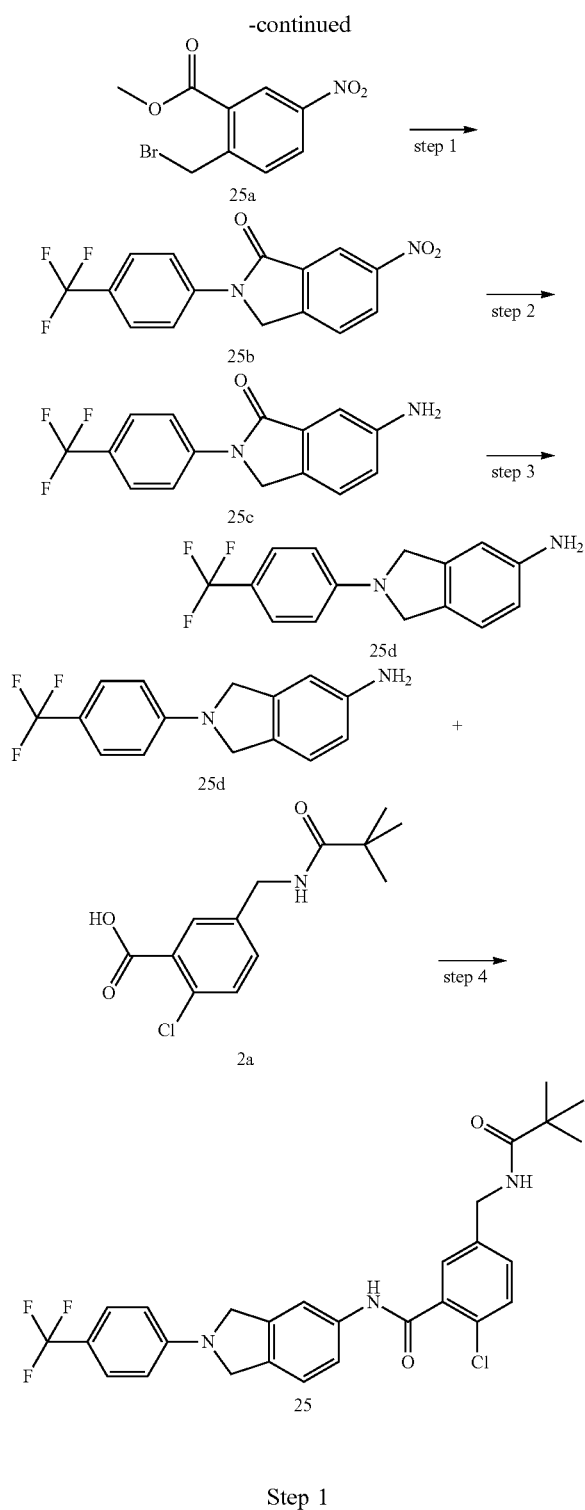

Step 1

6-Nitro-2-(4-(trifluoromethyl)phenyl)isoindolin-1-one

4-Aminobenzotrifluoride 24a (193 mg, 1.2 mmol) was dissolved in 3 mL ethanol, and then added with methyl 2-(bromomethyl)-5-nitro-benzoate 25a (274 mg, 1.0 mmol) and N,N-diisopropylethylamine (258 mg, 2.0 mmol). The reaction mixture was heated to 110° C. and stirred for 16 hours. The reaction solution was cooled to room temperature, and filtered. The filter cake were dried to obtain the title compound 6-nitro-2-(4-(trifluoromethyl)phenyl)isoindolin-1-one 25b (70 mg, 21.7%) as a yellow solid.

MS m/z (ESI): 321.0 [M−1]

Step 2

6-Amino-2-(4-(trifluoromethyl)phenyl)isoindolin-1-one

6-Nitro-2-(4-(trifluoromethyl)phenyl)isoindolin-1-one 25b (70 mg, 0.098 mmol) was dissolved in 10 mL of a mixture of tetrahydrofuran and methanol (V:V=1:1), and then added with Raney nickel (7 mg). The reaction mixture was stirred for 1 hour under a hydrogen atmosphere. The reaction mixture was filtered with celatom. The filtrate was concentrated under reduced pressure to obtain the crude title compound 6-amino-2-(4-(trifluoromethyl)phenyl)isoindolin-1-one 25c (64 mg) as a white solid which was used in the next step without further purification.

MS m/z (ESI): 293.1 (M+1)

Step 3

2-(4-(Trifluoromethyl)phenyl)isoindolin-5-amine

6-Amino-2-(4-(trifluoromethyl)phenyl)isoindolin-1-one 25c (64 mg, 0.22 mmol) was dissolved in 10 mL tetrahydrofuran, and then added with lithium aluminium hydride (51 mg, 1.32 mmol). The reaction mixture was heated to 65° C., and stirred for 16 hours. The reaction mixture was added with 0.1 mL sodium hydroxide solution (15%) and 0.4 mL water followed by magnesium sulfate, and stirred for another 5 minutes. The mixture was filtered, and extracted with ethyl acetate. The organic phase was concentrated under reduced pressure, and the residues were purified by thin layer chromatography (TLC) with elution system A to obtain the title compound 2-(4-(trifluoromethyl)phenyl)isoindolin-5-amine 25d (11 mg, 18.0%) as a gray solid.

MS m/z (ESI): 279.1 [M+1]

Step 4

2-Chloro-5-((2,2-dimethylpropanoylamino)methyl)-N-(2-(4-(trifluoromethyl)phenyl)isoindolin-5-yl)benzamide 2-(4-(Trifluoromethyl)phenyl)isoindolin-5-amine 25d (11 mg, 0.04 mmol), 2-chloro-5-((2,2-dimethylpropanoylamino)methyl)benzoic acid 2a (11 mg, 0.04 mmol), 1-ethyl-(3-dimethylaminopropyl) carbodiimide hydrochloride (12 mg, 0.06 mmol), 1-hydroxybenzotriazole (6 mg, 0.04 mmol) and triethylamine (17 mg, 0.16 mmol) were added in 5 mL of N,N-dimethylformamide, successively. The reaction mixture was stirred for 16 hours and then concentrated under reduced pressure. The residues were purified by thin layer chromatography (TLC) with elution system A to obtain the title compound 2-chloro-5-((2,2-dimethylpropanoylamino)methyl)-N-(2-(4-(trifluoromethyl)phenyl)isoindolin-5-yl)benzamide 25 (6 mg, 28.6%) as a white solid.

MS m/z (ESI): 530.1 [M+1]

$^1$H NMR (400 MHz, DMSO-$d_6$): δ 10.61 (s, 1H), 8.18 (t, 1H), 7.89 (s, 1H), 7.60-7.50 (m, 4H), 7.42-7.34 (m, 3H), 6.80 (d, 2H), 4.68 (d, 4H), 4.30 (d, 2H), 1.14 (s, 9H).

Example 26

2-(Difluoromethyl)-5-(((2-fluoro-2-methyl-propanoyl)amino)methyl)-N-(2-(4-(trifluoromethyl)phenyl)isoindolin-5-yl)nicotinamide

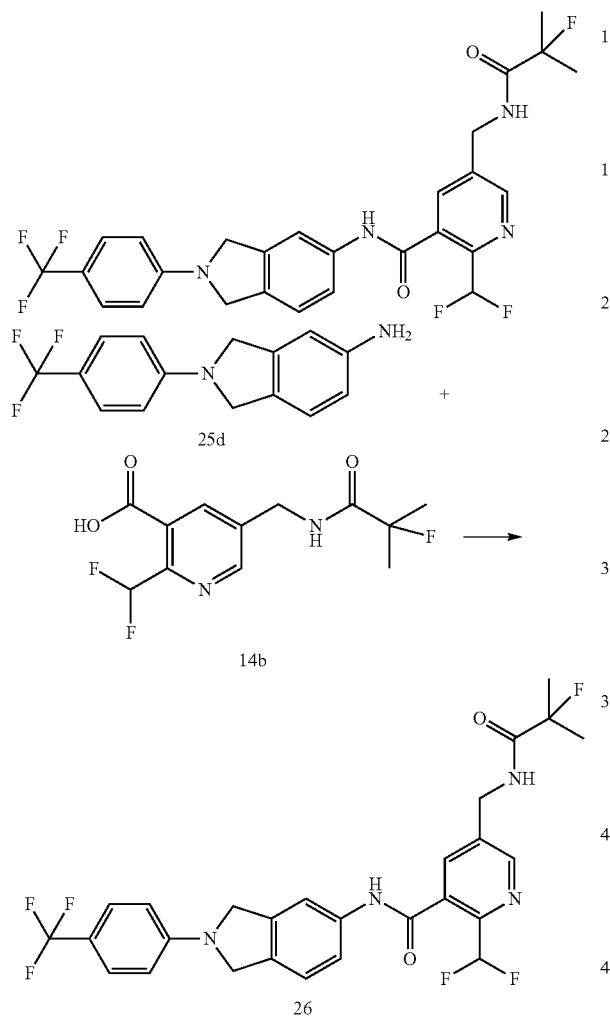

2-(4-(Trifluoromethyl)phenyl)isoindolin-5-amine 25d (63 mg, 0.23 mmol) was dissolved in 5 mL of N,N-dimethylformamide, and added with 2-(difluoromethyl)-5-(((2-fluoro-2-methyl-propanoyl)amino)methyl)nicotinic acid 14b (66 mg, 0.23 mmol), 1-ethyl-(3-dimethylaminopropyl) carbodiimide hydrochloride (67 mg, 0.35 mmol), 1-hydroxybenzotriazole (27 mg, 0.23 mmol) and triethylamine (93 mg, 0.92 mmol), successively. The reaction mixture was stirred for 16 hours and then concentrated under reduced pressure. The residues were purified by thin layer chromatography (TLC) with elution system A to obtain the title compound 2-(difluoromethyl)-5-(((2-fluoro-2-methyl-propanoyl)amino)methyl)-N-(2-(4-(trifluoromethyl)phenyl) isoindolin-5-yl)nicotinamide 26 (50 mg, 39.7%) as a white solid.

MS m/z (ESI): 551.1 [M+1]

$^1$H NMR (400 MHz, DMSO-$d_6$): δ 10.79 (s, 1H), 8.87 (s, 1H), 8.70 (s, 1H), 8.00 (s, 1H), 7.87 (s, 1H), 7.57 (d, 3H), 7.42 (d, 1H), 7.16 (t, 1H), 6.80 (d, 2H), 4.69 (d, 4H), 4.66 (d, 2H), 1.53 (s, 3H), 1.48 (s, 3H).

Example 27

2-(Difluoromethyl)-5-(((2-fluoro-2-methyl-propanoyl)amino)methyl)-N-(1-(2-methoxyethyl)-2-(4-(trifluoromethyl)phenyl)-1H-indol-5-yl)nicotinamide

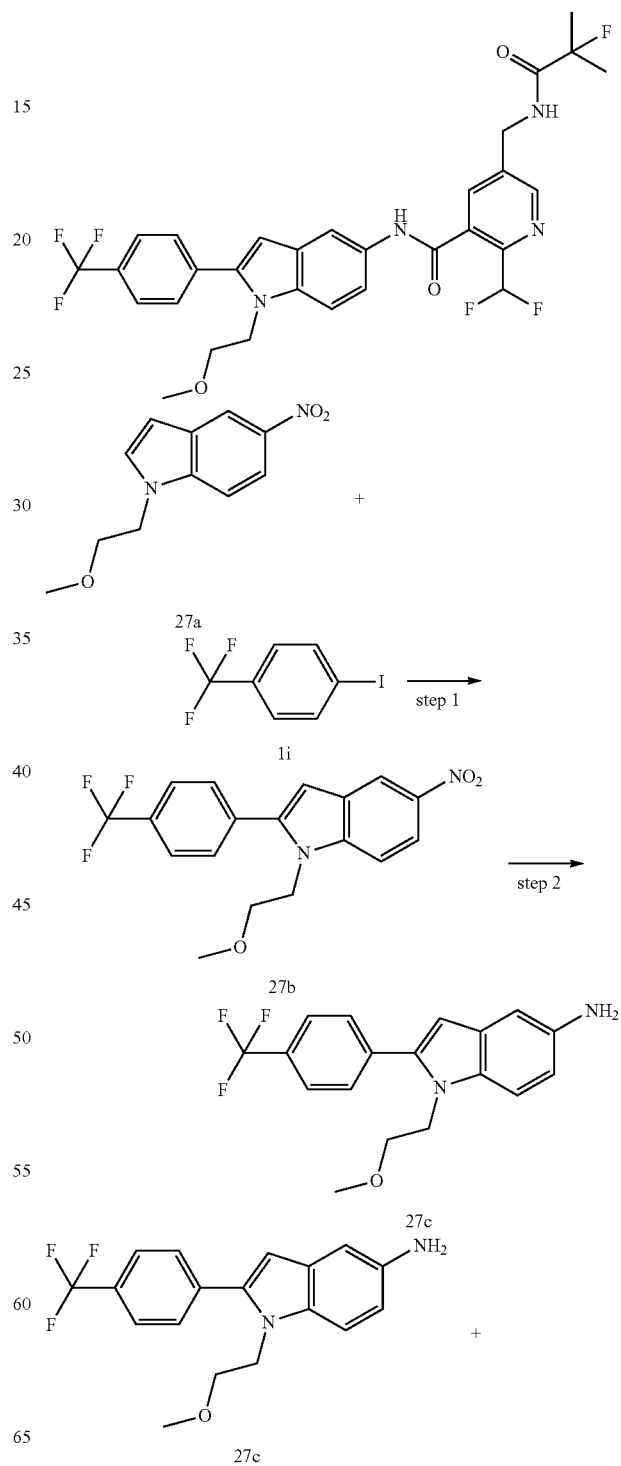

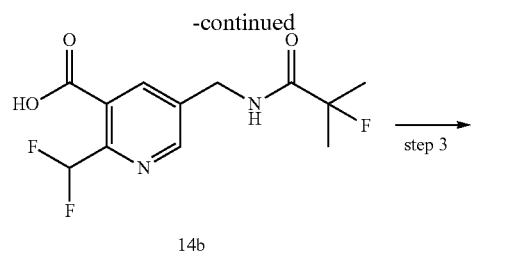

14b

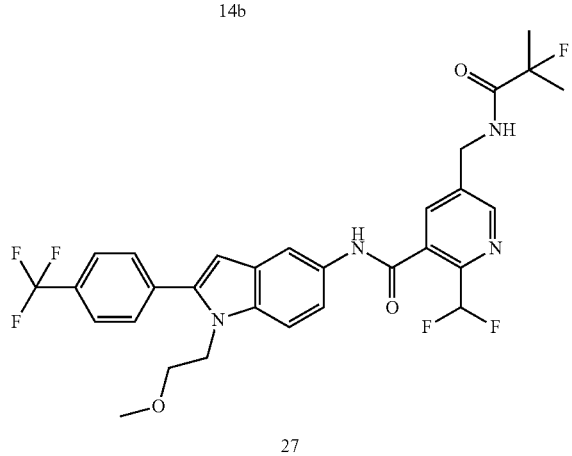

27

Step 1

1-(2-Methoxyethyl-5-nitro-2-(4-(trifluoromethyl)phenyl)-1H-indole 1-(2-Methoxyethyl)-5-nitro-1H-indole 27a (2.2 g, 10 mmol, prepared according to the method disclosed in patent application publication "US20090076275") was dissolved in 10 mL N,N-dimethylacetamide, and then added with 1-iodo-4-(trifluoromethyl)benzene 1i (2.7 g, 10 mmol), triphenylphosphine (564 mg, 2.0 mmol), palladium acetate (225 mg, 1.0 mmol), and cesium acetate (3.8 g, 20 mmol), successively. The reaction mixture was heated to 140° C., and stirred for 18 hours under an argon atmosphere. The reaction mixture was concentrated under reduced pressure, and the residue was washed with ethyl acetate (5 mL×3). The filtrate was concentrated under reduced pressure, the residue was purified by silica gel column chromatography with elution system C to obtain the title compound 1-(2-methoxyethyl-5-nitro-2-(4-(trifluoromethyl)phenyl)-1H-indole 27b (300 mg, 8.2%) as a yellow solid.

MS m/z (ESI): 365.1 (M+1)

Step 2

1-(2-Methoxyethyl-5-amino-2-(4-(trifluoromethyl)phenyl)-1H-indole 1-(2-Methoxyethyl)-5-nitro-2-(4-(trifluoromethyl)phenyl)-1H-indole 27b (100 mg, 0.27 mmol) was dissolved in 20 mL of a mixture of tetrahydrofuran and methanol (V:V=1:1), and then added with Raney nickel (10 mg). The reaction mixture was stirred for 2 hours under a hydrogen atmosphere. The reaction mixture was filtered with celatom, and the filter cake was washed with ethyl acetate (30 mL). The filtrate was concentrated under reduced pressure to obtain the crude title compound 1-(2-methoxyethyl-5-amino-2-(4-(trifluoromethyl)phenyl)-1H-indole 27c (90 mg) as a yellow oil which was used in the next step without further purification.

MS m/z (ESI): 335.1 [M+1]

Step 3

2-(Difluoromethyl)-5-(((2-fluoro-2-methyl-propanoyl)amino)methyl)-N-(1-(2-methoxyethyl)-2-(4-(trifluoromethyl)phenyl)-1H-indol-5-yl)nicotinamide 1-(2-Methoxyethyl-5-amino-2-(4-(trifluoromethyl)phenyl)-1H-indole 27c (150 mg, 0.44 mmol), 2-(difluoromethyl)-5-(((2-fluoro-2-methyl-propanoyl)amino)methyl) nicotinic acid 14b (128 mg, 0.44 mmol), 1-ethyl-(3-dimethylaminopropyl)carbodiimide hydrochloride (169 mg, 0.88 mmol), 1-hydroxybenzotriazole (6 mg, 0.04 mmol) and triethylamine (178 mg, 1.76 mmol) were dissolved in 10 mL N,N-dimethylacetamide, successively. The reaction mixture was heated to 75° C. and stirred for 2 hours. The reaction mixture was concentrated under reduced pressure, and the residues were purified by thin layer chromatography (TLC) with elution system A to obtain the title compound 2-(difluoromethyl)-5-(((2-fluoro-2-methyl-propanoyl)amino)methyl)-N-(1-(2-methoxyethyl)-2-(4-(trifluoromethyl)phenyl)-1H-indol-5-yl)nicotinamide 27 (60 mg, 22.4%) as a yellow solid.

MS m/z (ESI): 607.3[M+1]

$^1$H NMR (400 MHz, DMSO-d$_6$): δ10.624 (s, 1H), 8.879 (s, 1H), 8.692 (s, 1H), 8.021-8.062 (m, 2H), 7.871-7.921 (m, 4H), 7.592-7.614 (m, 1H), 7.421-7.438 (m, 1H), 7.192-7.416 (m, 1H), 6.689 (s, 1H), 4.376-4.815 (m, 4H), 3.548-3.575 (m, 2H), 3.058-3.575 (s, 3H), 1.443-1.541 (d, 6H)

Example 28

2-(Difluoromethyl)-N-(1-ethyl-2-(3-(trifluoromethyl)phenyl)-1H-indol-5-yl)-5-(((2-fluoro-2-methyl-propanoyl)amino)methyl)-nicotinamide

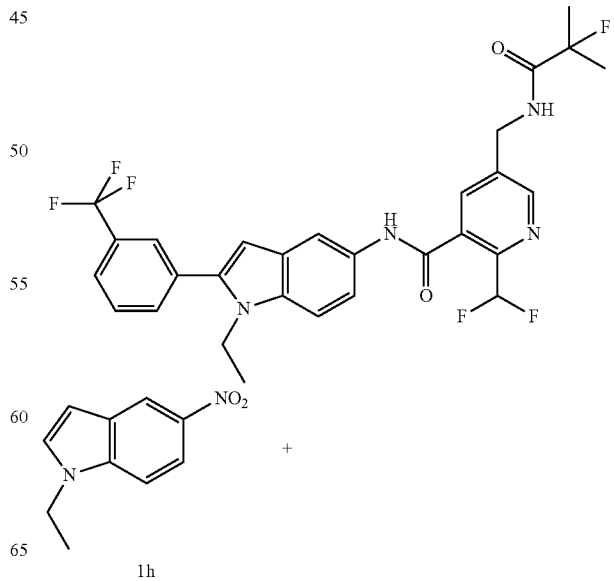

1h

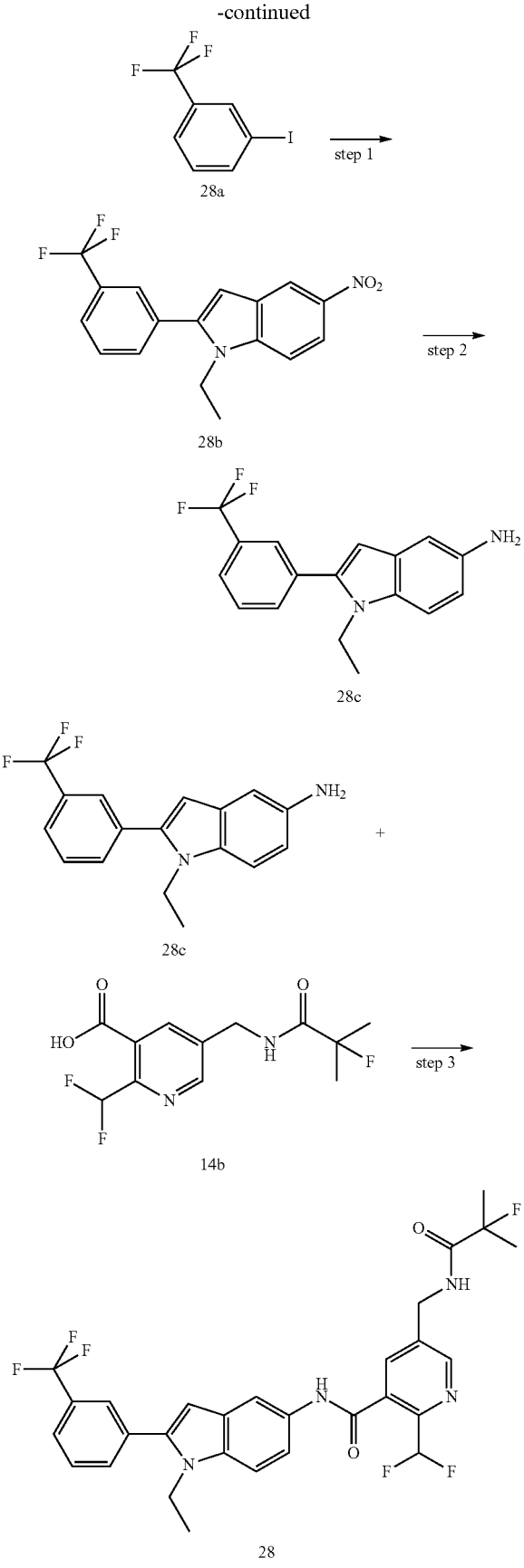

Step 1

1-Ethyl-5-nitro-2-(3-(trifluoromethyl)phenyl)-1H-indole

1-Ethyl-5-nitro-1H-indole 1h (500 mg, 2.63 mmol) was dissolved in 5 mL N,N-dimethylacetamide, and then added with 1-iodo-3-(trifluoromethyl)benzene 28a (860 mg, 3.16 mmol), triphenylphosphine (140 mg, 0.53 mmol), palladium acetate (119 mg, 0.13 mmol), and cesium acetate (2.0 g, II mmol), successively. The reaction mixture was heated to 140° C. and stirred for 16 hours under an argon atmosphere. The reaction solution was added with 40 mL of water, and extracted with ethyl acetate (40 mL×2). The organic phases were combined and dried over anhydrous sodium sulfate, and filtered. The filtrate was concentrated under reduced pressure, and the residue was purified by silica gel column chromatography with elution system C to obtain the title compound 1-ethyl-5-nitro-2-(3-(trifluoromethyl)phenyl)-1H-indole 28b (100 mg, 11.4%) as a yellow solid.

MS m/z (ESI): 335.1 [M+1]

Step 2

1-Ethyl-5-amino-2-(3-(trifluoromethyl)phenyl)-1H-indole

1-Ethyl-5-nitro-2-(3-(trifluoromethyl)phenyl)-1H-indole 28b (110 mg, 0.33 mmol) was dissolved in a mixture of 8 mL of tetrahydrofuran and methanol (V:V=1:1), and then added with Raney nickel (30 mg). The reaction mixture was stirred for 2 hours under a hydrogen atmosphere. The reaction mixture was filtered with celatom, and the filtrate was concentrated under reduced pressure to obtain the crude title compound 1-ethyl-5-amino-2-(3-(trifluoromethyl)phenyl)-1H-indole-28c (100 mg) as a light yellow solid which was used in the next step without further purification.

MS m/z (ESI): 305.1 [M+1]

Step 3

2-(Difluoromethyl)-N-(1-ethyl-2-(3-(trifluoromethyl)phenyl)-1H-indol-5-yl)-5-(((2-fluoro-2-methyl-propanoyl)amino)methyl)nicotinamide 1-Ethyl-5-amino-2-(3-(trifluoromethyl)phenyl)-1H-indole 28c (50 mg, 0.16 mmol), 2-(difluoromethyl)-5-(((2-fluoro-2-methyl-propanoyl)amino)methyl)nicotinic acid 14b (50 mg, 0.16 mmol), 1-ethyl-(3-dimethylaminopropyl) carbodiimide hydrochloride (70 mg, 0.33 mmol) and 1-hydroxybenzotriazole (25 mg, 0.16 mmol) were added into 3 mL N,N-dimethylacetamide, successively. The reaction mixture was heated to 40° C. and stirred for 4 hours. The reaction mixture was concentrated under reduced pressure, and the residue was purified by thin layer chromatography (TLC) with elution system A to obtain the title compound 2-(difluoromethyl)-N-(1-ethyl-2-(3-(trifluoromethyl)phenyl)-1H-indol-5-yl)-5-(((2-fluoro-2-methyl-propanoyl) amino)methyl)nicotinamide 28 (20 mg, 21.1%) as a yellow solid.

MS m/z (ESI): 575.5 [M−1]

$^1$H NMR (400 MHz, DMSO-d$_6$): δ 10.59 (s, 1H), 8.85 (s, 1H), 8.67 (s, 1H), 8.03 (d, 2H), 7.85-7.83 (m, 1H), 7.81-7.79 (m, 2H), 7.56 (d, 1H), 7.44 (d, 1H), 6.68 (s, 1H), 4.46 (d, 2H), 4.22-4.18 (m, 2H), 2.87 (s, 1H), 2.72 (s, 1H), 1.52 (s, 3H), 1.46 (s, 3H), 1.22 (t, 3H)

Example 29

2-(Difluoromethyl)-5-(((2-fluoro-2-methyl-propanoyl)amino)methyl)-N-(2-(4-(trifluoromethyl)phenyl)benzofuran-5-yl)nicotinamide

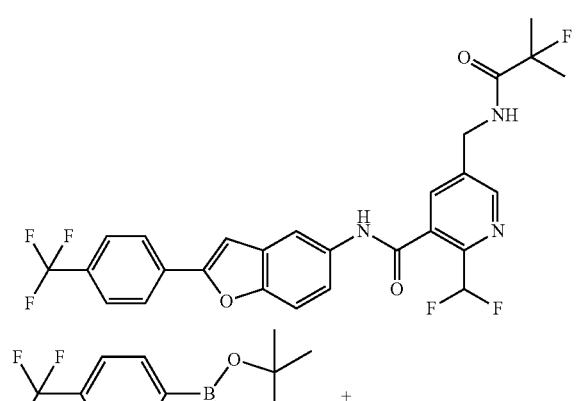

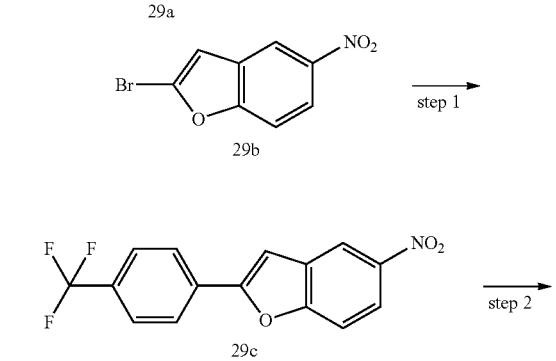

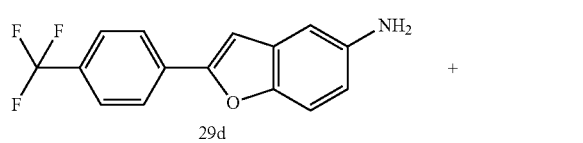

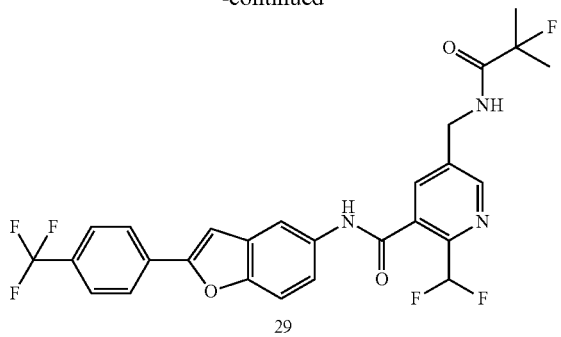

Step 1

5-Nitro-2-(4-(trifluoromethyl)phenyl)benzofuran 4-(Trifluoromethyl)(pinacolboryl)benzene 29a (170 mg, 0.62 mmol) was dissolved in a mixture of 6 mL of 1,4-dioxane and water (V:V=5:1), and then added with 2-bromo-5-nitro-benzofuran 29b (100 mg, 0.43 mmol, prepared according to the method disclosed in "*European Journal of Organic Chemistry* 2013, 2013(9), 1644-1648"), [1,1'-Bis(diphenylphosphino)ferrocene]dichloropalladium(II) (30 mg, 0.04 mmol) and sodium carbonate (88 mg, 0.83 mmol). The reaction mixture was heated to 100° C., and stirred for 16 hours under an argon atmosphere. The reaction solution was added with 50 mL of dichloromethane, and filtered with celatom. The filtrate was concentrated under reduced pressure, and the residue was purified by thin layer chromatography (TLC) with elution system C to obtain the title compound 5-nitro-2-(4-(trifluoromethyl)phenyl)benzofuran 29c (80 mg) as a light yellow solid which was used in the next step without further purification.

Step 2

5-Amino-2-(4-(trifluoromethyl)phenyl)benzofuran

5-Nitro-2-(4-(trifluoromethyl)phenyl)benzofuran 29c (40 mg, 0.13 mmol) was dissolved in a mixture of 10 mL of tetrahydrofuran and water (V:V=1:1), and then added with Raney nickel (40 mg). The reaction mixture was stirred for 2 hours under a hydrogen atmosphere. The reaction mixture was filtered with celatom, and the filtrate was concentrated under reduced pressure to obtain the title compound 5-amino-2-(4-(trifluoromethyl)phenyl)benzofuran 29d (36 mg) as a light yellow solid which was used in the next step without further purification.

MS m/z (ESI): 278.2 [M+1]

Step 3

2-(Difluoromethyl)-5-(((2-fluoro-2-methyl-propanoyl)amino)methyl)-N-(2-(4-(trifluoromethyl)phenyl)benzofuran-5-yl)nicotinamide 5-Amino-2-(4-(trifluoromethyl)phenyl)benzofuran 29d (33 mg, 0.12 mmol), 2-(difluoromethyl)-5-(((2-fluoro-2-methyl-propanoyl)amino)methyl)nicotinic acid 14b (35 mg, 0.12 mmol), 1-ethyl-(3-dimethylaminopropyl)carbodiimide hydrochloride (45 mg, 0.24 mmol) and 1-hydroxybenzotriazole (16 mg, 0.12 mmol) were added into 3 mL N,N-dimethylacetamide, successively. The reaction mixture was heated to 40° C. and stirred for 2 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(2-(4-(trifluoromethyl)phenyl)benzofuran-5-yl)nicotinamide 29 (20 mg, 30.3%) as a white solid.

MS m/z (ESI): 550.3 [M+1]

$^1$H NMR (400 MHz, DMSO-$d_6$): δ 10.7 (s, 1H), 8.71 (s, 1H), 8.49 (t, 1H), 8.12 (s, 1H), 8.03 (s, 1H), 7.93-7.88 (m, 2H), 7.86-7.80 (m, 2H), 7.61-7.56 (m, 1H), 7.46-7.42 (m, 1H), 7.31-7.01 (m, 1H), 7.15 (s, 1H), 4.44-4.38 (m, 2H), 1.55-1.49 (m, 6H).

Example 30

2-(Difluoromethyl)-5-(((2-fluoro-2-methyl-propanyl)amino)methyl)-N-(1-tetrahydrofuran-3-yl-2-(4-(trifluoromethyl)phenyl)-1H-indol-5-yl)nicotinamide

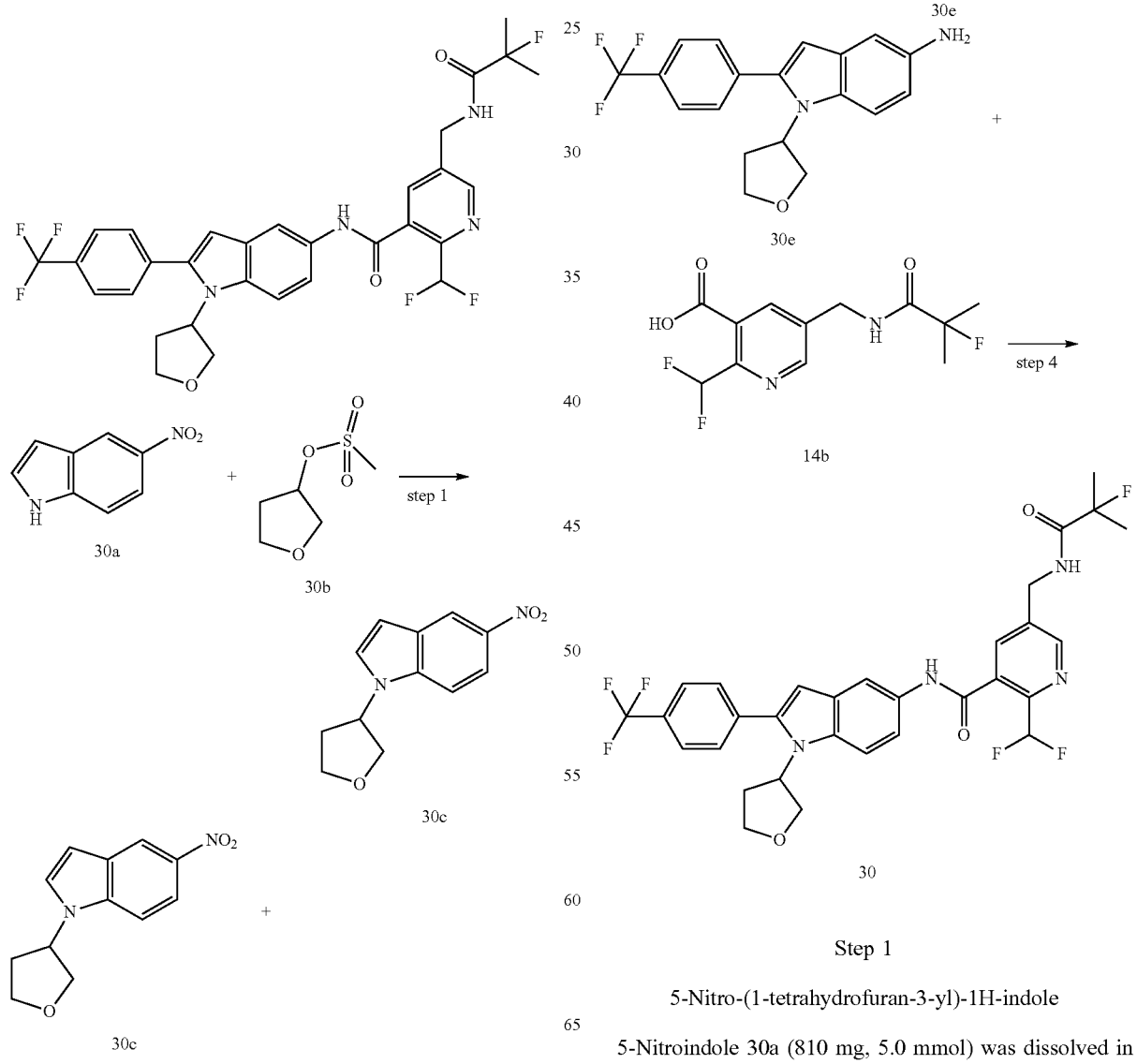

Step 1

5-Nitro-(1-tetrahydrofuran-3-yl)-1H-indole

5-Nitroindole 30a (810 mg, 5.0 mmol) was dissolved in 10 m of N, N-dimethylacetamide under an ice bath, and then added with sodium hydride (300 mg, 7.5 mmol). The reaction solution was warmed up to room temperature and then stirred for 10 minutes. Tetrahydrofuran-3-yl methanesulfonate 30b (1.66 g, 10.0 mmol, prepared according to the method disclosed in "*Journal of Organic Chemistry*, 2008, 73(14), 5397-5409") was added and the mixture was heated to 50° C., and stirred for 16 hours. The reaction mixture was added with 100 mL of water, and mixed well, then extracted with ethyl acetate (100 mL×3). The organic phases were combined and washed with saturated sodium chloride solution (50 mL), dried over anhydrous sodium sulfate, and filtered. The filtrate was concentrated under reduced pressure to obtain the title compound 5-nitro-1-tetrahydrofuran-3-yl-1H-indole 30c (1.16 g) as a white solid which was used in the next step without further purification.

MS m/z (ESI): 233.1 [M+1]

Step 2

5-Nitro-1-(tetrahydrofuran-3-yl)-2-(4-(trifluoromethyl)phenyl)-1H-indole

5-Nitro-1-(tetrahydrofuran-3-yl)-1H-indole 30c (1.16 g, 5.0 mmol) was dissolved in 10 mL N,N-dimethylacetamide, and then added with 1-iodo-4-(trifluoromethyl)benzene 1i (1.36 g, 5.0 mmol), triphenylphosphine (282 mg, 1.0 mmol), palladium acetate (113 mg, 0.5 mmol) and cesium acetate (1.9 g, 10 mmol), successively. The reaction mixture was heated to 140° C. and stirred for 18 hours under an argon atmosphere. The reaction mixture was concentrated under reduced pressure, and the residue was purified by silica gel column chromatography with elution system C to obtain the title compound 5-nitro-1-(tetrahydrofuran-3-yl)-2-(4-(trifluoromethyl)phenyl)-1H-indole 30d (200 mg, 10.6%) as a yellow solid.

MS m/z (ESI): 377.1 [M+1]

Step 3

5-Amino-1-(tetrahydrofuran-3-yl)-2-(4-(trifluoromethyl)phenyl)-1H-indole

5-Nitro-1-(tetrahydrofuran-3-yl)-2-(4-(trifluoromethyl)phenyl)-1H-indole 30d (100 mg, 0.27 mmol) was dissolved in 10 mL of tetrahydrofuran, and then added with Raney nickel (10 mg). The reaction mixture was stirred for 2 hours under a hydrogen atmosphere. The reaction mixture was filtered with celatom, and the filter cake was washed with ethyl acetate (30 mL). The filtrate was concentrated under reduced pressure to obtain the title compound 5-amino-1-(tetrahydrofuran-3-yl)-2-(4-(trifluoromethyl)phenyl)-1H-indole 30e (85 mg, 92.4%) as a yellow solid.

MS m/z (ESI): 347.1 [M+1]

Step 4

2-(Difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide 5-Amino-1-(tetrahydrofuran-3-yl)-2-(4-(trifluoromethyl)phenyl)-1H-indole 30e (70 mg, 0.20 mmol), 2-(difluoromethyl)-5-(((2-fluoro-2-methyl-propanoyl)amino)methyl) nicotinic acid 14b (58 mg, 0.20 mmol), 1-ethyl-(3-dimethylaminopropyl) carbodiimide hydrochloride (58 mg, 0.30 mmol), 1-hydroxybenzotriazole (3 mg, 0.02 mmol) and N,N-diisopropylethylamine (52 mg, 0.40 mmol) were added in 10 mL of N,N-dimethylacetamide, successively. The reaction mixture was stirred for 2 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide 30 (20 mg, 16.1%) as a light yellow solid.

MS m/z (ESI): 619.2[M+1]

$^1$H NMR (400 MHz, DMSO-d$_6$): δ 10.64 (s, 1H), 8.87 (s, 1H), 8.69 (t, 1H), 8.13 (s, 1H), 8.01 (s, 1H), 8.01-7.91 (m, 2H), 7.78-7.76 (m, 2H), 7.72-7.69 (m, 1H), 7.40-7.39 (m, 1H), 7.18 (t, 1H), 6.65 (s, 1H), 5.13 (m, 1H), 4.68-4.67 (m, 2H), 4.48-4.46 (m, 1H), 4.32-4.17 (m, 1H), 3.96-3.91 (m, 1H), 3.67-3.65 (m, 1H), 2.40-2.33 (m, 2H), 1.54-1.42 (d, 6H).

Example 31

(S)-2-(Difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide

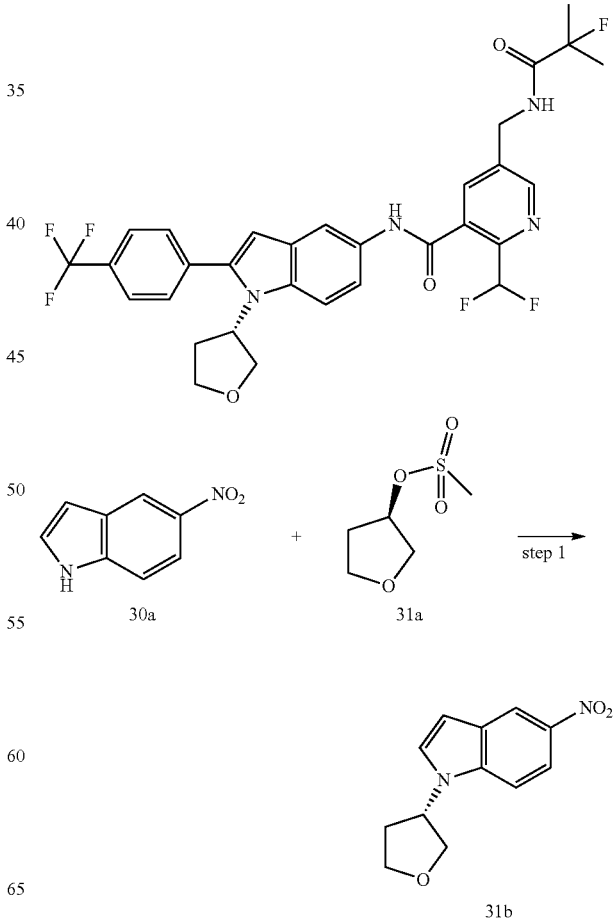

-continued

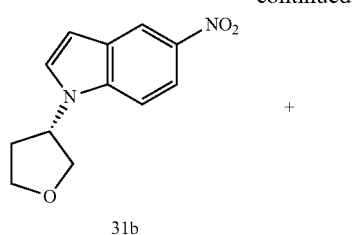

31b

+

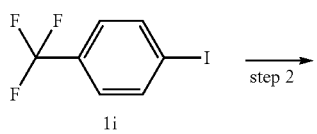

1i

→ step 2

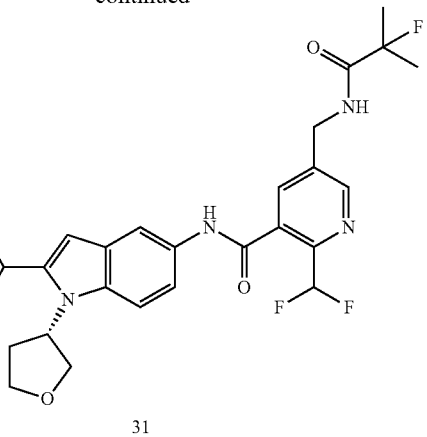

31

Step 1

(S)-5-Nitro-1-(tetrahydrofuran-3-yl)-1H-indole

5-Nitroindole 30a (9.0 g, 55.3 mmol) and caesium carbonate (36.0 g, 110.6 mmol) were dissolved in 100 mL of N,N-dimethylacetamide, and then added with (R) tetrahydrofuran-3-yl methanesulfonate 31a (18.4 g, 110.6 mmol, prepared according to the method disclosed in "*Nature Chemical Biology*, 2008, 4(11), 691-699"). The to reaction mixture was heated to 70° C., and stirred for 16 hours. The reaction solution was poured into 400 mL of ice-water. A lot of solid was precipitated and then filtered out. The filter cake was dissolved in ethyl acetate and filtered. The filtrate was dried over anhydrous sodium sulfate, and then filtered. The filtrate was concentrated under reduced pressure to obtain the title compound (S)-5-nitro-1-(tetrahydrofuran-3-yl)-1H-indole 31b (12 g, 93.8%) as a yellow solid.

MS m/z (ESI): 233.0 [M+1]

Step 2

(S)-5-Nitro-1-(tetrahydrofuran-3-yl)-2-(4-(trifluoromethyl)phenyl)-1H-indole (S)-5-Nitro-1-(tetrahydrofuran-3-yl)-1H-indole 31b (2.0 g, 8.6 mmol) was dissolved in mL of N,N-dimethylacetamide, and then added with 1-iodo-4-(trifluoromethyl)benzene 1i (2.58 g, 9.5 mmol), triphenylphosphine (450 mg, 1.7 mmol), palladium acetate (97 mg, 0.4 mmol) and cesium acetate (5.0 g, 25.9 mmol), successively. The reaction mixture was heated to 140° C., and stirred for 18 hours under an argon atmosphere. The reaction solution was added with 200 mL of water, and extracted with ethyl acetate (200 mL×2). The organic phases were combined and dried over anhydrous sodium sulfate, and filtered. The filtrate was concentrated under reduced pressure, and the residue was purified by silica gel column chromatography with elution system C to obtain the title compound (S)-5-nitro-1-(tetrahydrofuran-3-yl)-2-(4-(trifluoromethyl)phenyl)-1H-indole 31c (200 mg, 5.3%) as a yellow solid.

MS m/z (ESI): 377.1 [M+1]

Step 3

(S)-5-Amino-1-(tetrahydrofuran-3-yl)-2-(4-(trifluoromethyl)phenyl)-1H-indole (S)-5-Nitro-1-(tetrahydrofuran-3-yl)-2-(4-(trifluoromethyl)phenyl)-1H-indole 31c (200 mg, 0.53 mmol) was 31d 31d

+

14b

→ step 4 dissolved in a mixture of 10 mL of tetrahydrofuran and methanol (V:V=1:1), and then added with Raney nickel (20 mg). The reaction mixture was stirred for 2 hours under a hydrogen atmosphere. The reaction mixture was filtered with celatom, and the filtrate was concentrated under reduced pressure to obtain the title compound (S)-5-amino-1-(-tetrahydrofuran-3-yl)-2-(4-(trifluoromethyl)phenyl)-1H-indole 31d (130 mg, 70.7%) as a light yellow solid.

MS m/z (ESI): 347.2 [M+1]

Step 4

(S)-2-(Difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide (S)-5-Amino-1-(tetrahydrofuran-3-yl)-2-(4-(trifluoromethyl)phenyl)-1H-indole 31d (130 mg, 0.38 mmol), 2-(difluoromethyl)-5-(((2-fluoro-2-methyl-propanoyl)amino)methyl)nicotinic acid 14b (58 mg, 0.20 mmol), 1-ethyl-(3-dimethylaminopropyl) carbodiimide hydrochloride (58 mg, 0.30 mmol), 1-hydroxybenzotriazole (4 mg, 0.03 mmol) and triethylamine (139 mg, 1.38 mmol) were added into 5 mL of N,N-dimethylacetamide, successively. The reaction mixture was stirred for 16 hours. The reaction mixture was concentrated under reduced pressure, and the residue was purified by silica gel column chromatography with elution system A to obtain the title compound (S)-2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide 31 (100 mg, 46.9%) as a white solid.

MS m/z (ESI): 619.3[M+1]

$^1$H NMR (400 MHz, DMSO-$d_6$): δ 10.63 (s, 1H), 8.86 (s, 1H), 8.68 (s, 1H), 8.12 (s, 1H), 8.01-8.12 (d, 1H), 7.89-7.91 (d, 2H), 7.75-7.77 (d, 2H), 7.69-7.71 (d, 1H), 7.39-7.40 (d, 1H), 7.31 (t, 1H), 6.64 (s, 1H), 4.46-4.48 (d, 2H), 4.32-4.35 (m, 1H), 4.13-4.17 (m, 1H), 3.91-3.95 (m, 1H), 3.65-3.67 (m, 1H), 2.42-2.45 (m, 1H), 2.32-2.36 (m, 1H), 1.98-2.04 (m, 1H), 1.54 (s, 3H), 1.48 (s, 3H).

Example 32

(R)-2-(Difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide

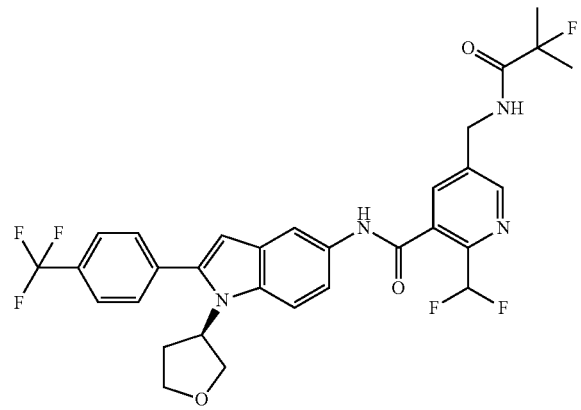

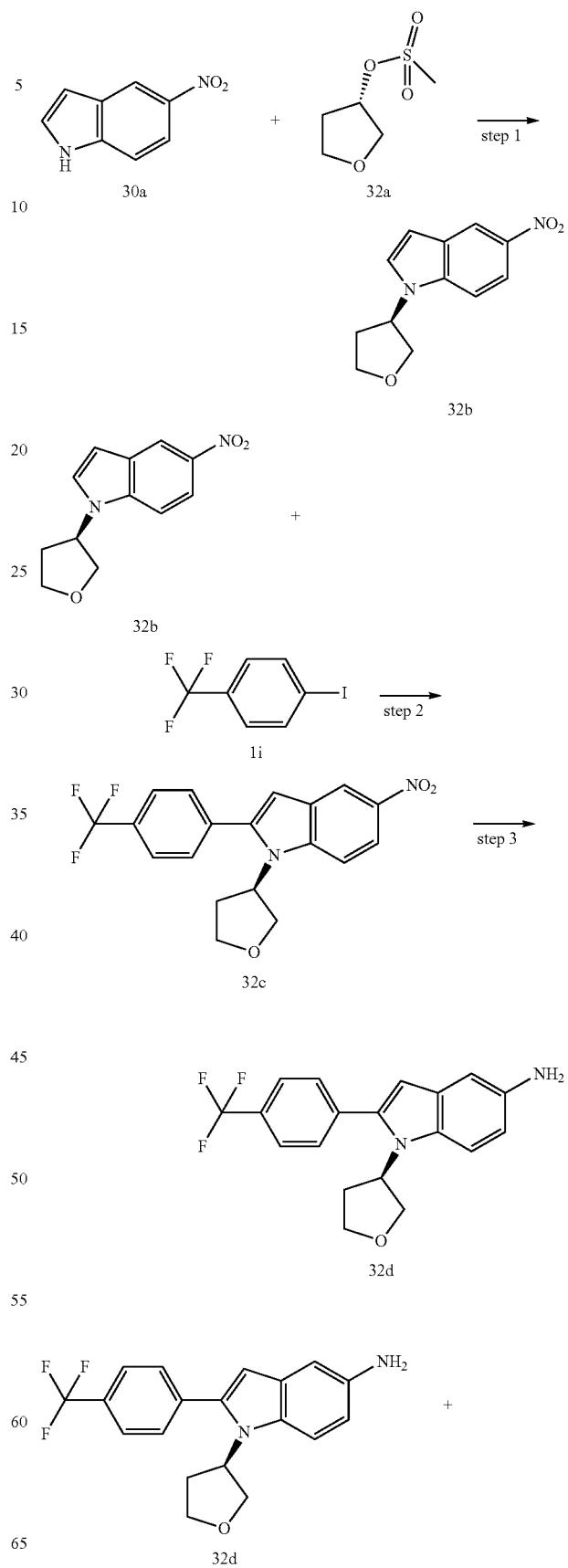

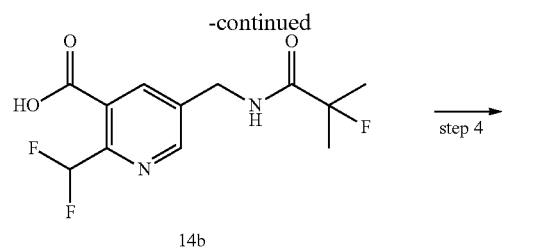

14b

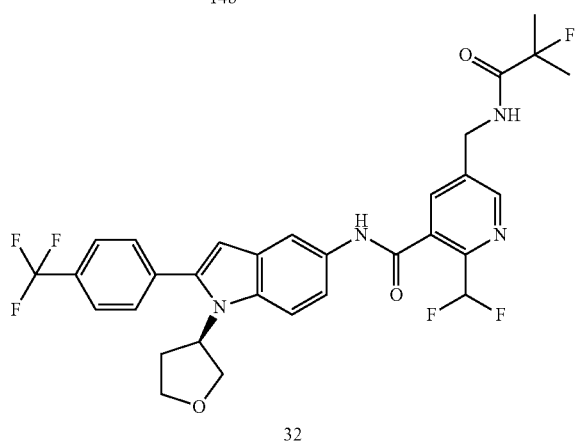

32

Step 1

(R)-5-Nitro-1-(tetrahydrofuran-3-yl)-1H-indole

5-Nitroindole 30a (5.0 g, 30.8 mmol) and cesium carbonate (20.0 g, 61.3 mmol) were dissolved in 70 mL of N,N-dimethylacetamide, and then added with (S)-tetrahydrofuran-3-yl methanesulfonate 32a (10.0 g, 60.2 mmol, prepared according to the method disclosed in "*Nature Chemical Biology*, 2008, 4(11), 691-699"). The reaction mixture was heated to 70° C., and stirred for 16 hours. The reaction solution was poured into 400 mL of ice-water. A lot of solid was precipitated and filtered out. The filter cake was washed with water (50 mL×3), and dried to obtain the title compound (R)-5-nitro-1-(tetrahydrofuran-3-yl)-1H-indole 32b (7.0 g) as a yellow solid which was used in the next step without further purification.

MS m/z (ESI): 233.0 [M+1]

Step 2

(R)-5-Nitro-1-(tetrahydrofuran-3-yl)-2-(4-(trifluoromethyl)phenyl)-1H-indole (R)-5-Nitro-1-(tetrahydrofuran-3-yl)-1H-indole 32b (2.0 g, 8.6 mmol) was dissolved in 80 mL of N, N-dimethylacetamide, and then added with 1-iodo-4-(trifluoromethyl)benzene 1i (2.34 g, 8.6 mmol), triphenylphosphine (485 mg, 1.7 mmol), palladium acetate (200 mg, 0.86 mmol) and cesium acetate (2.5 g, 12.9 mmol), successively. The reaction mixture was heated to 140° C., and stirred for 18 hours under an argon atmosphere. The reaction mixture was concentrated under reduced pressure, and the residue was purified by TLC with elution system C to obtain the title compound (R)-5-nitro-1-(tetrahydrofuran-3-yl)-2-(4-(trifluoromethyl)phenyl)-1H-indole 32c (300 mg, 9.4%) as yellow solid.

MS m/z (ESI): 377.3 [M+1]

Step 3

(R)-5-Amino-1-(tetrahydrofuran-3-yl)-2-(4-(trifluoromethyl)phenyl)-1H-indole (R)-5-Nitro-1-(tetrahydrofuran-3-yl)-2-(4-(trifluoromethyl)phenyl)-1H-indole 32c (200 mg, 0.53 mmol) was dissolved in a mixture of 10 mL of tetrahydrofuran and methanol (V:V=1:1), and then added with Raney nickel (20 mg). The reaction mixture was stirred for 2 hours under a hydrogen atmosphere. The reaction mixture was filtered with celatom, and the filtrate was concentrated under reduced pressure to obtain the title compound (R)-5-amino-1-(tetrahydrofuran-3-yl)-2-(4-(trifluoromethyl)phenyl)-1H-indole 32d (184 mg) as a yellow solid which was used in the next step without further purification.

MS m/z (ESI): 347.0 [M+1]

Step 4

(R)-2-(Difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide (R)-5-Amino-1-(tetrahydrofuran-3-yl)-2-(4-(trifluoromethyl)phenyl)-1H-indole 32d (160 mg, 0.55 mmol), 2-(difluoromethyl)-5-(((2-fluoro-2-methyl-propanoyl)amino)methyl)nicotinic acid 14b (190 mg, 0.55 mmol), 1-ethyl-(3-dimethylaminopropyl) carbodiimide hydrochloride (158 mg, 0.83 mmol), 1-hydroxybenzotriazole (7 mg, 0.05 mmol) and N,N-diisopropylethylamine (142 mg, 1.1 mmol) were added in 10 mL of N,N-dimethylacetamide, successively. The reaction mixture was stirred for 2 hours. The reaction mixture was concentrated under reduced pressure, and the residue was purified by silica gel column chromatography with elution system A to obtain the title compound (R)-2-(difluoromethyl)-5-(((2-fluoro-2-methyl-propanoyl)amino)methyl)-N-(1-(tetrahydrofuran-3-yl)-2-(4-(trifluoromethyl)phenyl)-1H-indol-5-yl)nicotinamide 32 (100 mg, 29.4%) as a white solid.

MS m/z (ESI): 619.2[M+1]

$^1$H NMR (400 MHz, DMSO-d$_6$): δ 10.64 (s, 1H), 8.88 (s, 1H), 8.69 (t, 1H), 8.13 (s, 1H), 8.01 (s, 1H), 7.91-7.89 (m, 2H), 7.78-7.76 (m, 2H), 7.71-7.69 (m, 1H), 7.40-7.39 (m, 1H), 7.31 (t, 1H), 6.65 (s, 1H), 5.13 (m, 1H), 4.48-4.46 (m, 2H), 4.34-4.30 (m, 1H), 4.17-4.14 (m, 1H), 3.95-3.93 (m, 1H), 3.67-3.65 (m, 1H), 2.45-2.33 (m, 2H), 1.53-1.48 (d, 6H).

Example 33

N-(2-(3-Chlorophenyl)-1-methyl-1H-indol-5-yl)-2-(difluoromethyl)-5-(((2-fluoro-2-methyl-propanoyl)amino)methyl)nicotinamide

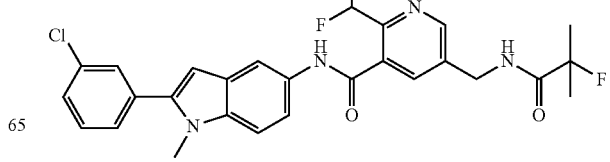

145

-continued

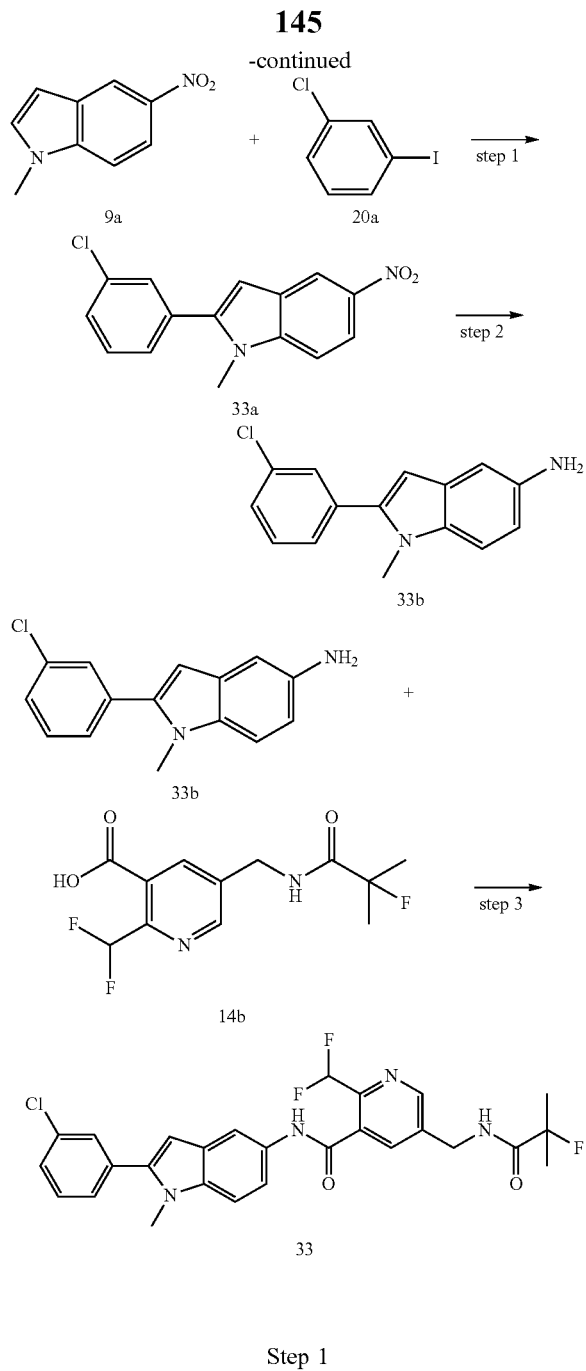

146

Step 2

2-(3-Chlorophenyl)-1-methyl-1H-indol-5-amine 2-(3-Chlorophenyl)-1-methyl-5-nitro-1H-indole 33a (300 mg, 1.05 mmol) was dissolved in a mixture of 20 mL of tetrahydrofuran and methanol (V:V=1:1), and then added with Raney nickel (30 mg). The reaction mixture was stirred for 2 hours under a hydrogen atmosphere. The reaction mixture was filtered with celatom. The filtrate was concentrated under reduced pressure to obtain the crude title compound 2-(3-chlorophenyl)-1-methyl-1H-indol-5-amine 33b (269 mg) as a yellow solid which was used in the next step without further purification.

MS m/z (ESI): 257.1 [M+1]

Step 3

N-(2-(3-Chlorophenyl)-1-methyl-1H-indol-5-yl)-2-(difluoromethyl)-5-(((2-fluoro-2-methyl-propanoyl)amino)methyl)nicotinamide 2-(3-Chlorophenyl)-1-methyl-1H-indol-5-amine 33b (269 mg, 1.05 mmol), 2-(difluoromethyl)-5-(((2-fluoro-2-methyl-propanoyl)amino)methyl)nicotinic acid 14b (305 mg, 1.05 mmol), 1-ethyl-(3-dimethylaminopropyl) carbodiimide hydrochloride (302 mg, 1.58 mmol), 1-hydroxybenzotriazole (14 mg, 0.10 mmol) and N,N-diisopropylethylamine (271 mg, 2.1 mmol) were added in 10 mL of N,N-dimethylacetamide successively. The reaction mixture was stirred for 16 hours. The reaction mixture was concentrated under reduced pressure, and the residues were purified by silica gel column chromatography with elution system A to obtain the title compound N-(2-(3-chlorophenyl)-1-methyl-1H-indol-5-yl)-2-(difluoromethyl)-5-(((2-fluoro-2-methyl-propanoyl)amino)methyl)nicotinamide 33 (30 mg, 5.4% for two steps) as a white solid.

MS m/z (ESI): 529.1 [M+1]

$^1$H NMR (400 MHz, DMSO-d$_6$): δ 10.60 (s, 1H), 8.87 (s, 1H), 8.69 (s, 1H), 8.06 (d, 2H), 7.69 (s, 1H), 7.56-7.51 (m, 4H), 7.45-7.44 (m, 1H), 7.20 (s, 1H), 6.69 (s, 1H), 4.48-4.46 (m, 2H), 3.77 (s, 3H), 1.54 (s, 3H), 1.48 (s, 3H)

Example 34

2-Chloro-N-(2-(4-fluorophenyl)-1-methyl-1H-indol-5-yl)-5-(((1-(trifluoromethyl)cyclopropanecarbonyl)amino)methyl)benzamide

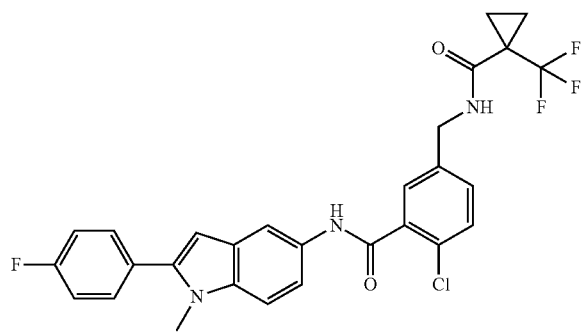

Step 1

2-(3-Chlorophenyl)-1-methyl-5-nitro-1H-indole

1-Methyl-5-nitro-1H-indole 9a (2.0 g, 11.4 mmol) was dissolved in 20 mL N,N-dimethylacetamide, and then added with 1-chloro-3-iodo-benzene 20a (2.7 g, 11.3 mmol), triphenylphosphine (620 mg, 2.2 mmol), palladium acetate (250 mg, 1.1 mmol), and cesium acetate (4.2 g, 22.0 mmol), successively. The reaction mixture was heated to 140° C., and stirred for 18 hours under an argon atmosphere. The reaction mixture was concentrated under reduced pressure, and the residue was purified by TLC with elution system B to obtain the title compound 2-(3-chlorophenyl)-1-methyl-5-nitro-1H-indole 33a (300 mg, 9.5%) as a light yellow solid.

MS m/z (ESI): 287.1 [M+1]

147
-continued

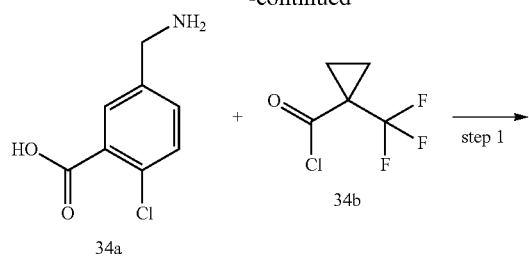

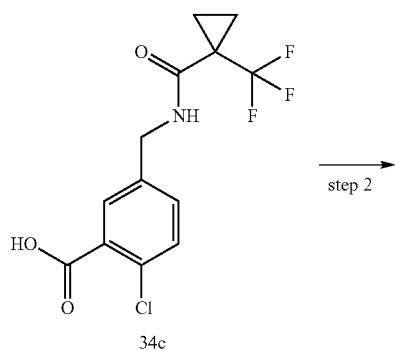

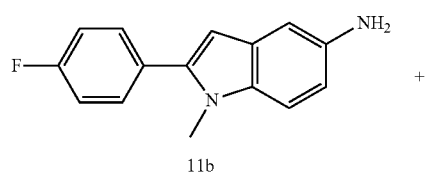

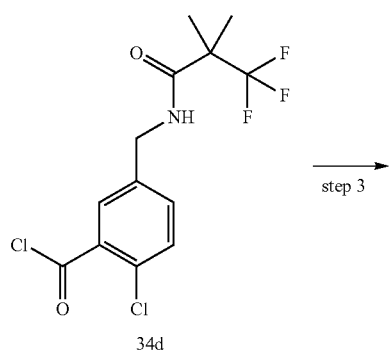

148
-continued

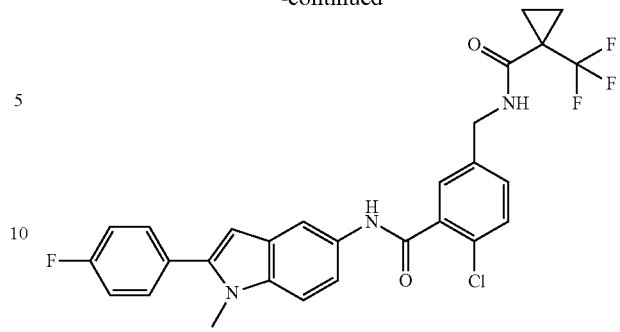

Step 1

2-Chloro-5-(((1-(trifluoromethyl)cyclopropanecarbonyl)amino)methyl)benzoic acid 5-(aminomethyl)-2-chloro-benzoic acid 34a (1.5 g, 6.8 mmol, prepared according to the method disclosed in PCT Patent Application Publication "WO2011048004") and N,N-diisopropylethylamine (2.63 g, 20.3 mmol) were dissolved in 4 mL dicloromethane, and cooled 0° C. under an ice bath. 1-(trifluoromethyl)cyclopropanecarbonyl chloride 34b (1.28 g, 7.5 mmol, prepared according to the method disclosed in PCT Patent Application Publication "WO2005023773") was added and the reaction mixture was warmed up to room temperature and stirred for 5 hours. The reaction mixture was concentrated under reduced pressure to obtain the crude title compound 2-chloro-5-(((1-(trifluoromethyl)cyclopropanecarbonyl)amino)methyl)benzoic acid 34c (2.4 g) as a light yellow oil which was used in the next step without further purification.

MS m/z (ESI): 320.1 [M−1]

Step 2

2-Chloro-5-(((1-(trifluoromethyl)cyclopropanecarbonyl)amino)methyl)benzoyl chloride 2-chloro-5-(((1-(trifluoromethyl)cyclopropanecarbonyl)amino)methyl)benzoic acid 34c (200 mg, 0.62 mmol) and thionyl chloride (222 mg, 1.86 mmol) were dissolved in 20 mL of dicloromethane, and then added with one drop of N,N-dimethylformamide. The reaction mixture was stirred for 3 hours. The reaction mixture was concentrated under reduced pressure to obtain the crude title compound 2-chloro-5-(((1-(trifluoromethyl)cyclopropanecarbonyl)amino)methyl)benzoyl chloride 34d (210 mg) as a light yellow oil which was used in the next step without further purification.

Step 3

2-Chloro-N-(2-(4-fluorophenyl)-1-methyl-1H-indol-5-yl)-5-(((1-(trifluoromethyl)cyclopropanecarbonyl)amino)methyl)benzamide 2-(4-Fluorophenyl)-1-methyl-5-amino-1H-indole 11b (85 mg, 0.35 mmol) was dissolved in 10 mL of dicloromethane, and then added with 2-chloro-5-(((1-(trifluoromethyl)cyclopropanecarbonyl)amino)methyl)benzoyl chloride 34d (120 mg, 0.35 mmol) and N,N-diisopropylethylamine (90 mg, 0.70 mmol). The reaction mixture was stirred for 2 hours. The reaction mixture was concentrated under reduced pressure, and the residue was purified by thin layer chromatography (TLC) with elution system A to obtain the title compound 2-chloro-N-(2-(4-fluorophenyl)-1-methyl-1H-indol-5-yl)-5-(((1-(trifluoromethyl)cyclopropanecarbonyl)amino)methyl)benzamide 34 (20 mg, 10.5%) as a light yellow solid.

MS m/z (ESI): 544.3 [M+1]

$^1$H NMR (400 MHz, DMSO-d$_6$): δ 10.37 (s, 1H), 8.47 (s, 1H), 8.06 (s, 1H), 7.66-7.64 (m, 2H), 7.53-7.35 (m, 7H), 6.58 (s, 1H), 4.34-4.32 (m, 2H), 3.73 (s, 3H), 1.34-1.24 (m, 4H).

Example 35

N-(2-(3-Chlorophenyl)-1-methyl-1H-pyrrolo[3,2-b]pyridin-5-yl)-2-(difluoromethyl)-5-(((2-fluoro-2-methyl-propanoylamino)methylnicotinamide

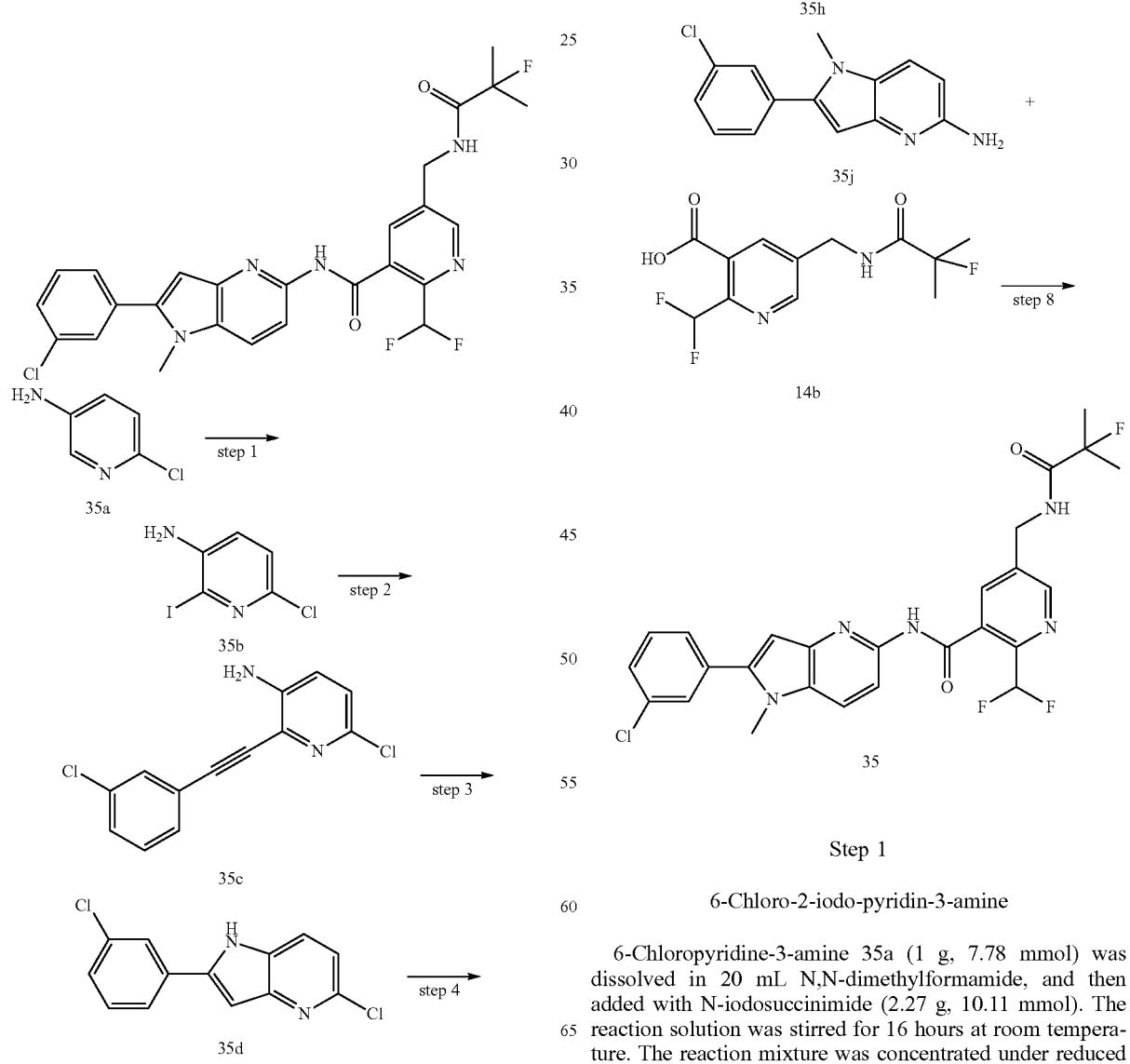

Step 1

6-Chloro-2-iodo-pyridin-3-amine

6-Chloropyridine-3-amine 35a (1 g, 7.78 mmol) was dissolved in 20 mL N,N-dimethylformamide, and then added with N-iodosuccinimide (2.27 g, 10.11 mmol). The reaction solution was stirred for 16 hours at room temperature. The reaction mixture was concentrated under reduced pressure. The residue was purified by thin layer chromatography (TLC) with elution system C to obtain the title compound 6-chloro-2-iodo-pyridin-3-amine 35b (1.37 g, 69.2%) as a brown solid.

Step 2

6-Chloro-2-(2-(3-chlorophenyl)ethynyl)pyridin-3-amine

6-Chloro-2-iodo-pyridin-3-amine 35b (1.37 g, 5.38 mmol), 3-chlorophenylacetylene (882 mg, 6.46 mmol), Bis (triphenylphosephine)palladium(II) chloride (378 mg, 0.54 mmol), cuprous iodide (205 mg, 1.08 mmol) and N,N-diisopropylethylamine (1.39 g, 10.76 mmol) were added into 10 mL of N,N-dimethylformamide. The reaction mixture was stirred for 16 hours at 100° C. under an argon atmosphere. The reaction mixture was concentrated under reduced pressure. The residue was purified by thin layer chromatography (TLC) with elution system C to obtain the title compound 6-chloro-2-((3-chlorophenyl)ethynyl)pyridin-3-amine 35c (871 mg, 61.6%) as a brown solid.

Step 3

5-Chloro-2-(3-chlorophenyl)-1H-pyrrolo[3,2-b]pyridine

6-Chloro-2-((3-chlorophenyl)ethynyl)pyridin-3-amine 35c (871 mg, 3.32 mmol) and potassium tert-butanolate (746 mg, 6.64 mmol) was dissolved in 20 mL of N,N-dimethylformamide. The resulting mixture was stirred for 16 hours at 70° C. The reaction mixture was concentrated under reduced pressure. The residue was added with 10 mL of ethyl acetate, and filtered. The filtrate was concentrated under reduced pressure to obtain the crude title compound 5-chloro-2-(3-chlorophenyl)-1H-pyrrolo[3,2-b]pyridine 35d (1.17 g) as a yellow solid which was used in the next step without further purification.

Step 4

5-Chloro-2-(3-chlorophenyl)-1-methyl-1H-pyrrolo[3,2-b]pyridine

5-Chloro-2-(3-chlorophenyl)-1H-pyrrolo[3,2-b]pyridine 35d (1.17 g, 4.46 mmol) was dissolved in 15 mL N,N-dimethylformamide, and then added with 60% sodium hydride (268 mg, 6.69 mmol). The reaction mixture was stirred for 30 minutes at room temperature. Iodomethane (761 mg, 5.36 mmol) was added and continually stirred for 2 hours at room temperature. The reaction mixture was concentrated under reduced pressure. The residue was purified by thin layer chromatography (TLC) with elution system C to obtain the title compound 5-chloro-2-(3-chlorophenyl)-1-methyl-1H-pyrrolo[3,2-b]pyridine 35e (650 mg, 52.8%) as a yellow solid.

Step 5

2-(3-Chlorophenyl)-N-(4-methoxybenzyl)-1-methyl-1H-pyrrolo[3,2-b]pyridin-5-amine 5-Chloro-2-(3-chlorophenyl)-1-methyl-1H-pyrrolo[3,2-b]pyridine 35e (276 mg, 1.0 mmol), 4-methoxybenzylamine (172 mg, 1.25 mmol), Tris(dibenzylideneacetone)dipalladium (92 mg, 0.1 mmol), (±)-2,2'-Bis(diphenylphosphino)-1,1'-binaphthyl (125 mg, 0.2 mmol), and potassium phosphate (425 mg, 2 mmol) were dissolved in 15 mL of 1,4-dioxane. The reaction mixture was stirred for 16 hours at 100° C. under an argon atmosphere. The reaction mixture was concentrated under reduced pressure. The residue was purified by thin layer chromatography (TLC) with elution system A to obtain the title compound 2-(3-chlorophenyl)-N-(4-methoxybenzyl)-1-methyl-1H-pyrrolo[3,2-b]pyridin-5-amine 35f (221 mg, 58.5%) as a yellow solid.

Step 6

N-(2-(3-Chlorophenyl)-1-methyl-1H-pyrrolo[3,2-b]pyridin-5-yl)-2,2,2-trifluoro-acetamide 2-(3-Chlorophenyl)-N-(4-methoxybenzyl)-1-methyl-1H-pyrrolo[3,2-b]pyridin-5-amine 35f (221 mg, 0.58 mmol) was dissolved in 5 mL of trifluoroacetic acid. The resulting mixture was stirred for 16 hours at 60° C. The reaction mixture was concentrated under reduced pressure to obtain the crude title compound N-(2-(3-chlorophenyl)-1-methyl-1H-pyrrolo[3,2-b]pyridin-5-yl)-2,2,2-trifluoroacetamide 35h (207 mg) as a brown oil which was used in the next step without further purification.

Step 7

2-(3-Chlorophenyl)-1-methyl-1H-pyrrolo[3,2-b]pyridine-5-amine

N-(2-(3-Chlorophenyl)-1-methyl-1H-pyrrolo[3,2-b]pyridin-5-yl)-2,2,2-trifluoroacetamide 35h (207 mg, 0.58 mmol) and potassium carbonate (162 mg, 1.17 mmol) were dissolved in 10 mL ethanol. The reaction mixture was stirred for 1 hour at 80° C. The reaction mixture was concentrated under reduced pressure. The residue was purified by thin layer chromatography (TLC) with elution system A to obtain the title compound 2-(3-chlorophenyl)-1-methyl-1H-pyrrolo[3,2-b]pyridine-5-amine 35j (30 mg, 20%) as a light yellow solid.

Step 8

N-(2-(3-Chlorophenyl)-1-methyl-1H-pyrrolo[3,2-b]pyridin-5-yl)-2-(difluoromethyl)-5-(((2-fluoro-2-methyl-propanoyl)amino)methyl)nicotinamide 2-(Difluoromethyl)-5-(((2-fluoro-2-methyl-propanoyl)amino)methyl)nicotinic acid 14b (34 mg, 0.12 mmol) and 2-(3-chlorophenyl)-1-methyl-1H-pyrrolo[3,2-b]pyridine-5-amine 35j (30 mg, 0.12 mmol) were dissolved in 15 mL of N,N-Dimethylformamide, and then added with triethylamine (47 mg, 0.46 mmol), 1-hydroxybenzotriazole (16 mg, 0.12 mmol) and 1-ethyl-(3-dimethylaminopropyl) carbodiimide hydrochloride (34 mg, 0.17 mmol). The reaction mixture was stirred for 16 hours at room temperature. The reaction mixture was concentrated under reduced pressure, and the residue was purified by thin layer chromatography (TLC) with elution system A to obtain the title compound N-(2-(3-chlorophenyl)-1-methyl-1H-pyrrolo[3,2-b]pyridin-5-yl)-2-(difluoromethyl)-5-(((2-fluoro-2-methyl-propanoyl)amino)methyl)nicotinamide 35 (3 mg, 4.8%) as an off-white solid.

MS m/z (ESI): 530.1 [M+1]

$^1$H NMR (400 MHz, CDCl$_3$): δ 8.63 (s, 1H), 8.34 (s, 1H), 7.96 (s, 1H), 7.82 (s, 1H), 7.54-7.43 (m, 4H), 7.31 (s, 1H), 6.93 (s, 1H), 6.42 (s, 1H), 4.43 (s, 2H), 3.83 (s, 3H), 1.64 (s, 3H), 1.59 (s, 3H).

Example 36

N-(2-(3-Chlorophenyl)-1-methyl-1H-pyrrolo[2,3-c]pyridin-5-yl)-2-(difluoromethyl)-5-(((2-fluoro-2-methyl-propanoyl)amino)methyl)nicotinamide

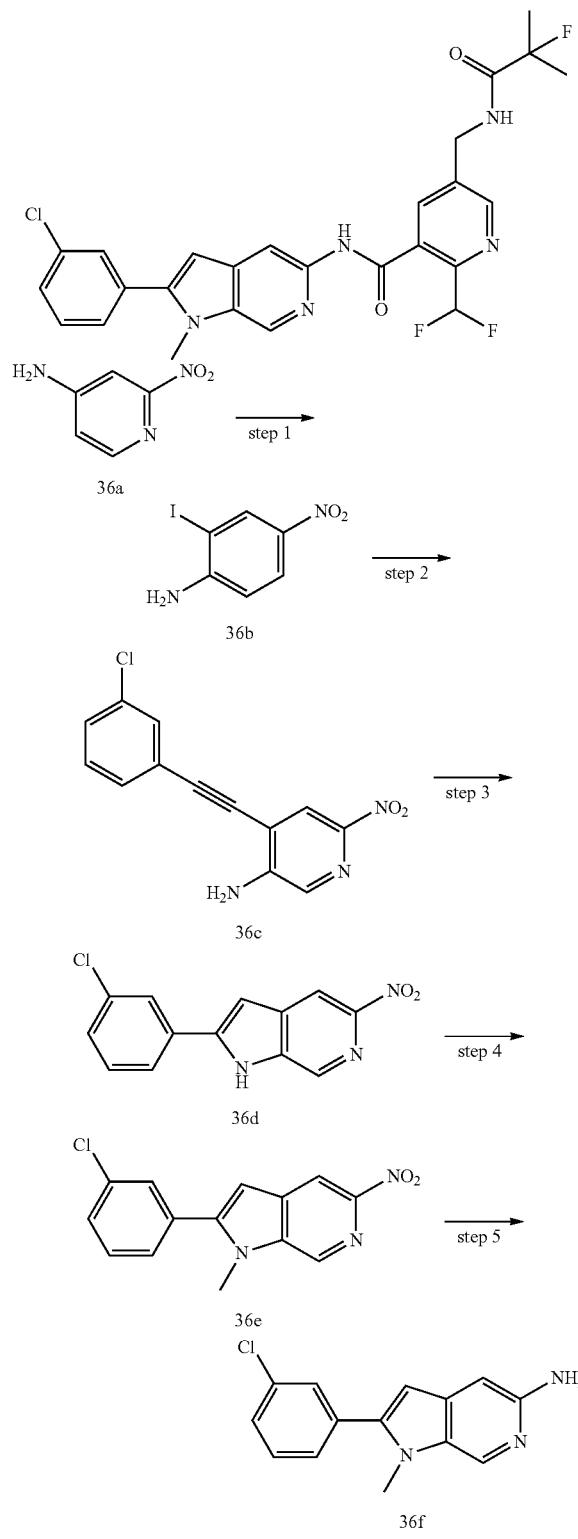

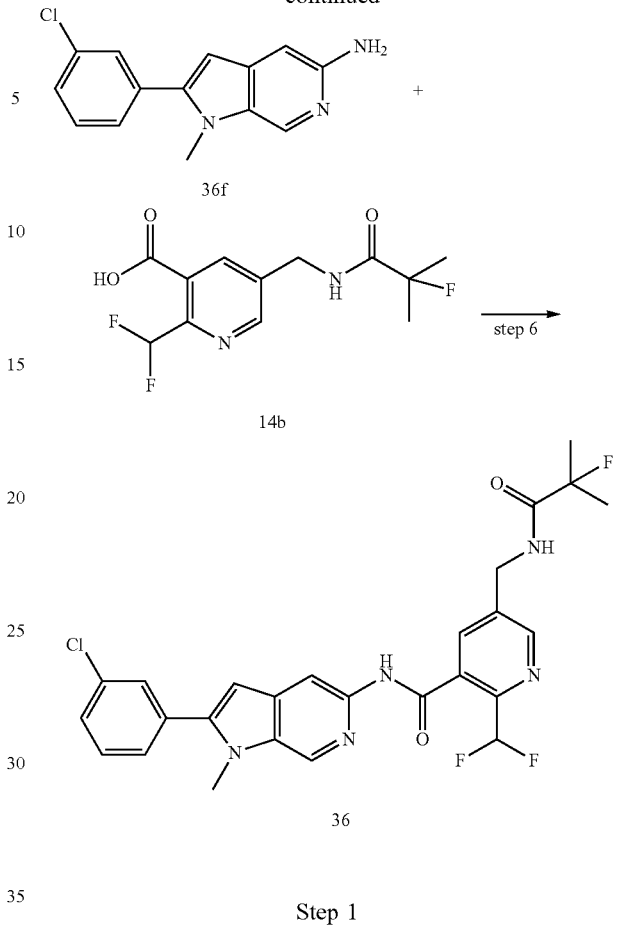

Step 1

4-Iodo-6-nitro-pyridine-3-amine

5-Amino-2-nitropyridine 36a (1 g, 7.2 mmol), potassium iodate (770 mg, 3.6 mmol) and potassium iodide (1.2 g, 7.2 mmol) were added in 30 mL of sulfuric acid (2N), successively. The reaction solution was stirred for 16 hours at 80° C. and then cooled to room temperature. The reaction mixture was adjusted to pH 10 with 2N sodium hydroxide aqueous solution. An amount of solid was precipitated and filtered out. The filter cake was washed with water, and dried to obtain the title compound 4-iodo-6-nitro-pyridin-3-amine 36b (1.5 g, 79%) as a yellow solid.

Step 2

4-((3-Chlorophenyl)ethynyl)-6-nitro-pyridine-3-amine

4-Iodo-6-nitro-pyridine-3-amine 36b (1.5 g, 5.7 mmol), 3-chlorophenylacetylene (850 mg, 6.2 mmol), cuprous iodide (1.1 g, 5.7 mmol), (1,1'-Bis(diphenylphosphino)ferrocene) dichloropalladium(II) (834 mg, 1.14 mmol) and triethylamine (1.6 mL, 11.4 mmol) were added into 20 mL of N,N-dimethylformamide, successively. The reaction mixture was stirred for 16 hours under an argon atmosphere. The reaction mixture was concentrated under reduced pressure. The residue was purified by silica gel column chromatography with elution system A to obtain the title compound 4-((3-chlorophenyl)ethynyl)-6-nitro-pyridine-3-amine 36c (1.5 g, 97%) as a yellow solid.

Step 3

2-(3-Chlorophenyl)-5-nitro-1H-pyrrolo[2,3-c]pyridine 4-((3-Chlorophenyl)ethynyl)-6-nitro-pyridine-3-amine 36c (200 mg, 0.73 mmol), potassium tertbutanolate (123 mg, 1.1 mmol) and 10 mL of N,N-dimethylformamide were added in a 50 mL flask. The resulting mixture was stirred for 16 hours at 60° C. The reaction mixture was concentrated under reduced pressure to obtain the crude title compound 2-(3-chlorophenyl)-5-nitro-1H-pyrrolo[2,3-c]pyridine 36d (300 mg) as a brown oil which was used in the next step without further purification.

Step 4

2-(3-Chlorophenyl)-1-methyl-5-nitro-1H-pyrrolo[2,3-c]pyridine 2-(3-Chlorophenyl)-5-nitro-1H-pyrrolo[2,3-c]pyridine 36d (300 mg, 1.1 mmol), iodomethane (233 mg, 1.64 mmol), cesium carbonate (717 mg, 2.2 mmol) and 10 mL of N,N-dimethylformamide were added in a 100 mL flask. The reaction mixture was stirred for 16 hours at room temperature. The reaction mixture was concentrated under reduced pressure. The residue was purified by thin layer chromatography (TLC) with elution system A to obtain the title compound 2-(3-chlorophenyl)-1-methyl-5-nitro-1H-pyrrolo(2,3-c)pyridine 36e (50 mg, 15.8%) as a yellow solid.

Step 5

2-(3-Chlorophenyl)-1-methyl-1H-pyrrolo[2,3-c]pyridine-5-amine 2-(3-Chlorophenyl)-1-methyl-5-nitro-1H-pyrrolo[2,3-c]pyridine 36e (50 mg, 0.17 mmol), Raney nickel (5 mg) and 10 mL of tetrahydrofuran were added in a 50 mL flask. The reaction mixture was stirred for 2 hours at room temperature under a hydrogen atmosphere. The reaction mixture was filtered. The filtrate was concentrated under reduced pressure to obtain the title compound 2-(3-chlorophenyl)-1-methyl-1H-pyrrolo[2,3-c]pyridine-5-amine 36f (40 mg, 88.9%) as a light yellow solid.

Step 6

N-(2-(3-Chlorophenyl)-1-methyl-1H-pyrrolo[2,3-c]pyridin-5-yl)-2-(difluoromethyl)-5-(((2-fluoro-2-methyl-propanoyl)amino)methyl)nicotinamide 2-(Difluoromethyl)-5-(((2-fluoro-2-methyl-propanoyl)amino)methyl)nicotinic acid 14b (45 mg, 0.16 mmol), 2-(3-chlorophenyl)-1-methyl-1H-pyrrolo[2,3-c]pyridin-5-amine 36f (40 mg, 0.16 mmol), 1-hydroxybenzotriazole (2.2 mg, 0.016 mmol), 1-ethyl-3-(3-dimethylaminopropyl)carbodiimide hydrochloride (46 mg, 0.24 mmol) and N,N-diisopropylethylamine (31 mg, 0.24 mmol) were dissolved in N,N-dimethylformamide. The reaction mixture was stirred for 2 hours at 70° C. The reaction mixture was concentrated under reduced pressure, and the residue was purified by thin layer chromatography (TLC) with elution system A to obtain the title compound N-(2-(3-chlorophenyl)-1-methyl-1H-pyrrolo[2,3-c]pyridin-5-yl)-2-(difluoromethyl)-5-(((2-fluoro-2-methyl-propanoyl)amino)methyl)nicotinamide 36 (20 mg, 23.5%) as light yellow solid.

MS m/z (ESI): 530.1 [(M+1])

$^1$H NMR (400 MHz, DMSO-d$_6$): δ 11.15 (s, 1H), 8.82-8.80 (m, 1H), 8.67 (s, 1H), 8.07-8.05 (m, 3H), 7.75 (s, 1H), 7.66-7.65 (m, 1H), 7.57-7.55 (m, 2H), 7.21 (s, 1H), 6.72 (s, 1H), 4.46-4.44 (d, 2H), 3.83 (s, 3H), 1.53 (s, 3H), 1.48 (s, 3H).

Example 37

N-(2-(3-Chlorophenyl)-1-ethyl-1H-pyrrolo[3,2-b]pyridin-5-yl)-2-(difluoromethyl)-5-(((2-fluoro-2-methyl-propanoyl)amino)methyl)nicotinamide

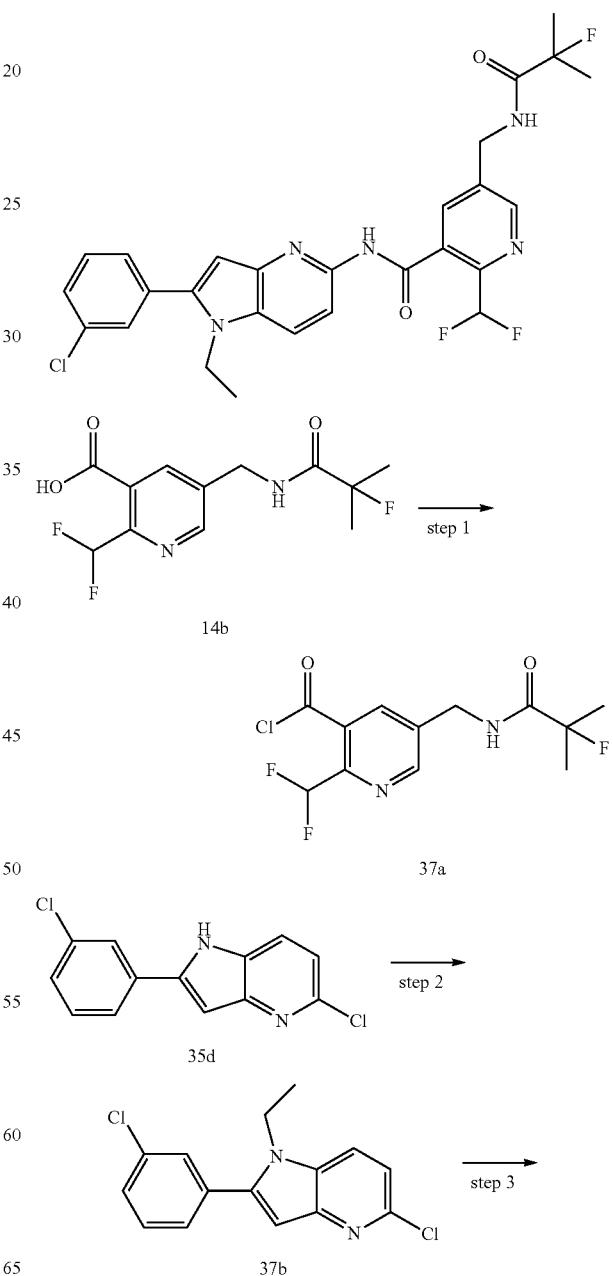

-continued

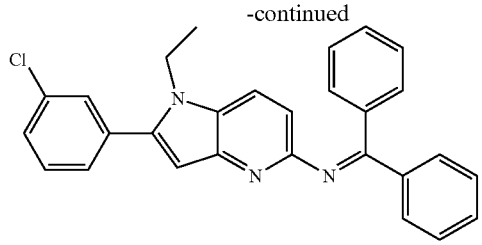

37c

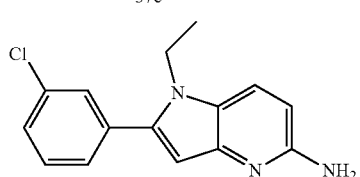

37d

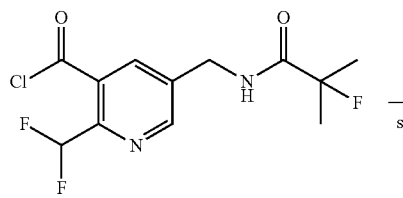

37a

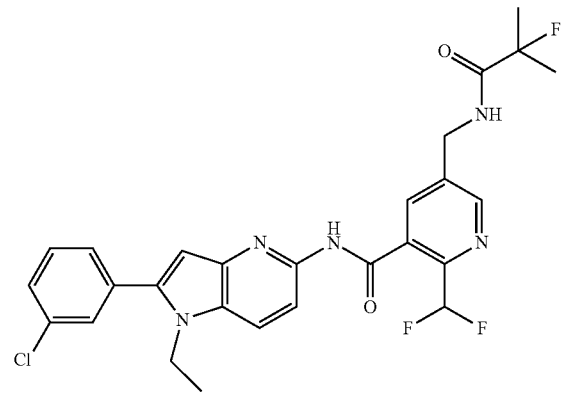

37

Step 1

2-(Difluoromethyl)-5-(((2-fluoro-2-methyl-propanoyl)amino)methyl)nicotinoyl chloride 2-(Difluoromethyl)-5-(((2-fluoro-2-methyl-propanoyl)amino)methyl)nicotinic acid 14 b (1.5 g, 5.17 mmol) was dissolved in 10 mL of dichloromethane, and then added with thionyl chloride (1.2 mL, 15.5 mmol) and 2 drops of N,N-dimethylformamide. The reaction solution was stirred for 1 hour at room temperature. The reaction mixture was concentrated under reduced pressure to obtain the crude title compound 2-(difluoromethyl)-5-(((2-fluoro-2-methyl-propanoyl)amino)methyl)nicotinoyl chloride 37a (1.6 g) as a white solid which was used in the next step without further purification.

Step 2

5-Chloro-2-(3-chlorophenyl)-1-ethyl-1H-pyrrolo[3,2-b]pyridine

5-Chloro-2-(3-chlorophenyl)-1H-pyrrolo[3,2-b]pyridine 35d (0.87 g, 3.32 mmol) was dissolved in 20 mL of N,N-dimethylformamide, and then added with 60% sodium hydride (0.2 g, 4.98 mmol). The reaction mixture was stirred for 30 minutes at room temperature, and then added with iodoethane (0.62 g, 3.98 mmol) and continually stirred for another 2 hours at room temperature. The reaction mixture was added with 10 mL of water, and concentrated under reduced pressure. The residue was purified by thin layer chromatography (TLC) with elution system A to obtain the title compound 5-chloro-2-(3-chlorophenyl)-1-ethyl-1H-pyrrolo[3,2-b]pyridine 37b (0.35 g, 36.3%) as a yellow oil.

Step 3

(2-(3-Chlorophenyl)-N-(diphenymethylenyl)-1-ethyl-1H-pyrrolo[3,2-b]pyridine-5-amine 5-Chloro-2-(3-chlorophenyl)-1-ethyl-1H-pyrrolo[3,2-b]pyridine 37b (30 mg, 0.1 mmol), benzophenone imine (22 mg, 0.12 mmol), tris(dibenzylideneacetone)dipalladium (9.5 mg, 0.01 mmol), 4,5-bis(diphenylphosphino)-9,9-dimethyxanthene (12 mg, 0.021 mmol) and potassium phosphate (44 mg, 0.21 mmol) were dissolved in 2 mL of 1,4-dioxane. The resulting mixture was stirred for 16 hours at 100° C. under an argon atmosphere. The reaction mixture was concentrated under reduced pressure. The residue was added with a little tetrahydrofuran, and filtered. The filtrate was concentrated under reduced pressure to obtain the crude title compound (2-(3-chlorophenyl)-N-(diphenylmethylenyl)-1-ethyl-1H-pyrrolo[3,2-b]pyridin-5-amine 37c (50 mg) as a gray solid which was used in the next step without further purification.

Step 4

2-(3-Chlorophenyl)-1-ethyl-1H-pyrrolo[3,2-b]pyridin-5-amine (2-(3-Chlorophenyl)-N-(diphenylmethylenyl)-1-ethyl-1H-pyrrolo[3,2-h]pyridin-5-amine 37c (50 mg, 0.12 mmol) was dissolved in 10 mL of tetrahydrofuran, and then added with 4 mL of 2 M hydrochloric acid solution. The reaction mixture was stirred for 2 hours at room temperature. The reaction mixture was concentrated under reduced pressure, and then adjusted to pH>7 with saturated sodium bicarbonate solution. The mixture was concentrated under reduced pressure, and the residue was purified by thin layer chromatography (TLC) with elution system A to obtain the crude title compound 2-(3-chlorophenyl)-1-ethyl-1H-pyrrolo[3,2-b]pyridine-5-amine 37d (62 mg) as a yellow solid which was used in the next step without further purification.

Step 5

N-(2-(3-Chlorophenyl)-1-ethyl-1H-pyrrolo[3,2-b]pyridin-5-yl)-2-(difluoromethyl)-5-(((2-fluoro-2-methyl-propanoyl)amino)methyl)nicotinamide 2-(Difluoromethyl)-5-(((2-fluoro-2-methyl-propanoyl)amino)methyl)nicotinoyl chloride 37a (13.5 mg, 0.044 mmol) was dissolved in 10 mL of dichloromethane, and then added with triethylamine (94 mg, 0.088 mmol) and 2-(3- chlorophenyl)-1-ethyl-1H-pyrrolo[3,2-b]pyridine-5-amine 37d (11.9 mg, 0.044 mmol). The reaction mixture was stirred for 3 hours at room temperature. The reaction mixture was concentrated under reduced pressure, and the residue was purified by thin layer chromatography (TLC) with elution system C to obtain the title compound N-(2-(3-chlorophenyl)-1-ethyl-1H-pyrrolo[3,2-b]pyridin-5-yl)-2-(difluoromethyl)-5-(((2-fluoro-2-methyl-propanoyl)amino)methyl)nicotinamide 37 (5 mg, 20.8%) as a white solid.

MS m/z (ESI): 544.1 [M+1]

$^1$H NMR (400 MHz, CDCl$_3$): δ 13.16 (s, 1H), 8.84-8.82 (d, 2H), 8.72-8.70 (d, 1H), 8.26-8.24 (d, 1H), 7.57-7.52 (m, 3H), 7.43-7.42 (d, 1H), 7.36-7.31 (m, 2H), 6.81 (s, 1H), 4.71-4.69 (d, 2H), 4.39-4.33 (m, 2H), 1.64 (s, 3H), 1.59 (s, 3H), 1.44-1.42 (m, 3H).

Example 38

2-(Difluoromethyl)-5-((2-methylpropanoylamino)methyl)-N-(2-(4-(trifluoromethyl)phenyl)benzo[d]oxazol-5-yl)nicotinamide

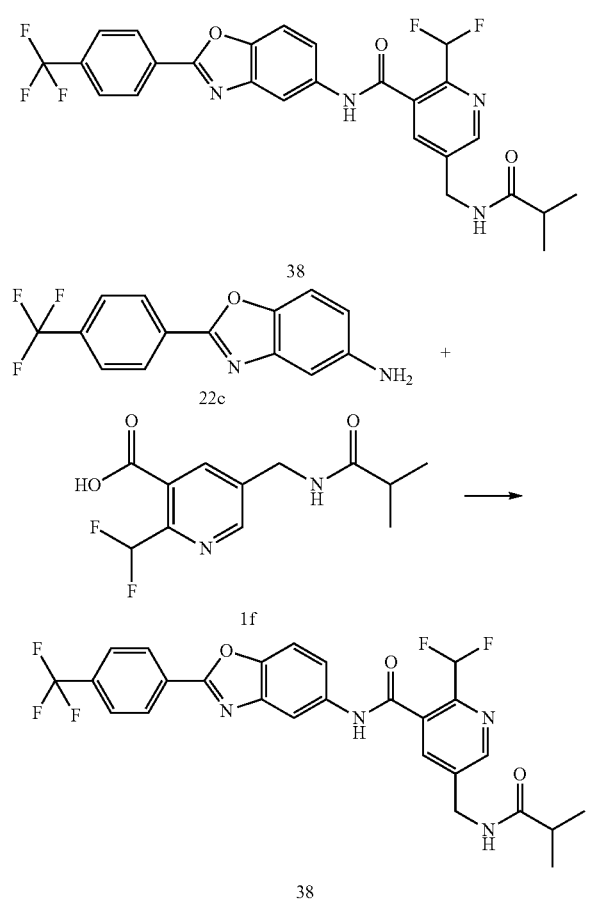

2-(4-(Trifluoromethyl)phenyl)benzo[d]oxazol-5-amine 22c (120 mg, 0.44 mmol) was dissolved in 5 mL of N,N-dimethylformamide, and then added with 2-(difluoromethyl)-5-((2-methylpropanoylamino)methyl)nicotinic acid 1f (100 mg, 0.37 mmol), 1-(3-dimethylaminopropyl)-3-ethylcarbodiimide hydrochloride (140 mg, 0.74 mmol), 1-hydroxybenzotriazole (5 mg, 0.037 mmol) and triethylamime (200 μL, 1.47 μmol). The resulting mixture was heated to 70° C., and stirred for 3 hours. The reaction solution was cooled to room temperature. The reaction mixture was concentrated under reduced pressure, and the residue was purified by silica gel column chromatography with elution system A to obtain the title compound 2-(difluoromethyl)-5-((2-methylpropanoylamino)methyl)-N-(2-(4-(trifluoromethyl)phenyl)benzo[d]oxazol-5-yl)nicotinamide 38 (60 mg, 30.6%) as a white solid.

MS m/z (ESI): 533.2[M+1]

$^1$H NMR (400 MHz, DMSO-d$_6$): δ 11.00 (s, 1H), 8.81 (s, 1H), 8.61 (t, 1H), 8.21-8.27 (m, 3H), 8.10 (s, 1H), 7.83 (d, 1H), 7.72 (d, 3H), 7.22 (t, 1H), 4.44 (d, 2H), 2.49 (d, 1H), 1.06 (d, 6H).

Example 39

2-(Difluoromethyl)-5-((2-methylpropanoylamino)methyl)-N-(2-(4-(trifluoromethyl)phenyl)benzofuran-5-yl)nicotinamide

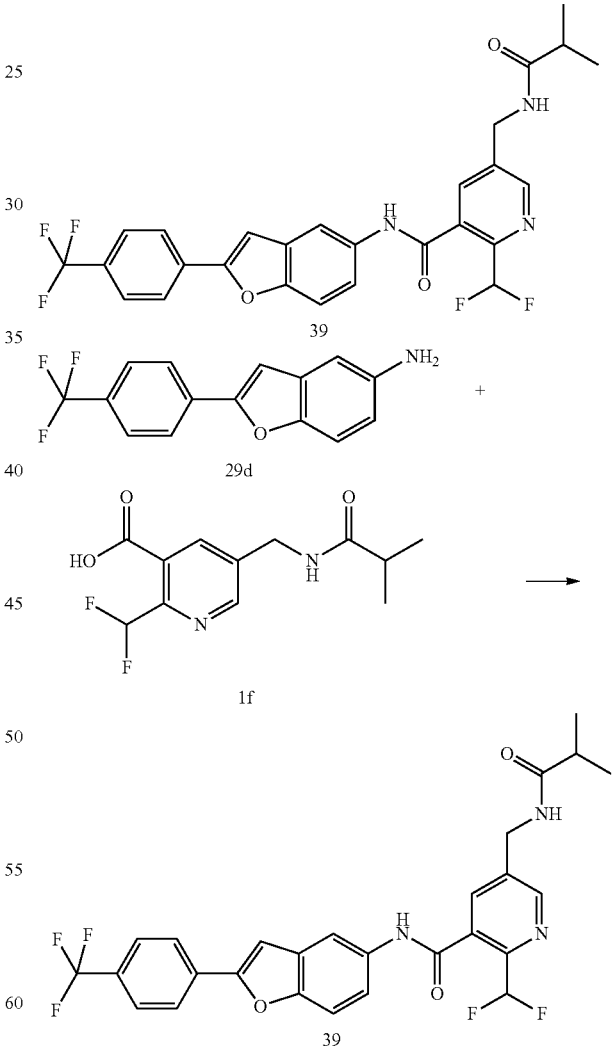

5-Amino-2-(4-(trifluoromethyl)phenyl)benzofuran 29d (70 mg, 0.25 mmol), 2-(difluoromethyl)-5-((2-methylpropanoylamino)methyl)nicotinic acid 1f (69 mg, 0.25 mmol), 1-(3-dimethylaminopropyl)-3-ethylcarbodiimide hydrochloride (97 mg, 0.51 mmol), 1-hydroxybenzotriazole (3 mg, 0.025 mmol) and triethylamime (140 μL, 0.80 μmol) were added in 5 mL of N,N-dimethylformamide, successively. The resulting mixture was heated to 70° C. and stirred for 2 hours. The reaction mixture was concentrated under reduced pressure, and the residue was purified by thin layer chromatography (TLC) with elution system A to obtain the title compound 2-(difluoromethyl)-5-((2-methylpropanoylamino)methyl)-N-(2-(4-(trifluoromethyl)phen yl)benzofuran-5-yl)nicotinamide 39 (70 mg, 52.2%) as an off-white solid.

MS m/z (ESI): 532.2 [M+1]

$^1$H NMR (400 MHz, DMSO-$d_6$): δ 10.81 (s, 1H), 8.70 (s, 1H), 8.48 (s, 1H), 8.20 (s, 1H), 8.15 (d, 2H), 8.04 (s, 1H), 7.89 (d, 2H), 7.73 (s, 1H), 7.69 (s, 1H), 7.59 (s, 1H), 7.19 (s, 1H), 4.44 (d, 2H), 2.47 (d, 1H), 1.06 (d, 6H).

Example 40

2-(Difluoromethyl)-5-((2-methylpropanoylamino)methyl)-N-(2-(4-(trifluoromethyl)phenyl)isoindolin-5-yl)nicotinamide 2-(4-(Trifluoromethyl)phenyl)isoindoline-5-amine 25d (10 mg, 0.036 mmol) and 2-(difluoromethyl)-5-((2-methylpropanoylamino)methyl)nicotinic acid 1f (10 mg, 0.036 mmol) were dissolved in 5 mL of N,N-dimethylformamide, and then added with 1-(3-dimethylaminopropyl)-3-ethylcarbodiimide hydrochloride (11 mg, 0.054 mmol) and 1-hydroxybenzotriazole (5 mg, 0.036 mmol). The resulting mixture was stirred for 1 hour. The reaction mixture was concentrated under reduced pressure, and the residue was purified by thin layer chromatography (TLC) with elution system A to obtain the title compound 2-(difluoromethyl)-5-((2-methylpropanoylamino)methyl)-N-(2-(4-(trifluoromethyl)phen yl)isoindolin-5-yl)nicotinamide 40 (10 mg, 52.6%) as a white solid.

MS m/z (ESI): 533.1 [M+1]

$^1$H NMR (400 MHz. DMSO-$d_6$): δ 10.62 (s, 1H), 8.66 (s, 1H), 8.44 (d, 1H), 8.07 (s, 1H), 8.00 (s, 1H), 7.88-7.85 (m, 4H), 7.54 (d, 1H), 7.47 (d, 1H), 7.42 (t, 1H), 4.60 (s, 4H), 4.41 (d, 2H), 3.18-3.17 (m, 1H), 1.05 (s, 6H)

Example 41

2-Chloro-5-(((1-methylcyclopropanecarbonyl)amino)methyl)-N-(2-(4-(trifluoromethyl)phenyl)benzo[d]oxazol-5-yl)benzamide

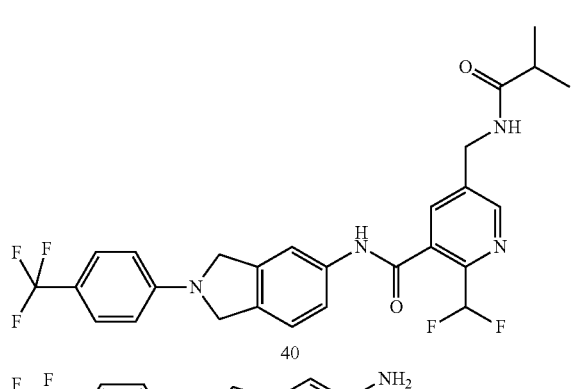

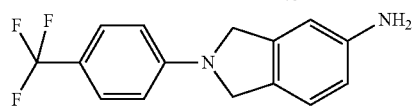

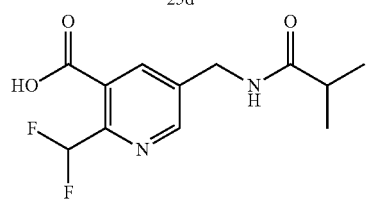

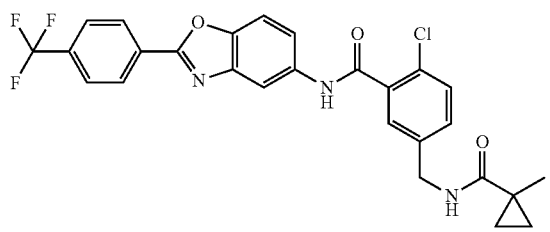

41

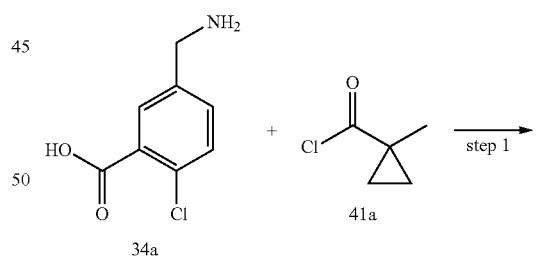

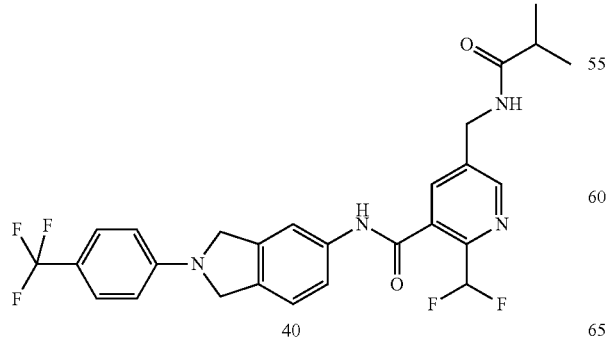

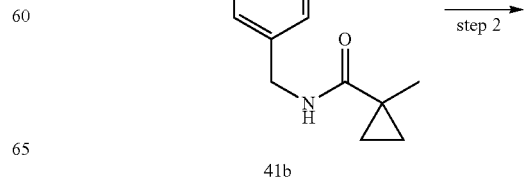

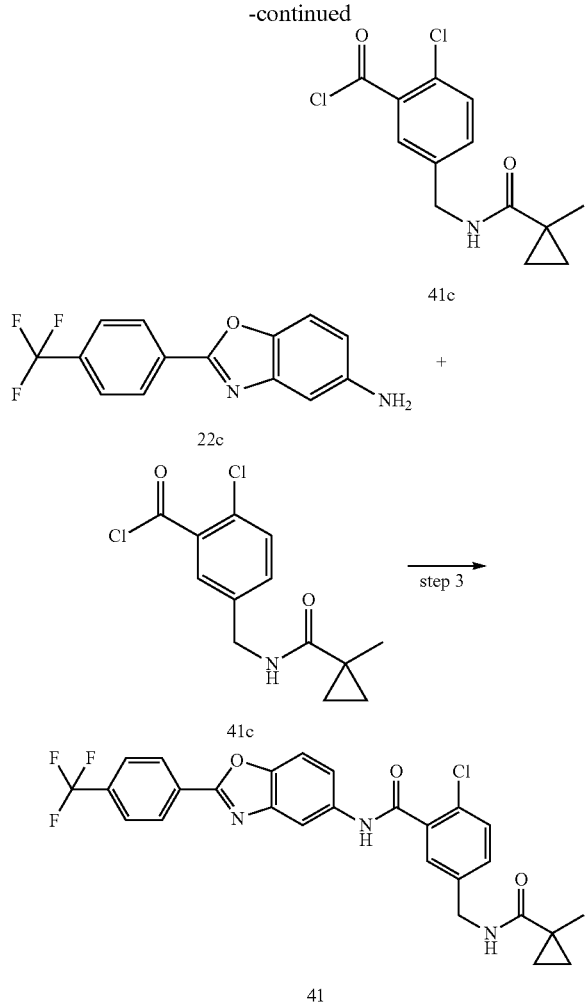

Step 1

2-Chloro-5-(((1-methylcyclopropanecarbonyl)amino)methyl)benzoic acid 5-(Aminomethyl)-2-chloro-benzoic acid 34a (1.5 g, 6.8 mmol, prepared according to the method disclosed in PCT Patent Application Publication "WO2011048004") and triethylamine (3.2 mL, 23.2 mmol) were dissolved in 15 mL of tetrahydrofuran, and then cooled to 0° C. under an ice bath. A solution of 1-methylcyclopropanecarbonyl chloride 41a (890 mg, 7.47 mmol, prepared according to the method disclosed in "*Journal of Medicinal Chemistry*, 2014, 57(22), 9323-9342") in 5 mL of tetrahydrofuran was added to the above mixture dropwise. The reaction mixture was warmed up to room temperature, and then stirred for 1 hour. The reaction mixture was concentrated under reduced pressure to obtain the crude title compound 2-chloro-5-(((1-methylcyclopropanecarbonyl)amino)methyl)benzoic acid 41b (4.78 g,) as a white solid which was used in the next step without further purification.

MS m/z (ESI): 266.1 [M−1]

Step 2

2-Chloro-5-(((1-methylcyclopropanecarbonyl)amino)methyl)benzoyl chloride

2-Chloro-5-(((1-methylcyclopropanecarbonyl)amino)methyl)benzoic acid 41b (200 mg, 0.75 mmol) was dissolved in 10 mL of dichloromethane, and then added with thionyl chloride (0.2 mL, 2.75 mmol). The reaction solution was stirred for 15 minutes at room temperature. The reaction mixture was concentrated under reduced pressure to obtain the title compound 2-chloro-5-(((1-methylcyclopropanecarbonyl)amino)methyl)benzoyl chloride 41c crude (220 mg) as yellow oil which was used in the next step without further purification.

Step 3

2-Chloro-5-(((1-methylcyclopropanecarbonyl)amino)methyl)-N-(2-(4-(trifluoromethyl)phenyl)benzo[d]oxazol-5-yl)benzamide 2-(4-(trifluoromethyl)phenyl)benzo[d]oxazol-6-amine 22c (90 mg, 0.33 mmol) and triethylamine (90 μL, 0.65 μmol) were dissolved in 5 mL of tetrahydrofuran, and then added with a solution of 2-chloro-5-(((1-methylcyclopropanecarbonyl)amino)methyl)benzoyl chloride 41c (220 mg, 0.72 mmol) in 5 mL of tetrahydrofuran dropwise. The reaction mixture was stirred for 30 minutes. The reaction mixture was filtered and concentrated under reduced pressure. The residue was purified by thin layer chromatography (TLC) with elution system A to obtain the title compound 2-chloro-5-(((1-methylcyclopropanecarbonyl)amino)methyl)-N-(2-(4-(trifluoromethyl)phenyl)benzo[d]oxazol-5-yl)benzamide 41 (30 mg, 17.4% for two steps) as a yellow solid.

MS m/z (ESI): 528.3 [M+1]

$^1$H NMR (400 MHz, DMSO-d$_6$): δ 10.78 (s, 1H), 8.42 (d, 2H), 8.33 (s, 1H), 8.23 (t, 1H), 8.01 (d, 2H), 7.84 (d, 1H), 7.72 (d, 1H), 7.54 (d, 1H), 7.49 (s, 1H), 7.39 (d, 1H), 4.31 (d, 2H), 1.30 (s, 3H), 0.97 (d, 2H), 0.54 (d, 2H).

Example 42

N-(2-(4-Chlorophenyl)-1-ethyl-1H-indol-5-yl)-2-(difluoromethyl)-5-(((1-methylcyclopropanecarbonyl)amino)methyl)nicotinamide

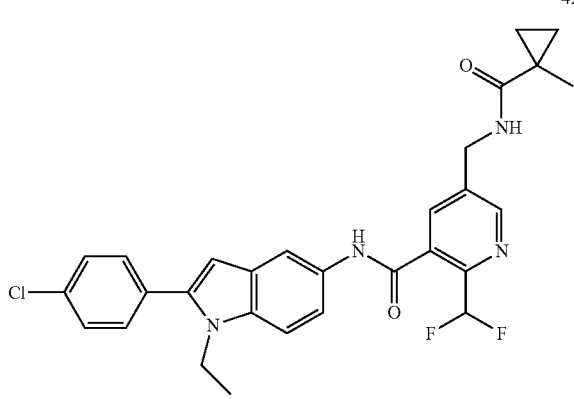

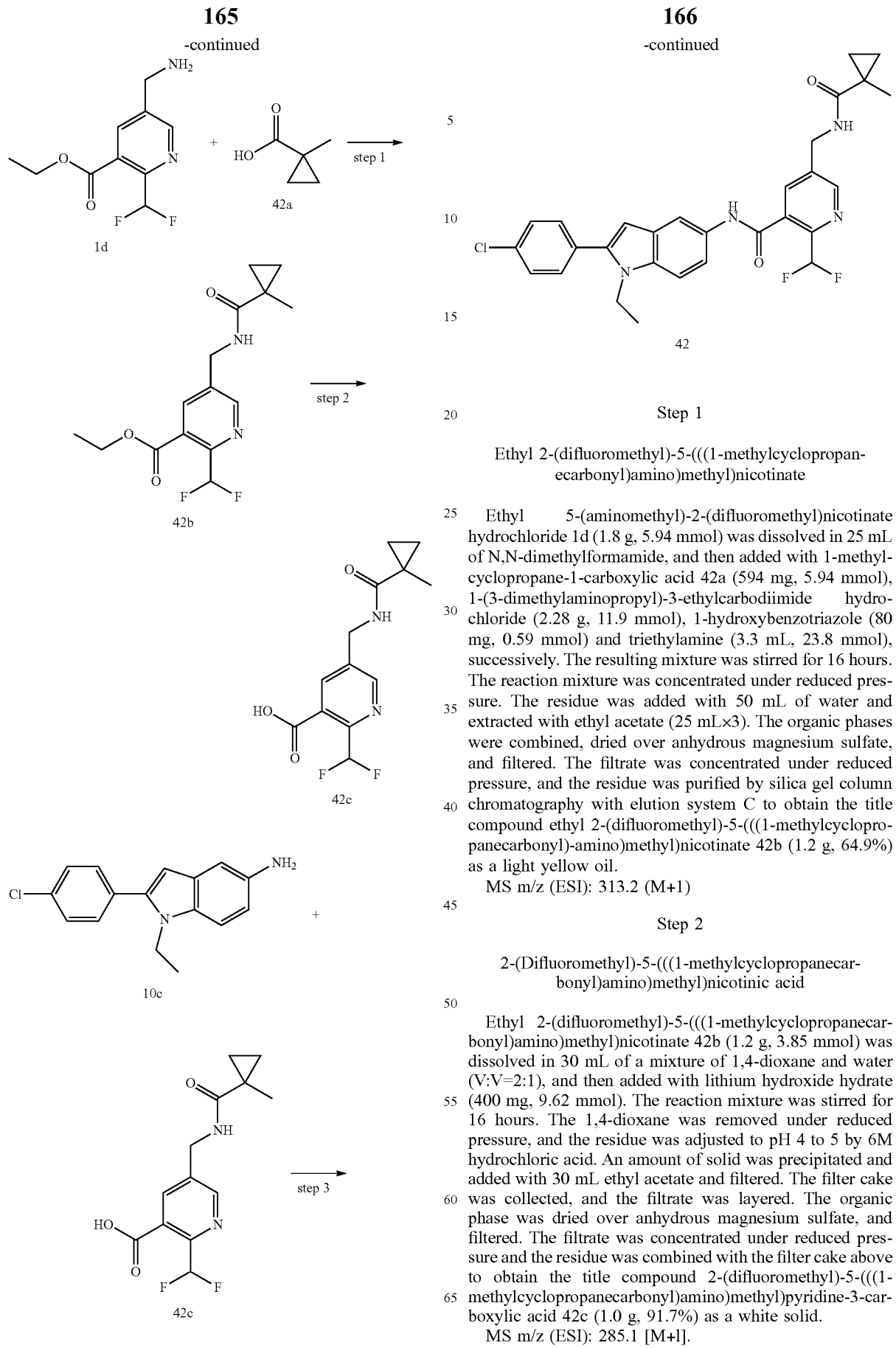

Step 1

Ethyl 2-(difluoromethyl)-5-(((1-methylcyclopropan-ecarbonyl)amino)methyl)nicotinate Ethyl 5-(aminomethyl)-2-(difluoromethyl)nicotinate hydrochloride 1d (1.8 g, 5.94 mmol) was dissolved in 25 mL of N,N-dimethylformamide, and then added with 1-methyl-cyclopropane-1-carboxylic acid 42a (594 mg, 5.94 mmol), 1-(3-dimethylaminopropyl)-3-ethylcarbodiimide hydrochloride (2.28 g, 11.9 mmol), 1-hydroxybenzotriazole (80 mg, 0.59 mmol) and triethylamine (3.3 mL, 23.8 mmol), successively. The resulting mixture was stirred for 16 hours. The reaction mixture was concentrated under reduced pressure. The residue was added with 50 mL of water and extracted with ethyl acetate (25 mL×3). The organic phases were combined, dried over anhydrous magnesium sulfate, and filtered. The filtrate was concentrated under reduced pressure, and the residue was purified by silica gel column chromatography with elution system C to obtain the title compound ethyl 2-(difluoromethyl)-5-(((1-methylcyclopropanecarbonyl)-amino)methyl)nicotinate 42b (1.2 g, 64.9%) as a light yellow oil.

MS m/z (ESI): 313.2 (M+1)

Step 2

2-(Difluoromethyl)-5-(((1-methylcyclopropanecarbonyl)amino)methyl)nicotinic acid Ethyl 2-(difluoromethyl)-5-(((1-methylcyclopropanecarbonyl)amino)methyl)nicotinate 42b (1.2 g, 3.85 mmol) was dissolved in 30 mL of a mixture of 1,4-dioxane and water (V:V=2:1), and then added with lithium hydroxide hydrate (400 mg, 9.62 mmol). The reaction mixture was stirred for 16 hours. The 1,4-dioxane was removed under reduced pressure, and the residue was adjusted to pH 4 to 5 by 6M hydrochloric acid. An amount of solid was precipitated and added with 30 mL ethyl acetate and filtered. The filter cake was collected, and the filtrate was layered. The organic phase was dried over anhydrous magnesium sulfate, and filtered. The filtrate was concentrated under reduced pressure and the residue was combined with the filter cake above to obtain the title compound 2-(difluoromethyl)-5-(((1-methylcyclopropanecarbonyl)amino)methyl)pyridine-3-carboxylic acid 42c (1.0 g, 91.7%) as a white solid.

MS m/z (ESI): 285.1 [M+l].

Step 3

N-(2-(4-Chlorophenyl)-1-ethyl-1H-indol-5-yl)-2-(difluoromethyl)-5-(((1-methylcyclopropanecarbonyl)amino)methyl)nicotinamide 2-(Difluoromethyl)-5-(((1-methylcyclopropanecarbonyl)amino)methyl)nicotinic acid 42c (52 mg, 0.19 mmol), 1-ethyl-2-(4-chlorophenyl)-5-amino-1H-indole 10c (50 mg, 0.19 mmol), 1-(3-dimethylaminopropyl)-3-ethylcarbodiimide hydrochloride (71 mg, 0.37 mmol), 1-hydroxybenzotriazole (2.5 mg, 18.5 µmol) and triethylamine (100 µL, 0.74 mmol) were dissolved in 5 mL of N,N-dimethylformamide. The reaction mixture was heated to 70° C. and stirred for 2 hours. The reaction mixture was cooled to room temperature and then concentrated under reduced pressure. The residue was purified by thin layer chromatography (TLC) with elution system A to obtain the title compound N-(2-(4-chlorophenyl)-1-ethyl-1H-indol-5-yl)-2-(difluoromethyl)-5-(((1-methylcyclopropanecarbonyl)amino)methyl)nicotinamide 42 (40 mg, 40.4%) as a yellow solid.

MS m/z (ESI): 538.2 [M+1]

$^1$H NMR (400 MHz, DMSO-$d_6$): δ 10.62 (s, 1H), 8.69 (s, 1H), 8.31 (s, 1H), 8.04 (d, 2H), 7.55-7.69 (m, 3H), 7.44 (d, 2H), 7.19 (t, 1H), 6.60 (s, 1H), 4.43 (d, 2H), 4.22 (d, 2H), 1.32 (s, 3H), 1.20 (t, 3H), 1.00 (s, 3H), 0.56 (s, 2H).

Example 43

2-(Difluoromethyl)-5-(((1-methylcyclopropanecarbonyl)amino)methyl)-N-(2-(4-(trifluoromethyl)phenyl)benzo[d]oxazol-5-yl)nicotinamide

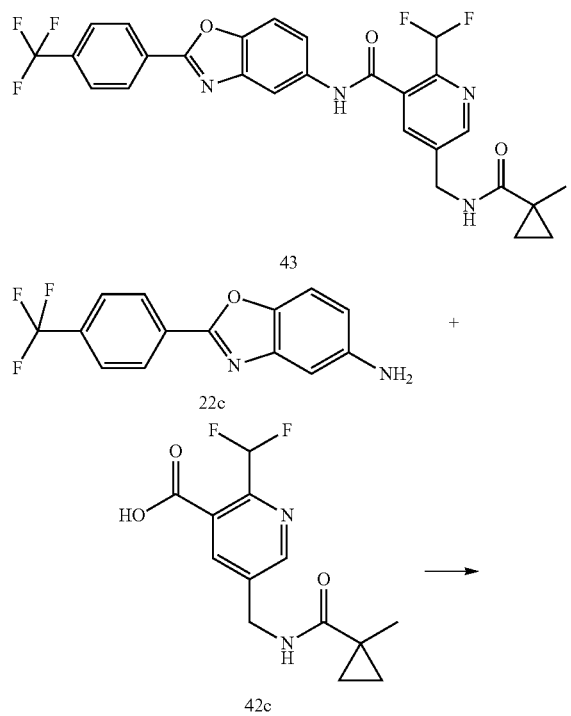

2-(4-(Trifluoromethyl)phenyl)benzo[d]oxazol-5-amine 22c (50 mg, 0.18 mmol) was dissolved in 5 mL of N,N-dimethylformamide, and then added with 2-(difluoromethyl)-5-(((1-methylcyclopropanecarbonyl)amino)methyl)nicotinic acid 42c (51 mg, 0.18 mmol), 1-(3-dimethylaminopropyl)-3-ethylcarbodiimide hydrochloride (75 mg, 0.39 mmol), 1-hydroxybenzotriazole (2.4 mg, 0.018 mmol) and triethylamine (0.1 mL, 720 µmol). The reaction mixture was heated to 70° C., and stirred for 2 hours. The reaction mixture was cooled to room temperature and, then concentrated under reduced pressure. The residue was purified by thin layer chromatography (TLC) with elution system A to obtain the title compound 2-(difluoromethyl)-5-(((1-methylcyclopropanecarbonyl)amino)methyl)-N-(2-(4-(trifluoromethyl)phenyl)benzo[d]oxazol-5-yl)nicotinamide 43 (20 mg, 20.4%) as a yellow solid.

MS m/z (ESI): 545.3 [M+1]

$^1$H NMR (400 MHz, DMSO-$d_6$): δ 10.95 (s, 1H), 8.70 (d, 1H), 8.43 (d, 2H), 8.30 (t, 2H), 8.03 (d, 3H), 7.87 (d, 1H), 7.72 (d, 1H), 7.19 (t, 1H), 4.43 (d, 2H), 1.31 (s, 3H), 0.99 (d, 2H), 0.56 (d, 2H).

Example 44

N-(2-(4-Chlorophenyl)-1-methyl-1H-pyrrolo(2,3-b)pyridin-5-yl)-2-(difluoromethyl)-5-(((2-fluoro-2-methyl-propanoyl)amino)methyl)nicotinamide

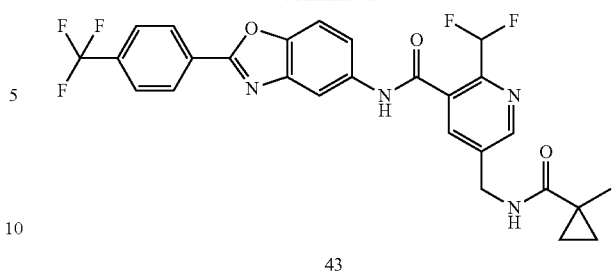

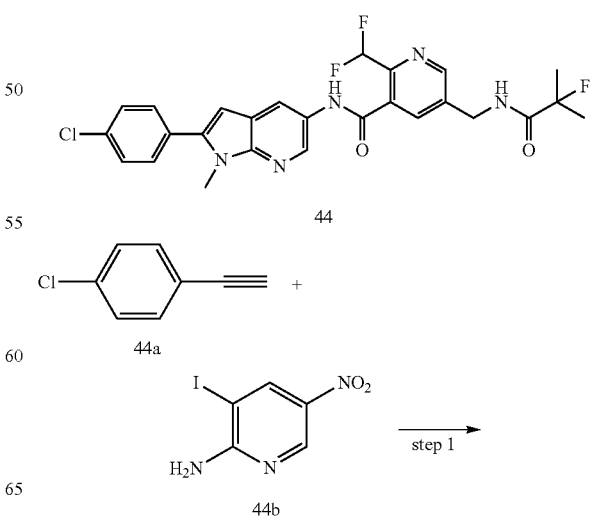

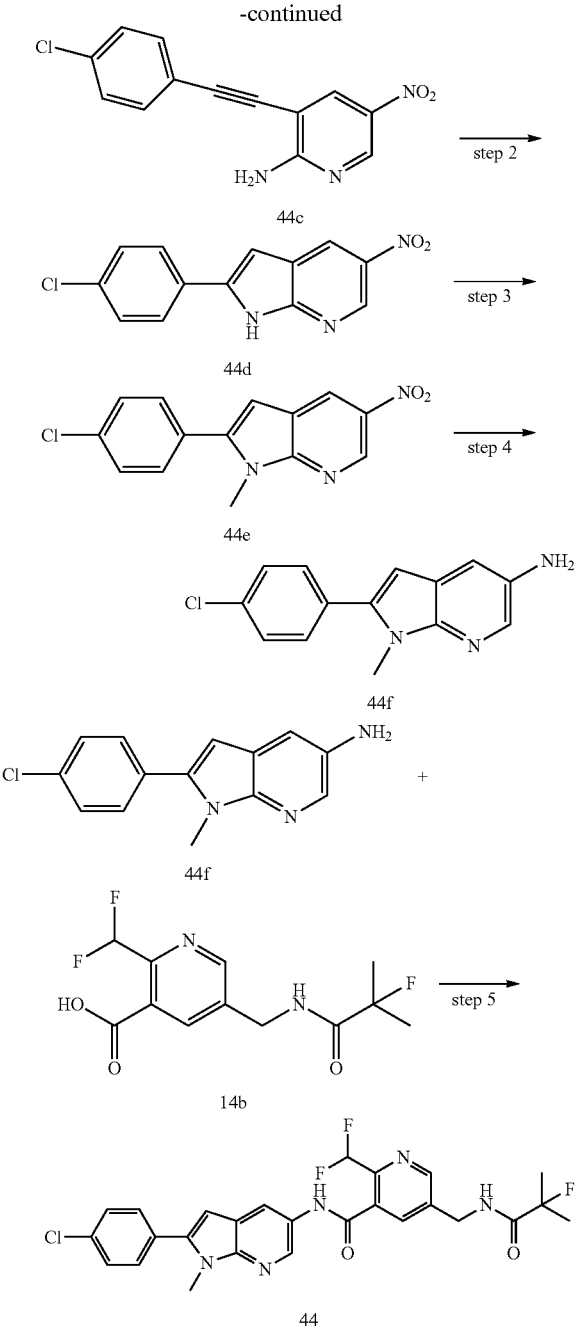

anhydrous sodium sulfate, and filtered. The filtrate was concentrated under reduced pressure. The residue was purified by thin layer chromatography (TLC) with elution system A to obtain the title compound 3-((4-chlorophenyl) ethynyl)-5-nitro-pyridine-2-amine 44c (250 mg, 80.9%) as a yellow solid.

MS m/z (ESI): 272.0 [M−1]

Step 2

2-(4-Chlorophenyl)-5-nitro-1H-pyrrolo(2,3-b)pyridine 3-(4-Chlorophenyl)ethynyl)-5-nitro-pyridine-2-amine 44c (160 mg, 0.58 mmol) and potassium tertbutanolate (746 mg, 6.64 mmol) were dissolved in 10 mL of N,N-dimethylformamide. The reaction mixture was heated to 70° C. and stirred for 3 hours. The reaction mixture was concentrated under reduced pressure. The residue was mixed with 50 mL of ethyl acetate, and filtered. The filtrate was concentrated under reduced pressure to obtain the crude title compound 2-(4-chlorophenyl)-5-nitro-1H-pyrrolo(2,3-b)pyridine 44d (160 mg) as a yellow solid which was used in the next step without further purification.

MS m/z (ESI): 273.0 [M−1]

Step 3

2-(4-Chlorophenyl)-1-methyl-5-nitro-1H-pyrrolo[2,3-b]pyridine 2-(4-Chlorophenyl)-5-nitro-1H-pyrrolo[2,3-b]pyridine 44d (160 mg, 0.58 mmol) was dissolved in 5 mL N,N-dimethylformamide, and then added with cesium carbonate (380 mg, 1.17 mmol) and iodomethane (73 μL, 1.17 mmol. The reaction mixture was stirred for 3 hours. The reaction mixture was concentrated under reduced pressure. The residue was purified by thin layer chromatography (TLC) with elution system C to obtain the title compound 2-(4-chlorophenyl)-1-methyl-5-nitro-1H-pyrrolo[2,3-b]pyridine 44e (30 mg, 17.9% for two steps) as a yellow solid.

MS m/z (ESI): 290.0 [M+1]

Step 4

2-(4-Chlorophenyl)-1-methyl-1H-pyrrolo[2,3-b]pyridine-5-amine 2-(4-Chlorophenyl)-1-methyl-5-nitro-1H-pyrrolo[2,3-b]pyridine 44e (50 mg, 0.17 mmol) was dissolved in a mixture of 10 mL of tetrahydrofuran and methanol (V:V=1:1), and then added with Raney nickel (30 mg). The reaction mixture was stirred for 1 hour under a hydrogen atmosphere. The reaction mixture was filtered with celatom, and the filtrate was concentrated under reduced pressure to obtain the crude title compound 2-(4-chlorophenyl)-1-methyl-1H-pyrrolo[2,3-b]pyridin-5-amine 44f (45 mg) as a light yellow solid which was used in the next step without further purification.

MS m/z (ESI): 259.1 [M+1]

Step 5

N-(2-(4-Chlorophenyl)-1-methyl-1H-pyrrolo[2,3-b]pyridin-5-yl)-2-(difluoromethyl)-5-(((2-fluoro-2-methyl-propanoyl)amino)methyl)nicotinamide 2-(4-Chlorophenyl)-1-methyl-1H-pyrrolo[2,3-b]pyridin-5-amine 44f (50 mg, 0.17 mmol), 2-(difluoromethyl)-5-(((2-

Step 1

3-((4-Chlorophenyl)ethynyl)-5-nitro-pyridine-2-amine

2-Amino-3-iodo-5-nitro-pyridine 44b (300 mg, 1.13 mmol), 4-chlorophenylacetylene 44a (325 mg, 2.38 mmol), bis(triphenylphosphine)palladium(II) chloride (40 mg, 56.5 μmol), cuprous iodide (11 mg, 56.5 μmol) and triethylamine (1.6 mL, 11.3 mmol) were added into 20 mL of N,N-dimethylformamide, successively. The reaction mixture was stirred for 16 hours under an argon atmosphere. The reaction mixture was added with 100 mL of ethyl acetate, and washed with water (50 mL×2). The organic phases were dried over fluoro-2-methyl-propanoyl)amino)methyl)nicotinic acid 14b (50 mg, 0.17 mmol), 1-ethyl-(3-dimethylaminopropyl)-3carbodiimide hydrochloride (67 mg, 0.35 mmol) and 1-hydroxybenzotriazole (2.3 mg, 17.4 µmol) were added in 5 mL of N,N-dimethylformamide, successively. The reaction mixture was stirred for 2 hours. The reaction mixture was concentrated under reduced pressure, and the residue was purified by thin layer chromatography (TLC) with elution system A to obtain the title compound N-(2-(4-chlorophenyl)-1-methyl-1H-pyrrolo[2,3-b]pyridin-5-yl)-2-(difluoromethyl)-5-(((2-fluoro-2-methyl-propanoyl)amino)methyl) nicotinamide 44 (3 mg, 3.3%) as a yellow solid.

MS m/z (ESI): 531.1 [M+1]

$^1$H NMR (400 MHz, DMSO-d$_6$): δ 10.86 (s, 1H), 8.71 (s, 1H), 8.51 (t, 1H), 8.20-8.27 (m, 2H), 8.05 (s, 2H), 7.82 (d, 1H), 7.71 (d, 2H), 7.19 (t, 1H), 6.55 (s, 1H), 4.47 (d, 2H), 3.83 (s, 3H), 1.54 (s, 3H), 1.48 (s, 3H).

Example 45

N-(2-(4-Chlorophenyl)benzo[d]oxazol-5-yl)-2-(difluoromethyl)-5-((2-methylpropanoylamino)methyl) nicotinamide

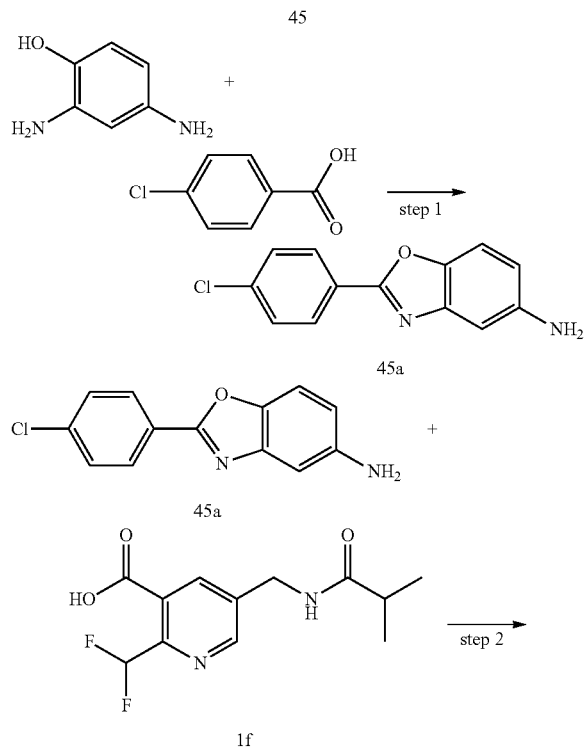

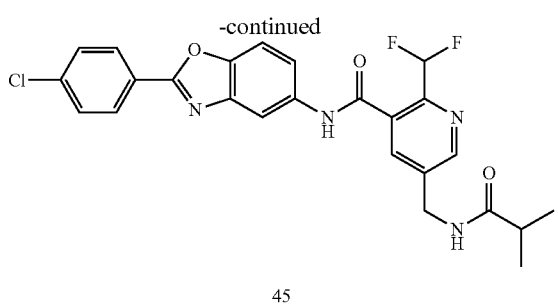

Step 1

2-(4-Chlorophenyl) benzo[d]oxazol-5-amine 2,4-Diaminophenol (800 mg, 6.45 mmol) and 4-chlorobenzoic acid (1.1 g, 7.1 mmol) were dissolved in 10 ml of polyphosphoric acid. The reaction mixture was heated to 95° C. and stirred for 16 hours. The reaction mixture was cooled to room temperature and poured into 50 mL ice-water and adjusted to pH 7 with addition of sodium hydroxide solution dropwise. The mixture was extracted with ethyl acetate (30 mL×3). The organic phases were combined, dried over anhydrous sodium sulfate, and filtered. The filtrate was concentrated under reduced pressure, and the residue was purified by thin layer chromatography (TLC) with elution system A to obtain the title compound 2-(4-chlorophenyl) benzo[d]oxazol-5-amine 45a (90 mg, 5.7%) as a gray solid.

MS m/z (ESI): 259.1 [M+1]

Step 2

N-(2-(4-Chlorophenyl)benzo[d]oxazol-5-yl)-2-(difluoromethyl)-5-((2-methylpropanoylamino)methyl) nicotinamide 2-(4-Chlorophenyl)benzo[d]oxazol-5-amine 45a (80 mg, 0.33 mmol) and 2-(difluoromethyl)-5-((2-methylpropanoylamino)methyl)nicotinic acid 1f (81 mg, 0.30 mmol) were dissolved in 5 mL of N,N-dimethylformamide, and then added with 1-(3-dimethylaminopropyl)-3-ethyl-carbodiimide hydrochloride (67 mg, 0.35 mmol), 1-hydroxybenzotriazole 4 mg, 0.030 mmol) and triethylamine (0.16 mL, 1.19 µmol). The reaction mixture was heated to 70° C. and stirred for 3 hours. The reaction mixture was cooled to room temperature, and then concentrated under reduced pressure. The residue was purified by thin layer chromatography (TLC) with elution system A to obtain the title compound N-(2-(4-chlorophenyl) benzo[d]oxazol-5-yl)-2-(difluoromethyl)-5-((2-methylpropanoylamino)methyl)nicotinamide 45 (6 mg, 4.1%) as brown solid.

MS m/z (ESI): 499.2 [M+1]

$^1$H NMR (400 MHz, DMSO-d$_6$): δ 10.96 (s, 1H), 8.70 (s, 1H), 8.51 (t, 1H), 8.20-8.27 (m, 3H), 8.05 (s, 1H), 7.82 (d, 1H), 7.71 (d, 3H), 7.20 (t, 1H), 4.44 (d, 2H), 2.49 (d, 1H), 1.06 (d, 6H).

Example 46

(S)-N-(2-(4-Chlorophenyl)-1-(-tetrahydrofuran-3-yl)-1H-indol-5-yl)-2-(difluoromethyl)-5-(((2-fluoro-2-methyl-propanoyl)amino)methyl)nicotinamide

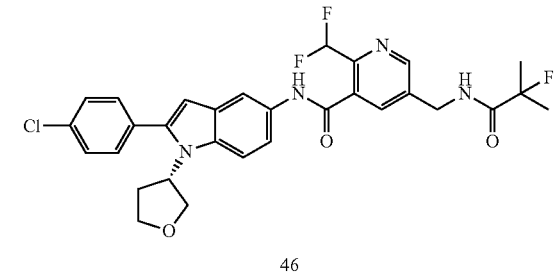 [SMILES: CC(C)(F)C(=O)NCc1cnc(C(F)F)c(C(=O)Nc2ccc3c(c2)cc(-c2ccc(Cl)cc2)n3[C@H]2CCOC2)c1]

46

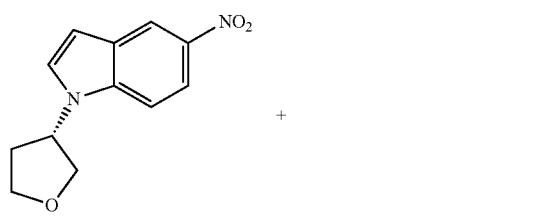

31b

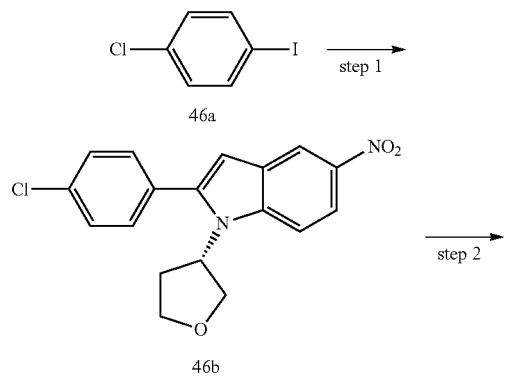

46b

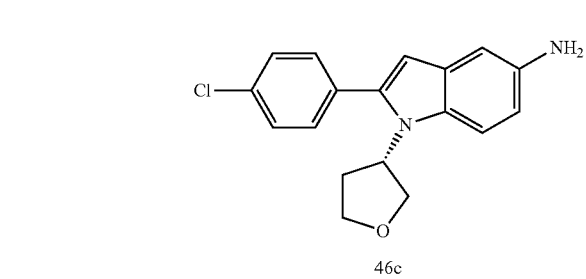

46c

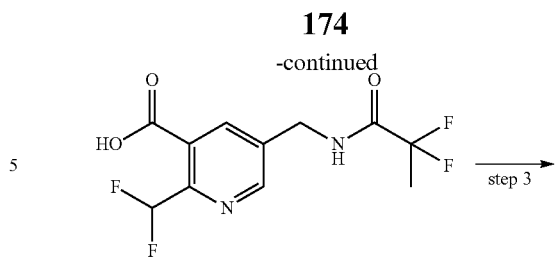

14b

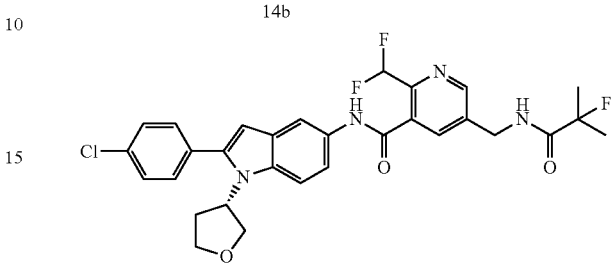

46

Step 1

(S)-2-(4-chlorophenyl)-5-nitro-1-(tetrahydrofuran-3-yl)-1H-indole (S)-5-Nitro-1-(tetrahydrofuran-3-yl)-1H-indole 31b (2.0 g, 8.6 mmol) was dissolved in 15 mL of N, N-dimethylacetamide, and then added with 4-chloro-iodo-benzene 46a (2.3 g, 9.5 mmol), triphenylphosphine (450 mg, 1.7 mmol), palladium acetate (97 mg, 0.4 mmol), and cesium acetate (4.1 g, 21.6 mmol), successively. The reaction mixture was heated to 140° C. and stirred for 18 hours under an argon atmosphere. The reaction solution was cooled to room temperature and added with 200 mL water, then extracted with ethyl acetate (200 mL×1). The organic phase was dried over anhydrous sodium sulfate, and filtered. The filtrate was concentrated under reduced pressure to obtain the title compound (S)-2-(4-chlorophenyl)-5-nitro-1-(tetrahydrofuran-3-yl)-1H-indole 46b (100 mg, 3.4%) as a yellow solid.

MS m/z (ESI): 343.1 [M+1]

Step 2

(S)-2-(4-Chlorophenyl)-1-(tetrahydrofuran-3-yl)-1H-indol-5-amine (S)-2-(4-Chlorophenyl)-5-nitro-1-(tetrahydrofuran-3-yl)-1H-indole 46b (70 mg, 0.20 mmol) was dissolved in 10 mL mixture of tetrahydrofuran and methanol (V:V=1:1), and then added with Raney nickel (20 mg). The reaction mixture was stirred for 3 hours under a hydrogen atmosphere. The reaction mixture was filtered with celatom. The filtrate was concentrated under reduced pressure to obtain the crude title compound (S)-2-(4-chlorophenyl)-1-(tetrahydrofuran-3-yl)-1H-indol-5-amine 46c (64 mg) as a yellow solid which was used in the next step without further purification.

MS m/z (ESI): 313.1 [M+1]

Step 3

(S)-N-(2-(4-Chlorophenyl)-1-(tetrahydrofuran-3-yl)-1H-indol-5-yl)-2-(difluoromethyl)-5-(((2-fluoro-2-methyl-propanoyl)amino)methyl)nicotinamide (S)-2-(4-Chlorophenyl)-1-(tetrahydrofuran-3-yl)-1H-indol-5-amine 46c (64 mg, 0.21 mmol), 2-(difluoromethyl)-

5-(((2-fluoro-2-methyl-propanoyl)amino)methyl)nicotinic acid 14b (100 mg, 0.35 mmol), 1-ethyl-(3-dimethylaminopropyl)carbodiimide hydrochloride (63 mg, 0.69 mmol), 1-hydroxybenzotriazole (4.7 mg, 0.03 mmol) and triethylamine (0.2 mL, 1.38 mmol) were added in 5 mL of N,N-dimethylformamide successively. The reaction mixture was stirred for 16 hours. The reaction mixture was concentrated under reduced pressure, and the residue was purified by thin layer chromatography (TLC) with elution system A to obtain the title compound (S)-N-(2-(4-chlorophenyl)-1-(tetrahydrofuran-3-yl)-1H-indol-5-yl)-2-(difluoromethyl)-5-(((2-fluoro-2-methyl-propanoyl)amino)methyl)nicotinamide 46 (30 mg, 14.9%) as a yellow solid.

MS m/z (ESI): 586.2 [M+1]

$^1$H NMR (400 MHz, DMSO-$d_6$): δ 10.61 (s, 1H), 8.86 (br, 1H), 8.69 (d, 1H), 8.09 (d, 1H), 8.01 (s, 1H), 7.67 (d, 2H), 7.61 (d, 2H), 7.55 (d, 1H), 7.36 (d, 1H), 7.18 (t, 1H), 6.55 (s, 1H), 5.11 (br, 1H), 4.47 (d, 2H), 4.32 (t, 1H), 4.13 (dd, 1H), 3.91 (t, 1H), 3.66 (d, 1H), 2.36-2.45 (m, 1H), 2.26-2.32 (m, 1H), 1.54 (s, 3H), 1.48 (s, 3H).

Example 47

(R)-N-(2-(4-Chlorophenyl)-1-(tetrahydrofuran-3-yl)-1H-indol-5-yl)-2-(difluoromethyl)-5-(((2-fluoro-2-methyl-propanoyl)amino)methyl)nicotinamide

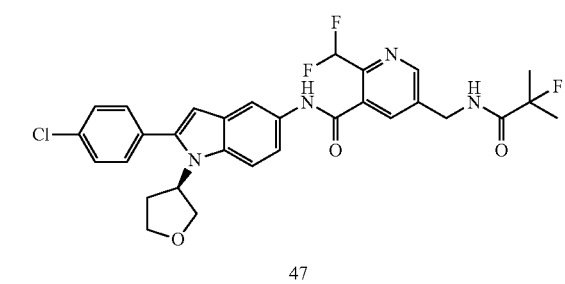 [SMILES: CC(C)(F)C(=O)NCc1cnc(C(F)F)c(C(=O)Nc2ccc3c(c2)cc(-c2ccc(Cl)cc2)n3[C@@H]2CCOC2)c1]

47

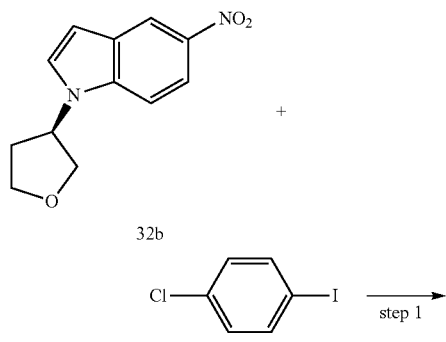

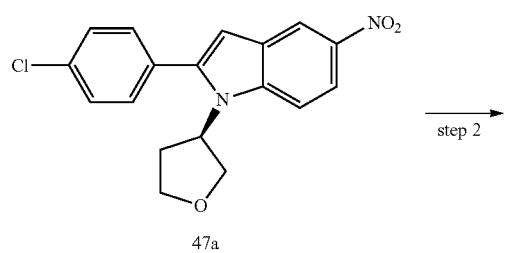

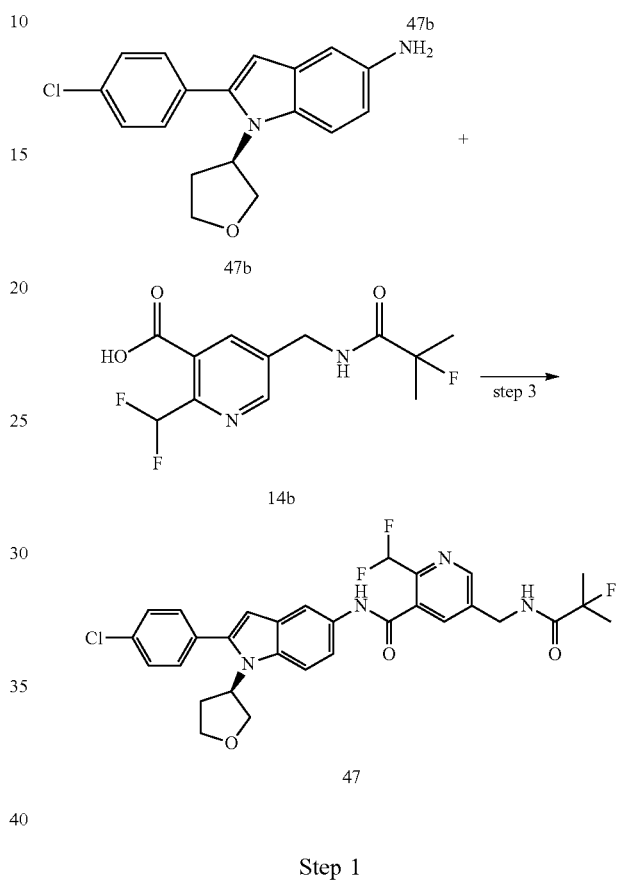

Step 1

(R)-2-(4-Chlorophenyl)-5-nitro-1-(tetrahydrofuran-3-yl)-1H-indole (R)-5-Nitro-1-(tetrahydrofuran-3-yl)-1H-indole 32b (2.0 g, 8.6 mmol) was dissolved in 30 mL N, N-dimethylacetamide, and then added with 4-chloro-iodo-benzene 46a (2.1 g, 8.6 mmol), triphenylphosphine (508 mg, 1.8 mmol), palladium acetate (200 mg, 0.86 mmol), and cesium acetate (3.5 g, 18 mmol), successively. The reaction mixture was heated to 140° C. and stirred for 18 hours under an argon atmosphere. The reaction mixture was concentrated under reduced pressure, and the residue was purified by thin layer chromatography (TLC) with elution system B to obtain the title compound (R)-2-(4-chlorophenyl)-5-nitro-1-(tetrahydrofuran-3-yl)-1H-indole 47a (280 mg, 9.0%) as a yellow solid.

MS m/z (ESI): 343.9 [M+1]

Step 2

(R)-2-(4-Chlorophenyl)-1-(tetrahydrofuran-3-yl)-1H-indol-5-amine (R)-2-(4-Chlorophenyl)-5-nitro-1-(tetrahydrofuran-3-yl)-1H-indole 47a (280 mg, 0.82 mmol) was dissolved in 20 mL, and then added with Raney nickel (28 mg). The reaction mixture was stirred for 3 hours under a hydrogen atmosphere. The reaction mixture was filtered with celatom. The filtrate was concentrated under reduced pressure to obtain the crude title compound (R)-2-(4-chlorophenyl)-1-(tetrahydrofuran-3-yl)-1H-indol-5-amine 47b (230 mg) as a yellow solid which was used in the next step without further purification.

MS m/z (ESI): 313.1 [M+1]

Step 3

(R)-N-(2-(4-Chlorophenyl)-1-(tetrahydrofuran-3-yl)-1H-indol-5-yl)-2-(difluoromethyl)-5-(((2-fluoro-2-methyl-propanoyl)amino)methyl)nicotinamide (R)-2-(4-Chlorophenyl)-1-(tetrahydrofuran-3-yl)-1H-indol-5-amine 46c (230 mg, 0.74 mmol), 2-(difluoromethyl)-5-(((2-fluoro-2-methyl-propanoyl)amino)methyl)nicotinic acid 14b (213 mg, 0.74 mmol), 1-ethyl-(3-dimethylaminopropyl) carbodiimide hydrochloride (211 mg, 1.1 mmol), 1-hydroxybenzotriazole (10 mg, 0.074 mmol) and N,N-diisopropylethylamine (200 mg, 1.47 mmol) were added in 5 mL of N,N-dimethylformamide, successively. The reaction mixture was stirred for 16 hours. The reaction mixture was concentrated under reduced pressure, and the residue was purified by thin layer chromatography (TLC) with elution system A to obtain the title compound (R)-N-(2-(4-chlorophenyl)-1-(tetrahydrofuran-3-yl)-1H-indol-5-yl)-2-(difluoromethyl)-5-(((2-fluoro-2-methyl-propanoyl)amino)methyl)nicotinamide 47 (100 mg, 23.3%) as a white solid.

MS m/z (ESI): 586.3 [M+1]

$^1$H NMR (400 MHz, DMSO-$d_6$): δ 10.61 (s, 1H), 8.86 (t, 1H), 8.68 (s, 1H), 8.09 (s, 1H), 8.01 (s, 1H), 7.76 (d, 1H), 7.61 (d, 2H), 7.55 (d, 2H), 7.38 (d, 1H), 7.18 (t, 1H), 6.55 (s, 1H), 5.10 (br, 1H), 4.47 (d, 2H), 4.31 (t, 1H), 4.13 (d, 1H), 3.92 (t, 1H), 3.65 (dd, 1H), 2.40 (d, 1H), 2.32 (d, 1H), 1.54 (s, 3H), 1.48 (s, 3H).

Example 48

2-(Difluoromethyl)-5-(((2-fluoro-2-methyl-propanoyl)amino)methyl)-N-(2-(3-(trifluoromethyl)phenyl)benzofuran-5-yl)nicotinamide

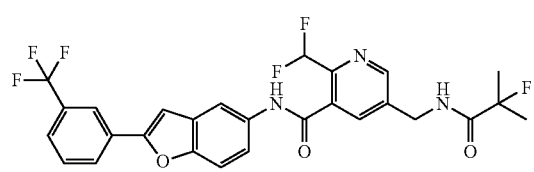

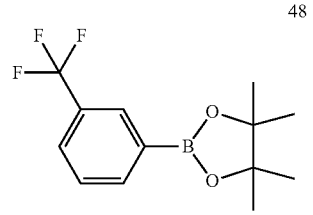

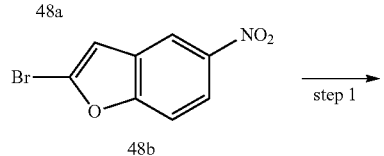

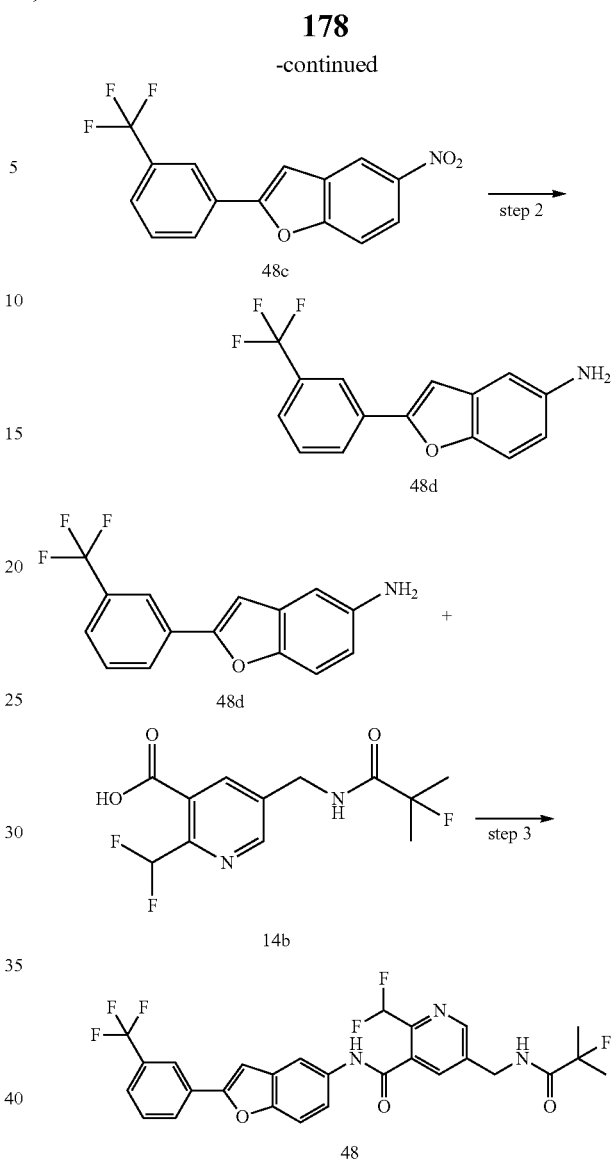

Step 1

5-Nitro-2-(3-(trifluoromethyl)phenyl)benzofuran 3-(Trifluoromethyl)(pinacolboryl)benzene 48a (143 mg, 0.53 mmol) and 2-bromo-5-nitro-benzofuran 48b (85 mg, 0.35 mmol, prepared according to the method disclosed in "Organic & Biomolecular Chemistry, 2013, 11(24), 4095-4101") were dissolved in a mixture of 6 mL of 1,4-dioxane and water (V:V=5:1), and then added with (1,1'-Bis(diphenylphosphino)ferrocene)-dichloropalladium(II) (26 mg, 0.036 mmol) and sodium carbonate (75 mg, 0.71 mmol). The reaction mixture was heated to 100° C. and stirred for 16 hours under an argon atmosphere. The reaction mixture was cooled to room temperature. The reaction mixture was filtered and the filtrate was concentrated under reduced pressure. The residue was purified by thin layer chromatography (TLC) with elution system C to obtain the title compound 5-nitro-2-(3-(trifluoromethyl)phenyl)benzofuran 48 (64 mg, 64.0%) as a yellow solid.

Step 2

2-(3-(Trifluoromethyl)phenyl)benzofuran-5-amine

5-Nitro-2-(3-(trifluoromethyl)phenyl)benzofuran 48c (64 mg, 0.21 mmol) was dissolved in a mixture of 10 mL of tetrahydrofuran and methanol (V:V=1:1), and then added with Raney nickel (20 mg). The reaction mixture was stirred for 2 hours under a hydrogen atmosphere. The reaction mixture was filtered with celatom. The filtrate was concentrated under reduced pressure to obtain the title compound 2-(3-(trifluoromethyl)phenyl)benzofuran-5-amine 48d (45 mg, 77.6%) as a yellow oil.

Step 3

2-(Difluoromethyl)-5-(((2-fluoro-2-methyl-propanoyl)amino)methyl)-N-(2-(3-(trifluoromethyl)phenyl)benzofuran-5-yl)nicotinamide 2-(3-(Trifluoromethyl)phenyl)benzofuran-5-amine 48d (23 mg, 0.083 mmol), 2-(difluoromethyl)-5-(((2-fluoro-2-methyl-propanoyl)amino)methyl)nicotinic acid 14b (24 mg, 0.083 mmol), 1-ethyl-(3-dimethylaminopropyl)-carbodiimide hydrochloride (32 mg, 0.17 mmol) and 1-hydroxybenzotriazole (11.2 mg, 0.083 mmol) were added in 3 mL N,N-dimethylacetamide, successively. The reaction mixture was heated to 40° C. The reaction mixture was stirred for 3 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(2-(3-(trifluoromethyl)phenyl)benzofuran-5-yl)nicotinamide 48 (10 mg, 21.7%) as a light yellow solid.

MS m/z (ESI): 550.1 [M+1]

$^1$H NMR (400 MHz, DMSO-$d_6$): δ 8.68 (s, 1H), 8.15-8.11 (d, 2H), 8.04-8.00 (d, 3H), 7.61-7.52 (m, 3H), 7.39-7.38 (d, 1H), 7.15-6.85 (m, 3H), 4.58-4.57 (d, 2H), 1.64 (s, 3H), 1.58 (s, 3H).

Example 49

2-(Difluoromethyl)-5-(((2-fluoro-2-methyl-propanoyl)amino)methyl)-N-(2-(3-(trifluoromethyl)phenyl)isoindolin-5-yl)nicotinamide

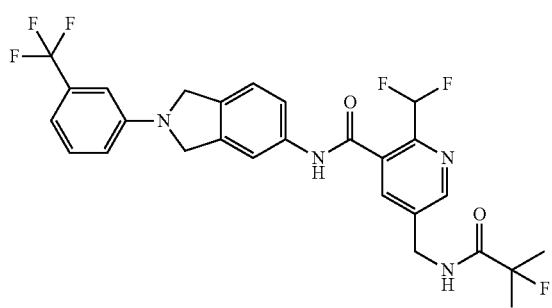

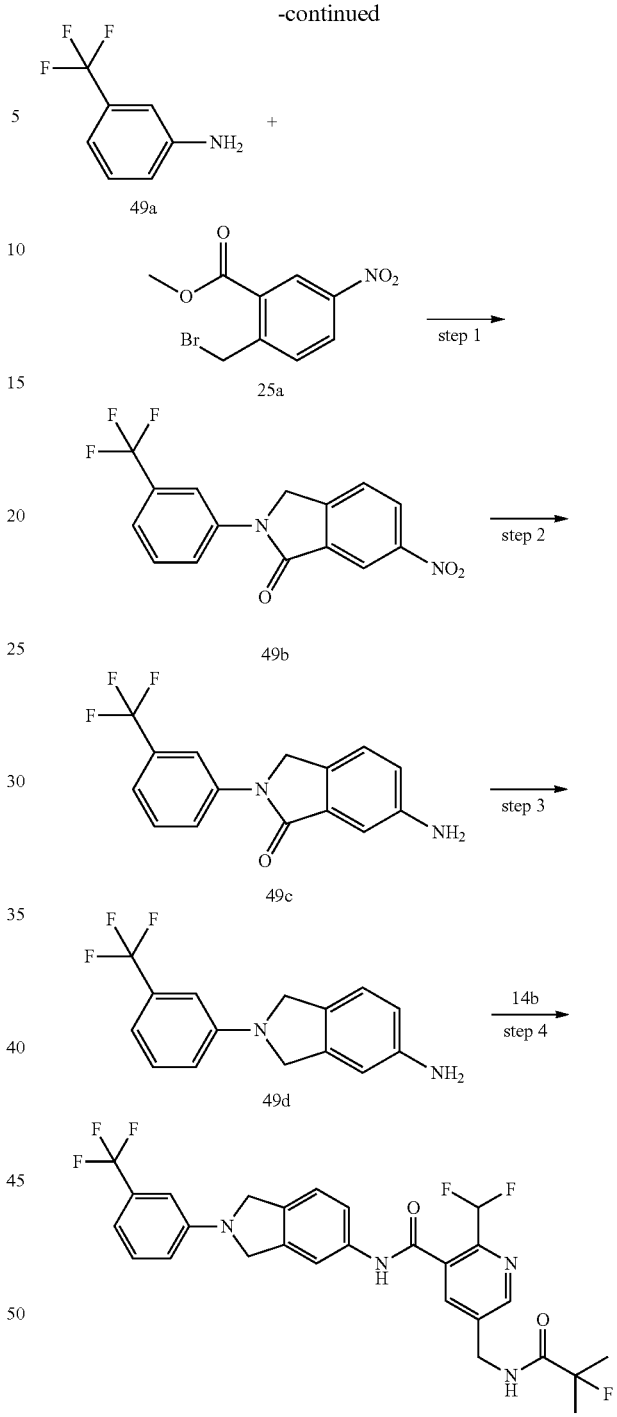

Step 1

6-Nitro-2-(3-(trifluoromethyl)phenyl)isoindolin-1-one 3-(Trifluoromethyl)aniline 49a (773 mg, 4.8 mmol) was dissolved in 15 mL acetic acid, and then added with methyl 2-(bromomethyl)-5-nitro-benzoate 25a (1.1 g, 4.0 mmol). The reaction mixture was heated to 110° C. and stirred for 16 hours. The reaction mixture was cooled to room temperature. An amount of solid was precipitated and filtered out. The filter cake was dried to obtain the title compound 6-nitro-2-(3-(trifluoromethyl)phenyl)isoindolin-1-one 49b (300 mg, 23.2%) as a white solid.

MS m/z (ESI): 323.0 [M+1]

Step 2

6-Amino-2-(3-(trifluoromethyl)phenyl)isoindolin-1-one

6-Nitro-2-(3-(trifluoromethyl)phenyl)isoindolin-1-one 49b (300 mg, 0.93 mmol) was dissolved in a mixture of 40 mL of tetrahydrofuran and methanol (V:V=1:1), and then added with Raney nickel (30 mg). The reaction mixture was stirred for 16 hours under a hydrogen atmosphere. The reaction mixture was filtered with celatom, and the filter cake was washed with 30 mL of ethyl acetate. The filtrate was combined and concentrated under reduced pressure to obtain the crude title compound 6-amino-2-(3-(trifluoromethyl)-phenyl)isoindolin-1-one 49c (272 mg) as a black solid which was used in the next step without further purification.

MS m/z (ESI): 293.2 [M+1]

Step 3

2-(3-(Trifluoromethyl)phenyl)isoindolin-5-amine

Lithium aluminium hydride (70 mg, 1.86 mmol) was added into 10 mL tetrahydrofuran, and then cooled under ice bath. The solution was slowly added with a 10 mL solution of 6-amino-2-(3-(trifluoromethyl)phenyl)isoindolin-1-one 49c (271 mg, 0.93 mmol) in tetrahydrofuran dropwise. The ice bath was removed and the reaction mixture was heated to 65° C. and then stirred for 1 hour. The reaction mixture was added with 2 mL of 1 M sodium hydroxide solution and filtered. The filter cake was washed with 20 mL of ethyl acetate. The filtrate was combined and concentrated under reduced pressure to obtain the crude title compound 2-(3-(trifluoromethyl)phenyl)isoindolin-5-amine 49d (258 mg) as a black solid which was used in the next step without further purification.

MS m/z (ESI): 279.1 [M+1]

Step 4

2-(Difluoromethyl)-5-(((2-fluoro-2-methyl-propanoyl)amino)methyl)-N-(2-(3-(trifluoromethyl)phenyl)isoindolin-5-yl)nicotinamide 2-(3-(Trifluoromethyl)phenyl)isoindolin-5-amine 49d (258 mg, 0.93 mmol), 2-(difluoromethyl)-5-(((2-fluoro-2-methyl-propanoyl)amino)methyl)nicotinic acid 14b (270 mg, 0.93 mmol), 1-ethyl-(3-dimethylaminopropyl)-carbodiimide hydrochloride (357 mg, 01.86 mmol), 1-hydroxybenzotriazole (13 mg, 0.093 mmol) and triethylamime (375 mg, 3.72 mmol) were added in 5 mL of N,N-dimethylacetamide, successively. The reaction mixture was stirred for 2 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(2-(3-(trifluoromethyl)phenyl)isoindolin-5-yl)nicotinamide 49 (25 mg, 4.9% for three steps) as a yellow solid.

MS m/z (ESI): 551.2 [M+1]

$^1$H NMR (400 MHz, DMSO-$d_6$): δ 10.79 (s, 1H), 8.87 (br, 1H), 8.69 (s, 1H), 8.00 (s, 1H), 7.84 (s, 1H), 7.58 (d, 1H), 7.47 (t, 1H), 7.41 (d, 1H), 7.16 (s, 1H), 6.97 (t, 2H), 6.89 (s, 1H), 4.68 (d, 3H), 4.47 (d, 2H), 4.39-4.44 (m, 1H), 1.54 (s, 3H), 1.48 (s, 3H).

Example 50

2-(Difluoromethyl)-5-(((2-fluoro-2-methyl-propanoyl)amino)methyl)-N-(2-(3-(trifluoromethyl)phenyl)-2H-indazol-5-yl)nicotinamide

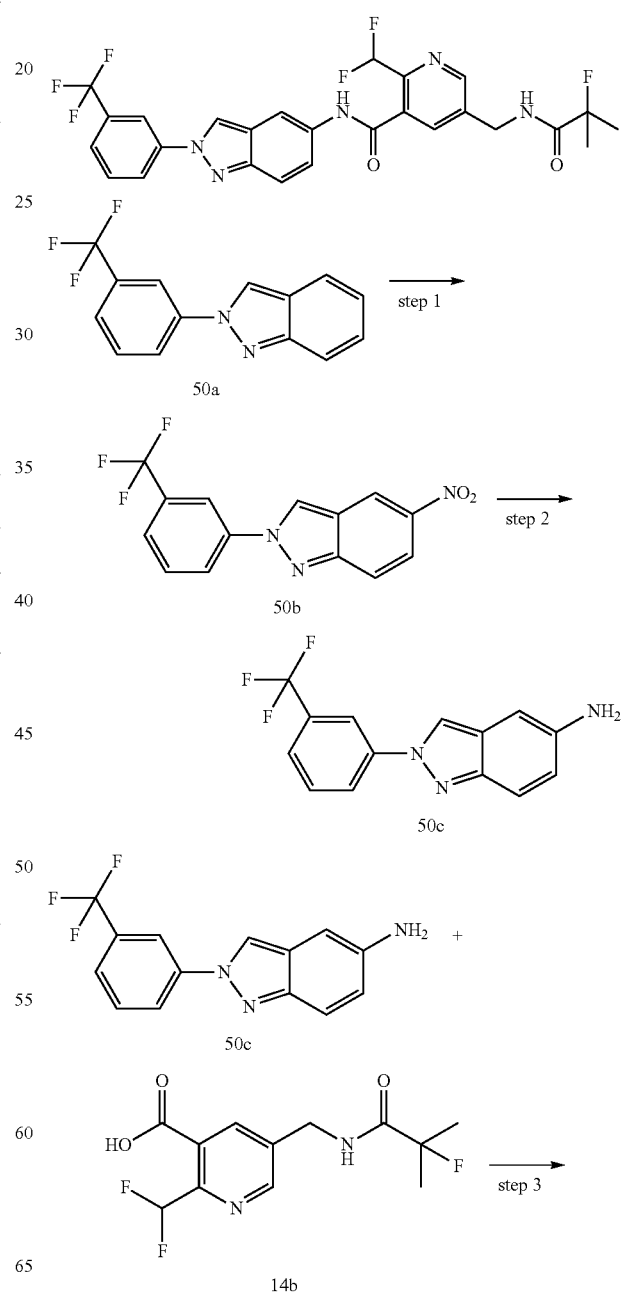

-continued

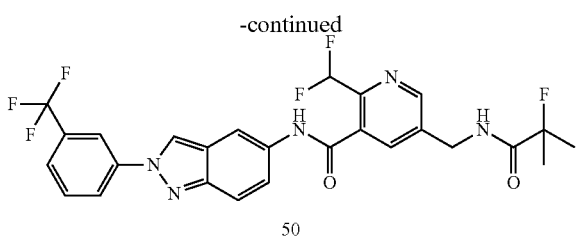

50

Step 1

5-Nitro-2-(3-(trifluoromethyl)phenyl)-2H-indazole 2-(3-(Trifluoromethyl)phenyl)indazole 50a (28 mg, 0.11 mmol) and sodium nitrate (14.5 mg, 0.17 mmol) were added in 1 mL of concentrated sulfuric acid. The reaction mixture was heated to 70° C. and stirred for 0.5 hour. The reaction mixture was cooled to room temperature and then poured into 20 mL of saturated sodium carbonate solution, then extracted with ethyl acetate (30 mL×3). The organic phases were combined, dried over anhydrous sodium sulfate, and filtered. The filtrate was concentrated under reduced pressure to obtain the title compound 5-nitro-2-(3-(trifluoromethyl)-phenyl)-2H-indazole 50b (30 mg, 91.5%) as a yellow solid.

MS m/z (ESI): 308.1 [M+1]

Step 2

2-(3-(Trifluoromethyl)phenyl)-2H-indazol-5-amine

5-Nitro-2-(3-(trifluoromethyl)phenyl)-2H-indazole 50b (30 mg, 0.098 mmol) was dissolved in a mixture of 10 mL of tetrahydrofuran and methanol (V:V=1:1), and then added with Raney nickel (10 mg). The reaction mixture was stirred for 1 hour under a hydrogen atmosphere. The reaction mixture was filtered with celatom. The filtrate was concentrated under reduced pressure to obtain the crude title compound 2-(3-(trifluoromethyl)phenyl)-2H-indazol-5-amine 50c (25 mg, 92.6%) as a yellow solid.

MS m/z (ESI): 278.1 [M+1]

Step 3

2-(Difluoromethyl)-5-(((2-fluoro-2-methyl-propanoyl)amino)methyl)-N-(2-(3-(trifluoromethyl)phenyl)-2H-indazol-5-yl)nicotinamide 2-(3-(Trifluoromethyl)phenyl)-2H-indazol-5-amine 50c (25 mg, 0.090 mmol), 2-(difluoromethyl)-5-(((2-fluoro-2-methyl-propanoyl)amino)methyl)nicotinic acid 14b (26 mg, 0.090 mmol), 1-ethyl-(3-dimethylaminopropyl) carbodiimide hydrochloride (35 mg, 0.18 mmol), 1-hydroxybenzotriazole (1.2 mg, 9.02 µmol) and triethylamime (50 µL, 0.36 mmol) were added in 5 mL of N,N-dimethylacetamide, successively. The reaction mixture was stirred for 2 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(2-(3-(trifluoromethyl)phenyl)indazol-5-yl)nicotinamide 50 (14 mg, 28.6%) as a yellow solid.

MS m/z (ESI): 550.2 [M+i]

$^1$H NMR (400 MHz, DMSO-d$_6$): δ 10.80 (s, 1H), 9.30 (s, 1H), 8.89 (br, 1H), 8.70 (s, 1H), 8.44 (d, 2H), 8.37 (s, 1H), 7.85 (s, 1H), 7.76-7.81 (m, 2H), 7.77 (d, 1H), 7.48 (d, 1H), 7.20 (t, 1H), 4.47 (d, 2H), 1.54 (s, 3H), 1.48 (s, 3H).

Example 51

N-(2-(4-Chlorophenyl)-1-ethyl-1H-benzo[d]imidazol-5-yl)-2-(difluoromethyl)-5-((2-methylpropanoylamino)methyl)nicotinamide

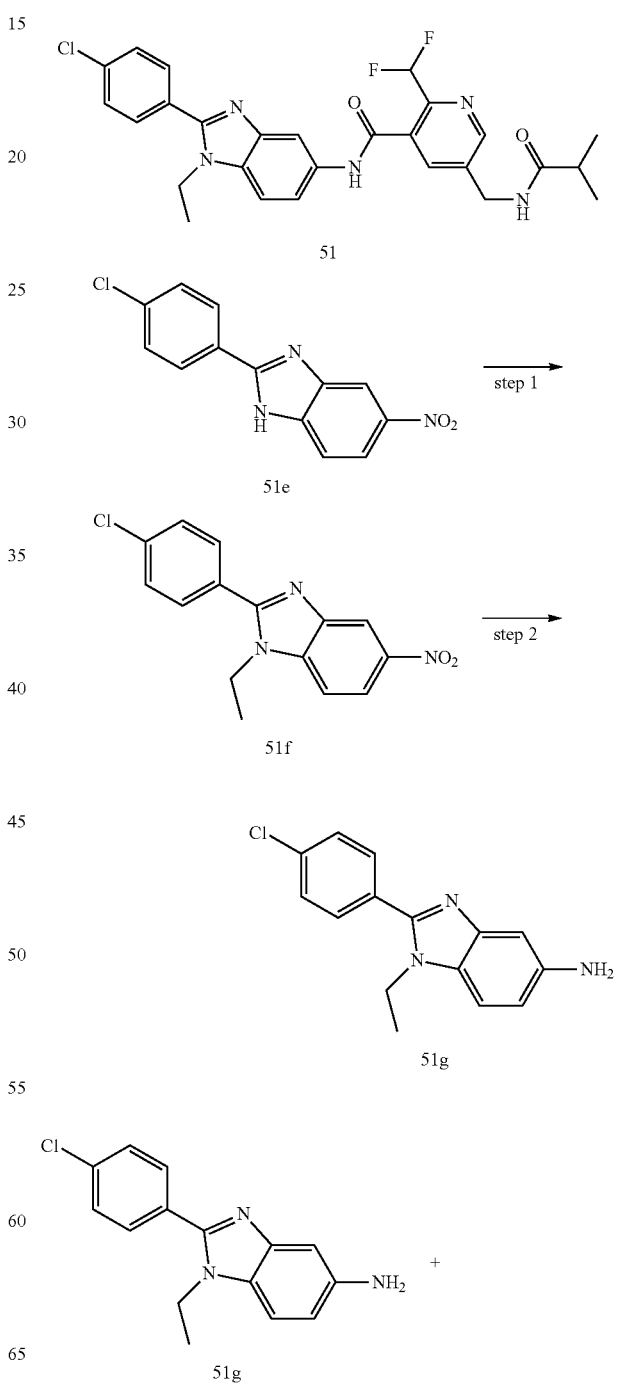

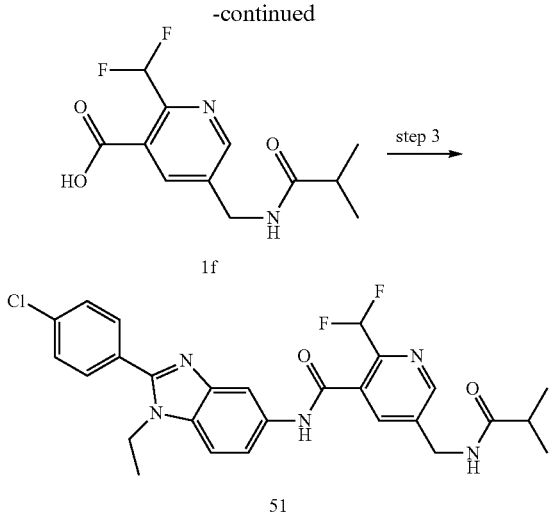

Step 1

2-(4-Chlorophenyl)-1-ethyl-5-nitro-benzo[d]imidazole 2-(4-Chlorophenyl)-5-nitro-1H-benzo[d]imidazole 51e (600 mg, 2.29 mmol, prepared according to the method disclosed in "*Monatshefte fuer Chemie*. 2009, 140(5), 547-552") was dissolved in 40 mL of N,N-dimethylformamide, and then added with sodium hydride (87 mg, 2.29 mmol). The reaction mixture was stirred for 0.5 hour, and then added with iodoethane (512 mg, 3.28 mmol) and continually stirred for another 3 hours. After the reaction was completed, the reaction mixture was quenched with 30 mL of water, and extracted with ethyl acetate (30 mL×3), washed with saturated sodium chloride solution (30 mL×2), dried over anhydrous sodium sulphate, and filtered. The filtrate was concentrated under reduced pressure, and the residue was purified by thin layer chromatography (TLC) with elution system A to obtain the title compound 2-(4-chlorophenyl)-1-ethyl-5-nitro-benzo[d]imidazole 51f (540 mg, 82.0%) as a yellow viscous material.

MS m/z (ESI): 302.1 [M+1]

Step 2

2-(4-Chlorophenyl)-1-ethyl-1H-benzo[d]imidazol-5-amine 2-(4-Chlorophenyl)-1-ethyl-5-nitro-1-1H-benzo[d]imidazole 51f (150 mg, 0.49 mmol) was dissolved in 10 mL methanol, and then added with Raney nickel (15 mg). The reaction mixture was stirred for 14 hours at room temperature under a hydrogen atmosphere. The reaction mixture was filtered. The filtrate was concentrated under reduced pressure to obtain the crude title 2-(4-chlorophenyl)-1-ethyl-1H-benzo[d]imidazol-5-amine 51g (100 mg) as a brownish viscous material which was used in the next step without further purification.

MS m/z (ESI): 272.2 [M+1]

Step 3

N-(2-(4-Chlorophenyl)-1-ethyl-1H-benzo[d]imidazol-5-yl)-2-(difluoromethyl)-5-((2-methylpropanoylamino)methyl)nicotinamide 2-(4-Chlorophenyl)-1-ethyl-benzo[d]imidazol-5-amine 51g (50 mg, 0.87 mmol), 2-(difluoromethyl)-5-((2-methylpropanoylamino)methyl)nicotinic acid 1f (80 mg, 0.87 mmol), 1-hydroxybenzotriazole (25 mg, 0.87 μmol), and 1-ethyl-3-(3-dimethylaminopropyl)-carbodiimide hydrochloride (70 mg, 0.367 mmol) were added in 3 mL of N,N-dimethylacetamide, successively. The reaction mixture was stirred for 3.5 hours at 40° C. The reaction mixture was concentrated under reduced pressure, and the residue was purified by thin layer chromatography (TLC) with elution system A to obtain the title compound N-(2-(4-chlorophenyl)-1-ethyl-1H-benzo[d]imidazol-5-yl)-2-(difluoromethyl)-5-((2-methylpropanoylamino)methyl)-nicotinamide 51 (40 mg, 40%) as a light yellow solid.

MS m/z (ESI): 526.7 [M+1]

$^{1}$H NMR (400 MHz, DMSO-d$_{6}$): δ 10.50 (br, 1H), 8.89 (s, 1H), 8.77 (s, 1H), 8.55 (s, 1H), 8.13 (d, 2H), 8.10 (s, 1H), 7.66 (d, 1H), 7.58 (d, 1H), 7.56 (s, 2H), 6.47 (s, 1H), 4.51 (s, 2H), 4.15 (m, 2H), 2.71 (m, 1H), 1.30 (m, 3H), 1.15 (m, 6H).

Example 52

2-Chloro-N-(2-(4-chlorophenyl)-1-ethyl-1H-benzo[d]imidazol-5-yl)-5-((2,2-dimethylpropanoylamino)methyl)benzamide

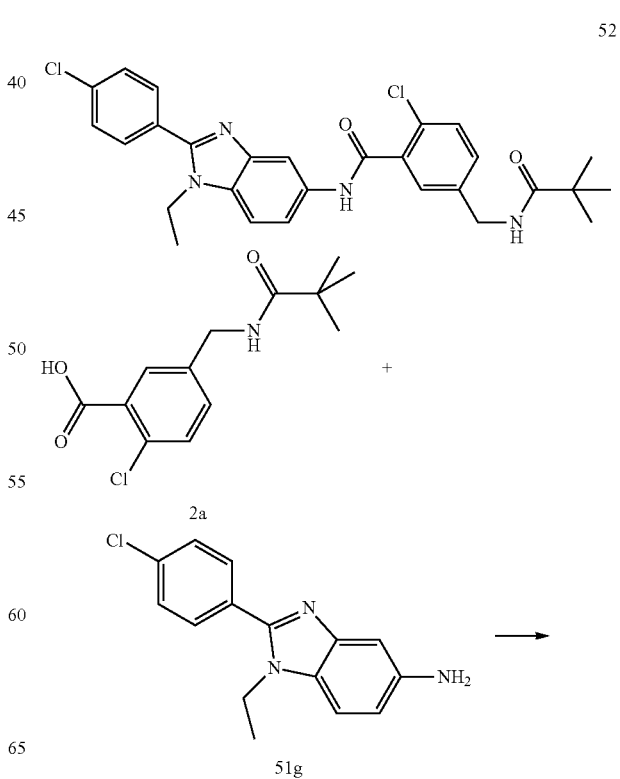

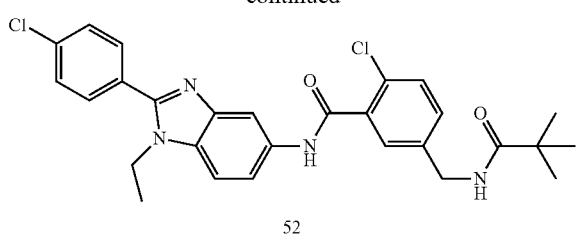

2-(4-Chlorophenyl)-1-ethyl-1H-benzo[d]imidazol-5-amine 51g (50 mg, 0.87 mmol), 2-chloro-5-((2,2-dimethylpropanoylamino)methyl)benzoic acid 2a (100 mg, 0.87 mmol), 1-hydroxybenzotriazole (25 mg, 0.87 μmol), and 1-ethyl-3-(3-dimethylaminopropyl)-carbodiimide hydrochloride (70 mg, 0.367 mmol) were added in 3 mL of N,N-dimethylformamide, successively. The reaction mixture was stirred for 3.5 hours at 40° C. The reaction mixture was concentrated under reduced pressure, and the residue was purified by thin layer chromatography (TLC) with elution system A to obtain the title compound 2-chloro-N-(2-(4-chlorophenyl)-1-ethyl-1H-benzo[d]imidazol-5-yl)-5-((2,2-dimethylpropanoylamino)methyl)benzamide 52 (10 mg, 10.7%) as an earthy yellow solid.

MS m/z (ESI): 523.2 [M+1]

$^1$H NMR (400 MHz, DMSO-$d_6$): δ 10.39 (br, 1H), 8.18 (d, 2H), 8.10 (s, 1H), 7.70 (s, 1H), 7.66 (d, 1H), 7.58 (m, 2H), 7.56-7.53 (m, 3H), 4.26 (s, 2H), 4.16 (m, 2H), 1.30 (m, 4H), 1.21 (s, 9H).

Example 53

2-Chloro-N-(2-(5-chloropyridin-2-yl)-1H-benzo[d]imidazol-5-yl)-5-((2,2-dimethylpropanoylamino)methyl)benzamide

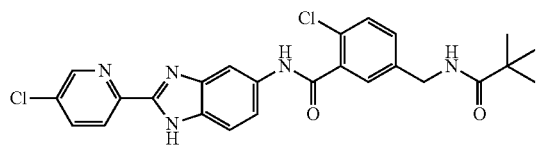

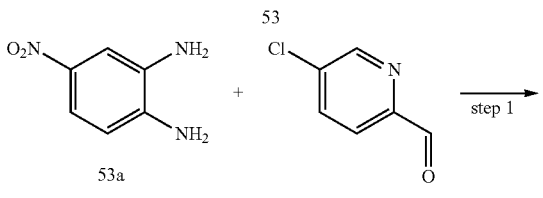

Step 1

2-(5-Chloropyridin-2-yl)-5-nitro-1H-benzo[d]imidazole

4-Nitrobenzene-1,2-diamine 53a (400 mg, 2.6 mmol, 5-chloropyridine-2-carbaldehyde 53b (92 mg, 0.65 mmol) and 10 mL of 6 N hydrochloric acid were mixed well. The resulting mixture was stirred for 12 hours at 65° C. The reaction mixture was filtered, and the filter cake was washed with water (20 mL) and dried to obtain the crude title compound 2-(5-chloropyridin-2-yl)-5-nitro-1H-benzo[d]imidazole 53c (350 mg) as a yellow solid which was used in the next step without further purification.

MS m/z (ESI): 275.1 [M+1]

Step 2

2-(5-Chloropyridin-2-yl)-1H-benzo[d]imidazol-5-amine 2-(5-Chloro-2-pyridyl)-5-nitro-1H-benzo[d]imidazole 53c (120 mg, 0.44 mmol) was dissolved in 20 mL of tetrahydrofuran and 20 mL of methanol, and then added with Raney nickel (100 mg). The reaction mixture was stirred for 12 hours under a hydrogen atmosphere. The reaction mixture was filtered. The filtrate was concentrated under reduced pressure to obtain the crude title 2-(5-chloropyridin-2-yl)-1H-benzo[d]imidazol-5-amine 53d (110 mg) as a black-yellow oil which was used in the next step without further purification.

MS m/z (ESI): 245.1 [M+1]

Step 3

2-Chloro-N-(2-(5-chloropyridin-2-yl)-1H-benzo[d]imidazol-5-yl)-5-((2,2-dimethylpropanoylamino)methyl)benzamide 2-Chloro-5-((2,2-dimethylpropanoylamino)methyl)benzoyl chloride 2b (58 mg, 0.20 mmol) was dissolved in 10 mL of tetrahydrofuran, and then added with N,N-diisopropylethylamine (53 mg, 0.41 mmol) and 2-(5-chloropyridin-2-yl)-1H-benzo[d]imidazol-5-amine 53d (50 mg, 0.20 mmol). The resulting mixture was stirred for 12 hours. The reaction mixture was concentrated under reduced pressure, and the residue was purified by thin layer chromatography (TLC) with elution system A to obtain the title compound 2-chloro-N-(2-(5-chloropyridin-2-yl)-1H-benzo[d]imidazol-5-yl)-5-((2,2-dimethylpropanoylamino)methyl)benzamide 53 (20 mg, 20%) as a light yellow solid.

MS m/z (ESI): 496.1 [M+1]

$^1$H NMR (400 MHz, DMSO-d$_6$): δ 10.82 (s, 1H), 8.71 (s, 1H), 8.35 (d, 1H), 8.18 (s, 1H), 8.13 (s, 1H), 7.95 (d, 1H), 7.57-7.52 (m, 5H), 5.5 (s, 1H), 4.30 (d, 2H), 1.13 (s, 9H).

Example 54

2-(Difluoromethyl)-5-((2-methylpropanoylamino)methyl)-N-(2-(4-(trifluoromethyl)phenyl)benzo[d]thiazol-6-yl)nicotinamide

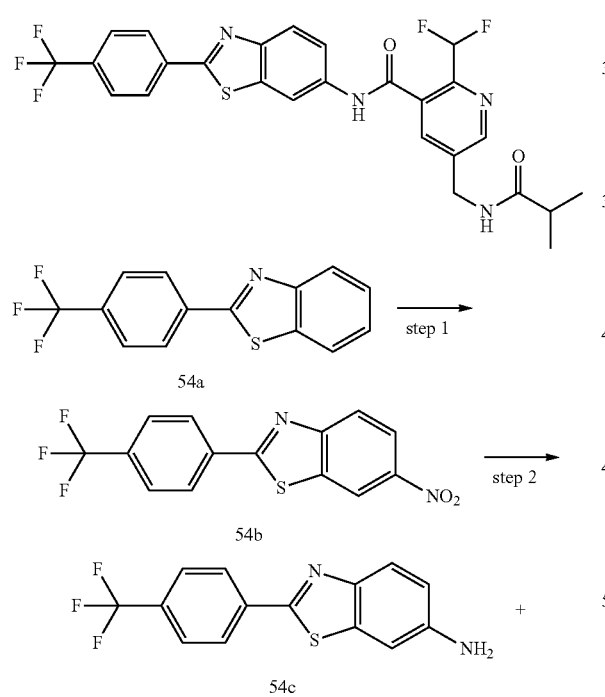

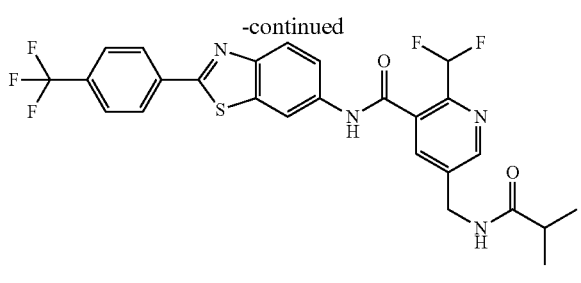

Step 1

6-Nitro-2-(4-(trifluoromethyl)phenyl)benzo[d]thiazole

Sodium nitrate (27 mg, 0.32 mmol) and 1 mL of concentrated sulfuric acid were mixed, and then added with 2-(4-(trifluoromethyl)phenyl) benzo[d]thiazole 54a (50 mg, 0.18 mmol, prepared according to the method disclosed in "*Journal of Molecular Structure*, 2012, 1011, 81-93") slowly with the temperature maintained below 75° C. Upon completion of the addition, the reaction mixture was stirred for 1 hour at 70° C. The reaction mixture was adjusted to pH 9 with sodium hydroxide solution (50%), and then added with 50 mL of ethyl acetate and 20 mL of water. The organic phase was concentrated under reduced pressure to obtain the crude title compound 6-nitro-2-(4-(trifluoromethyl)phenyl benzo[d]thiazole 54b (58 mg) as a yellow solid which was used in the next step without further purification.

MS m/z (ESI): 325.1 [M+1]

Step 2

2-(4-(Trifluoromethyl)phenyl)benzo[d]thiazole-6-amine

6-Nitro-2-(4-(trifluoromethyl)phenyl) benzo[d]thiazole 54b (58 mg, 0.179 mmol) was dissolved in 5 mL of tetrahydrofuran and 5 mL of methanol, and then added with Raney nickel (5 mg). The reaction mixture was stirred for 20 minutes under a hydrogen atmosphere. The reaction mixture was filtered. The filtrate was concentrated under reduced pressure to obtain the crude title compound 2-(4-(trifluoromethyl)phenyl)benzo[d]thiazole-6-amine 54c (53 mg) as a light yellow solid which was used in the next step without further purification.

MS m/z (ESI): 295.1 [M+1]

Step 3

2-(Difluoromethyl)-5-((2-methylpropanoylamino)methyl)-N-(2-(4-(trifluoromethyl)phenyl) benzo[d]thiazol-6-yl)nicotinamide 2-(4-(Trifluoromethyl)phenyl) benzo[d]thiazole-6-amine 54c (53 mg, 0.18 mmol), 2-(difluoromethyl)-5-((2-methylpropanoylamino)methyl)nicotinic acid 1f (49 mg, 0.18 mmol), 1-hydroxybenzotriazole (25 mg, 0.18 mmol) and 1-ethyl-3-(3-dimethylaminopropyl) carbodiimide hydrochloride (52 mg, 0.27 mmol) were added in 5 mL of N,N-dimethylacetamide. The reaction mixture was stirred for 1 hour at 40° C. The reaction mixture was concentrated under reduced pressure, and the residue was purified by thin layer chromatography (TLC) with elution system A to obtain the title compound 2-(difluoromethyl)-5-((2-methylpropanoylamino)methyl)-N-(2-(4-(trifluoromethyl)phenyl)benzo[d]thiazol-6-yl)nicotinamide 54 (20 mg, 20%) as a yellow solid.

MS m/z (ESI): 529.2 [M+1]

$^1$H NMR (400 MHz, DMSO-$d_6$): δ 10.60 (s, 1H), 8.67 (s, 1H), 8.45 (d, 1H), 8.08 (s, 1H), 8.00 (s, 1H), 7.89-7.87 (m, 4H), 7.54 (d, 1H), 7.46 (d, 1H), 7.43 (t, 1H), 4.42 (d, 2H), 3.17-3.16 (m, 1H), 1.05 (s, 6H).

Example 55

2-Chloro-N-(2-(4-chlorophenyl)-1-methyl-1H-benzo[d]imidazol-5-yl)-5-((2,2-dimethylpropanoylamino)methyl)benzamide

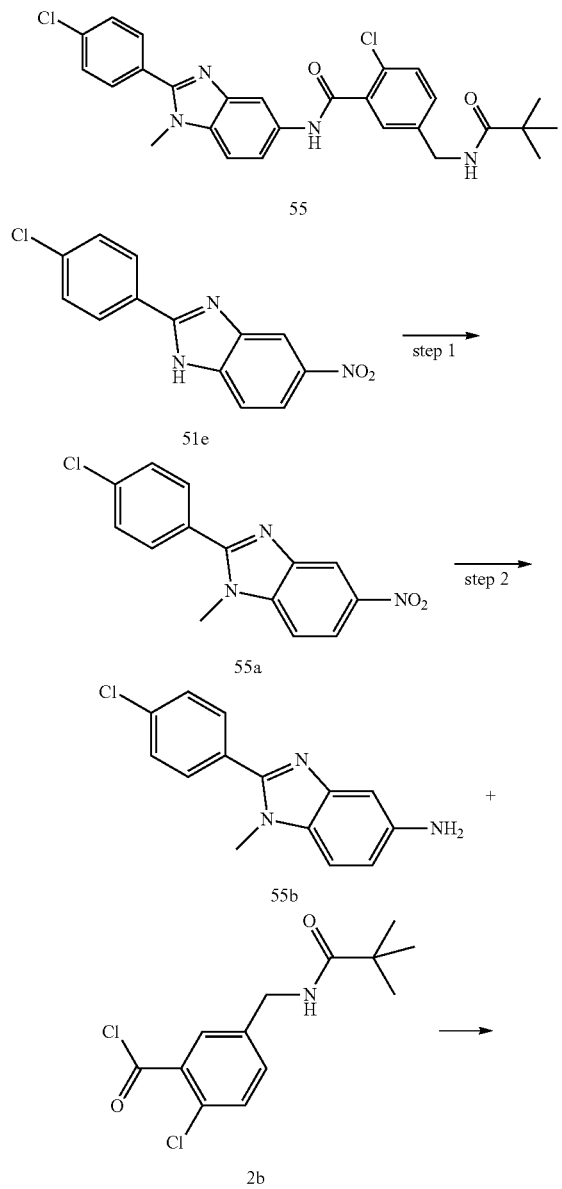

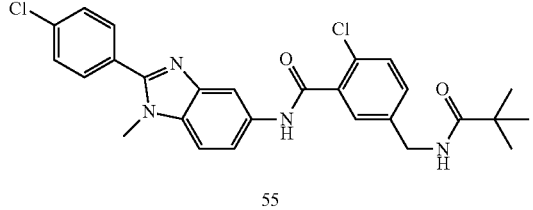

Step 1

2-(4-Chlorophenyl)-1-methyl-5-nitro-1H-benzo[d]imidazole 2-(4-Chlorophenyl)-5-nitro-1H-benzo[d]imidazole 51e (600 mg, 2.2 mmol), iodomethane (0.47 mg, 3.3 mmol) and cesium carbonate (2.15 g, 6.6 mmol) were mixed. The reaction mixture was stirred for 12 hours. After the reaction was completed, the reaction mixture was poured into 50 mL of water, and filtered. The filtrate cake was washed with water (20 mL), and dried to obtain the crude title compound 2-(4-chlorophenyl)-1-methyl-5-nitro-1H-benzo[d]imidazole 55a (0.35 g) as a yellow solid which was used in the next step without further purification.

MS m/z (ESI): 288.2 [M+1]

Step 2

2-(4-Chlorophenyl)-1-methyl-1H-benzo[d]imidazol-5-amine 2-(4-Chlorophenyl)-1-methyl-5-nitro-1H-benzo[d]imidazole 55a (320 mg, 1.11 mmol) was dissolved in 1 mL of tetrahydrofuran and 1 mL of methanol, and then added with Raney nickel (50 mg). The reaction mixture was stirred for 12 hours under a hydrogen atmosphere. The reaction mixture was filtered. The filtrate was concentrated under reduced pressure to obtain the crude title compound 2-(4-chlorophenyl)-1-methyl-1H-benzo[d]imidazol-5-amine 55b (112 mg) as a yellow oil which was used in the next step without further purification.

MS m/z (ESI): 258.1 [M+1]

Step 3

2-Chloro-N-(2-(4-chlorophenyl)-1-methyl-1H-benzo[d]imidazol-5-yl)-5-((2,2-dimethylpropanoylamino)methyl)benzamide 2-(4-Chlorophenyl)-1-methyl-1H-benzo[d]imidazol-5-amine 55b (50 mg, 0.19 mmol) was dissolved in 10 mL of tetrahydrofuran, and then added with 2-chloro-5-((2,2-dimethylpropanoylamino)methyl)benzoyl chloride 2b (56 mg, 0.19 mmol), and N,N-diisopropylethylamine (52 mg, 0.39 mmol). The resulting mixture was stirred for 2 hours at 65° C. Ater the reaction was completed, the reaction mixture was concentrated under reduced pressure, and the residue was purified by thin layer chromatography (TLC) with elution system A and then by HPLC to obtain the title compound 2-chloro-N-(2-(4-chlorophenyl)-1-methyl-1H-benzo[d]imidazol-5-yl)-5-((2,2-dimethylpropanoylamino)methyl)benzamide 55 (10 mg, 10.1%) as a light yellow solid.

MS m/z (ESI): 509.1 [M+1]

$^1$H NMR (400 MHz, DMSO-d$_6$): δ 10.37 (br, 1H), 8.16 (d, 2H), 8.12 (s, 1H), 8.00 (s, 1H), 7.72 (s, 1H), 7.68 (d, 1H), 7.59 (m, 2H), 7.58-7.55 (m, 3H), 4.28 (d, 2H), 3.98 (s, 3H), 1.23 (s, 9H).

Example 56

2-(Difluoromethyl)-5-(((2-fluoro-2-methyl-propanoyl)amino)methyl)-N-(2-(3-(trifluoromethyl)phenyl)benzo[d]oxazol-5-yl)nicotinamide

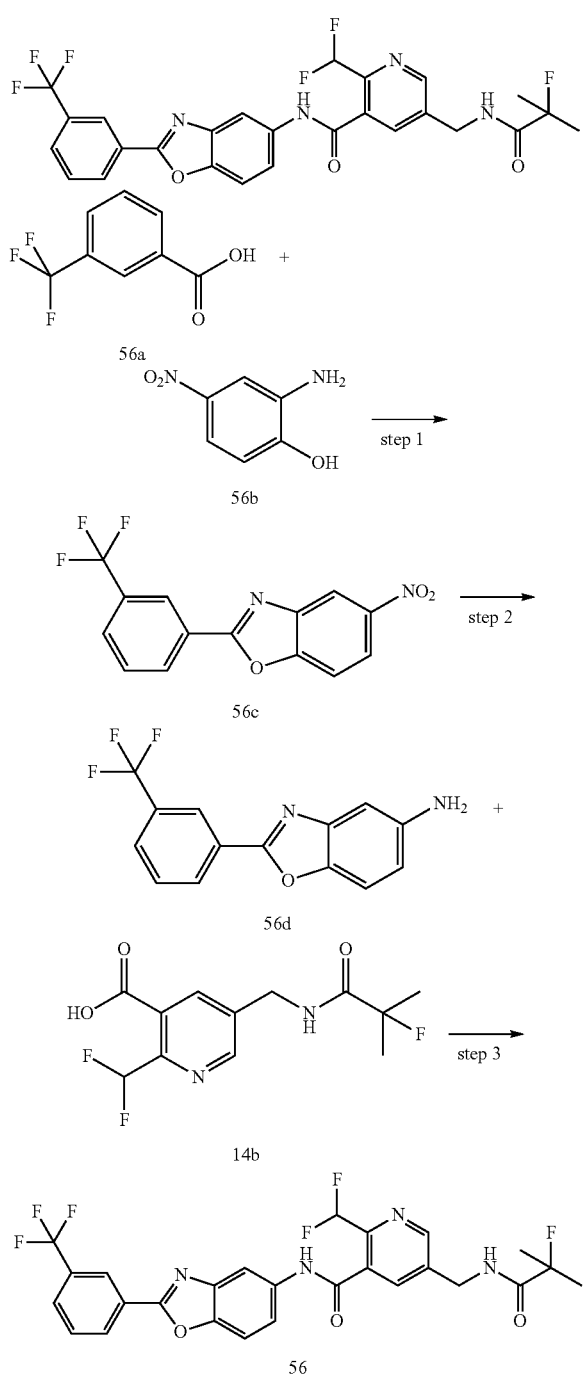

Step 1

5-Nitro-2-(3-(trifluoromethyl)phenyl)benzo[d]oxazole

To a flask, 10 mL of polyphosphoric acid was added and heated to 120° C. 3-(trifluoromethyl)benzoic acid 56a (1.48 g, 7.79 mmol) and 2-amino-4-nitro-phenol 56b (1.0 g, 6.49 mmol) were added portionwise. The resulting mixture was stirred for 12 hours at 120° C. The reaction mixture was cooled to room temperature, and poured into 50 mL of 1N sodium hydroxide solution. The solution was adjusted to pH 8 to 9 with 1N sodium hydroxide solution under an ice bath, and then extracted with ethyl acetate (50 mL×3), dried over anhydrous sodium sulfate, and filtered. The filtrate was concentrated under reduced pressure, and the residue was purified by thin layer chromatography (TLC) with elution system B to obtain the title compound 5-nitro-2-(3-(trifluoromethyl)phenyl) benzo[d]oxazole 56c (0.26 g, 10%) as a white solid.

MS m/z (ESI): 308.9 [M+1]

Step 2

2-(3-(Trifluoromethyl)phenyl)benzo[d]oxazole-5-amine

5-Nitro-2-(3-(trifluoromethyl)phenyl) benzo[d]oxazole 56c (100 mg, 0.3 mmol) was dissolved in 5 mL of tetrahydrofuran and 5 mL of methanol, and then added with Raney nickel (30 mg). The reaction mixture was stirred for 1 hour under a hydrogen atmosphere. The reaction mixture was filtered with celatom. The filtrate was concentrated under reduced pressure to obtain the crude title compound 2-(3-(trifluoromethyl)phenyl) benzo[d]oxazole-5-amine 56d (100 mg) as a yellow oil which was used in the next step without further purification.

MS m/z (ESI): 279.1 [M+1]

Step 3

2-(Difluoromethyl)-5-(((2-fluoro-2-methyl-propanoyl)amino)methyl)-N-(2-(3-(trifluoromethyl)phenyl)benzo[d]oxazol-5-yl)nicotinamide 2-(3-(Trifluoromethyl)phenyl) benzo[d]oxazole-5-amine 56d (100 mg, 0.325 mmol), 2-(difluoromethyl)-5-(((2-fluoro-2-methyl-propanoyl)amino)methyl)nicotinic acid 14b (94 mg, 0.325 mmol), 1-hydroxybenzotriazole (4.0 mg, 0.03 µmol), 1-ethyl-(3-dimethylaminopropyl)-carbodiimide hydrochloride (125 mg, 0.65 mmol) and triethylamime (0.18 mL, 1.3 mmol) were added in 10 mL of N,N-dimethylacetamide. The reaction mixture was stirred for 2 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(2-(3-(trifluoromethyl)phenyl)benzo[d]oxazol-5-yl)nicotinamide 56 (190 mg, 56%) as a light yellow solid.

MS m/z (ESI): 551.3 [M+1]

$^1$H NMR (400 MHz, DMSO-d$_6$): δ 10.94 (s, 1H), 8.88 (br, 1H), 8.71 (d, 1H), 8.51 (d, 1H), 8.46 (s, 1H), 8.27 (d, 1H), 8.05 (d, 2H), 7.89-7.97 (m, 1H), 7.84-7.88 (m, 1H), 7.72 (dd, 1H), 7.20 (t, 1H), 4.48 (d, 2H), 1.54 (s, 3H), 1.49 (s, 3H).

Example 57

2-Chloro-N-(2-(4-chlorophenyl)-3-oxo-isoindolin-5-yl)-5-((2,2-dimethylpropanoylamino)methyl)benzamide

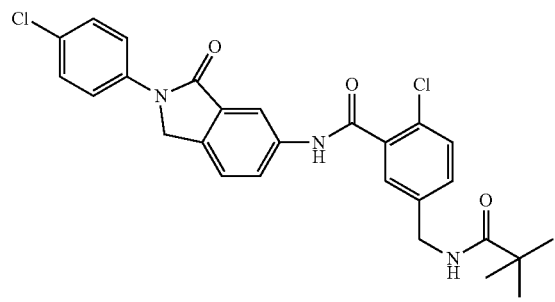

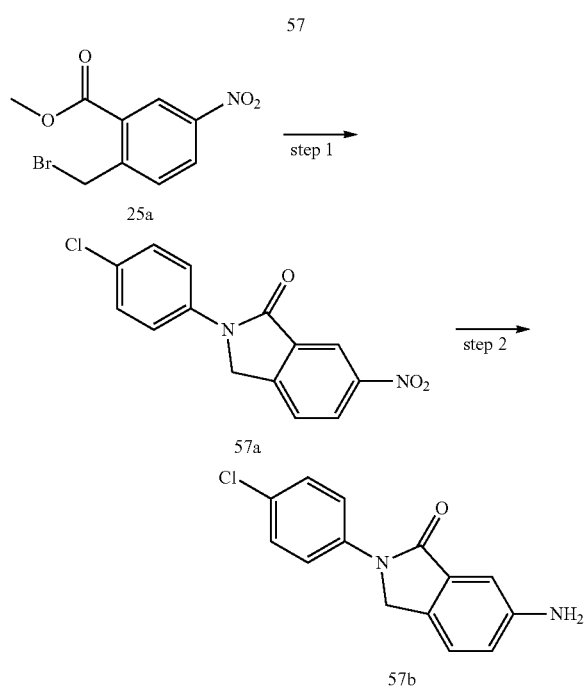

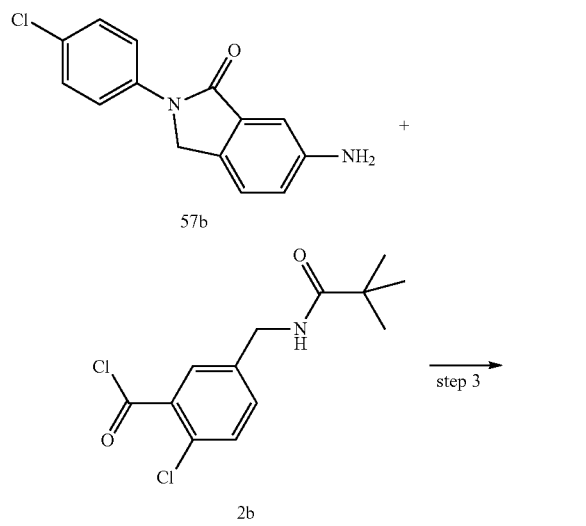

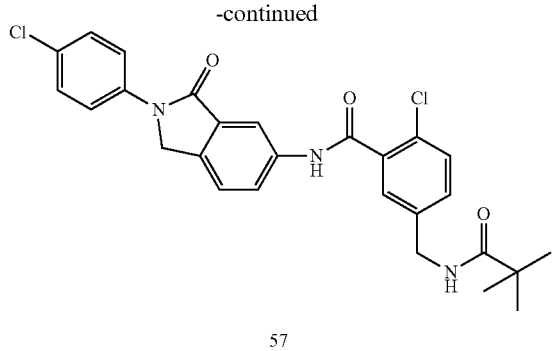

57

Step 1

2-(4-Chlorophenyl)-6-nitro-isoindolin-1-one

Methyl 2-(bromomethyl)-5-nitro-benzoate 25a (200 mg, 0.73 mmol), 4-chloroaniline (112 mg, 0.88 mmol) and N,N-diisopropylethylamine (113 mg, 0.88 mmol) were added in 5 mL of ethanol. The reaction mixture was heated to 110° C. and stirred for 16 hours. The reaction mixture was cooled to room temperature and filtered. The filter cake was washed with ethanol (0.5 mL×2) and dried to obtain the title compound 2-(4-chlorophenyl)-6-nitro-isoindolin-1-one 57a (160 mg, 76.2%) as a yellow solid.

MS m/z (ESI): 289.0 [M+1]

Step 2

6-Amino-2-(4-chlorophenyl)isoindolin-1-one 2-(4-Chlorophenyl)-6-nitro-isoindolin-1-one 57a (160 mg, 0.55 mmol) was dissolved in a mixture of 20 mL of tetrahydrofuran and methanol (V:V=1:1), and then added with Raney nickel (50 mg). The reaction mixture was stirred for 4 hours under a hydrogen atmosphere. The reaction mixture was filtered with celatom, and the filtrate was concentrated under reduced pressure to obtain the crude title compound 6-amino-2-(4-chlorophenyl)isoindolin-1-one 57b (160 mg) as a white solid which was used in the next step without further purification.

MS m/z (ESI): 259.1 [M+1]

Step 3

2-Chloro-N-(2-(4-chlorophenyl)-3-oxo-isoindolin-5-yl)-5-((2,2-dimethylpropanoylamino)methyl)benzamide 6-Amino-2-(4-chlorophenyl)isoindolin-1-one 57b (80 mg, 0.31 mmol) and triethylamine (0.2 mL, 1.49 mmol) were dissolved in 10 mL of acetonitrile, and then added with a 2 mL solution of 2-chloro-5-((2,2-dimethylpropanoylamino)methyl)benzoyl chloride 2b (74 mg, 0.26 mmol) in dichloromethane under an ice bath. The reaction mixture was stirred for 1 hour. The reaction mixture was concentrated under reduced pressure, and the residue was purified by thin layer chromatography (TLC) with elution system A to obtain the title compound 2-chloro-N-(2-(4-chlorophenyl)-3-oxo-isoindolin-5-yl)-5-((2,2-dimethyl propanoylamino)methyl)benzamide 57 (15 mg, 15.9% for two steps) as a light yellow solid.

MS m/z (ESI): 511.2[M+1]

¹H NMR (400 MHz, DMSO-d₆): δ 10.82 (s, 1H), 8.27 (s, 1H), 8.19 (t, 1H), 7.97 (d, 2H), 7.65 (d, 1H), 7.54 (d, 1H), 7.50-7.53 (m, 3H), 7.46 (s, 1H), 7.37 (d, 1H), 5.01 (s, 2H), 4.30 (s, 2H), 1.13 (s, 9H).

Example 58

2-Chloro-N-(3-oxo-2-(4-(trifluoromethyl)phenyl)isoindolin-5-yl)-5-((2,2-dimethyl-propanoyl)amino)methyl)-benzamide

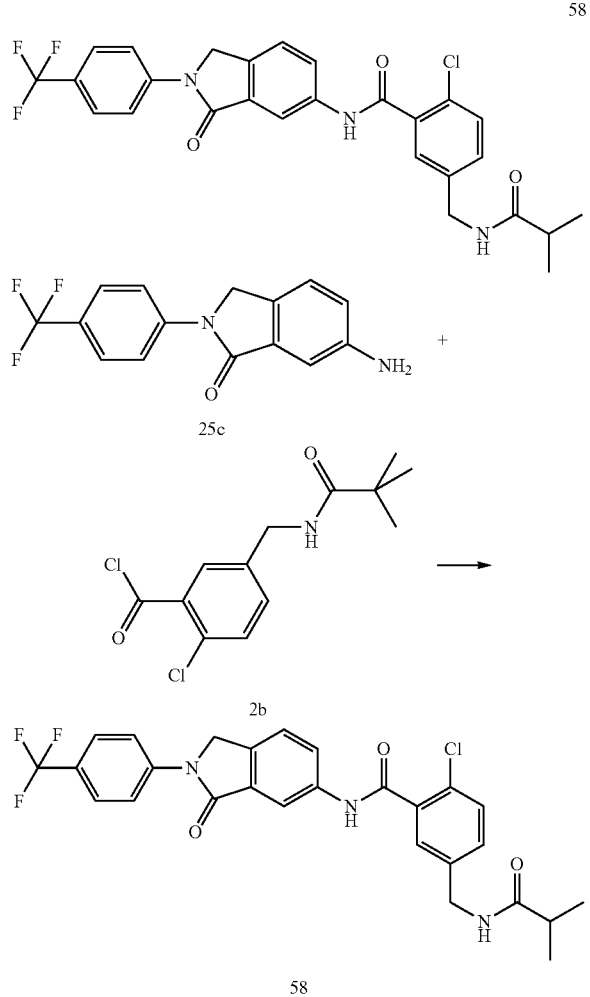

6-Amino-2-(4-(trifluoromethyl)phenyl)isoindolin-1-one 25c (82 mg, 0.28 mmol) and triethylamine (0.2 mL, 1.49 mmol) were dissolved in 10 mL of dichloromethane, and then added with a 10 mL solution of 2-chloro-5-((2,2-dimethylpropanoylamino)methyl)benzoyl chloride 2b (80 mg, 0.28 mmol) in dichloromethane under an ice bath. The reaction mixture was stirred for 1 hour. The reaction mixture was concentrated under reduced pressure, and the residue was purified by thin layer chromatography (TLC) with elution system A to obtain the title compound 2-chloro-N-(3-oxo-2-(4-(trifluoromethyl)phenyl)isoindolin-5-yl)-5-((2,2-dimethyl-propanoyl)amino)methyl)-benzamide 58 (4 mg, 2.6%) as a light yellow solid.

MS m/z (ESI): 544.1 [M+1]

¹H NMR (400 MHz, DMSO-d₆): δ 10.84 (s, 1H), 8.30 (d, 1H), 8.17 (d, 3H), 7.87 (d, 1H), 7.82 (s, 2H), 7.70 (d, 1H), 7.55 (d, 1H), 7.47 (s, 1H), 7.38 (d, 1H), 5.08 (s, 2H), 4.30 (d, 2H), 1.13 (s, 9H)

Example 59

2-(Difluoromethyl)-5-(((2-fluoro-2-methyl-propanoyl)amino)methyl)-N-(3-oxo-2-(3-(trifluoromethyl)phenyl)isoindolin-5-yl)nicotinamide

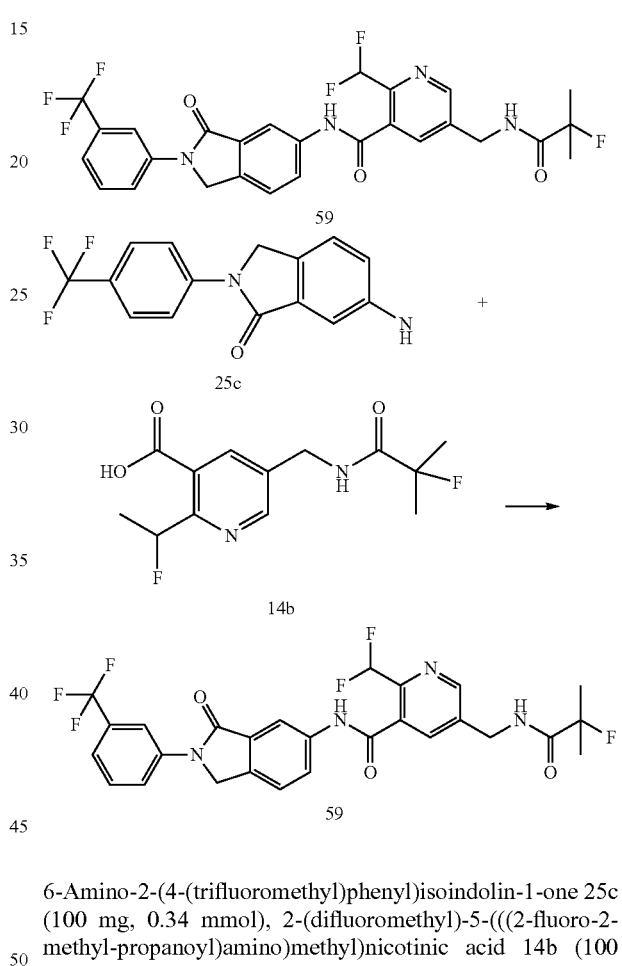

6-Amino-2-(4-(trifluoromethyl)phenyl)isoindolin-1-one 25c (100 mg, 0.34 mmol), 2-(difluoromethyl)-5-(((2-fluoro-2-methyl-propanoyl)amino)methyl)nicotinic acid 14b (100 mg, 0.34 mmol), 1-ethyl-(3-dimethylaminopropyl)-carbodiimide hydrochloride (130 mg, 0.69 mmol), 1-hydroxybenzotriazole (5.0 mg, 37 μmol) and triethylamine (140 μL, 1.03 mmol) were added in 5 mL of N,N-dimethylacetamide. The reaction mixture was stirred for 16 hours. The reaction mixture was concentrated under reduced pressure, and the residue was purified by thin layer chromatography (TLC) with elution system A to obtain the title compound 2-(difluoromethyl)-5-(((2-fluoro-2-methyl-propanoyl)amino)methyl)-N-(3-oxo-2-(3-(trifluoromethyl)phenyl)isoindolin-5-yl)nicotinamide 59 (80 mg, 41.5%) as a light yellow solid.

MS m/z (ESI): 565.1 [M+1]

¹H NMR (400 MHz, DMSO-d₆): δ 11.02 (s, 1H), 8.89 (br, 1H), 8.71 (d, 1H), 8.45 (s, 1H), 8.27 (d, 1H), 8.13 (d, 1H), 8.06 (s, 1H), 7.91 (d, 1H), 7.70 (d, 2H), 7.55 (d, 1H), 7.20 (t, 1H), 5.11 (s, 2H), 4.48 (d, 2H), 1.54 (s, 3H), 1.48 (s, 3H).

TEST EXAMPLES

Biological Assay

Test Example 1

The Inhibition Activity of the Present Compounds for Human mPGES1

The method described here is used for determining the inhibition activity of the present compounds for human mPGES1.

I. Materials and Apparatus
1. PGE2 Assay kit (Cisbio, #62P2APEB)
2. Prostaglandin H2 (Sigma, #P7867-1MG)
3. FlexStation3 microplate reader.

II. Experimental Procedure
1. Obtaining the membrane proteins of mPGES1 enzyme

The cell density of HEK-293 F was grown to $6 \times 10^5$ per milliliter and was transferred with the plasmid containing human mPGES1 gene by transfection reagent PEI the next day. The cells were continuously cultured for 72 hours at 37° C. with shaking. After centrifuging at 1100 g for 5 minutes, the cells were harvested. After ultrasonication in an ice bath and centrifugation at 5000 g for 10 minutes, the supernatant was obtained. The supernatant was centrifuged at 100000 g for 1 hour to obtain a precipitate. The precipitate was resuspended with storage buffer containing 10% glycerinum, subpackaged and frozen rapidly under liquid nitrogen, and stored at −80° C.

2. mPGES1 enzyme assay mPGES1 was diluted with assay buffer and added into plate at 49 μL/well supplemented with 1 μL of compound (the final concentration of each compound at seven gradient concentrations was 10000 nM, 1000 nM, 100 nM, 10 nM, 1 nM, 0.1 nM and 0.01 nM). Each well was added with 3.8 μL of 20 μg/mL PGH precooled on ice after shaking for 30 seconds and incubated for 7 minutes on ice. Then, each well was added with 53.8 μL of 6 mg/mL $SnCl_2$ to quench the reaction. The sample was diluted with dilute buffer at 1:400. 10 μl of diluted sample, 5 μL PGE2-d2 and 5 μL anti-PGE2 Cryptate were added to a black 384-well plate, and incubated at 4° C. overnight. HTRF was determined using Flexstation, and the $IC_{50}$ of the compounds was obtained by data processing software.

The inhibition activity of the present compounds on mPGES1 was tested by the assay described above. The $IC_{50}$ values are shown in Table I below.

TABLE 1

Inhibition ($IC_{50}$) of the present compounds on human mPGES1

| Example No. | IC50 (nM) |
|---|---|
| 1 | 8.26 |
| 5 | 21.97 |
| 7 | 6.02 |
| 8 | 3.88 |
| 9 | 15.64 |
| 10 | 11.15 |
| 11 | 5.14 |
| 13 | 7.43 |
| 14 | 4.59 |
| 15 | 23.44 |
| 16 | 9.31 |
| 17 | 2.68 |
| 18 | 5.15 |
| 19 | 8.12 |
| 20 | 3.54 |
| 21 | 8.24 |
| 22 | 6.69 |
| 23 | 4.73 |
| 24 | 17.22 |
| 25 | 11.86 |
| 26 | 3.38 |
| 27 | 4.77 |
| 30 | 2.99 |
| 31 | 2.95 |
| 30 | 1.73 |
| 31 | 4.12 |
| 32 | 2.24 |
| 33 | 5.33 |
| 34 | 7.75 |
| 35 | 4.07 |
| 36 | 4.19 |
| 37 | 6.46 |
| 38 | 5.43 |
| 39 | 3.68 |
| 40 | 22.44 |
| 41 | 25.65 |
| 42 | 7.21 |
| 43 | 15.96 |
| 45 | 49.39 |
| 46 | 2.71 |
| 47 | 5.72 |
| 48 | 3.58 |
| 49 | 8.29 |
| 54 | 47.09 |
| 55 | 29.78 |
| 56 | 7.74 |
| 57 | 6.75 |
| 58 | 8.51 |
| 59 | 1.18 |

Conclusion: The present compounds have significant inhibition activity on human mPGES1 protein.

Test Example 2

The Inhibition Activity of the Present Compounds on Guinea Pig mPGES1

The method described here was used for determining the inhibition activity of the present compounds for guinea pig mPGES1.

I. Materials and Apparatus
1. PGE2 Assay kit (Cisbio, #62P2APEB)
2. Prostaglandin H2 (Sigma, #P7867-1MG)
3. FlexStation3 microplate reader.

II. Experimental Procedure
1. Obtain the membrane proteins of mPGES1 enzyme

The cell density of HEK-293 F was grown to $6 \times 10^5$ per milliliter and was transferred with the plasmid containing human mPGES1 gene by transfection reagent PEI the next day. The cells were continuously cultured for 72 hours at 37° C. with shaking. After centrifuging at 1100 g for 5 minutes, the cells were harvested. After ultrasonication in an ice bath and centrifugation at 5000 g for 10 minutes, the supernatant was obtained. The supernatant was centrifuged at 100000 g for 1 hour to obtain a precipitate. The precipitate was resuspended with storage buffer containing 10% glycerinum, subpackaged and frozen rapidly under liquid nitrogen, and storage at −80° C.

2. mPGES1 enzyme assay mPGES1 was diluted with assay buffer and added into a plate at 49 μL/well supplemented with 1 μL of compound (the final concentration of each compound at seven gradient concentrations was 10000 nM, 1000 nM, 100 nM, 10 nM, 1 nM, 0.1 nM and 0.01 nM). Each well was added with 3.8 μL of 20 μg/mL PGH precooled on ice after shaking for 30 seconds and incubated for 7 minutes on ice. Then, each well was added with 53.8 μL of 6 mg/mL $SnCl_2$ to quench the reaction. The sample was diluted with dilute buffer at 1:400.

10 μl of diluted sample, 5 μL PGE2-d2 and 5 μL anti-PGE2 Cryptate were added to a black 384-well plate, and incubated at 4° C. overnight. HTRF was determined using Flexstation, and the $IC_{50}$ of the compounds was obtained by data processing software. The inhibition activity of the present compounds on mPGES1 was tested by the assay described above. The $IC_{50}$ values are shown in table 2 below.

TABLE 2

The inhibition ($IC_{50}$) of the present compounds on guinea pig mPGES1

| Example No. | $IC_{50}$ (nM) |
|---|---|
| 11 | 710.60 |
| 14 | 91.18 |
| 18 | 152.50 |
| 20 | 74.73 |
| 32 | 16.86 |
| 33 | 107.60 |
| 35 | 39.88 |
| 36 | 137.30 |
| 37 | 141.10 |

Conclusion: The present compounds have significant activity against guinea pig mPGES1 protein.

Test Example 3

The Inhibition Activity of the Present Compounds on the Secretion of PGE2 by A549 Cells Stimulated with IL-1β

The method described here was used for determining the inhibition activity of the present compounds on the secretion of PGE2 by A549 cells stimulated with IL-1β.

I. Materials and Apparatus

1. PGE2 Assay kit (Cisbio, #62P2APEB)

2. IL-1β (Peprotech, # AF-200-01B)

3. Cell line: A549 (ATCC: CCL-185)

4. FlexStation3 microplate reader.

II. Experimental Procedure

On the first day, A549 cells were inoculated in a 96-well plate at 40000/well. On the second day, the culture medium in the 96-well plate was removed and then added with 90 μL of compound diluted with culture medium (the concentration of each compound at seven gradient concentrations was 11111 nM, 11111 nM, 111 nM, 11.11 nM, 1.11 nM, 0.11 nM and 0.011 nM). The cells were incubated for 30 minutes at 37° C. in an incubator, and then added with IL-1β to a final concentration of 0.2 ng/mL. Then, the cells were incubated for another 24 hours at 37° C. On the third day, 10 μl of supernatant, 5 μL of PGE2-d2 and 5 μL of anti-PGE2 Cryptate were added into a black 384-well plate, and then incubated at 4° C. overnight. HTRF was determined using Flexstation, and the $IC_{50}$ of the compounds was obtained by data processing software.

The inhibition activity of the present compounds on the secretion of PGE2 by A549 cells stimulated with IL-1β was determined by the assay described above. The $IC_{50}$ values are shown in Table 3 below.

TABLE 3

The inhibition activity ($IC_{50}$) of the present compounds on the secretion of PGE2 by A549 cells stimulated with IL-1β

| Example No. | $IC_{50}$ (nM) |
|---|---|
| 1 | 3.55 |
| 4 | 26.87 |
| 5 | 12.40 |
| 6 | 68.10 |
| 7 | 10.44 |
| 8 | 19.15 |
| 9 | 11.85 |
| 10 | 12.31 |
| 11 | 16.30 |
| 13 | 16.67 |
| 14 | 20.46 |
| 15 | 33.31 |
| 16 | 26.18 |
| 17 | 12.14 |
| 18 | 17.19 |
| 19 | 42.60 |
| 20 | 12.57 |
| 21 | 57.42 |
| 22 | 38.80 |
| 23 | 49.02 |
| 24 | 45.65 |
| 25 | 47.63 |
| 26 | 46.05 |
| 27 | 13.44 |
| 30 | 19.17 |
| 31 | 32.39 |
| 30 | 7.18 |
| 31 | 17.00 |
| 32 | 18.83 |
| 33 | 12.78 |
| 34 | 12.21 |
| 35 | 31.56 |
| 36 | 13.22 |
| 37 | 22.45 |
| 38 | 42.85 |
| 39 | 30.53 |
| 40 | 16.87 |
| 43 | 58.18 |
| 45 | 25.91 |
| 46 | 24.70 |
| 47 | 18.93 |
| 48 | 14.13 |
| 49 | 23.97 |
| 52 | 55.20 |
| 54 | 58.53 |
| 56 | 27.49 |
| 57 | 6.22 |
| 58 | 2.18 |
| 59 | 20.52 |

Conclusion: The present compounds have significant inhibition activity on the secretion of PGE2 by A549 cells stimulated with IL-1β.

Pharmacokinetics Assay

Test Example 4

The Pharmacokinetics Assay of the Present Compounds

1. Abstract

Rats were used as test animals. The drug concentration in plasma at different time points was determined by LC/MS/MS after administration of the compounds of Example 8, Example 11, Example 14, Example 17, Example 20, Example 27, Example 33, Example 35, Example 36, Example 37 and Example 48 to rats. The pharmacokinetic behavior of the present compounds was studied and evaluated in rats.

2. Protocol 2.1 Samples

Compounds of Example 8, Example 11, Example 14, Example 17, Example 20, Example 27, Example 33, Example 35, Example 36, Example 37 and Example 48.

2.2 Test Animals

Forty four (44) healthy adult Sprague-Dawley (SD) rats, half male and half female, which were purchased from SINO-BRITSH SIPPR/BK LAB. ANIMAL LTD., CO, with Certificate No.: SCXK (Shanghai) 2008-0016, were divided into 11 groups, with 4 rats in each group.

2.3 Preparation of the Test Compounds

The appropriate amount of test compounds was weighed, and mixed with 25 µL Tween 80 and Labrasol to prepare a 0.6 mg/mL suspension by ultrasonication.

2.4 Administration

After an overnight fast, 44 SD rats, half male and half female, were divided into 11 groups, and administered intragastrically at a dose of 5.0 mg/kg and an administration volume of 10 mL/kg.

3. Process

Blood (0.1 mL) was sampled from the orbital sinus before administration and 0.5 h, 1.0 h, 2.0 h, 4.0 h, 6.0 h, 8.0 h, 11.0 h, and 24.0 h after administration. The samples were stored in EDTA anticoagulation tubes, and centrifuged for 5 minutes at 3,500 rpm to separate the blood plasma. The plasma samples were stored at −20° C. The rats were fed 2 hours after administration.

The plasma concentration of the test compounds in rat after intragastric administration was determined by LC-MS/MS. The linearity of the method is 5.00-2000 ng/mL and 1.00-2000 ng/ml, and the minimum of quantification is 5.00 ng/mL and 1.00 ng/mL.

Plasma samples were analyzed after pretreatment by protein precipitation.

4. Results of Pharmacokinetic Parameters

Pharmacokinetic parameters of the present compounds are shown as follows.

Conclusion: The present compounds have good pharmacokinetic data and significant pharmacokinetic absorption effect.

The invention claimed is:

1. A compound of formula (III), formula (IV), or formula (V), or a tautomer, mesomer, racemate, enantiomer, diastereomer, or mixture thereof, or pharmaceutically acceptable salt thereof:

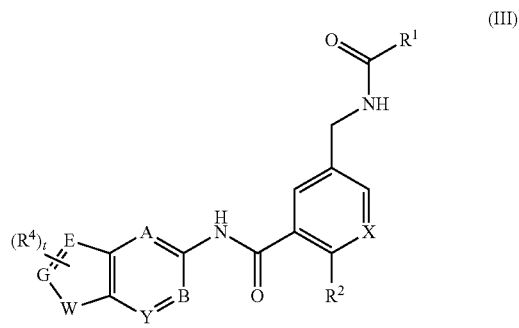

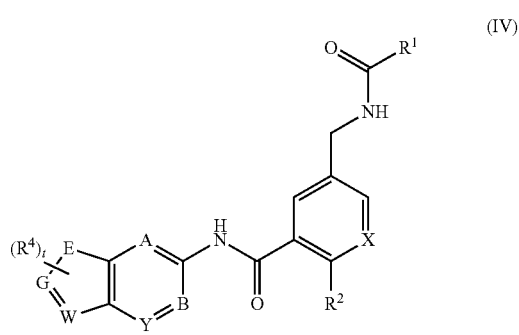

| Example No | Plasma Conc. Cmax (ng/mL) | Area Under Curve AUC (ng/mL*h) | Half-Life T½ (h) | Mean Residence Time MRT (h) | Clearance CLz/F (ml/min/kg) | Apparent Distribution Volume Vz/F (ml/kg) |
|---|---|---|---|---|---|---|
| 8 | 346 ± 155 | 2899 ± 1342 | 4.69 ± 3.74 | 8.21 ± 4.88 | 32.7 ± 13.1 | 10470 ± 4664 |
| 11 | 572 ± 167 | 7231 ± 5319 | 5.27 ± 3.25 | 10.4 ± 5.1 | 19.2 ± 14.1 | 5829 ± 1144 |
| 14 | 150 ± 56 | 1787 ± 984 | 4.15 ± 1.59 | 9.25 ± 2.24 | 56.7 ± 25.4 | 17936 ± 3118 |
| 17 | 155 ± 26 | 2002 ± 650 | 5.44 ± 1.23 | 10.4 ± 1.9 | 45.3 ± 15.3 | 20169 ± 2601 |
| 20 | 681 ± 195 | 8242 ± 2285 | 5.94 ± 2.00 | 11.1 ± 3.0 | 10.7 ± 2.7 | 5412 ± 1815 |
| 27 | 193 ± 23 | 1176 ± 247 | 2.46 ± 0.59 | 5.32 ± 1.03 | 73.3 ± 15.3 | 15091 ± 1533 |
| 33 | 557 ± 80 | 5721 ± 1210 | 3.72 ± 0.38 | 7.60 ± 1.09 | 15 2 ± 3 8 | 4823 ± 961 |
| 35 | 1513 ± 517 | 37418 ± 36701 | 11.3 ± 14.5 | 18.8 ± 20.6 | 4.69 ± 3.72 | 1853 ± 576 |
| 36 | 459 ± 157 | 3537 ± 1968 | 3.69 ± 2.40 | 6.56 ± 3.01 | 30.4 ± 17.0 | 7218 ± 1340 |
| 37 | 2349 ± 676 | 23174 ± 14236 | 4.49 ± 2.93 | 7.34 ± 3.76 | 5.44 ± 4.31 | 1388 ± 170 |
| 48 | 263 ± 66 | 2259 ± 767 | 2.30 ± 0.76 | 6.30 ± 1.62 | 41.0 ± 16.7 | 7528 ± 1689 |

-continued

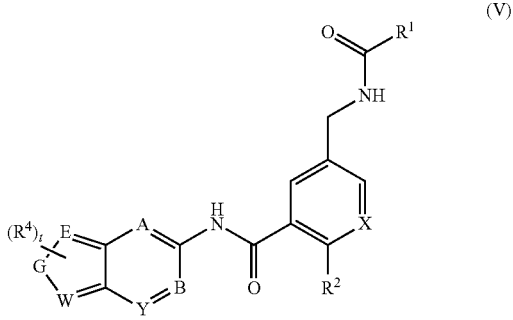

(V)

wherein:
X is —CH— or N;
each of E, G and W is independently selected from the group consisting of $CR^a$, $NR^b$, and N;
$R^a$ and $R^b$ are each independently selected from the group consisting of hydrogen, halogen, alkoxy, cyano, nitro, alkyl, cycloalkyl, heterocyclyl, —C(O)$OR_5$, —OC(O)$R^5$, —NHS(O)$_m R^5$, —C(O)$R^5$, —NHC(O)$R^5$, —NHC(O)$OR^5$, —$NR^6R^7$, —OC(O)$NR^6R^7$ and —C(O)$NR^6R^7$, wherein the alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)$OR^5$, —OC(O)$R^5$, —NHS(O)$_m R^5$, —C(O)$R^5$, —NHC(O)$R^5$, —NHC(O)$OR^5$, —$NR^6R^7$, —OC(O)$NR^6R^7$ and —C(O)$NR^6R^7$;
each of A, B and Y is —CH—;
$R^1$ is selected from the group consisting of alkyl and cycloalkyl, wherein the alkyl or cycloalkyl is optionally further substituted by one or more groups selected from the group consisting of alkyl, halogen and haloalkyl;
$R^2$ is selected from the group consisting of halogen and haloalkyl;
$R^4$ is selected from the group consisting of aryl and heteroaryl, wherein the aryl and heteroaryl are each optionally further substituted by one or more groups selected from the group consisting of halogen, alkoxy, hydroxyl, cyano, nitro, alkyl, haloalkyl, hydroxyalkyl, cycloalkyl, heterocyclyl, aryl, heteroaryl, —C(O)$OR^5$, —OC(O)$R^5$, —NHS(O)$_m R^5$, —C(O)$R^5$, —NHC(O)$R^5$, —NHC(O)$OR^5$, —$NR^6R^7$, —OC(O)$NR^6R^7$ and —C(O)$NR^6R^7$;
$R^5$ is selected from the group consisting of alkyl, alkenyl, alkynyl, cycloalkyl, heterocyclyl, aryl and heteroaryl, wherein the alkyl, cycloalkyl, aryl and heteroaryl are each optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group;
$R^6$ and $R^7$ are each independently selected from the group consisting of hydrogen, alkyl, alkoxy, cycloalkyl, heterocyclyl, aryl and heteroaryl, wherein the alkyl, alkoxy, cycloalkyl, heterocyclyl, aryl and heteroaryl are each independently and optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group; or $R^6$ and $R^7$ are taken together with the nitrogen atom to which they are attached to form a heterocyclyl, wherein the heterocyclyl optionally contains one or more heteroatoms selected from the group consisting of N, O and S (O)$_m$, and wherein the heterocyclyl is optionally further substituted by one or more groups selected from the group consisting of alkyl, halogen, hydroxyl, alkoxy, hydroxyalkyl, cycloalkyl, heterocyclyl, aryl, heteroaryl, carboxylic acid and carboxylate group;
m is 0, 1 or 2; and
t is 0 or 1.

2. The compound of formula (III), formula (IV), or formula (V), or the tautomer, mesomer, racemate, enantiomer, diastereomer, or mixture thereof, or pharmaceutically acceptable salt thereof according to claim 1, being a compound of formula (VI), or a tautomer, mesomer, racemate, enantiomer, diastereomer, or mixture thereof, or pharmaceutically acceptable salt thereof:

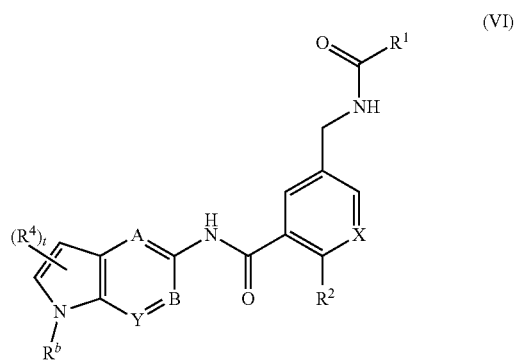

(VI)

wherein:
X is —CH— or N;
$R^b$ is selected from the group consisting of hydrogen, halogen, alkoxy, cyano, nitro, alkyl, cycloalkyl, heterocyclyl, —C(O)$OR^5$, —OC(O)$R^5$, —NHS(O)$_m R^5$, —C(O)$R^5$, —NHC(O)$R^5$, —NHC(O)$OR^5$, —$NR^6R^7$, —OC(O)$NR^6R^7$ and —C(O)$NR^6R^7$, wherein the alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)$OR^5$, —OC(O)$R^5$, —NHS(O)$_m R^5$, —C(O)$R^5$, —NHC(O)$R^5$, —NHC(O)$OR^5$, —$NR^6R^7$, —OC(O)$NR^6R^7$ and —C(O)$NR^6R^7$; and
A, B, Y, t, $R^1$ to $R^2$ and $R^4$ to $R^7$ are as defined in claim 1.

3. The compound of formula (III), formula (IV), or formula (V), or the tautomer, mesomer, racemate, enantiomer, diastereomer, or mixture thereof, or pharmaceutically acceptable salt thereof according to claim 1, being a compound of formula (VII), or a tautomer, mesomer, racemate, enantiomer, diastereomer, or mixture thereof, or pharmaceutically acceptable salt thereof:

(VII)

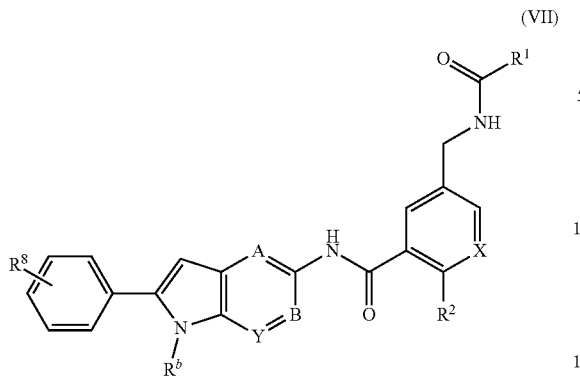

wherein:

X is —CH— or N;

R$^b$ is selected from the group consisting of hydrogen, halogen, alkoxy, cyano, nitro, alkyl, cycloalkyl, heterocyclyl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein the alkyl, cycloalkyl and heterocyclyl are each optionally further substituted by one or more groups selected from the group consisting of halogen, hydroxy, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$;

R$^8$ is selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$; and A, B, Y, R$^1$ to R$^2$ and R$^5$ to R$^7$ are as defined in claim 1.

4. A compound of formula (I), or the tautomer, mesomer, racemate, enantiomer, diastereomer, or mixture thereof, or pharmaceutically acceptable salt thereof:

(I)

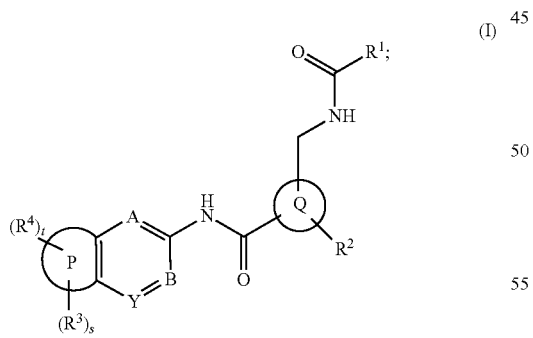

wherein ring Q is selected from the group consisting of phenyl and pyridine;

R$^1$ is selected from the group consisting of alkyl and cycloalkyl, wherein the alkyl or cycloalkyl is optionally further substituted by one or more groups selected from the group consisting of alkyl, halogen and haloalkyl;

R$^2$ is selected from the group consisting of halogen and haloalkyl;

wherein the group

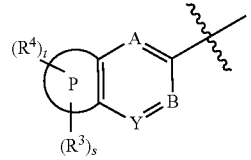

is selected from the group consisting of:

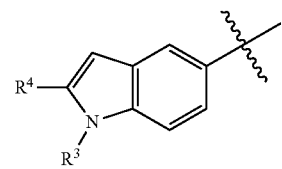

,

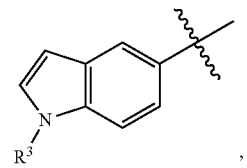

,

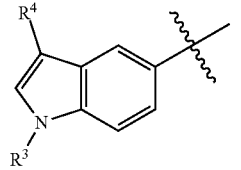

,

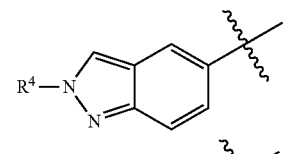

,

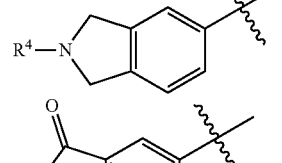

,

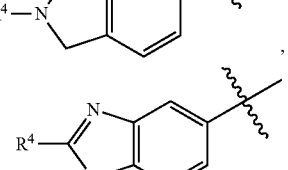

, and

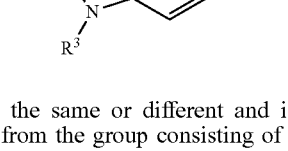

, each R$^3$ is the same or different and is independently selected from the group consisting of hydrogen, halogen, alkoxy, cyano, nitro, alkyl, cycloalkyl, heterocyclyl, oxo, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein the alkyl, cycloalkyl and heterocyclyl are each optionally further substituted by one or more groups selected from the group consisting of halogen, hydroxyl, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$;

R[4] is selected from the group consisting of aryl and heteroaryl, wherein the aryl and heteroaryl are each optionally further substituted by one or more groups selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR[5], —OC(O)R[5], —NHS(O)$_m$R[5], —C(O)R[5], —NHC(O)R[5], —NHC(O)OR[5], —NR[6]R[7], —OC(O)NR[6]R[7] and —C(O)NR[6]R[7];

R[5] is selected from the group consisting of alkyl, alkenyl, alkynyl, cycloalkyl, heterocyclyl, aryl and heteroaryl, wherein the alkyl, cycloalkyl, aryl and heteroaryl are each optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group;

R[6] and R[7] are each independently selected from the group consisting of hydrogen, alkyl, alkoxy, cycloalkyl, heterocyclyl, aryl and heteroaryl, wherein the alkyl, alkoxy, cycloalkyl, heterocyclyl, aryl and heteroaryl are each independently and optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group; or R[6] and R[7] are taken together with the nitrogen atom to which they are attached to form a heterocyclyl, wherein the heterocyclyl optionally contains one or more heteroatoms selected from the group consisting of N, O and S(O)$_m$, and wherein the heterocyclyl is optionally further substituted by one or more groups selected from the group consisting of alkyl, halogen, hydroxyl, alkoxy, hydroxyalkyl, cycloalkyl, heterocyclyl, aryl, heteroaryl, carboxylic acid and carboxylate group; and m is 0, 1 or 2.

5. The compound of formula (III), formula (IV), or formula (V), or the tautomer, mesomer, racemate, enantiomer, diastereomer, or mixture thereof, or pharmaceutically acceptable salt thereof according to claim 1, wherein R[1] is selected from the group consisting of alkyl and haloalkyl.

6. A compound selected from the group consisting of:

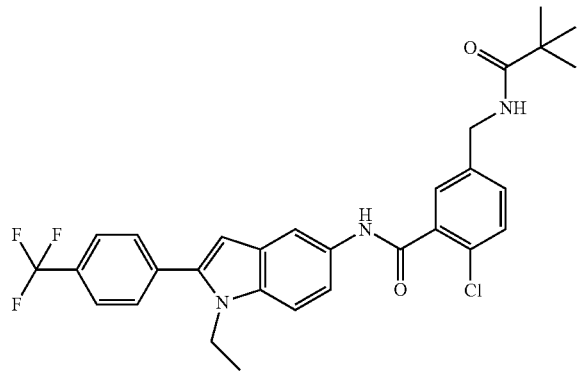

2

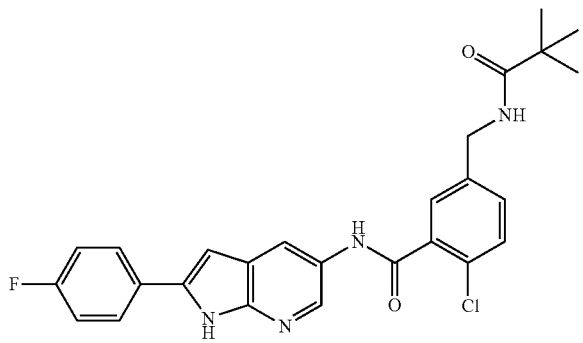

3

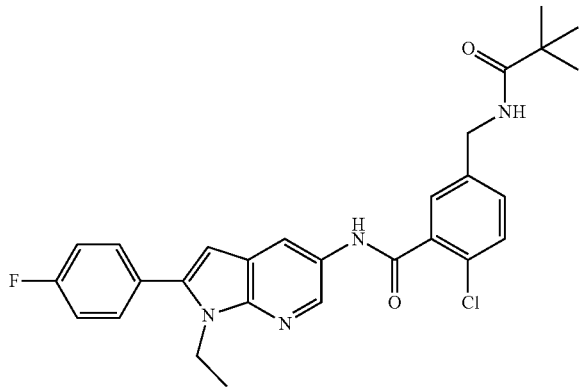

4

-continued

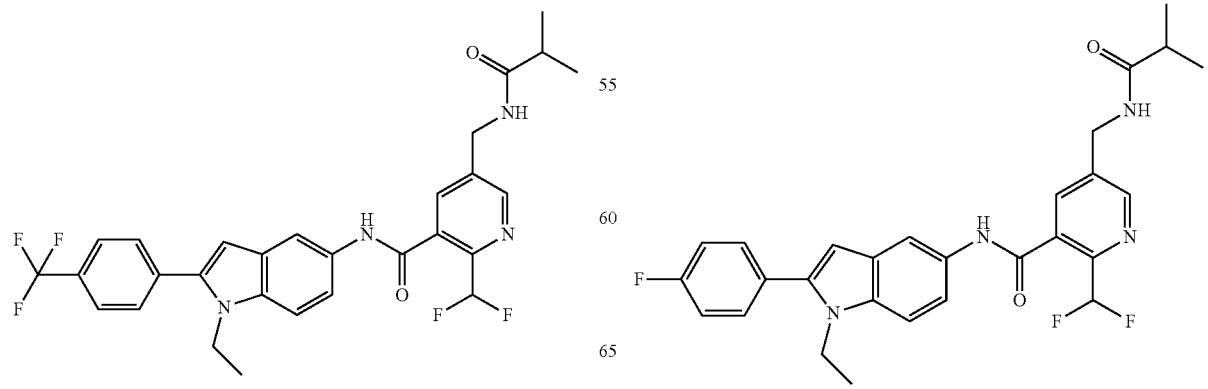

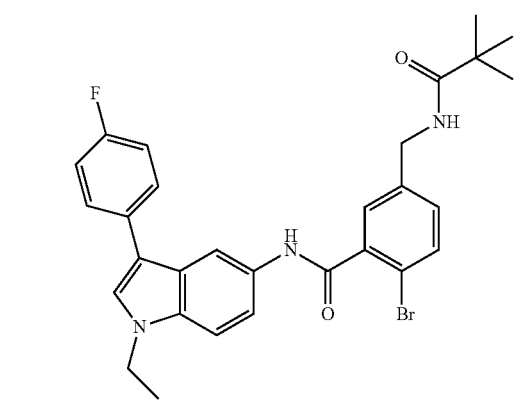
6
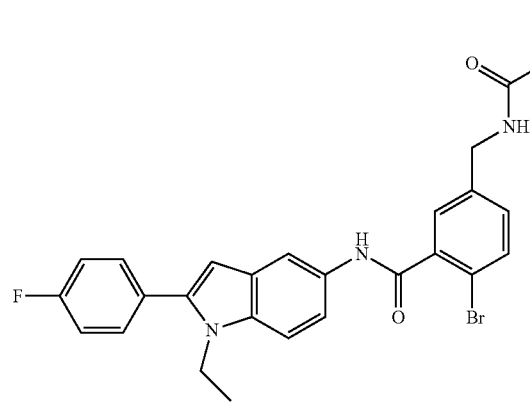
7
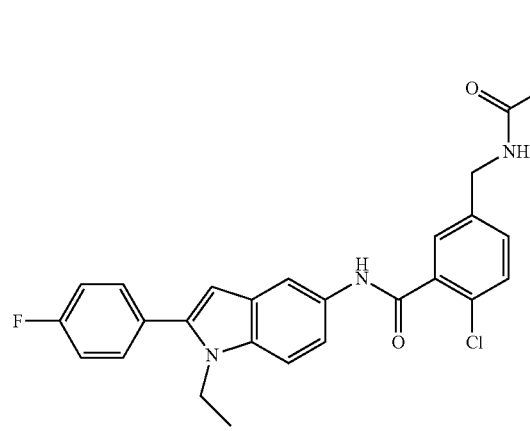
8
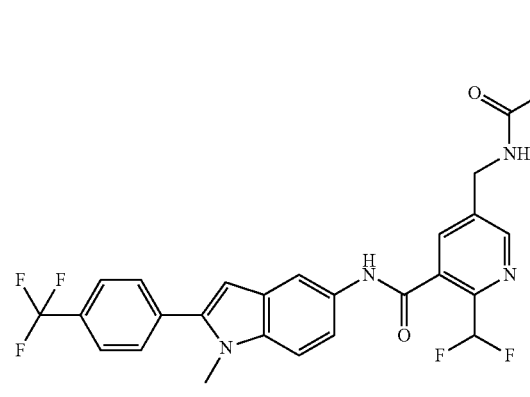
9
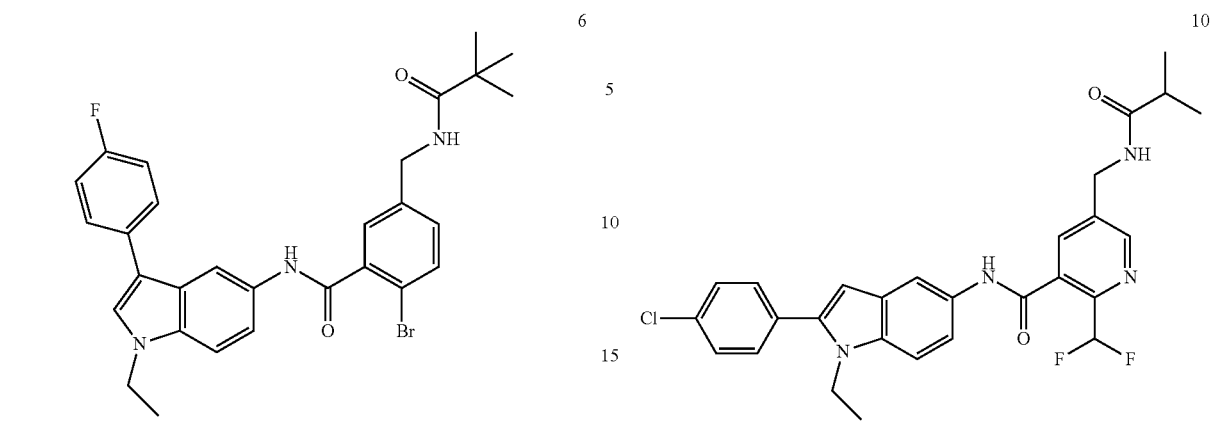
10
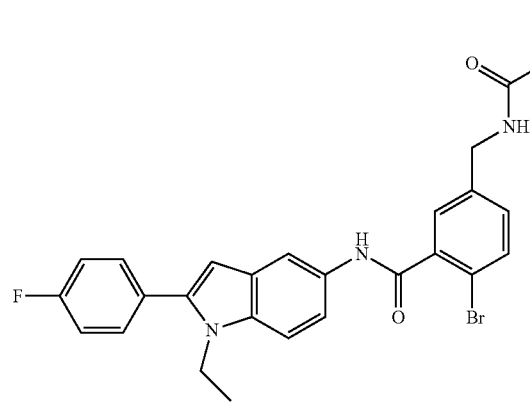
11
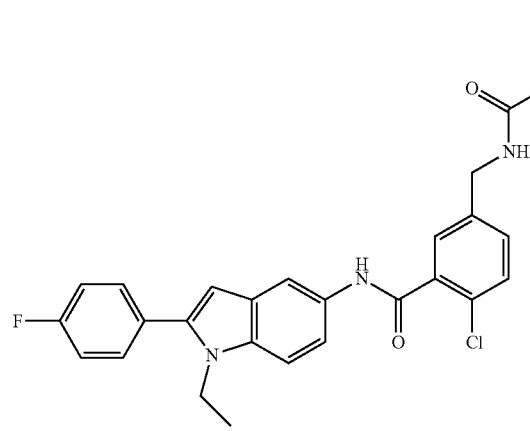
12
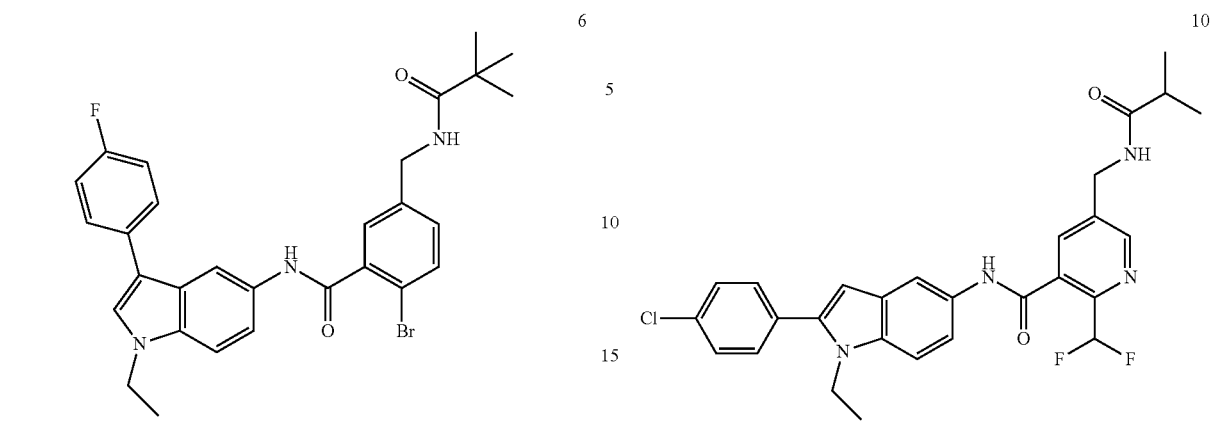
13

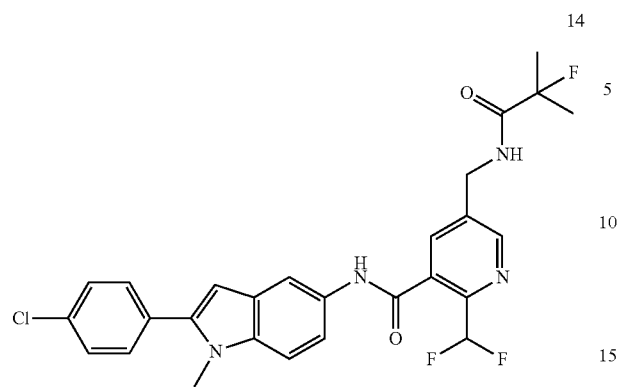
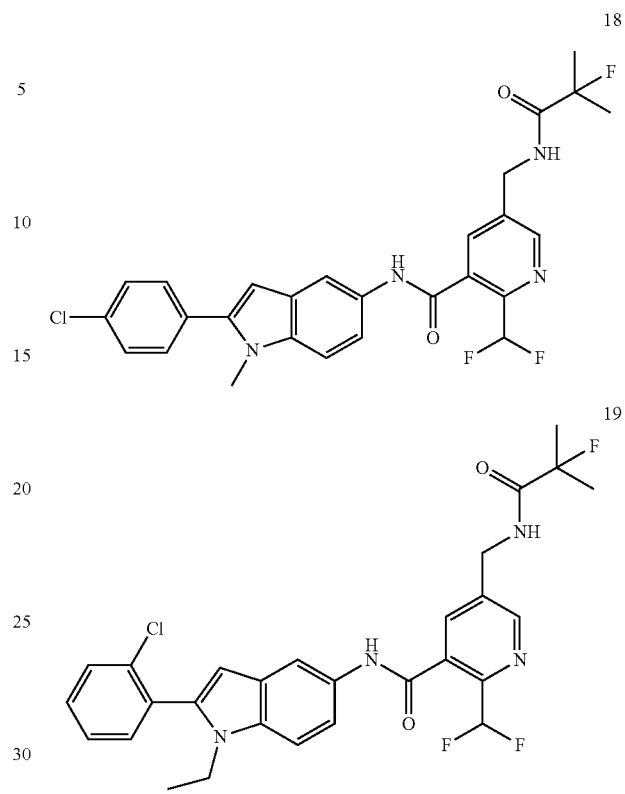
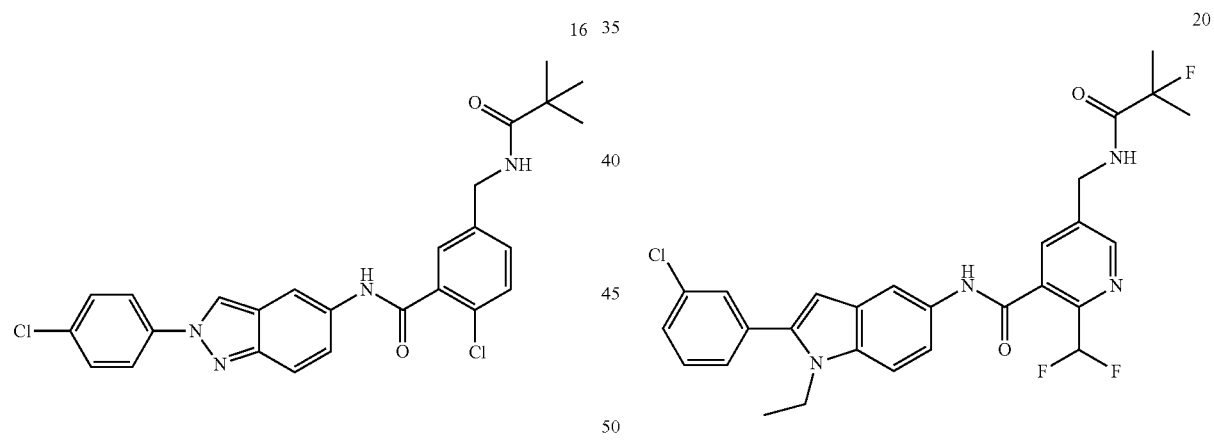
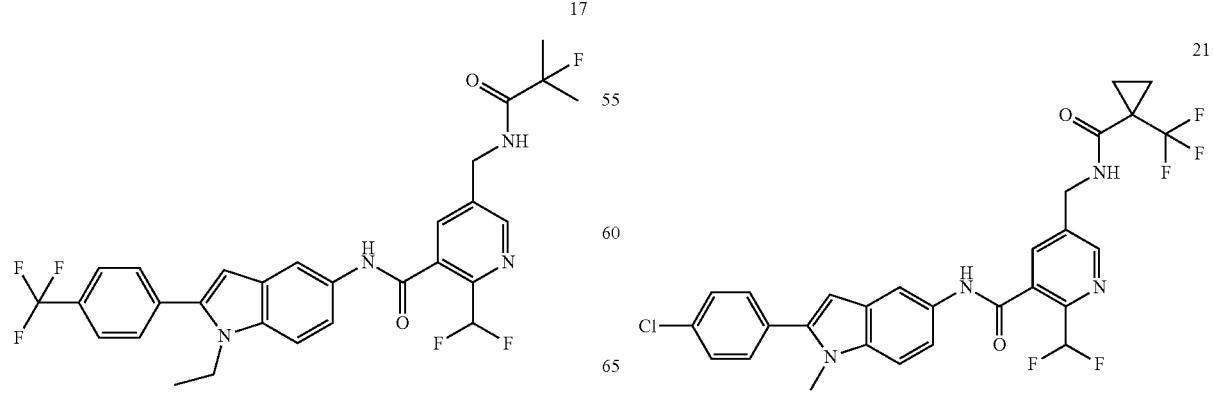

22
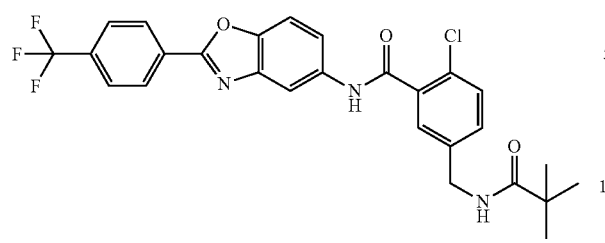
23
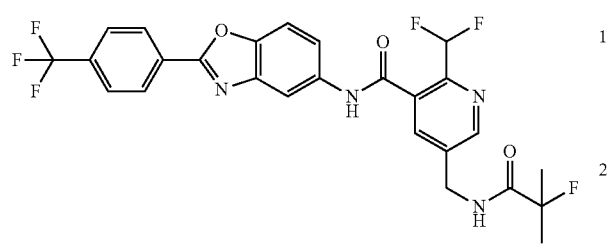
24
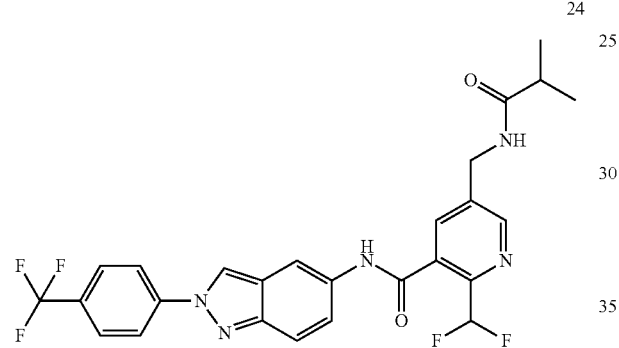
25
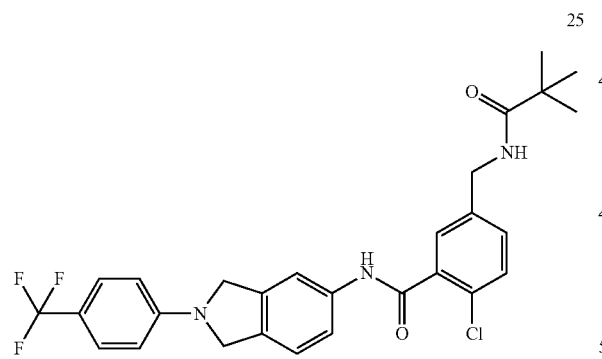
26
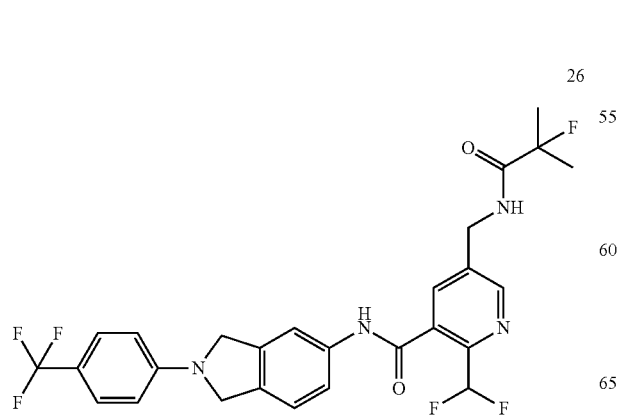
27
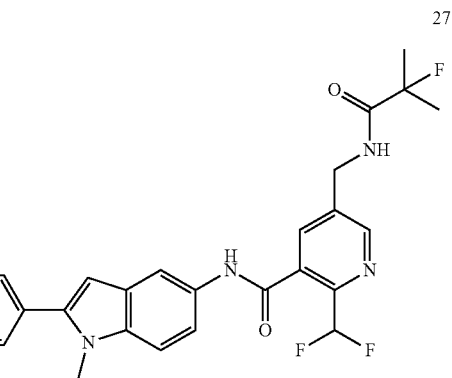
28
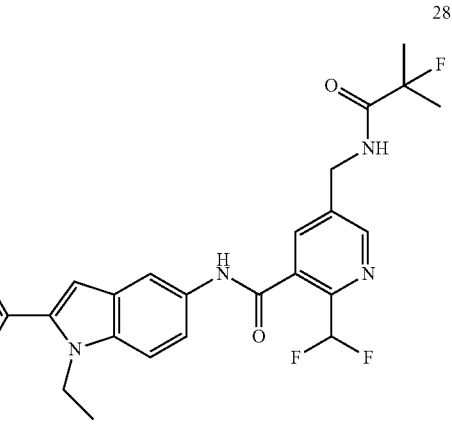
29
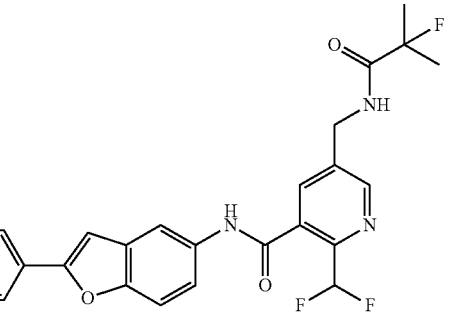
30
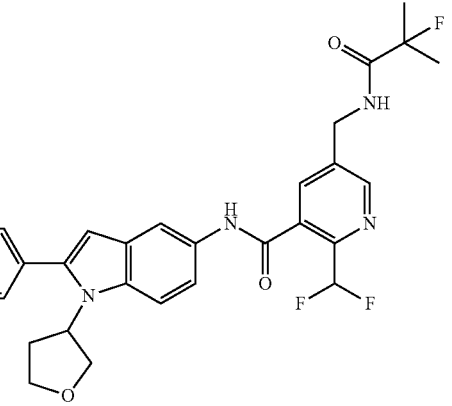

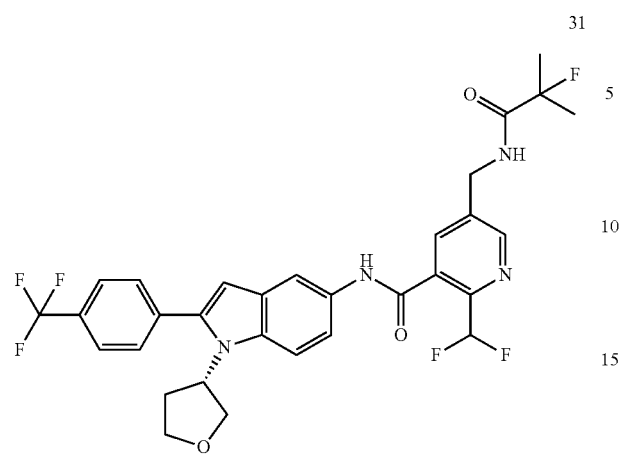
31
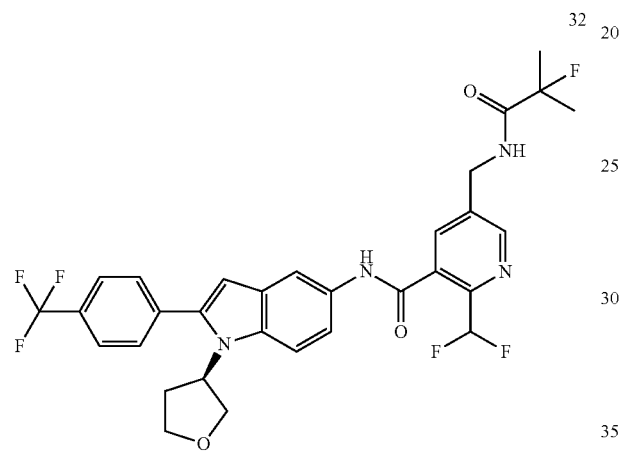
32
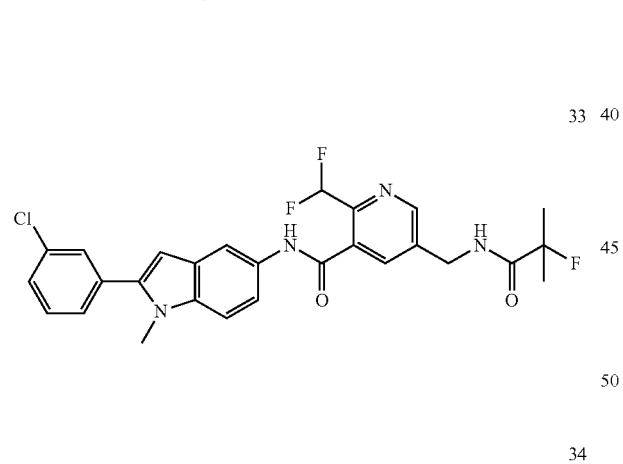
33
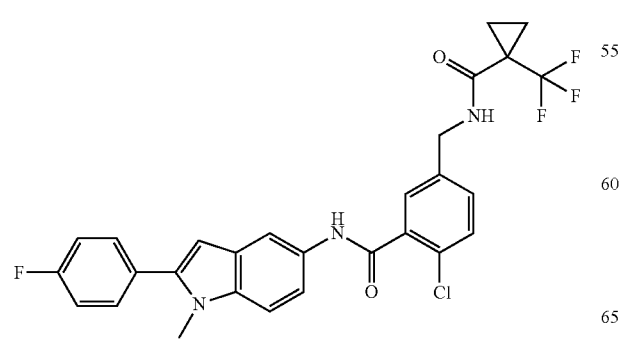
34
35
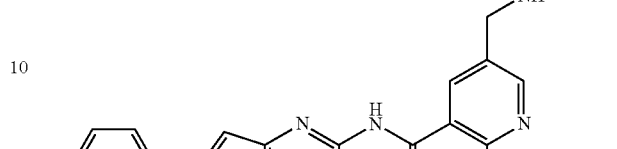
36
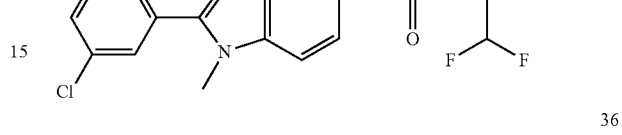
37
38

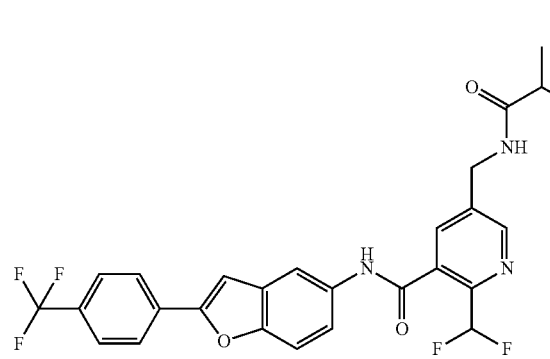
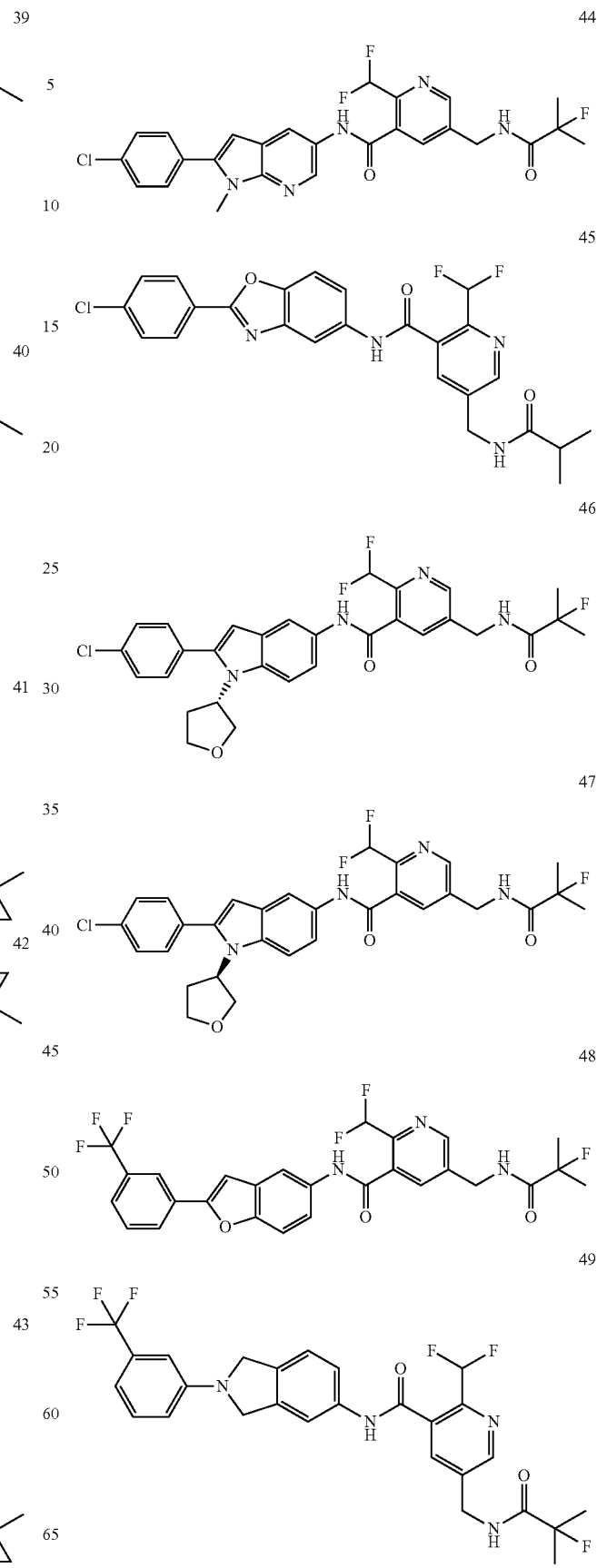

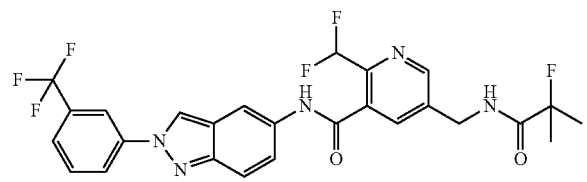
50
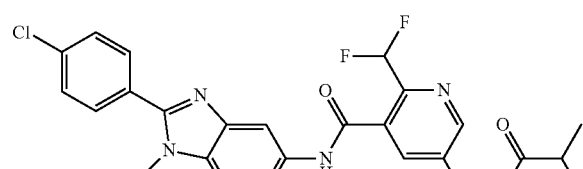
51
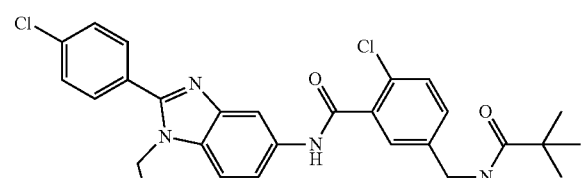
52
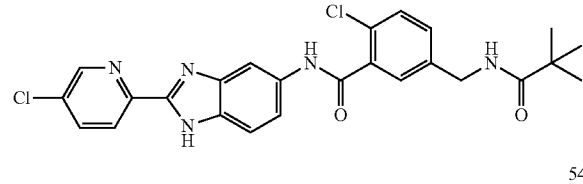
53
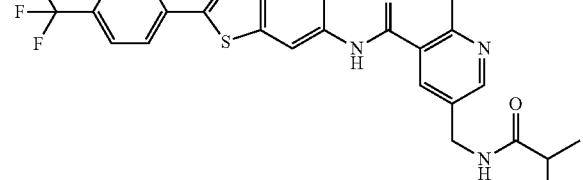
54
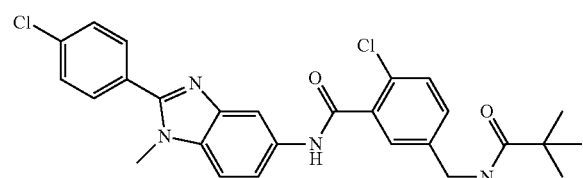
55
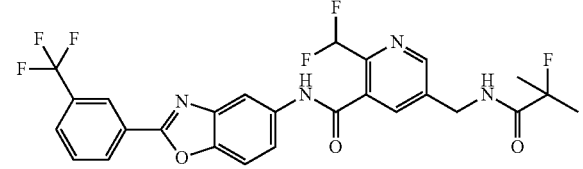
56
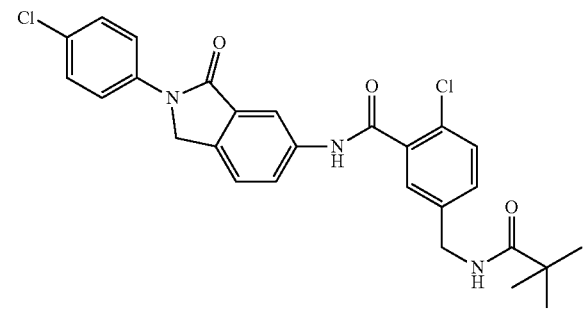
57
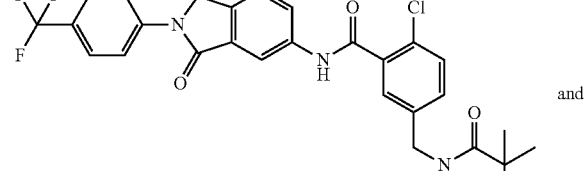
58
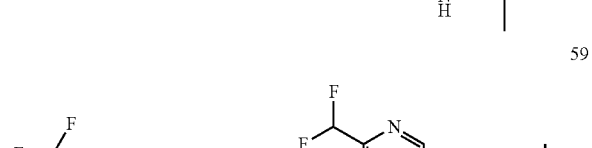
59
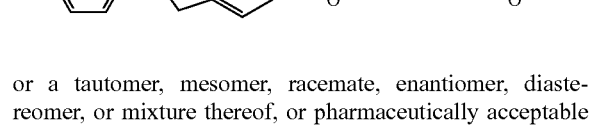
or a tautomer, mesomer, racemate, enantiomer, diastereomer, or mixture thereof, or pharmaceutically acceptable salt thereof.
7. A process for preparing a compound of formula (I), or a tautomer, mesomer, racemate, enantiomer, diastereomer, or mixture thereof, or pharmaceutically acceptable salt, comprising:
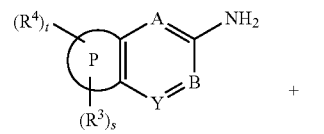
(IA)
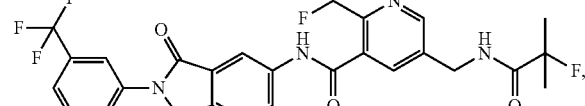
(IB)

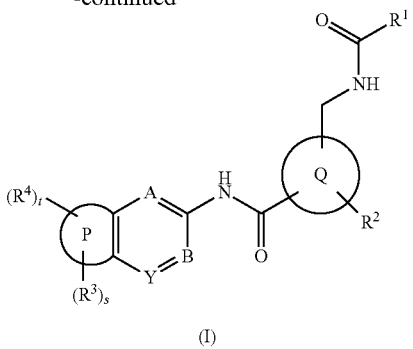

(I)

reacting a compound of formula (IA) or a salt thereof with a compound of formula (IB) to give the compound of formula (I);

wherein:
$R^c$ is hydroxy or halogen; and wherein:
ring P is selected from the group consisting of five-membered heteroaryl and five-membered heterocyclyl;
ring Q is selected from the group consisting of aryl and heteroaryl;
each of A, B and Y is —CH—;
$R^1$ is selected from the group consisting of alkyl and cycloalkyl, wherein the alkyl or cycloalkyl is optionally further substituted by one or more groups selected from the group consisting of alkyl, halogen and haloalkyl;
$R^2$ is selected from the group consisting of halogen and haloalkyl;
each $R^3$ is the same or different and is independently selected from the group consisting of hydrogen, halogen, alkoxy, cyano, nitro, alkyl, cycloalkyl, heterocyclyl, oxo, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, wherein the alkyl, cycloalkyl and heterocyclyl are each optionally further substituted by one or more groups selected from the group consisting of halogen, hydroxyl, alkoxy, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$;
$R^4$ is selected from the group consisting of aryl and heteroaryl, wherein the aryl and heteroaryl are each optionally further substituted by one or more groups selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$;
$R^5$ is selected from the group consisting of alkyl, alkenyl, alkynyl, cycloalkyl, heterocyclyl, aryl and heteroaryl, wherein the alkyl, cycloalkyl, aryl and heteroaryl are each optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group;
$R^6$ and $R^7$ are each independently selected from the group consisting of hydrogen, alkyl, alkoxy, cycloalkyl, heterocyclyl, aryl and heteroaryl, wherein the alkyl, alkoxy, cycloalkyl, heterocyclyl, aryl and heteroaryl are each independently and optionally further substituted by one or more groups selected from the group consisting of alkyl, halogen, hydroxyl, hydroxyalkyl, alkoxy, cycloalkyl, heterocyclyl, aryl, heteroaryl, carboxylic acid and carboxylate group; or
$R^6$ and $R^7$ are taken together with the nitrogen atom to which they are attached to form a heterocyclyl, wherein the heterocyclyl optionally contains one or more heteroatoms selected from the group consisting of N, O and S (O)$_m$, and wherein the heterocyclyl is optionally further substituted by one or more groups selected from the group consisting of alkyl, halogen, hydroxyl, alkoxy, hydroxyalkyl, cycloalkyl, heterocyclyl, aryl, heteroaryl, carboxylic acid and carboxylate group;
m is 0, 1 or 2;
s is 0, 1, 2, or 3; and
t is 0 or 1.

8. A pharmaceutical composition comprising a therapeutically effective amount of the compound of formula (III), formula (IV), or formula (V), or the tautomer, mesomer, racemate, enantiomer, diastereomer, or mixture thereof, or pharmaceutically acceptable salt thereof according to claim 1, and a pharmaceutically acceptable carrier, diluent or excipient.

9. The compound of formula (III), formula (IV), or formula (V), or the tautomer, mesomer, racemate, enantiomer, diastereomer, or mixture thereof, or pharmaceutically acceptable salt thereof according to claim 1, wherein $R^4$ is selected from the group consisting of aryl and heteroaryl, wherein the aryl and heteroaryl are each optionally further substituted by one or more groups selected from the group consisting of halogen, alkoxy, hydroxyl, cyano, nitro, alkyl, haloalkyl, hydroxyalkyl, cycloalkyl, heterocyclyl, aryl, heteroaryl, —C(O)OR$^5$, —OC(O)R$^5$, —NHS(O)$_m$R$^5$, —C(O)R$^5$, —NHC(O)R$^5$, —NHC(O)OR$^5$, —NR$^6$R$^7$, —OC(O)NR$^6$R$^7$ and —C(O)NR$^6$R$^7$, and the haloalkyl is trifluoromethyl.

10. The compound of formula (III), formula (IV), or formula (V), or the tautomer, mesomer, racemate, enantiomer, diastereomer, or mixture thereof, or pharmaceutically acceptable salt thereof according to claim 5, wherein $R^1$ is selected from the group consisting of tertiary butyl, isopropyl,

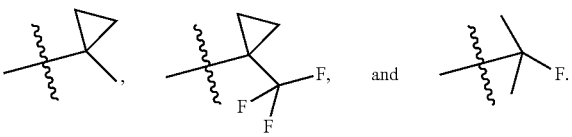

11. A method of inhibiting microsomal prostaglandin E synthase-1 in a subject in need thereof, the method comprising administering to the subject the pharmaceutical composition of claim 8.

12. A method of inhibiting microsomal prostaglandin E synthase-1, the method comprising contacting microsomal prostaglandin E synthase-1 with the compound of formula (III), formula (IV), or formula (V), or the tautomer, mesomer, racemate, enantiomer, diastereomer, or mixture thereof, or pharmaceutically acceptable salt thereof according to claim 1, thereby inhibiting microsomal prostaglandin E synthase-1.

13. A method of treating a disease or disorder in a subject in need thereof, the method comprising administering to the subject the pharmaceutical composition of claim 8, wherein the disease or disorder is selected from the group consisting of inflammatory pain and osteoarthritis.

14. A pharmaceutical composition comprising a therapeutically effective amount of the compound, or the tautomer, mesomer, racemate, enantiomer, diastereomer, or mixture thereof, or pharmaceutically acceptable salt thereof according to claim 6, and a pharmaceutically acceptable carrier, diluent or excipient.

15. A method of inhibiting microsomal prostaglandin E synthase-1 in a subject in need thereof, the method comprising administering to the subject the pharmaceutical composition of claim 14.

16. A method of treating a disease or disorder in a subject in need thereof, the method comprising administering to the subject the pharmaceutical composition of claim 14, wherein the disease or disorder is selected from the group consisting of inflammatory pain and osteoarthritis.

* * * * *